US008841438B2

(12) United States Patent
Tenenbaum et al.

(10) Patent No.: US 8,841,438 B2
(45) Date of Patent: Sep. 23, 2014

(54) TRANS-ACTING RNA SWITCHES

(75) Inventors: Scott A. Tenenbaum, Selkirk, NY (US);
Francis J. Doyle, II, Albany, NY (US);
Ajish George, Timonium, MD (US);
Christopher Zaleski, Huntington, NY (US)

(73) Assignee: The Research Foundation of the University of New York, Albany, NY (US)

( * ) Notice: Subject to any disclaimer, the term of this patent is extended or adjusted under 35 U.S.C. 154(b) by 0 days.

(21) Appl. No.: 13/321,816

(22) PCT Filed: May 21, 2010

(86) PCT No.: PCT/US2010/035870
§ 371 (c)(1),
(2), (4) Date: Jun. 12, 2012

(87) PCT Pub. No.: WO2010/135716
PCT Pub. Date: Nov. 25, 2010

(65) Prior Publication Data
US 2012/0252876 A1    Oct. 4, 2012

Related U.S. Application Data

(60) Provisional application No. 61/180,670, filed on May 22, 2009.

(51) Int. Cl.
| C07H 21/04 | (2006.01) |
| C07H 21/02 | (2006.01) |
| C12N 15/63 | (2006.01) |
| C12N 15/85 | (2006.01) |

(52) U.S. Cl.
USPC ....... 536/24.5; 536/23.1; 435/320.1; 435/325

(58) Field of Classification Search
CPC . A61K 2300/00; A61K 31/7088; A61K 48/00
See application file for complete search history.

(56) References Cited

U.S. PATENT DOCUMENTS

| 5,554,528 A | 9/1996 | Harrison et al. |
| 5,593,863 A | 1/1997 | Eberwine et al. |
| 7,338,762 B2 * | 3/2008 | Gorenstein et al. .......... 435/6.11 |
| 2005/0282190 A1 | 12/2005 | Shi et al. |

FOREIGN PATENT DOCUMENTS

| WO | WO-2004/046321 A2 | 6/2004 |
| WO | WO-2007/041213 A2 | 4/2007 |

OTHER PUBLICATIONS

Gorgoni et al. (2005) "The stem-loop binding protein stimulates histone translation at an early step in the initiation pathway" *RNA* 11: 1030-1042.
International Search Report of the International Searching Authority for PCT/US2010/035870, dated Aug. 20, 2010, 4 pages.
Written Opinion of the International Searching Authority for PCT/US2010/035870, dated Aug. 20, 2010, 7 pages.
Childs J. L. "Oligonucleotide directed misfolding of RNA inhibits *Candida albicans* group I intron splicing," *PNAS,* 2002, vol. 99, No. 17, pp. 11091-11096.
Isaacs et al. "Engineered riboregulators enable post-transcriptional control of gene expression," *Nature Biotechnology,* 2004, vol. 22, No. 7, pp. 841-847.
Khattab et al. "Improved Targeting of the Flanks of a DNA Stem Using α-Oligodeoxynucleotides—The Enhanced Effect of an Intercalator," *Nucleosides & Nucleotides,* 1998, vol. 17, No. 12, pp. 2351-2365.
Sando et al. "Doubly Catalytic Sensing of HIV-1-Related CCR5 Sequence in Prokaryotic Cell-Free Translation System Using Riboregulator-Controlled Luciferase Activity," *J. Am. Chem. Soc.,* 2005, vol. 127, No. 15, pp. 5300-5301.
Silverman S. K. "Nucleic Acid Switches and Sensors," Nucleic Acid Switches and Sensors Springer, 233 Spring Street, New York, NY 10013, United States Series : Molecular Biology Intelligence Unit, 2006, 133 pages.
Vickers et al. "Enhancement of ribosomal frameshifting by oligonucleotides targeted to the HIV *gag-pol* region," *Nucleic Acids Research,* 1992, vol. 20, No. 15, pp. 3945-3953.
Supplementary European Search Report for European Application No. EP 10778508.1, dated Jan. 23, 2014, 11 pages.

* cited by examiner

*Primary Examiner* — Amy Bowman
(74) *Attorney, Agent, or Firm* — Goodwin Procter LLP

(57) ABSTRACT

Disclosed are RNA constructs which function to activate or inactivate a biological process, e.g., may be designed for attachment to a polypeptide coding region. Such RNA constructs modulate translation of a polypeptide from the coding region in response to the presence of a target polynucleotide in an expression environment. Such RNA constructs include a weakened stem-loop structure which, when bound to the target polynucleotide, assumes stem-loop secondary structure and associates with an RNA binding protein. Association with the RNA binding protein modulates translation of the polypeptide coding region. Such RNA constructs also have three-way junction joining regions 3' and 5' of the stem-loop structure.

17 Claims, 157 Drawing Sheets

| | start | end | origin |
|---|---|---|---|
| 1. | 450 | 470 | >gi|72398502|gb|DQ073573.1| Craterostigma plantagineum histone H3.3 mRNA |
| 2. | 438 | 458 | >gi|221130418|ref|XM_002154434.1| PREDICTED: Hydra magnipapillata similar to Histone H3.3B CG8989-PA (LOC100206107); mRNA |
| 3. | 438 | 458 | >gi|28317599|gb|AY223124.1| Schistosoma japonicum clone ZZD1425 mRNA sequence |
| 4. | 408 | 428 | >gi|56755656|gb|AY814275.1| Schistosoma japonicum clone SJCHGC01603 unknown mRNA |
| 5. | 376 | 396 | >gi|60603025|gb|AY812081.1| Schistosoma japonicum SJCHGC05779 protein mRNA; partial cds |
| 6. | 484 | 504 | >gi|12276044|gb|AF304122.1|AF304122 Caenorhabditis elegans histone H3 (20113) mRNA |
| 7. | 494 | 514 | >gi|71981222|ref|NM_069733.2| Caenorhabditis elegans HIStone family member (his-45) (his-45) mRNA |
| 8. | 357 | 377 | >gi|71986946|ref|NM_069753.2| Caenorhabditis elegans HIStone family member (his-64) (his-64) mRNA |
| 9. | 416 | 436 | >gi|71989465|ref|NM_068800.2| Caenorhabditis elegans HIStone family member (his-61) (his-61) mRNA |
| 10. | 431 | 451 | >gi|133930986|ref|NM_069731.3| Caenorhabditis elegans HIStone family member (his-48) (his-48) mRNA |
| 11. | 388 | 408 | >gi|193203235|ref|NM_060240.3| Caenorhabditis elegans HIStone family member (his-67) (his-67) mRNA |
| 12. | 438 | 458 | >gi|193205286|ref|NM_064491.5| Caenorhabditis elegans HIStone family member (his-11) (his-11) mRNA |
| 13. | 363 | 383 | >gi|193206351|ref|NM_068802.4| Caenorhabditis elegans HIStone family member (his-60) (his-60) mRNA |
| 14. | 385 | 405 | >gi|193208310|ref|NM_072897.3| Caenorhabditis elegans HIStone family member (his-18) (his-18) mRNA |
| 15. | 466 | 486 | >gi|193208694|ref|NM_074632.2| Caenorhabditis elegans HIStone family member (his-2) (his-2) mRNA |
| 16. | 431 | 451 | >gi|212646063|ref|NM_069739.4| Caenorhabditis elegans HIStone family member (his-58) (his-58) mRNA |
| 17. | 499 | 519 | >gi|170572148|ref|XM_001891966.1| Brugia malayi histone H3 partial mRNA |
| 18. | 429 | 449 | >gi|170572152|ref|XM_001891968.1| Brugia malayi histone H2A partial mRNA |
| 19. | 439 | 459 | >gi|170572156|ref|XM_001891970.1| Brugia malayi histone H4 partial mRNA |
| 20. | 492 | 512 | >gi|170572314|ref|XM_001892027.1| Brugia malayi Histone H2B 2 partial mRNA |
| 21. | 491 | 511 | >gi|13919642|gb|AY028698.1| Trichinella spiralis histone H3 mRNA |
| 22. | 1561 | 1581 | >gi|786116|gb|L41834.1|ENXNUPR Ensis minor (clone 1/6) nuclear protein mRNA |
| 23. | 594 | 614 | >gi|170047065|ref|XM_001851007.1| Culex quinquefasciatus tetratricopeptide repeat protein; tpr; mRNA |
| 24. | 404 | 424 | >gi|195356859|ref|XM_002044819.1| Drosophila sechellia GM16912 (Dsec\GM16912); mRNA |

Figure 11B

| 25. | 371 | 391 | >gi\|195356889\|ref\|XM_002044830.1\| Drosophila sechellia GM16472 (Dsec\GM16472); mRNA |
| --- | --- | --- | --- |
| 26. | 404 | 424 | >gi\|195356893\|ref\|XM_002044832.1\| Drosophila sechellia GM16470 (Dsec\GM16470); mRNA |
| 27. | 415 | 435 | >gi\|195388881\|ref\|XM_002053071.1\| Drosophila virilis GJ23521 (Dvir\GJ23521); mRNA |
| 28. | 657 | 677 | >gi\|156545682\|ref\|XM_001604326.1\| PREDICTED: Nasonia vitripennis similar to histone H1 (LOC100120772); mRNA |
| 29. | 686 | 706 | >gi\|47551076\|ref\|NM_214549.1\| Strongylocentrotus purpuratus early histone H1 (LOC373342); mRNA |
| 30. | 745 | 765 | >gi\|47551088\|ref\|NM_214558.1\| Strongylocentrotus purpuratus histone H1-beta (LOC373354); mRNA |
| 31. | 420 | 440 | >gi\|115635580\|ref\|XM_001175478.1\| PREDICTED: Strongylocentrotus purpuratus similar to H4 histone protein (LOC752036); mRNA |
| 32. | 506 | 526 | >gi\|115671086\|ref\|XM_001178342.1\| PREDICTED: Strongylocentrotus purpuratus similar to histone H3 (LOC754375); mRNA |
| 33. | 418 | 438 | >gi\|115671088\|ref\|XM_001178624.1\| PREDICTED: Strongylocentrotus purpuratus similar to H4 histone protein (LOC754403); mRNA |
| 34. | 468 | 488 | >gi\|115671090\|ref\|XM_001178716.1\| PREDICTED: Strongylocentrotus purpuratus similar to histone H2B (LOC754417); mRNA |
| 35. | 506 | 526 | >gi\|115678952\|ref\|XM_001175488.1\| PREDICTED: Strongylocentrotus purpuratus similar to histone H3 (LOC752264); mRNA |
| 36. | 417 | 437 | >gi\|115679019\|ref\|XM_001175935.1\| PREDICTED: Strongylocentrotus purpuratus similar to H4 histone protein (LOC752682); mRNA |
| 37. | 463 | 483 | >gi\|115679021\|ref\|XM_001176085.1\| PREDICTED: Strongylocentrotus purpuratus similar to histone H2A (LOC752697); mRNA |
| 38. | 417 | 437 | >gi\|115699559\|ref\|XM_001176666.1\| PREDICTED: Strongylocentrotus purpuratus similar to H4 histone protein (LOC753233); mRNA |
| 39. | 387 | 407 | >gi\|115712049\|ref\|XM_001177620.1\| PREDICTED: Strongylocentrotus purpuratus similar to H4 histone protein (LOC753158); mRNA |
| 40. | 463 | 483 | >gi\|115725408\|ref\|XM_001175793.1\| PREDICTED: Strongylocentrotus purpuratus similar to histone H2A (LOC752307); mRNA |
| 41. | 417 | 437 | >gi\|115727659\|ref\|XM_001177753.1\| PREDICTED: Strongylocentrotus purpuratus similar to H4 histone protein (LOC754000); mRNA |
| 42. | 674 | 694 | >gi\|115836849\|ref\|XR_025642.1\| PREDICTED: Strongylocentrotus purpuratus similar to early histone H1 (LOC752088); mRNA |
| 43. | 420 | 440 | >gi\|115925694\|ref\|XM_001178996.1\| PREDICTED: Strongylocentrotus purpuratus similar to H4 histone protein (LOC759686); mRNA |
| 44. | 506 | 526 | >gi\|115944486\|ref\|XM_001175699.1\| PREDICTED: Strongylocentrotus purpuratus similar to histone H3 (LOC757440); mRNA |
| 45. | 417 | 437 | >gi\|115950535\|ref\|XM_001178802.1\| PREDICTED: Strongylocentrotus purpuratus similar to H4 histone protein (LOC759351); mRNA |
| 46. | 462 | 482 | >gi\|115958725\|ref\|XM_001179746.1\| PREDICTED: Strongylocentrotus purpuratus similar to histone H2A (LOC760111); mRNA |

Figure 11C

| 47. | 417 | 437 | >gi|115959075|ref|XM_001176582.1| PREDICTED: Strongylocentrotus purpuratus similar to H4 histone protein (LOC758518); mRNA |
| --- | --- | --- | --- |
| 48. | 418 | 438 | >gi|115963938|ref|XM_001178381.1| PREDICTED: Strongylocentrotus purpuratus similar to H4 histone protein (LOC759306); mRNA |
| 49. | 506 | 526 | >gi|115963942|ref|XM_001178654.1| PREDICTED: Strongylocentrotus purpuratus similar to histone H3 (LOC759352); mRNA |
| 50. | 470 | 490 | >gi|115963944|ref|XM_001178738.1| PREDICTED: Strongylocentrotus purpuratus similar to histone H2B (LOC759371); mRNA |
| 51. | 387 | 407 | >gi|115968876|ref|XM_001175583.1| PREDICTED: Strongylocentrotus purpuratus similar to H4 histone protein (LOC757410); mRNA |
| 52. | 417 | 437 | >gi|115970232|ref|XM_001177556.1| PREDICTED: Strongylocentrotus purpuratus similar to H4 histone protein (LOC759028); mRNA |
| 53. | 674 | 694 | >gi|115973493|ref|XR_025658.1| PREDICTED: Strongylocentrotus purpuratus similar to early histone H1 (LOC758970); mRNA |
| 54. | 490 | 510 | >gi|198424614|ref|XM_002128346.1| PREDICTED: Ciona intestinalis similar to His3:CG31613 CG31613-PA (LOC100175370); mRNA |
| 55. | 487 | 507 | >gi|198424616|ref|XM_002128978.1| PREDICTED: Ciona intestinalis similar to His3:CG31613 CG31613-PA (LOC100183198); mRNA |
| 56. | 443 | 463 | >gi|219409246|ref|XM_002202402.1| Branchiostoma floridae hypothetical protein (BRAFLDRAFT_113575) mRNA |
| 57. | 478 | 498 | >gi|219435123|ref|XM_002215306.1| Branchiostoma floridae hypothetical protein (BRAFLDRAFT_121770) mRNA |
| 58. | 432 | 452 | >gi|219440622|ref|XM_002218045.1| Branchiostoma floridae hypothetical protein (BRAFLDRAFT_114570) mRNA |
| 59. | 1183 | 1203 | >gi|219446307|ref|XM_002220875.1| Branchiostoma floridae hypothetical protein (BRAFLDRAFT_83007) mRNA |
| 60. | 443 | 463 | >gi|219467359|ref|XM_002231261.1| Branchiostoma floridae hypothetical protein (BRAFLDRAFT_266634) mRNA |
| 61. | 552 | 572 | >gi|219467380|ref|XM_002231271.1| Branchiostoma floridae hypothetical protein (BRAFLDRAFT_266644) mRNA |
| 62. | 782 | 802 | >gi|219475159|ref|XM_002234919.1| Branchiostoma floridae hypothetical protein (BRAFLDRAFT_128327) mRNA |
| 63. | 619 | 639 | >gi|219475662|ref|XM_002235155.1| Branchiostoma floridae hypothetical protein (BRAFLDRAFT_268216) mRNA |
| 64. | 369 | 389 | >gi|219477239|ref|XM_002235893.1| Branchiostoma floridae hypothetical protein (BRAFLDRAFT_283927) mRNA |
| 65. | 215 | 235 | >gi|219480247|ref|XM_002237298.1| Branchiostoma floridae hypothetical protein (BRAFLDRAFT_269245) mRNA; partial cds |
| 66. | 389 | 409 | >gi|219480257|ref|XM_002237303.1| Branchiostoma floridae hypothetical protein (BRAFLDRAFT_129140) mRNA |
| 67. | 621 | 641 | >gi|219480297|ref|XM_002237322.1| Branchiostoma floridae hypothetical protein (BRAFLDRAFT_284648) mRNA |
| 68. | 432 | 452 | >gi|219481533|ref|XM_002237895.1| Branchiostoma floridae hypothetical protein (BRAFLDRAFT_115929) mRNA |

Figure 11D

| 69. | 432 | 452 | >gi|219481535|ref|XM_002237896.1| Branchiostoma floridae hypothetical protein (BRAFLDRAFT_115931) mRNA |
|---|---|---|---|
| 70. | 432 | 452 | >gi|219481537|ref|XM_002237897.1| Branchiostoma floridae hypothetical protein (BRAFLDRAFT_129351) mRNA |
| 71. | 404 | 424 | >gi|219481578|ref|XM_002237916.1| Branchiostoma floridae hypothetical protein (BRAFLDRAFT_269579) mRNA |
| 72. | 455 | 475 | >gi|219481580|ref|XM_002237917.1| Branchiostoma floridae hypothetical protein (BRAFLDRAFT_115926) mRNA |
| 73. | 378 | 398 | >gi|219481584|ref|XM_002237919.1| Branchiostoma floridae hypothetical protein (BRAFLDRAFT_115927) mRNA |
| 74. | 881 | 901 | >gi|219481589|ref|XM_002237921.1| Branchiostoma floridae hypothetical protein (BRAFLDRAFT_115930) mRNA |
| 75. | 432 | 452 | >gi|219482187|ref|XM_002238199.1| Branchiostoma floridae hypothetical protein (BRAFLDRAFT_129443) mRNA |
| 76. | 432 | 452 | >gi|219484360|ref|XM_002239207.1| Branchiostoma floridae hypothetical protein (BRAFLDRAFT_129777) mRNA |
| 77. | 455 | 475 | >gi|219484385|ref|XM_002239219.1| Branchiostoma floridae hypothetical protein (BRAFLDRAFT_285546) mRNA |
| 78. | 378 | 398 | >gi|219484389|ref|XM_002239221.1| Branchiostoma floridae hypothetical protein (BRAFLDRAFT_285548) mRNA |
| 79. | 378 | 398 | >gi|219484393|ref|XM_002239223.1| Branchiostoma floridae hypothetical protein (BRAFLDRAFT_129780) mRNA |
| 80. | 799 | 819 | >gi|219484396|ref|XM_002239224.1| Branchiostoma floridae hypothetical protein (BRAFLDRAFT_129781) mRNA |
| 81. | 429 | 449 | >gi|219484398|ref|XM_002239225.1| Branchiostoma floridae hypothetical protein (BRAFLDRAFT_129784) mRNA |
| 82. | 312 | 332 | >gi|219493289|ref|XM_002243348.1| Branchiostoma floridae hypothetical protein (BRAFLDRAFT_271938) mRNA; partial cds |
| 83. | 618 | 638 | >gi|219500497|ref|XM_002246634.1| Branchiostoma floridae hypothetical protein (BRAFLDRAFT_288719) mRNA |
| 84. | 386 | 406 | >gi|219500531|ref|XM_002246650.1| Branchiostoma floridae hypothetical protein (BRAFLDRAFT_116571) mRNA |
| 85. | 623 | 643 | >gi|219512547|ref|XM_002251185.1| Branchiostoma floridae hypothetical protein (BRAFLDRAFT_290231) mRNA |
| 86. | 497 | 517 | >gi|28277997|gb|BC046078.1| Danio rerio H2A histone family; member X; mRNA (cDNA clone MGC:56329 IMAGE:5603679) |
| 87. | 497 | 517 | >gi|41055101|ref|NM_201073.1| Danio rerio H2A histone family; member X (h2afx); mRNA |
| 88. | 409 | 429 | >gi|60688614|gb|BC091558.1| Danio rerio zgc:114046; mRNA (cDNA clone MGC:114046 IMAGE:7417024) |
| 89. | 454 | 474 | >gi|62531204|gb|BC093343.1| Danio rerio MID1 interacting protein 1; mRNA (cDNA clone MGC:112497 IMAGE:7411962) |
| 90. | 656 | 676 | >gi|63100661|gb|BC095255.1| Danio rerio zgc:110425; mRNA (cDNA clone MGC:110425 IMAGE:7224636) |

Figure 11E

| 91. | 450 | 470 | >gi\|66267280\|gb\|BC095260.1\| Danio rerio zgc:110434; mRNA (cDNA clone MGC:110434 IMAGE:7226287) |
|---|---|---|---|
| 92. | 429 | 449 | >gi\|66267342\|gb\|BC095697.1\| Danio rerio zgc:112234; mRNA (cDNA clone MGC:112234 IMAGE:7223605) |
| 93. | 656 | 676 | >gi\|66472223\|ref\|NM_001020746.1\| Danio rerio zgc:110425 (zgc:110425); mRNA |
| 94. | 450 | 470 | >gi\|66773150\|ref\|NM_001024396.1\| Danio rerio zgc:110434 (zgc:110434); mRNA |
| 95. | 469 | 489 | >gi\|67677879\|gb\|BC097060.1\| Danio rerio zgc:113984; mRNA (cDNA clone MGC:113984 IMAGE:7448238) |
| 96. | 482 | 502 | >gi\|67678180\|gb\|BC097059.1\| Danio rerio zgc:113983; mRNA (cDNA clone MGC:113983 IMAGE:7226638) |
| 97. | 482 | 502 | >gi\|68448482\|ref\|NM_001025171.1\| Danio rerio zgc:113983 (zgc:113983); mRNA |
| 98. | 461 | 481 | >gi\|71051768\|gb\|BC098891.1\| Danio rerio zgc:114037; mRNA (cDNA clone MGC:114037 IMAGE:7276112) |
| 99. | 461 | 481 | >gi\|73611921\|ref\|NM_001031826.1\| Danio rerio zgc:114037 (zgc:114037); mRNA |
| 100. | 469 | 489 | >gi\|90855767\|ref\|NM_001025176.3\| Danio rerio zgc:113984 (zgc:113984); mRNA |
| 101. | 688 | 708 | >gi\|112418947\|gb\|BC122272.1\| Danio rerio zgc:153405; mRNA (cDNA clone MGC:153405 IMAGE:8125128) |
| 102. | 688 | 708 | >gi\|113679268\|ref\|NM_001045378.1\| Danio rerio zgc:153405 (zgc:153405); mRNA |
| 103. | 356 | 376 | >gi\|115292018\|gb\|BC122463.1\| Danio rerio zgc:154164; mRNA (cDNA clone MGC:154164 IMAGE:7268729) |
| 104. | 356 | 376 | >gi\|115529378\|ref\|NM_001076749.1\| Danio rerio zgc:154164 (zgc:154164); mRNA |
| 105. | 428 | 448 | >gi\|116284275\|gb\|BC124434.1\| Danio rerio zgc:112234; mRNA (cDNA clone MGC:153715 IMAGE:8132014) |
| 106. | 428 | 448 | >gi\|116812892\|ref\|NM_001024398.2\| Danio rerio zgc:112234 (zgc:112234); mRNA |
| 107. | 428 | 448 | >gi\|125808565\|ref\|XM_686974.2\| PREDICTED: Danio rerio hypothetical LOC563612 (LOC563612); mRNA |
| 108. | 355 | 375 | >gi\|125820535\|ref\|XM_001331295.1\| PREDICTED: Danio rerio hypothetical LOC791651 (LOC791651); mRNA |
| 109. | 656 | 676 | >gi\|125820539\|ref\|XM_001331131.1\| PREDICTED: Danio rerio hypothetical LOC791652 (LOC791652); mRNA |
| 110. | 408 | 428 | >gi\|125820557\|ref\|XM_001335354.1\| PREDICTED: Danio rerio similar to histone cluster 2; H2ab (LOC100001004); mRNA |
| 111. | 482 | 502 | >gi\|125855354\|ref\|XM_687893.2\| PREDICTED: Danio rerio hypothetical LOC564560 (LOC564560); mRNA |
| 112. | 416 | 436 | >gi\|125855692\|ref\|XM_001338920.1\| PREDICTED: Danio rerio similar to Mid1ip1 protein (LOC100004768); mRNA |

Figure 11F

| 113. | 387 | 407 | >gi|125855698|ref|XM_001339097.1| PREDICTED: Danio rerio similar to Histone H4 replacement CG3379-PC (LOC100004918); mRNA |
|---|---|---|---|
| 114. | 471 | 491 | >gi|125858883|gb|BC129430.1| Danio rerio zgc:113984; mRNA (cDNA clone MGC:158753 IMAGE:7888467) |
| 115. | 475 | 495 | >gi|125859006|gb|BC129333.1| Danio rerio zgc:158629; mRNA (cDNA clone MGC:158629 IMAGE:7071116) |
| 116. | 442 | 462 | >gi|133778769|gb|BC134206.1| Danio rerio zgc:163047; mRNA (cDNA clone MGC:163047 IMAGE:7281853) |
| 117. | 364 | 384 | >gi|141795352|gb|BC135092.1| Danio rerio zgc:163040; mRNA (cDNA clone MGC:163040 IMAGE:7225744) |
| 118. | 602 | 622 | >gi|141796183|gb|BC135096.1| Danio rerio zgc:163061; mRNA (cDNA clone MGC:163061 IMAGE:7430610) |
| 119. | 602 | 622 | >gi|147905489|ref|NM_001089531.1| Danio rerio zgc:163061 (zgc:163061); mRNA |
| 120. | 442 | 462 | >gi|148227933|ref|NM_001089564.1| Danio rerio zgc:163047 (zgc:163047); mRNA |
| 121. | 364 | 384 | >gi|148229710|ref|NM_001089569.1| Danio rerio zgc:163040 (zgc:163040); mRNA |
| 122. | 379 | 399 | >gi|148744728|gb|BC142859.1| Danio rerio zgc:165555; mRNA (cDNA clone MGC:165555 IMAGE:7233506) |
| 123. | 379 | 399 | >gi|148922914|ref|NM_001098761.1| Danio rerio zgc:165555 (zgc:165555); mRNA |
| 124. | 442 | 462 | >gi|152001090|gb|BC146737.1| Danio rerio zgc:165551; mRNA (cDNA clone MGC:165551 IMAGE:7219026) |
| 125. | 431 | 451 | >gi|152012638|gb|BC150432.1| Danio rerio zgc:173585; mRNA (cDNA clone MGC:173585 IMAGE:7239302) |
| 126. | 448 | 468 | >gi|152012854|gb|BC150436.1| Danio rerio zgc:173652; mRNA (cDNA clone MGC:173652 IMAGE:7225612) |
| 127. | 440 | 460 | >gi|152012906|gb|BC150451.1| Danio rerio guanine nucleotide binding protein (G protein); gamma 5; mRNA (cDNA clone MGC:173883 IMAGE:7279453) |
| 128. | 475 | 495 | >gi|154146239|ref|NM_001100173.1| Danio rerio zgc:158629 (zgc:158629); mRNA |
| 129. | 427 | 447 | >gi|156229880|gb|BC152000.1| Danio rerio zgc:171937; mRNA (cDNA clone MGC:171937 IMAGE:7448383) |
| 130. | 479 | 499 | >gi|156229911|gb|BC152073.1| Danio rerio zgc:158629; mRNA (cDNA clone MGC:173434 IMAGE:7891820) |
| 131. | 428 | 448 | >gi|156230360|gb|BC151966.1| Danio rerio zgc:171759; mRNA (cDNA clone MGC:171759 IMAGE:8124576) |
| 132. | 430 | 450 | >gi|156230433|gb|BC152107.1| Danio rerio zgc:173587; mRNA (cDNA clone MGC:173587 IMAGE:7448995) |
| 133. | 435 | 455 | >gi|156230877|gb|BC152106.1| Danio rerio zgc:114046; mRNA (cDNA clone MGC:173586 IMAGE:7437930) |
| 134. | 431 | 451 | >gi|156616355|ref|NM_001102632.1| Danio rerio zgc:173585 (zgc:173585); mRNA |

Figure 11G

| 135. | 448 | 468 | >gi|156938296|ref|NM_001103164.1| Danio rerio zgc:173652 (zgc:173652); mRNA |
|---|---|---|---|
| 136. | 473 | 493 | >gi|157423408|gb|BC153403.1| Danio rerio zgc:113984; mRNA (cDNA clone MGC:173558 IMAGE:7416180) |
| 137. | 427 | 447 | >gi|157954457|ref|NM_001109835.1| Danio rerio zgc:171937 (zgc:171937); mRNA |
| 138. | 430 | 450 | >gi|157954459|ref|NM_001109836.1| Danio rerio zgc:173587 (zgc:173587); mRNA |
| 139. | 1585 | 1605 | >gi|158253514|gb|BC154136.1| Danio rerio zgc:173552; mRNA (cDNA clone MGC:173552 IMAGE:7448991) |
| 140. | 1585 | 1605 | >gi|162138957|ref|NM_001111216.1| Danio rerio zgc:173552 (zgc:173552); mRNA |
| 141. | 364 | 384 | >gi|189516395|ref|XM_001337623.2| PREDICTED: Danio rerio hypothetical LOC100004971 (LOC100004971); mRNA |
| 142. | 452 | 472 | >gi|189516411|ref|XM_001344951.2| PREDICTED: Danio rerio similar to His3:CG31613 CG31613-PA (LOC100006146); mRNA |
| 143. | 538 | 558 | >gi|189516418|ref|XM_001922570.1| PREDICTED: Danio rerio similar to histone cluster 2; H2be (LOC100149997); mRNA |
| 144. | 441 | 461 | >gi|189516420|ref|XM_001345077.2| PREDICTED: Danio rerio similar to Mid1ip1 protein (LOC100006331); mRNA |
| 145. | 345 | 365 | >gi|189516422|ref|XM_687827.3| PREDICTED: Danio rerio similar to Histone H4 replacement CG3379-PC (LOC564494); mRNA |
| 146. | 697 | 717 | >gi|189516423|ref|XM_001337389.2| PREDICTED: Danio rerio similar to histone cluster 1; H2bb (LOC100004810); mRNA |
| 147. | 890 | 910 | >gi|189516424|ref|XM_694699.3| PREDICTED: Danio rerio similar to Histone H1.5 (Histone H1a) (LOC571135); mRNA |
| 148. | 476 | 496 | >gi|189516425|ref|XM_001337548.2| PREDICTED: Danio rerio similar to His3:CG31613 CG31613-PA (LOC100004914); mRNA |
| 149. | 452 | 472 | >gi|189516429|ref|XM_677616.3| PREDICTED: Danio rerio similar to His3:CG31613 CG31613-PA; transcript variant 1 (LOC556568); mRNA |
| 150. | 422 | 442 | >gi|189516430|ref|XM_685118.3| PREDICTED: Danio rerio similar to histone cluster 2; H2bc (LOC573116); mRNA |
| 151. | 457 | 477 | >gi|189521839|ref|XM_694200.3| PREDICTED: Danio rerio hypothetical LOC570692 (LOC570692); mRNA |
| 152. | 454 | 474 | >gi|189521840|ref|XM_688063.3| PREDICTED: Danio rerio similar to His3:CG31613 CG31613-PA (LOC564732); mRNA |
| 153. | 414 | 434 | >gi|189521843|ref|XM_687880.3| PREDICTED: Danio rerio similar to histone cluster 1; H2bb (LOC564549); mRNA |
| 154. | 434 | 454 | >gi|189521845|ref|XM_001334835.2| PREDICTED: Danio rerio similar to histone cluster 2; H2ab (LOC100000574); mRNA |
| 155. | 366 | 386 | >gi|189521846|ref|XM_687692.3| PREDICTED: Danio rerio similar to Histone H4 replacement CG3379-PC (LOC564352); mRNA |
| 156. | 449 | 469 | >gi|189521847|ref|XM_001335100.2| PREDICTED: Danio rerio similar to Mid1ip1 protein (LOC100000783); mRNA |

Figure 11H

| 157. | 465 | 485 | >gi|189521848|ref|XM_001335267.2| PREDICTED: Danio rerio similar to His3:CG31613 CG31613-PA (LOC100000930); mRNA |
|---|---|---|---|
| 158. | 485 | 505 | >gi|189521851|ref|XM_001922828.1| PREDICTED: Danio rerio similar to His3:CG31613 CG31613-PA (LOC100001294); mRNA |
| 159. | 688 | 708 | >gi|189521853|ref|XM_001922829.1| PREDICTED: Danio rerio similar to Histone H1.5 (Histone H1a) (LOC100149653); mRNA |
| 160. | 469 | 489 | >gi|189521857|ref|XM_001922833.1| PREDICTED: Danio rerio similar to His3:CG31613 CG31613-PA (LOC100148162); mRNA |
| 161. | 682 | 702 | >gi|189521859|ref|XM_001922838.1| PREDICTED: Danio rerio similar to Histone H1.5 (Histone H1a) (LOC100151261); mRNA |
| 162. | 450 | 470 | >gi|189521862|ref|XM_688696.2| PREDICTED: Danio rerio similar to histone cluster 2; H2ab (LOC565417); mRNA |
| 163. | 466 | 486 | >gi|189521865|ref|XM_688339.2| PREDICTED: Danio rerio similar to His3:CG31613 CG31613-PA (LOC565028); mRNA |
| 164. | 418 | 438 | >gi|189521870|ref|XM_001336287.2| PREDICTED: Danio rerio similar to histone cluster 1; H2bb (LOC100002115); mRNA |
| 165. | 361 | 381 | >gi|189521871|ref|XM_001336371.2| PREDICTED: Danio rerio similar to Histone H4 replacement CG3379-PC (LOC100002181); mRNA |
| 166. | 401 | 421 | >gi|189521872|ref|XM_694239.3| PREDICTED: Danio rerio similar to histone cluster 1; H2bb (LOC570727); mRNA |
| 167. | 481 | 501 | >gi|189521873|ref|XM_694212.2| PREDICTED: Danio rerio similar to His3:CG31613 CG31613-PA (LOC570703); mRNA |
| 168. | 477 | 497 | >gi|189522049|ref|XM_001922199.1| PREDICTED: Danio rerio zgc:173552 (zgc:173552); mRNA |
| 169. | 386 | 406 | >gi|189522051|ref|XM_702708.3| PREDICTED: Danio rerio similar to Histone H4 replacement CG3379-PC; transcript variant 2 (LOC562770); mRNA |
| 170. | 397 | 417 | >gi|189522052|ref|XM_001922227.1| PREDICTED: Danio rerio similar to histone cluster 1; H2bb (LOC794250); mRNA |
| 171. | 493 | 513 | >gi|189522060|ref|XM_001922325.1| PREDICTED: Danio rerio similar to LOC794406 protein (LOC100149321); mRNA |
| 172. | 406 | 426 | >gi|189536516|ref|XM_688419.3| PREDICTED: Danio rerio similar to histone cluster 1; H2bb (LOC565121); mRNA |
| 173. | 461 | 481 | >gi|189537808|ref|XM_683134.3| PREDICTED: Danio rerio hypothetical LOC559765 (LOC559765); mRNA |
| 174. | 1607 | 1627 | >gi|189537808|ref|XM_683134.3| PREDICTED: Danio rerio hypothetical LOC559765 (LOC559765); mRNA |
| 175. | 441 | 461 | >gi|189537813|ref|XM_684593.3| PREDICTED: Danio rerio similar to Mid1ip1 protein (LOC561187); mRNA |
| 176. | 475 | 495 | >gi|189537814|ref|XM_684517.3| PREDICTED: Danio rerio similar to LOC794406 protein (LOC561114); mRNA |
| 177. | 352 | 372 | >gi|189537815|ref|XM_684447.2| PREDICTED: Danio rerio similar to Histone H4 replacement CG3379-PC (LOC561044); mRNA |
| 178. | 425 | 445 | >gi|189537816|ref|XM_001923492.1| PREDICTED: Danio rerio similar to histone cluster 1; H2bb (LOC560974); mRNA |

Figure 11I

| | | |
|---|---|---|
| 179. | 440 | 460 >gi\|189537818\|ref\|XM_684297.3\| PREDICTED: Danio rerio similar to LOC794406 protein (LOC560897); mRNA |
| 180. | 431 | 451 >gi\|189537819\|ref\|XM_684153.3\| PREDICTED: Danio rerio similar to histone cluster 1; H2bb (LOC560748); mRNA |
| 181. | 366 | 386 >gi\|189537820\|ref\|XM_684085.2\| PREDICTED: Danio rerio similar to Histone H4 replacement CG3379-PC (LOC560685); mRNA |
| 182. | 472 | 492 >gi\|189537821\|ref\|XM_684015.3\| PREDICTED: Danio rerio similar to LOC794406 protein (LOC560616); mRNA |
| 183. | 441 | 461 >gi\|189537822\|ref\|XM_683938.3\| PREDICTED: Danio rerio similar to Mid1ip1 protein (LOC560527); mRNA |
| 184. | 366 | 386 >gi\|189537823\|ref\|XM_683785.3\| PREDICTED: Danio rerio similar to Histone H4 replacement CG3379-PC (LOC560380); mRNA |
| 185. | 737 | 757 >gi\|189537825\|ref\|XM_683282.3\| PREDICTED: Danio rerio similar to Mid1ip1 protein (LOC559892); mRNA |
| 186. | 378 | 398 >gi\|189537826\|ref\|XM_682981.2\| PREDICTED: Danio rerio similar to Histone H4 replacement CG3379-PC (LOC559623); mRNA |
| 187. | 427 | 447 >gi\|189537835\|ref\|XM_685927.3\| PREDICTED: Danio rerio hypothetical LOC562547 (LOC562547); mRNA |
| 188. | 423 | 443 >gi\|189537839\|ref\|XM_686935.3\| PREDICTED: Danio rerio similar to predicted protein (LOC563569); mRNA |
| 189. | 339 | 359 >gi\|189537841\|ref\|XM_001339363.2\| PREDICTED: Danio rerio similar to Histone H4 replacement CG3379-PC (LOC100005117); mRNA |
| 190. | 1047 | 1067 >gi\|189537842\|ref\|XM_001339430.2\| PREDICTED: Danio rerio similar to Mid1ip1 protein (LOC100005165); mRNA |
| 191. | 378 | 398 >gi\|189540119\|ref\|XM_687566.3\| PREDICTED: Danio rerio hypothetical LOC564216 (LOC564216); mRNA |
| 192. | 366 | 386 >gi\|189540120\|ref\|XM_001337312.2\| PREDICTED: Danio rerio hypothetical LOC100004665 (LOC100004665); mRNA |
| 193. | 425 | 445 >gi\|189540124\|ref\|XM_001338628.2\| PREDICTED: Danio rerio zgc:114046 (zgc:114046); mRNA |
| 194. | 428 | 448 >gi\|189540126\|ref\|XM_686987.3\| PREDICTED: Danio rerio similar to Mid1ip1 protein (LOC563625); mRNA |
| 195. | 402 | 422 >gi\|189540127\|ref\|XM_694057.2\| PREDICTED: Danio rerio similar to histone cluster 1; H2bb (LOC570561); mRNA |
| 196. | 420 | 440 >gi\|189540128\|ref\|XM_687633.2\| PREDICTED: Danio rerio similar to predicted protein (LOC564284); mRNA |
| 197. | 421 | 441 >gi\|189540130\|ref\|XM_001338071.2\| PREDICTED: Danio rerio similar to histone cluster 1; H2bb (LOC100005209); mRNA |
| 198. | 695 | 715 >gi\|189540131\|ref\|XM_687836.3\| PREDICTED: Danio rerio similar to Histone H1.5 (H1 VAR.5) (H1b) (LOC564503); mRNA |
| 199. | 438 | 458 >gi\|189540132\|ref\|XM_687955.2\| PREDICTED: Danio rerio similar to Mid1ip1 protein (LOC564621); mRNA |
| 200. | 558 | 578 >gi\|189540134\|ref\|XM_001337553.2\| PREDICTED: Danio rerio similar to His3:CG31613 CG31613-PA (LOC100004872); mRNA |

Figure 11J

| 201. | 412 | 432 | >gi|189540136|ref|XM_694133.3| PREDICTED: Danio rerio similar to Mid1ip1 protein (LOC570629); mRNA |
|---|---|---|---|
| 202. | 420 | 440 | >gi|189545296|ref|XM_686839.3| PREDICTED: Danio rerio similar to histone cluster 1; H2bb (LOC573293); mRNA |
| 203. | 460 | 480 | >gi|190337552|gb|BC163469.1| Danio rerio similar to histone cluster 2; H2be; mRNA (cDNA clone MGC:194989 IMAGE:9038659) |
| 204. | 460 | 480 | >gi|190338419|gb|BC163478.1| Danio rerio similar to histone cluster 2; H2be; mRNA (cDNA clone MGC:194998 IMAGE:9038657) |
| 205. | 460 | 480 | >gi|192451508|ref|NM_001128759.1| Danio rerio similar to histone cluster 2; H2be (LOC570661); mRNA |
| 206. | 640 | 660 | >gi|201090171|gb|BC169194.1| Danio rerio cDNA clone MGC:195633 IMAGE:9036907 |
| 207. | 449 | 469 | >gi|218931193|ref|NM_001142586.1| Danio rerio zgc:195633 (zgc:195633); mRNA |
| 208. | 378 | 398 | >gi|222824845|emb|AM422106.2| Danio rerio mRNA for histone h4 (h4 gene) |
| 209. | 378 | 398 | >gi|223005942|ref|NM_001105706.2| Danio rerio histone 1; H4; like (hist1h4l); mRNA |
| 210. | 504 | 524 | >gi|209730325|gb|BT046231.1| Salmo salar clone ssal-plnb-011-025 Histone H2A.x putative mRNA |
| 211. | 541 | 561 | >gi|223646389|gb|BT058240.1| Salmo salar clone Contig2506 Histone H2A.x putative mRNA |
| 212. | 513 | 533 | >gi|223649423|gb|BT059757.1| Salmo salar clone ssal-rgf-505-029 Histone H2A.x putative mRNA |
| 213. | 541 | 561 | >gi|223672236|gb|BT059940.1| Salmo salar clone ssal-rgg-511-256 Histone H2A.x putative mRNA |
| 214. | 347 | 367 | >gi|214223|gb|J00985.1|XELHIS4B Xenopus borealis h4 histone mRNA |
| 215. | 331 | 351 | >gi|214225|gb|J00986.1|XELHIS4L xenopus laevis h4 histone mrna |
| 216. | 53 | 73 | >gi|214581|gb|J00991.1|XELLHIS3 xenopus laevis h3 histone mrna |
| 217. | 611 | 631 | >gi|49256465|gb|BC074188.1| Xenopus laevis MGC82078 protein; mRNA (cDNA clone MGC:82078 IMAGE:7011567) |
| 218. | 449 | 469 | >gi|50603610|gb|BC077816.1| Xenopus laevis hypothetical LOC494591; mRNA (cDNA clone MGC:80455 IMAGE:5156013) |
| 219. | 438 | 458 | >gi|50603655|gb|BC077399.1| Xenopus laevis histone H2B; mRNA (cDNA clone MGC:81709 IMAGE:6865010) |
| 220. | 759 | 779 | >gi|51703455|gb|BC081020.1| Xenopus laevis MGC81615 protein; mRNA (cDNA clone MGC:81615 IMAGE:6863870) |
| 221. | 712 | 732 | >gi|52078445|gb|BC082371.1| Xenopus laevis hypothetical LOC494640; mRNA (cDNA clone MGC:81627 IMAGE:6864049) |
| 222. | 905 | 925 | >gi|54311378|gb|BC084765.1| Xenopus laevis hypothetical protein MGC81771; mRNA (cDNA clone MGC:81771 IMAGE:6866337) |
| 223. | 447 | 467 | >gi|77748126|gb|BC106331.1| Xenopus laevis hypothetical protein MGC130860; mRNA (cDNA clone MGC:130860 IMAGE:7205580) |
| 224. | 743 | 763 | >gi|122936413|gb|BC130125.1| Xenopus laevis hypothetical protein LOC100037078; mRNA (cDNA clone MGC:160660 IMAGE:6318752) |

Figure 11K

| | | |
|---|---|---|
| 225. | 464 | 484 >gi\|133737011\|gb\|BC133776.1\| Xenopus laevis hypothetical protein LOC100049126; mRNA (cDNA clone MGC:161039 IMAGE:7299620) |
| 226. | 449 | 469 >gi\|147898581\|ref\|NM_001094479.1\| Xenopus laevis hypothetical LOC494591 (LOC494591); mRNA |
| 227. | 759 | 779 >gi\|147901064\|ref\|NM_001094164.1\| Xenopus laevis MGC81615 protein (MGC81615); mRNA |
| 228. | 712 | 732 >gi\|147901298\|ref\|NM_001094488.1\| Xenopus laevis hypothetical LOC494640 (LOC494640); mRNA |
| 229. | 743 | 763 >gi\|147906636\|ref\|NM_001097802.1\| Xenopus laevis hypothetical protein LOC100037078 (LOC100037078); mRNA |
| 230. | 438 | 458 >gi\|148222088\|ref\|NM_001093284.1\| Xenopus laevis histone H2B (h2B); mRNA |
| 231. | 447 | 467 >gi\|148222885\|ref\|NM_001096215.1\| Xenopus laevis hypothetical protein MGC130860 (MGC130860); mRNA |
| 232. | 905 | 925 >gi\|148235652\|ref\|NM_001096795.1\| Xenopus laevis hypothetical protein MGC81771 (MGC81771); mRNA |
| 233. | 464 | 484 >gi\|148236632\|ref\|NM_001097959.1\| Xenopus laevis hypothetical protein LOC100049126 (LOC100049126); mRNA |
| 234. | 574 | 594 >gi\|160420284\|ref\|NM_001092630.1\| Xenopus laevis MGC82078 protein (MGC82078); mRNA |
| 235. | 458 | 478 >gi\|50604188\|gb\|BC077692.1\| Xenopus tropicalis histone 1; H2bk; mRNA (cDNA clone MGC:89948 IMAGE:7030528) |
| 236. | 458 | 478 >gi\|55742125\|ref\|NM_001006890.1\| Xenopus (Silurana) tropicalis histone 1; H2bk (hist1h2bk); mRNA |
| 237. | 432 | 452 >gi\|77621278\|emb\|CR760086.2\| Xenopus tropicalis finished cDNA; clone TNeu063l06 |
| 238. | 680 | 700 >gi\|77621394\|emb\|CR761779.2\| Xenopus tropicalis finished cDNA; clone TGas008a06 |
| 239. | 436 | 456 >gi\|77621403\|emb\|CR761789.2\| Xenopus tropicalis finished cDNA; clone TGas125k04 |
| 240. | 442 | 462 >gi\|77622098\|emb\|CR762147.2\| Xenopus tropicalis finished cDNA; clone TGas072c19 |
| 241. | 480 | 500 >gi\|77623308\|emb\|CR848416.2\| Xenopus tropicalis finished cDNA; clone TNeu117f13 |
| 242. | 424 | 444 >gi\|77623836\|emb\|CR855675.2\| Xenopus tropicalis finished cDNA; clone TGas058p09 |
| 243. | 463 | 483 >gi\|77623886\|emb\|CR855729.2\| Xenopus tropicalis finished cDNA; clone TGas081o10 |
| 244. | 459 | 479 >gi\|77626499\|emb\|CR760429.2\| Xenopus tropicalis finished cDNA; clone TNeu057j11 |
| 245. | 432 | 452 >gi\|77681530\|ref\|NM_001017251.2\| Xenopus (Silurana) tropicalis hypothetical protein LOC550005 (LOC550005); mRNA |
| 246. | 480 | 500 >gi\|77681654\|ref\|NM_001015968.2\| Xenopus (Silurana) tropicalis H2A histone family; member X (h2afx); mRNA |
| 247. | 680 | 700 >gi\|77682153\|ref\|NM_001016946.2\| Xenopus (Silurana) tropicalis hypothetical protein LOC549700 (LOC549700); mRNA |

Figure 11L

| | | |
|---|---|---|
| 248. | 436 | 456 >gi\|77682273\|ref\|NM_001030325.2\| Xenopus (Silurana) tropicalis hypothetical protein LOC594911 (LOC594911); mRNA |
| 249. | 442 | 462 >gi\|77682467\|ref\|NM_001030332.2\| Xenopus (Silurana) tropicalis hypothetical protein LOC594922 (LOC594922); mRNA |
| 250. | 463 | 483 >gi\|90017485\|ref\|NM_001016636.3\| Xenopus (Silurana) tropicalis histone cluster 2; H3c (hist2h3c); mRNA |
| 251. | 450 | 470 >gi\|163916080\|gb\|BC157346.1\| Xenopus tropicalis cDNA clone MGC:147886 IMAGE:7553386 |
| 252. | 435 | 455 >gi\|163916544\|gb\|BC157571.1\| Xenopus tropicalis hypothetical protein LOC100135279; mRNA (cDNA clone MGC:180869 IMAGE:7877341) |
| 253. | 435 | 455 >gi\|166158046\|ref\|NM_001113960.1\| Xenopus (Silurana) tropicalis hypothetical protein LOC100135279 (LOC100135279); mRNA |
| 254. | 430 | 450 >gi\|166796469\|gb\|BC159277.1\| Xenopus tropicalis hypothetical protein LOC100135279; mRNA (cDNA clone MGC:180484 IMAGE:7880774) |
| 255. | 441 | 461 >gi\|166796529\|gb\|BC158988.1\| Xenopus tropicalis hypothetical protein LOC100145139; mRNA (cDNA clone MGC:147637 IMAGE:7556374) |
| 256. | 1585 | 1605 >gi\|170287756\|gb\|BC160940.1\| Xenopus tropicalis histone cluster 2; H3c; mRNA (cDNA clone MGC:180899 IMAGE:7881440) |
| 257. | 441 | 461 >gi\|187608001\|ref\|NM_001126645.1\| Xenopus (Silurana) tropicalis hypothetical protein LOC100145139 (LOC100145139); mRNA |
| 258. | 361 | 381 >gi\|197246662\|gb\|BC168455.1\| Xenopus tropicalis hypothetical protein LOC549623; mRNA (cDNA clone MGC:147808 IMAGE:7534071) |
| 259. | 748 | 768 >gi\|95772088\|ref\|NM_001040643.1\| Gallus gallus histone 1; H1c (HIST1H1C); mRNA |
| 260. | 699 | 719 >gi\|118082576\|ref\|XM_425456.2\| PREDICTED: Gallus gallus similar to histone H1.02 - chicken (LOC427882); mRNA |
| 261. | 449 | 469 >gi\|118082579\|ref\|XM_001232832.1\| PREDICTED: Gallus gallus similar to histone protein Hist2h3c1 (LOC769809); mRNA |
| 262. | 433 | 453 >gi\|118082583\|ref\|XM_425459.2\| PREDICTED: Gallus gallus hypothetical LOC427885 (LOC427885); mRNA |
| 263. | 1234 | 1254 >gi\|118082585\|ref\|XM_001232870.1\| PREDICTED: Gallus gallus similar to histone H2B (LOC769845); mRNA |
| 264. | 364 | 384 >gi\|118082589\|ref\|XM_425458.2\| PREDICTED: Gallus gallus germinal histone H4 gene (LOC427884); mRNA |
| 265. | 476 | 496 >gi\|118082599\|ref\|XM_001232984.1\| PREDICTED: Gallus gallus similar to histone H2B (LOC769973); mRNA |
| 266. | 1080 | 1100 >gi\|118082601\|ref\|XM_416189.2\| PREDICTED: Gallus gallus similar to Histone H1.10 (Methylated DNA binding protein-2-H1) (MDBP-2-H1) (LOC417948); mRNA |
| 267. | 365 | 385 >gi\|118082603\|ref\|XM_001233008.1\| PREDICTED: Gallus gallus similar to histone H4 (LOC770005); mRNA |
| 268. | 478 | 498 >gi\|118082607\|ref\|XM_001233027.1\| PREDICTED: Gallus gallus similar to histone protein Hist2h3c1 (LOC770022); mRNA |
| 269. | 462 | 482 >gi\|118082616\|ref\|XM_001233116.1\| PREDICTED: Gallus gallus hypothetical protein LOC770092 (LOC770092); mRNA |

Figure 11M

| 270. | 427 | 447 | >gi|118082628|ref|XM_001233211.1| PREDICTED: Gallus gallus hypothetical protein LOC770170 (LOC770170); mRNA |
|---|---|---|---|
| 271. | 834 | 854 | >gi|118082630|ref|XM_001233226.1| PREDICTED: Gallus gallus similar to histone H2B (LOC770188); mRNA |
| 272. | 458 | 478 | >gi|118082638|ref|XM_416195.2| PREDICTED: Gallus gallus hypothetical LOC417955 (LOC417955); mRNA |
| 273. | 411 | 431 | >gi|118082646|ref|XM_001233336.1| PREDICTED: Gallus gallus similar to histone H2B (LOC770267); mRNA |
| 274. | 421 | 441 | >gi|118108125|ref|XM_425469.2| PREDICTED: Gallus gallus hypothetical LOC427895 (LOC427895); mRNA |
| 275. | 657 | 677 | >gi|67968863|dbj|AB168678.1| Macaca fascicularis testis cDNA clone: QtsA-14092; similar to human histone 2; H2aa (HIST2H2AA); mRNA; RefSeq: NM_003516.2 |
| 276. | 417 | 437 | >gi|67972229|dbj|AB179406.1| Macaca fascicularis testis cDNA clone: QtsA-19327; similar to human histone 1; H4j (HIST1H4J); mRNA; RefSeq: NM_021968.3 |
| 277. | 473 | 493 | >gi|90077479|dbj|AB171357.1| Macaca fascicularis brain cDNA clone: QorA-14467; similar to human histone 1; H2ag (HIST1H2AG); mRNA; RefSeq: NM_021064.3 |
| 278. | 454 | 474 | >gi|109015969|ref|XM_001096626.1| PREDICTED: Macaca mulatta similar to histone 2; H2ac (LOC705054); mRNA |
| 279. | 721 | 741 | >gi|109015972|ref|XM_001096734.1| PREDICTED: Macaca mulatta similar to histone H2A (LOC705170); mRNA |
| 280. | 616 | 636 | >gi|109016349|ref|XM_001104697.1| PREDICTED: Macaca mulatta similar to Histone H2B 291B (LOC714769); mRNA |
| 281. | 766 | 786 | >gi|109016354|ref|XM_001104774.1| PREDICTED: Macaca mulatta similar to H2B histone family; member F (LOC714818); mRNA |
| 282. | 406 | 426 | >gi|109017920|ref|XM_001081967.1| PREDICTED: Macaca mulatta similar to histone 3; H2ba (LOC693507); mRNA |
| 283. | 509 | 529 | >gi|109017922|ref|XM_001082086.1| PREDICTED: Macaca mulatta similar to histone 3; H2bb (LOC693635); mRNA |
| 284. | 489 | 509 | >gi|109017924|ref|XM_001082209.1| PREDICTED: Macaca mulatta similar to histone 2a (LOC693768); mRNA |
| 285. | 502 | 522 | >gi|109017926|ref|XM_001082339.1| PREDICTED: Macaca mulatta similar to histone 1; H2ai (predicted) (LOC694024); mRNA |
| 286. | 743 | 763 | >gi|109020394|ref|XM_001084245.1| PREDICTED: Macaca mulatta similar to CG31613-PA (LOC696204); mRNA |
| 287. | 673 | 693 | >gi|109020396|ref|XM_001084365.1| PREDICTED: Macaca mulatta similar to H2A histone family; member O (LOC696463); mRNA |
| 288. | 916 | 936 | >gi|109069843|ref|XM_001083516.1| PREDICTED: Macaca mulatta similar to Histone H1.1 (LOC694975); mRNA |
| 289. | 626 | 646 | >gi|109069845|ref|XM_001083629.1| PREDICTED: Macaca mulatta similar to histone 1; H2ai (predicted) (LOC695092); mRNA |
| 290. | 446 | 466 | >gi|109069855|ref|XM_001083954.1| PREDICTED: Macaca mulatta similar to histone 1; H2ai (predicted) (LOC695427); mRNA |

Figure 11N

| | | |
|---|---|---|
| 291. | 442 | 462 >gi\|109069857\|ref\|XM_001084059.1\| PREDICTED: Macaca mulatta similar to histone 2a (LOC695551); mRNA |
| 292. | 408 | 428 >gi\|109069859\|ref\|XM_001084180.1\| PREDICTED: Macaca mulatta similar to H2B histone family; member F (LOC695657); mRNA |
| 293. | 436 | 456 >gi\|109069861\|ref\|XM_001084296.1\| PREDICTED: Macaca mulatta similar to histone 1; H2ai (predicted) (LOC695891); mRNA |
| 294. | 715 | 735 >gi\|109069863\|ref\|XM_001084417.1\| PREDICTED: Macaca mulatta similar to Histone H1.2 (H1d) (LOC696005); mRNA |
| 295. | 524 | 544 >gi\|109069889\|ref\|XM_001086273.1\| PREDICTED: Macaca mulatta similar to Histone H2A type 1-C (LOC696629); mRNA |
| 296. | 770 | 790 >gi\|109069891\|ref\|XM_001086400.1\| PREDICTED: Macaca mulatta similar to Histone H1.4 (H1 VAR.2) (H1e) (LOC696754); mRNA |
| 297. | 479 | 499 >gi\|109069893\|ref\|XR_010212.1\| PREDICTED: Macaca mulatta similar to Histone H2B 291B (LOC696808); mRNA |
| 298. | 464 | 484 >gi\|109069894\|ref\|XM_001086509.1\| PREDICTED: Macaca mulatta similar to Histone H2B 291B (LOC696872); mRNA |
| 299. | 478 | 498 >gi\|109069896\|ref\|XM_001086637.1\| PREDICTED: Macaca mulatta similar to Histone H2B 291B (LOC696996); mRNA |
| 300. | 363 | 383 >gi\|109069900\|ref\|XM_001086761.1\| PREDICTED: Macaca mulatta similar to germinal histone H4 gene (LOC697115); mRNA |
| 301. | 898 | 918 >gi\|109069902\|ref\|XM_001086885.1\| PREDICTED: Macaca mulatta similar to Histone H2A type 1-D (H2A.3); transcript variant 1 (LOC697235); mRNA |
| 302. | 488 | 508 >gi\|109069904\|ref\|XM_001086987.1\| PREDICTED: Macaca mulatta similar to Histone H2A type 1-D (H2A.3); transcript variant 2 (LOC697235); mRNA |
| 303. | 476 | 496 >gi\|109069907\|ref\|XM_001087112.1\| PREDICTED: Macaca mulatta similar to Histone H2B 291B (LOC697469); mRNA |
| 304. | 455 | 475 >gi\|109069916\|ref\|XM_001087459.1\| PREDICTED: Macaca mulatta similar to Histone H2B 291B (LOC697857); mRNA |
| 305. | 795 | 815 >gi\|109069918\|ref\|XM_001087578.1\| PREDICTED: Macaca mulatta similar to histone 2a (LOC697977); mRNA |
| 306. | 806 | 826 >gi\|109069922\|ref\|XM_001087706.1\| PREDICTED: Macaca mulatta similar to histone 1; H2ai (predicted) (LOC698105); mRNA |
| 307. | 778 | 798 >gi\|109069924\|ref\|XM_001087823.1\| PREDICTED: Macaca mulatta similar to Histone H1.2 (H1d) (LOC698238); mRNA |
| 308. | 453 | 473 >gi\|109069928\|ref\|XM_001088184.1\| PREDICTED: Macaca mulatta similar to Histone H2B F (H2B 291A) (LOC698482); mRNA |
| 309. | 488 | 508 >gi\|109069930\|ref\|XM_001088298.1\| PREDICTED: Macaca mulatta similar to histone 1; H2ai (predicted) (LOC698615); mRNA |
| 310. | 456 | 476 >gi\|109069994\|ref\|XM_001092692.1\| PREDICTED: Macaca mulatta similar to H2B histone family; member F; transcript variant 2 (LOC701337); mRNA |
| 311. | 516 | 536 >gi\|109069996\|ref\|XM_001092808.1\| PREDICTED: Macaca mulatta similar to H2B histone family; member T (LOC701464); mRNA |
| 312. | 343 | 363 >gi\|109069999\|ref\|XM_001092924.1\| PREDICTED: Macaca mulatta similar to germinal histone H4 gene (LOC701574); mRNA |

Figure 11O

| | | |
|---|---|---|
| 313. | 473 | 493 >gi\|109070001\|ref\|XM_001093037.1\| PREDICTED: Macaca mulatta similar to Histone H2A type 1 (LOC701687); mRNA |
| 314. | 471 | 491 >gi\|109070004\|ref\|XM_001093153.1\| PREDICTED: Macaca mulatta similar to Histone H2A type 1 (LOC701826); mRNA |
| 315. | 491 | 511 >gi\|109070011\|ref\|XM_001090500.1\| PREDICTED: Macaca mulatta similar to H2B histone family; member F (LOC702227); mRNA |
| 316. | 571 | 591 >gi\|109070043\|ref\|XM_001095574.1\| PREDICTED: Macaca mulatta similar to histone 1; H2ai (predicted) (LOC703889); mRNA |
| 317. | 521 | 541 >gi\|109070045\|ref\|XM_001095673.1\| PREDICTED: Macaca mulatta similar to Histone H2A type 1 (LOC704006); mRNA |
| 318. | 501 | 521 >gi\|109070047\|ref\|XM_001095773.1\| PREDICTED: Macaca mulatta similar to H2A histone family; member E (LOC704127); mRNA |
| 319. | 470 | 490 >gi\|109070049\|ref\|XM_001095885.1\| PREDICTED: Macaca mulatta similar to Histone H2B F (H2B 291A) (LOC704241); mRNA |
| 320. | 358 | 378 >gi\|109070051\|ref\|XM_001095996.1\| PREDICTED: Macaca mulatta similar to germinal histone H4 gene (LOC704341); mRNA |
| 321. | 355 | 375 >gi\|109070055\|ref\|XM_001096216.1\| PREDICTED: Macaca mulatta similar to germinal histone H4 gene (LOC704565); mRNA |
| 322. | 472 | 492 >gi\|109070057\|ref\|XM_001096334.1\| PREDICTED: Macaca mulatta similar to Histone H2A type 1 (LOC704664); mRNA |
| 323. | 1655 | 1675 >gi\|109070059\|ref\|XM_001096566.1\| PREDICTED: Macaca mulatta similar to Histone H2B 291B (LOC704780); mRNA |
| 324. | 520 | 540 >gi\|109070061\|ref\|XM_001096671.1\| PREDICTED: Macaca mulatta similar to Histone H2A type 1 (LOC704994); mRNA |
| 325. | 767 | 787 >gi\|109070063\|ref\|XM_001096781.1\| PREDICTED: Macaca mulatta similar to Histone H1.5 (Histone H1a) (LOC705100); mRNA |
| 326. | 466 | 486 >gi\|109070065\|ref\|XM_001096897.1\| PREDICTED: Macaca mulatta similar to histone 1; H2ai (predicted) (LOC705220); mRNA |
| 327. | 340 | 360 >gi\|109070069\|ref\|XM_001097005.1\| PREDICTED: Macaca mulatta similar to germinal histone H4 gene (LOC705352); mRNA |
| 328. | 465 | 485 >gi\|109070073\|ref\|XM_001097227.1\| PREDICTED: Macaca mulatta similar to Histone H2A type 1; transcript variant 2 (LOC705469); mRNA |
| 329. | 438 | 458 >gi\|109073423\|ref\|XM_001086992.1\| PREDICTED: Macaca mulatta similar to testis-specific histone H2B (LOC698109); mRNA |
| 330. | 1212 | 1232 >gi\|109108925\|ref\|XM_001102040.1\| PREDICTED: Macaca mulatta similar to Histone H2A.x (H2a/x); transcript variant 2 (LOC703073); mRNA |
| 331. | 1107 | 1127 >gi\|109108927\|ref\|XM_001101949.1\| PREDICTED: Macaca mulatta similar to Histone H2A.x (H2a/x); transcript variant 1 (LOC703073); mRNA |
| 332. | 436 | 456 >gi\|114559138\|ref\|XM_524859.2\| PREDICTED: Pan troglodytes similar to Histone 2; H3c1 (LOC469476); mRNA |
| 333. | 487 | 507 >gi\|114559162\|ref\|XM_001166180.1\| PREDICTED: Pan troglodytes similar to Histone 2; H3c1 (LOC746430); mRNA |
| 334. | 588 | 608 >gi\|114559164\|ref\|XR_022033.1\| PREDICTED: Pan troglodytes similar to histone H2B/s (LOC746444); mRNA |

Figure 11P

| 335. | 503 | 523 | >gi\|114559165\|ref\|XM_001166304.1\| PREDICTED: Pan troglodytes similar to homeostatic thymus hormone alpha; transcript variant 3 (LOC746468); mRNA |
|---|---|---|---|
| 336. | 671 | 691 | >gi\|114559167\|ref\|XM_001166332.1\| PREDICTED: Pan troglodytes similar to homeostatic thymus hormone alpha; transcript variant 4 (LOC746468); mRNA |
| 337. | 390 | 410 | >gi\|114559169\|ref\|XM_001166270.1\| PREDICTED: Pan troglodytes similar to homeostatic thymus hormone alpha; transcript variant 2 (LOC746468); mRNA |
| 338. | 429 | 449 | >gi\|114559171\|ref\|XM_001166246.1\| PREDICTED: Pan troglodytes similar to homeostatic thymus hormone alpha; transcript variant 1 (LOC746468); mRNA |
| 339. | 516 | 536 | >gi\|114559174\|ref\|XR_022040.1\| PREDICTED: Pan troglodytes similar to histone H2B/s (LOC746491); mRNA |
| 340. | 861 | 881 | >gi\|114559175\|ref\|XM_001166412.1\| PREDICTED: Pan troglodytes similar to histone H2B (LOC746513); mRNA |
| 341. | 731 | 751 | >gi\|114559180\|ref\|XM_001166488.1\| PREDICTED: Pan troglodytes similar to histone H2A (LOC746557); mRNA |
| 342. | 492 | 512 | >gi\|114573045\|ref\|XM_525084.2\| PREDICTED: Pan troglodytes similar to Chain K; 2.9 Angstrom X-Ray Structure Of Hybrid Macroh2a Nucleosomes (LOC469700); mRNA |
| 343. | 440 | 460 | >gi\|114573046\|ref\|XM_525085.2\| PREDICTED: Pan troglodytes hypothetical LOC469701 (LOC469701); mRNA |
| 344. | 406 | 426 | >gi\|114573048\|ref\|XM_525086.2\| PREDICTED: Pan troglodytes hypothetical LOC469702 (LOC469702); mRNA |
| 345. | 481 | 501 | >gi\|114605723\|ref\|XM_518282.2\| PREDICTED: Pan troglodytes similar to histone 1; H2aa (LOC462486); mRNA |
| 346. | 546 | 566 | >gi\|114605724\|ref\|XM_527247.2\| PREDICTED: Pan troglodytes similar to histone 1; H2ba (LOC471869); mRNA |
| 347. | 917 | 937 | >gi\|114605748\|ref\|XM_527252.2\| PREDICTED: Pan troglodytes similar to histone H1 (LOC471874); mRNA |
| 348. | 768 | 788 | >gi\|114605749\|ref\|XM_527259.2\| PREDICTED: Pan troglodytes similar to Histone H1.4 (Histone H1b) (LOC471881); mRNA |
| 349. | 710 | 730 | >gi\|114605750\|ref\|XM_001172525.1\| PREDICTED: Pan troglodytes similar to histone H1 (LOC471878); mRNA |
| 350. | 868 | 888 | >gi\|114605752\|ref\|XM_518289.2\| PREDICTED: Pan troglodytes similar to histone H3; transcript variant 2 (LOC462493); mRNA |
| 351. | 1086 | 1106 | >gi\|114605754\|ref\|XM_001172544.1\| PREDICTED: Pan troglodytes similar to histone H3; transcript variant 1 (LOC462493); mRNA |
| 352. | 463 | 483 | >gi\|114605756\|ref\|XM_527255.2\| PREDICTED: Pan troglodytes similar to histone H3 (LOC471877); mRNA |
| 353. | 485 | 505 | >gi\|114605758\|ref\|XM_527254.2\| PREDICTED: Pan troglodytes similar to histone H3 (LOC471876); mRNA |
| 354. | 487 | 507 | >gi\|114605760\|ref\|XM_001172649.1\| PREDICTED: Pan troglodytes hypothetical protein LOC748424 (LOC748424); mRNA |
| 355. | 437 | 457 | >gi\|114605762\|ref\|XM_527258.2\| PREDICTED: Pan troglodytes similar to histone H2b-616 (LOC471880); mRNA |

Figure 11Q

| | | | |
|---|---|---|---|
| 356. | 794 | 814 | >gi\|114605763\|ref\|XM_527262.2\| PREDICTED: Pan troglodytes similar to Chain K; 2.9 Angstrom X-Ray Structure Of Hybrid Macroh2a Nucleosomes (LOC471884); mRNA |
| 357. | 622 | 642 | >gi\|114605765\|ref\|XM_527253.2\| PREDICTED: Pan troglodytes similar to histone H3 (LOC471875); mRNA |
| 358. | 455 | 475 | >gi\|114605766\|ref\|XM_527261.2\| PREDICTED: Pan troglodytes similar to histone H2b-616 (LOC471883); mRNA |
| 359. | 543 | 563 | >gi\|114605767\|ref\|XM_518286.2\| PREDICTED: Pan troglodytes similar to histone H2A (LOC462490); mRNA |
| 360. | 505 | 525 | >gi\|114605768\|ref\|XM_001172704.1\| PREDICTED: Pan troglodytes similar to Chain K; 2.9 Angstrom X-Ray Structure Of Hybrid Macroh2a Nucleosomes (LOC748495); mRNA |
| 361. | 408 | 428 | >gi\|114605770\|ref\|XM_001172713.1\| PREDICTED: Pan troglodytes similar to histone H2B (LOC748505); mRNA |
| 362. | 363 | 383 | >gi\|114605778\|ref\|XM_001172760.1\| PREDICTED: Pan troglodytes similar to histone H4 (LOC748540); mRNA |
| 363. | 799 | 819 | >gi\|114605783\|ref\|XM_518888.2\| PREDICTED: Pan troglodytes similar to histone H3 (LOC463171); mRNA |
| 364. | 779 | 799 | >gi\|114605785\|ref\|XM_001172808.1\| PREDICTED: Pan troglodytes similar to Histone H1.4 (Histone H1b) (LOC472227); mRNA |
| 365. | 453 | 473 | >gi\|114605789\|ref\|XM_518889.2\| PREDICTED: Pan troglodytes similar to histone H2b-616; transcript variant 2 (LOC463172); mRNA |
| 366. | 477 | 497 | >gi\|114605793\|ref\|XM_527604.2\| PREDICTED: Pan troglodytes similar to histone H3 (LOC472230); mRNA |
| 367. | 707 | 727 | >gi\|114605939\|ref\|XM_527257.2\| PREDICTED: Pan troglodytes similar to testicular H1 histone (LOC471879); mRNA |
| 368. | 487 | 507 | >gi\|114605941\|ref\|XM_518287.2\| PREDICTED: Pan troglodytes hypothetical LOC462491 (LOC462491); mRNA |
| 369. | 480 | 500 | >gi\|114605943\|ref\|XM_527266.2\| PREDICTED: Pan troglodytes similar to histone H2b-616 (LOC471888); mRNA |
| 370. | 458 | 478 | >gi\|114605964\|ref\|XM_518294.2\| PREDICTED: Pan troglodytes similar to histone H2B; transcript variant 2 (LOC462500); mRNA |
| 371. | 513 | 533 | >gi\|114605965\|ref\|XM_518295.2\| PREDICTED: Pan troglodytes similar to histone 1; H2bk (LOC462501); mRNA |
| 372. | 475 | 495 | >gi\|114605967\|ref\|XM_527272.2\| PREDICTED: Pan troglodytes similar to homeostatic thymus hormone alpha (LOC471894); mRNA |
| 373. | 373 | 393 | >gi\|114605969\|ref\|XM_001134995.1\| PREDICTED: Pan troglodytes similar to histone H4 (LOC735611); mRNA |
| 374. | 156 | 176 | >gi\|114605971\|ref\|XM_001135089.1\| PREDICTED: Pan troglodytes similar to histone H3 (LOC735660); mRNA |
| 375. | 920 | 940 | >gi\|114606004\|ref\|XM_527284.2\| PREDICTED: Pan troglodytes similar to Histone H1.5 (LOC471906); mRNA |
| 376. | 441 | 461 | >gi\|114606009\|ref\|XM_001137602.1\| PREDICTED: Pan troglodytes similar to histone H2b-616; transcript variant 2 (LOC462508); mRNA |

Figure 11R

| 377. | 1654 | 1674 | >gi|114606011|ref|XM_001137688.1| PREDICTED: Pan troglodytes similar to histone H2b-616; transcript variant 3 (LOC462508); mRNA |
|---|---|---|---|
| 378. | 438 | 458 | >gi|114606013|ref|XM_001137524.1| PREDICTED: Pan troglodytes similar to histone H2b-616; transcript variant 1 (LOC462508); mRNA |
| 379. | 453 | 473 | >gi|114606017|ref|XM_518299.2| PREDICTED: Pan troglodytes similar to histone H3 (LOC462506); mRNA |
| 380. | 2323 | 2343 | >gi|114606017|ref|XM_518299.2| PREDICTED: Pan troglodytes similar to histone H3 (LOC462506); mRNA |
| 381. | 462 | 482 | >gi|114606019|ref|XM_527285.2| PREDICTED: Pan troglodytes similar to histone H3 (LOC471907); mRNA |
| 382. | 473 | 493 | >gi|114606021|ref|XM_001137950.1| PREDICTED: Pan troglodytes similar to histone H2A.1 (LOC736529); mRNA |
| 383. | 486 | 506 | >gi|114606025|ref|XM_001138116.1| PREDICTED: Pan troglodytes hypothetical LOC471902; transcript variant 1 (LOC471902); mRNA |
| 384. | 365 | 385 | >gi|114606027|ref|XM_001138202.1| PREDICTED: Pan troglodytes similar to histone H4 (LOC736707); mRNA |
| 385. | 465 | 485 | >gi|114606031|ref|XM_527287.2| PREDICTED: Pan troglodytes similar to homeostatic thymus hormone alpha; transcript variant 2 (LOC471909); mRNA |
| 386. | 365 | 385 | >gi|114606033|ref|XM_518300.2| PREDICTED: Pan troglodytes similar to histone H4 (LOC462507); mRNA |
| 387. | 520 | 540 | >gi|114606035|ref|XM_527283.2| PREDICTED: Pan troglodytes similar to homeostatic thymus hormone alpha (LOC471905); mRNA |
| 388. | 504 | 524 | >gi|114606040|ref|XM_001138786.1| PREDICTED: Pan troglodytes similar to histone H2A (LOC737087); mRNA |
| 389. | 483 | 503 | >gi|114606050|ref|XM_518302.2| PREDICTED: Pan troglodytes similar to histone H2B (LOC462509); mRNA |
| 390. | 419 | 439 | >gi|114643775|ref|XM_520759.2| PREDICTED: Pan troglodytes similar to histone H4 (LOC465305); mRNA |
| 391. | 477 | 497 | >gi|55727406|emb|CR858221.1| Pongo abelii mRNA; cDNA DKFZp469C0528 (from clone DKFZp469C0528) |
| 392. | 477 | 497 | >gi|197101176|ref|NM_001131764.1| Pongo abelii histone cluster 2; H2be (HIST2H2BE); mRNA |
| 393. | 552 | 572 | >gi|31972|emb|X14850.1| Human H2A.X mRNA encoding histone H2A.X |
| 394. | 471 | 491 | >gi|306826|gb|L19778.1|HUMH2A1B Homo sapiens histone H2A.1b mRNA |
| 395. | 511 | 531 | >gi|306828|gb|L19779.1|HUMH2A2A Homo sapiens histone H2A.2 mRNA |
| 396. | 531 | 551 | >gi|2062703|gb|U90551.1|HSU90551 Human histone 2A-like protein (H2A/l) mRNA |
| 397. | 349 | 369 | >gi|3483909|gb|AF086564.1|HUMZE16D01 Homo sapiens full length insert cDNA clone ZE16D01 |
| 398. | 473 | 493 | >gi|12654706|gb|BC001193.1| Homo sapiens histone cluster 3; H2a; mRNA (cDNA clone IMAGE:3355200) |
| 399. | 711 | 731 | >gi|12803628|gb|BC002649.1| Homo sapiens histone cluster 1; H1c; mRNA (cDNA clone IMAGE:3608862) |
| 400. | 496 | 516 | >gi|12804444|gb|BC001629.1| Homo sapiens histone cluster 2; H2aa3; mRNA (cDNA clone IMAGE:3536984) |

Figure 11S

| 401. | 446 | 466 | >gi|15718713|ref|NM_003509.2| Homo sapiens histone cluster 1; H2ai (HIST1H2AI); mRNA |
|---|---|---|---|
| 402. | 437 | 457 | >gi|15718714|ref|NM_003510.2| Homo sapiens histone cluster 1; H2ak (HIST1H2AK); mRNA |
| 403. | 415 | 435 | >gi|15718715|ref|NM_021066.2| Homo sapiens histone cluster 1; H2aj (HIST1H2AJ); mRNA |
| 404. | 767 | 787 | >gi|15718716|ref|NM_005322.2| Homo sapiens histone cluster 1; H1b (HIST1H1B); mRNA |
| 405. | 447 | 467 | >gi|15718717|ref|NM_003511.2| Homo sapiens histone cluster 1; H2al (HIST1H2AL); mRNA |
| 406. | 464 | 484 | >gi|15718718|ref|NM_003514.2| Homo sapiens histone cluster 1; H2am (HIST1H2AM); mRNA |
| 407. | 430 | 450 | >gi|15718719|ref|NM_003519.3| Homo sapiens histone cluster 1; H2bl (HIST1H2BL); mRNA |
| 408. | 426 | 446 | >gi|15718720|ref|NM_003520.3| Homo sapiens histone cluster 1; H2bn (HIST1H2BN); mRNA |
| 409. | 454 | 474 | >gi|15718723|ref|NM_003533.2| Homo sapiens histone cluster 1; H3i (HIST1H3I); mRNA |
| 410. | 455 | 475 | >gi|15718724|ref|NM_003535.2| Homo sapiens histone cluster 1; H3j (HIST1H3J); mRNA |
| 411. | 450 | 470 | >gi|15718725|ref|NM_003536.2| Homo sapiens histone cluster 1; H3h (HIST1H3H); mRNA |
| 412. | 332 | 352 | >gi|15718726|ref|NM_003541.2| Homo sapiens histone cluster 1; H4k (HIST1H4K); mRNA |
| 413. | 341 | 361 | >gi|15718728|ref|NM_003546.2| Homo sapiens histone cluster 1; H4l (HIST1H4L); mRNA |
| 414. | 484 | 504 | >gi|15930225|gb|BC015544.1| Homo sapiens histone 2; H3c; mRNA (cDNA clone IMAGE:3913365) |
| 415. | 443 | 463 | >gi|16306565|ref|NM_003527.4| Homo sapiens histone cluster 1; H2bo (HIST1H2BO); mRNA |
| 416. | 332 | 352 | >gi|16306592|ref|NM_021968.3| Homo sapiens histone cluster 1; H4j (HIST1H4J); mRNA |
| 417. | 374 | 394 | >gi|16740964|gb|BC016336.1| Homo sapiens histone cluster 1; H4i; mRNA (cDNA clone IMAGE:4101102) |
| 418. | 460 | 480 | >gi|16741767|gb|BC016677.1| Homo sapiens histone cluster 1; H2ag; mRNA (cDNA clone MGC:17204 IMAGE:4342191) |
| 419. | 486 | 506 | >gi|16924218|gb|BC017379.1| Homo sapiens histone cluster 1; H2ac; mRNA (cDNA clone IMAGE:2988620) |
| 420. | 496 | 516 | >gi|17939536|gb|BC019308.1| Homo sapiens histone cluster 2; H2aa3; mRNA (cDNA clone IMAGE:2823572) |
| 421. | 390 | 410 | >gi|18088761|gb|BC020884.1| Homo sapiens histone cluster 4; H4; mRNA (cDNA clone IMAGE:4619662) |
| 422. | 343 | 363 | >gi|18105065|ref|NM_003495.2| Homo sapiens histone cluster 1; H4i (HIST1H4I); mRNA |

Figure 11T

| | | |
|---|---|---|
| 423. | 495 | 515 >gi\|19557649\|ref\|NM_021052.2\| Homo sapiens histone cluster 1; H2ae (HIST1H2AE); mRNA |
| 424. | 437 | 457 >gi\|19557652\|ref\|NM_021065.2\| Homo sapiens histone cluster 1; H2ad (HIST1H2AD); mRNA |
| 425. | 453 | 473 >gi\|19557655\|ref\|NM_003513.2\| Homo sapiens histone cluster 1; H2ab (HIST1H2AB); mRNA |
| 426. | 440 | 460 >gi\|19743828\|ref\|NM_003529.2\| Homo sapiens histone cluster 1; H3a (HIST1H3A); mRNA |
| 427. | 455 | 475 >gi\|19743834\|ref\|NM_003493.2\| Homo sapiens histone cluster 3; H3 (HIST3H3); mRNA |
| 428. | 408 | 428 >gi\|19924303\|ref\|NM_021062.2\| Homo sapiens histone cluster 1; H2bb (HIST1H2BB); mRNA |
| 429. | 464 | 484 >gi\|20336750\|ref\|NM_021063.2\| Homo sapiens histone cluster 1; H2bd (HIST1H2BD); transcript variant 1; mRNA |
| 430. | 458 | 478 >gi\|20336753\|ref\|NM_021058.3\| Homo sapiens histone cluster 1; H2bj (HIST1H2BJ); mRNA |
| 431. | 754 | 774 >gi\|20544161\|ref\|NM_005320.2\| Homo sapiens histone cluster 1; H1d (HIST1H1D); mRNA |
| 432. | 762 | 782 >gi\|20544164\|ref\|NM_005321.2\| Homo sapiens histone cluster 1; H1e (HIST1H1E); mRNA |
| 433. | 702 | 722 >gi\|20544167\|ref\|NM_005323.3\| Homo sapiens histone cluster 1; H1t (HIST1H1T); mRNA |
| 434. | 436 | 456 >gi\|21071022\|ref\|NM_003531.2\| Homo sapiens histone cluster 1; H3c (HIST1H3C); mRNA |
| 435. | 344 | 364 >gi\|21071023\|ref\|NM_003539.3\| Homo sapiens histone cluster 1; H4d (HIST1H4D); mRNA |
| 436. | 710 | 730 >gi\|21071025\|ref\|NM_005319.3\| Homo sapiens histone cluster 1; H1c (HIST1H1C); mRNA |
| 437. | 402 | 422 >gi\|21166386\|ref\|NM_003524.2\| Homo sapiens histone cluster 1; H2bh (HIST1H2BH); mRNA |
| 438. | 414 | 434 >gi\|21166387\|ref\|NM_003525.2\| Homo sapiens histone cluster 1; H2bi (HIST1H2BI); mRNA |
| 439. | 415 | 435 >gi\|21166388\|ref\|NM_003526.2\| Homo sapiens histone cluster 1; H2bc (HIST1H2BC); mRNA |
| 440. | 439 | 459 >gi\|21264566\|ref\|NM_003532.2\| Homo sapiens histone cluster 1; H3e (HIST1H3E); mRNA |
| 441. | 511 | 531 >gi\|21328454\|ref\|NM_003516.2\| Homo sapiens histone cluster 2; H2aa3 (HIST2H2AA3); mRNA |
| 442. | 522 | 542 >gi\|21396481\|ref\|NM_003512.3\| Homo sapiens histone cluster 1; H2ac (HIST1H2AC); mRNA |
| 443. | 407 | 427 >gi\|21396482\|ref\|NM_003522.3\| Homo sapiens histone cluster 1; H2bf (HIST1H2BF); mRNA |
| 444. | 412 | 432 >gi\|21396483\|ref\|NM_003523.2\| Homo sapiens histone cluster 1; H2be (HIST1H2BE); mRNA |

Figure 11U

| | | |
|---|---|---|
| 445. | 445 | 465 >gi|21396497|ref|NM_021018.2| Homo sapiens histone cluster 1; H3f (HIST1H3F); mRNA |
| 446. | 446 | 466 >gi|21396498|ref|NM_003537.3| Homo sapiens histone cluster 1; H3b (HIST1H3B); mRNA |
| 447. | 817 | 837 >gi|21411167|gb|BC031333.1| Homo sapiens histone cluster 1; H3d; mRNA (cDNA clone MGC:45668 IMAGE:3608479) |
| 448. | 409 | 429 >gi|21536482|ref|NM_003518.3| Homo sapiens histone cluster 1; H2bg (HIST1H2BG); mRNA |
| 449. | 479 | 499 >gi|21595675|gb|BC032756.1| Homo sapiens histone cluster 1; H2am; mRNA (cDNA clone IMAGE:5581631) |
| 450. | 454 | 474 >gi|21619974|gb|BC033095.1| Homo sapiens histone cluster 1; H3d; mRNA (cDNA clone IMAGE:5440523) |
| 451. | 429 | 449 >gi|21749539|dbj|AK091220.1| Homo sapiens cDNA FLJ33901 fis; clone CTONG2008321; highly similar to HISTONE H2B F |
| 452. | 438 | 458 >gi|21752674|dbj|AK093747.1| Homo sapiens cDNA FLJ36428 fis; clone THYMU2011564; highly similar to HISTONE H2B GL105 |
| 453. | 477 | 497 >gi|22027639|ref|NM_003528.2| Homo sapiens histone cluster 2; H2be (HIST2H2BE); mRNA |
| 454. | 414 | 434 >gi|27436923|ref|NM_003517.2| Homo sapiens histone cluster 2; H2ac (HIST2H2AC); mRNA |
| 455. | 390 | 410 >gi|28416433|ref|NM_175054.2| Homo sapiens histone cluster 4; H4 (HIST4H4); mRNA |
| 456. | 414 | 434 >gi|28558999|ref|NM_170610.2| Homo sapiens histone cluster 1; H2ba (HIST1H2BA); mRNA |
| 457. | 473 | 493 >gi|28872747|ref|NM_033445.2| Homo sapiens histone cluster 3; H2a (HIST3H2A); mRNA |
| 458. | 429 | 449 >gi|28872748|ref|NM_175055.2| Homo sapiens histone cluster 3; H2bb (HIST3H2BB); mRNA |
| 459. | 426 | 446 >gi|29171728|ref|NM_175065.2| Homo sapiens histone cluster 2; H2ab (HIST2H2AB); mRNA |
| 460. | 478 | 498 >gi|30047777|gb|BC050602.1| Homo sapiens histone cluster 1; H2ac; mRNA (cDNA clone IMAGE:6526471) |
| 461. | 728 | 748 >gi|31418312|gb|BC052981.1| Homo sapiens histone cluster 1; H3e; mRNA (cDNA clone IMAGE:6526461) |
| 462. | 484 | 504 >gi|31742502|ref|NM_021059.2| Homo sapiens histone cluster 2; H3c (HIST2H3C); mRNA |
| 463. | 578 | 598 >gi|33873655|gb|BC007518.2| Homo sapiens histone cluster 1; H3h; mRNA (cDNA clone IMAGE:3030790) |
| 464. | 532 | 552 >gi|33877793|gb|BC011694.2| Homo sapiens H2A histone family; member X; mRNA (cDNA clone MGC:19656 IMAGE:3139343) |
| 465. | 450 | 470 >gi|33989991|gb|BC056264.1| Homo sapiens histone 1; H2bg; mRNA (cDNA clone IMAGE:6668499); partial cds |
| 466. | 447 | 467 >gi|34782798|gb|BC005827.2| Homo sapiens histone cluster 2; H2bc; mRNA (cDNA clone MGC:1729 IMAGE:2989788) |

Figure 11V

| | | | |
|---|---|---|---|
| 467. | 473 | 493 | >gi\|34783150\|gb\|BC034487.2\| Homo sapiens histone cluster 1; H2ak; mRNA (cDNA clone MGC:26490 IMAGE:4825623) |
| 468. | 467 | 487 | >gi\|37590440\|gb\|BC058834.1\| Homo sapiens histone cluster 1; H3c; mRNA (cDNA clone IMAGE:6616012); with apparent retained intron |
| 469. | 522 | 542 | >gi\|38196985\|gb\|BC004915.2\| Homo sapiens H2A histone family; member X; mRNA (cDNA clone MGC:4759 IMAGE:3537648) |
| 470. | 517 | 537 | >gi\|38197230\|gb\|BC013416.2\| Homo sapiens H2A histone family; member X; mRNA (cDNA clone MGC:4703 IMAGE:3534359) |
| 471. | 453 | 473 | >gi\|38566171\|gb\|BC062305.1\| Homo sapiens histone cluster 1; H3f; mRNA (cDNA clone IMAGE:3162462); with apparent retained intron |
| 472. | 2322 | 2342 | >gi\|38566171\|gb\|BC062305.1\| Homo sapiens histone cluster 1; H3f; mRNA (cDNA clone IMAGE:3162462); with apparent retained intron |
| 473. | 471 | 491 | >gi\|38570130\|ref\|NM_021064.3\| Homo sapiens histone cluster 1; H2ag (HIST1H2AG); mRNA |
| 474. | 841 | 861 | >gi\|39812261\|ref\|NM_003530.3\| Homo sapiens histone cluster 1; H3d (HIST1H3D); mRNA |
| 475. | 351 | 371 | >gi\|40225911\|gb\|BC017361.2\| Homo sapiens histone cluster 1; H4j; mRNA (cDNA clone MGC:29783 IMAGE:4647914) |
| 476. | 440 | 460 | >gi\|42542575\|gb\|BC066247.1\| Homo sapiens histone cluster 1; H3a; mRNA (cDNA clone MGC:79342 IMAGE:7002070) |
| 477. | 343 | 363 | >gi\|42542579\|gb\|BC066250.1\| Homo sapiens histone cluster 1; H4i; mRNA (cDNA clone MGC:79353 IMAGE:7002105) |
| 478. | 440 | 460 | >gi\|42542796\|gb\|BC066245.1\| Homo sapiens histone cluster 1; H3a; mRNA (cDNA clone MGC:79340 IMAGE:7002068) |
| 479. | 440 | 460 | >gi\|42542798\|gb\|BC066246.1\| Homo sapiens histone cluster 1; H3a; mRNA (cDNA clone MGC:79341 IMAGE:7002069) |
| 480. | 454 | 474 | >gi\|45219795\|gb\|BC066884.1\| Homo sapiens histone cluster 1; H3i; mRNA (cDNA clone MGC:79346 IMAGE:7002077) |
| 481. | 443 | 463 | >gi\|45767727\|gb\|BC067492.1\| Homo sapiens histone cluster 1; H3f; mRNA (cDNA clone MGC:79345 IMAGE:7002073) |
| 482. | 343 | 363 | >gi\|45767733\|gb\|BC067497.1\| Homo sapiens histone cluster 1; H4i; mRNA (cDNA clone MGC:79354 IMAGE:7002106) |
| 483. | 471 | 491 | >gi\|45767869\|gb\|BC067782.1\| Homo sapiens histone 1; H2ag; mRNA (cDNA clone IMAGE:5314244); partial cds |
| 484. | 454 | 474 | >gi\|45768280\|gb\|BC067493.1\| Homo sapiens histone cluster 1; H3i; mRNA (cDNA clone MGC:79347 IMAGE:7002079) |
| 485. | 440 | 460 | >gi\|45768501\|gb\|BC067490.1\| Homo sapiens histone cluster 1; H3a; mRNA (cDNA clone MGC:79343 IMAGE:7002071) |
| 486. | 451 | 471 | >gi\|45768639\|gb\|BC067494.1\| Homo sapiens histone cluster 1; H3i; mRNA (cDNA clone IMAGE:7002080); containing frame-shift errors |
| 487. | 455 | 475 | >gi\|46575594\|gb\|BC069079.1\| Homo sapiens histone cluster 3; H3; mRNA (cDNA clone MGC:95354 IMAGE:7216893) |
| 488. | 767 | 787 | >gi\|46575677\|gb\|BC069101.1\| Homo sapiens histone cluster 1; H1b; mRNA (cDNA clone MGC:95376 IMAGE:7216915) |

Figure 11W

| 489. | 446 | 466 | >gi|46575762|gb|BC069133.1| Homo sapiens histone cluster 1; H3b; mRNA (cDNA clone MGC:95414 IMAGE:7216989) |
| --- | --- | --- | --- |
| 490. | 459 | 479 | >gi|46812686|gb|BC069193.1| Homo sapiens histone cluster 2; H2be; mRNA (cDNA clone MGC:78419 IMAGE:3936695) |
| 491. | 729 | 749 | >gi|46854339|gb|BC069492.1| Homo sapiens histone cluster 1; H1a; mRNA (cDNA clone MGC:96978 IMAGE:7262187) |
| 492. | 447 | 467 | >gi|47479842|gb|BC069306.1| Homo sapiens histone cluster 1; H2al; mRNA (cDNA clone MGC:97481 IMAGE:7262757) |
| 493. | 341 | 361 | >gi|47481358|gb|BC069392.1| Homo sapiens histone cluster 1; H4l; mRNA (cDNA clone MGC:97405 IMAGE:7262681) |
| 494. | 440 | 460 | >gi|47481370|gb|BC069303.1| Homo sapiens histone cluster 1; H3a; mRNA (cDNA clone MGC:97421 IMAGE:7262697) |
| 495. | 440 | 460 | >gi|48734858|gb|BC071668.1| Homo sapiens histone cluster 1; H2am; mRNA (cDNA clone IMAGE:4366993) |
| 496. | 402 | 422 | >gi|49257897|gb|BC073925.1| Homo sapiens histone cluster 2; H3; pseudogene 2; mRNA (cDNA clone IMAGE:5190019) |
| 497. | 355 | 375 | >gi|50368970|gb|BC075806.1| Homo sapiens histone cluster 1; H4i; mRNA (cDNA clone IMAGE:5225467) |
| 498. | 463 | 483 | >gi|52078381|gb|BC082269.1| Homo sapiens histone cluster 3; H2a; mRNA (cDNA clone IMAGE:6671338) |
| 499. | 435 | 455 | >gi|52078470|gb|BC082232.1| Homo sapiens histone cluster 1; H2bg; mRNA (cDNA clone IMAGE:3952039) |
| 500. | 477 | 497 | >gi|52426769|ref|NM_170745.3| Homo sapiens histone cluster 1; H2aa (HIST1H2AA); mRNA |
| 501. | 552 | 572 | >gi|52630339|ref|NM_002105.2| Homo sapiens H2A histone family; member X (H2AFX); mRNA |
| 502. | 483 | 503 | >gi|54673757|gb|BC085010.1| Homo sapiens histone cluster 1; H2ac; mRNA (cDNA clone IMAGE:5933682) |
| 503. | 487 | 507 | >gi|62739738|gb|BC093759.1| Homo sapiens histone cluster 1; H2bl; mRNA (cDNA clone IMAGE:7939604) |
| 504. | 486 | 506 | >gi|62739958|gb|BC093761.1| Homo sapiens histone cluster 1; H2bl; mRNA (cDNA clone IMAGE:7939606) |
| 505. | 402 | 422 | >gi|64653032|gb|BC096119.1| Homo sapiens histone cluster 1; H2bh; mRNA (cDNA clone MGC:116765 IMAGE:40002319) |
| 506. | 407 | 427 | >gi|64653042|gb|BC096123.1| Homo sapiens histone cluster 1; H2bf; mRNA (cDNA clone MGC:116769 IMAGE:40002357) |
| 507. | 402 | 422 | >gi|64654141|gb|BC096118.1| Homo sapiens histone cluster 1; H2bh; mRNA (cDNA clone MGC:116764 IMAGE:40002318) |
| 508. | 407 | 427 | >gi|64654145|gb|BC096120.1| Homo sapiens histone cluster 1; H2bf; mRNA (cDNA clone MGC:116766 IMAGE:40002352) |
| 509. | 402 | 422 | >gi|64654573|gb|BC096117.1| Homo sapiens histone cluster 1; H2bh; mRNA (cDNA clone MGC:116763 IMAGE:40002317) |
| 510. | 435 | 455 | >gi|68532404|gb|BC098112.1| Homo sapiens histone cluster 2; H2be; mRNA (cDNA clone MGC:119802 IMAGE:40014245) |

Figure 11X

| | | |
|---|---|---|
| 511. | 435 | 455 >gi\|68532406\|gb\|BC098289.1\| Homo sapiens histone cluster 2; H2be; mRNA (cDNA clone MGC:119804 IMAGE:40014249) |
| 512. | 458 | 478 >gi\|68532432\|gb\|BC096739.1\| Homo sapiens histone cluster 2; H2aa3; mRNA (cDNA clone MGC:120085 IMAGE:40021707) |
| 513. | 458 | 478 >gi\|68532499\|gb\|BC096705.1\| Homo sapiens histone cluster 2; H2aa3; mRNA (cDNA clone MGC:120083 IMAGE:40021705) |
| 514. | 408 | 428 >gi\|68532516\|gb\|BC096728.1\| Homo sapiens histone cluster 1; H2bb; mRNA (cDNA clone MGC:119805 IMAGE:40014250) |
| 515. | 458 | 478 >gi\|68532546\|gb\|BC098171.1\| Homo sapiens histone cluster 2; H2aa3; mRNA (cDNA clone MGC:120084 IMAGE:40021706) |
| 516. | 757 | 777 >gi\|75516610\|gb\|BC101593.1\| Homo sapiens histone cluster 1; H1a; mRNA (cDNA clone MGC:126642 IMAGE:8069099) |
| 517. | 503 | 523 >gi\|75516927\|gb\|BC101839.1\| Homo sapiens histone cluster 3; H3; mRNA (cDNA clone MGC:126888 IMAGE:8069345) |
| 518. | 503 | 523 >gi\|75517394\|gb\|BC101837.1\| Homo sapiens histone cluster 3; H3; mRNA (cDNA clone MGC:126886 IMAGE:8069343) |
| 519. | 436 | 456 >gi\|76825337\|gb\|BC107085.1\| Homo sapiens histone cluster 2; H2be; mRNA (cDNA clone MGC:129734 IMAGE:40014264) |
| 520. | 436 | 456 >gi\|76827221\|gb\|BC107084.1\| Homo sapiens histone cluster 2; H2be; mRNA (cDNA clone MGC:129733 IMAGE:40014260) |
| 521. | 454 | 474 >gi\|84570000\|gb\|BC110793.1\| Homo sapiens histone cluster 2; H2bf; mRNA (cDNA clone MGC:131639 IMAGE:5224812) |
| 522. | 454 | 474 >gi\|84992988\|ref\|NM_001024599.2\| Homo sapiens histone cluster 2; H2bf (HIST2H2BF); mRNA |
| 523. | 520 | 540 >gi\|85397583\|gb\|BC105129.1\| Homo sapiens histone cluster 1; H2ai; mRNA (cDNA clone MGC:132789 IMAGE:8144132) |
| 524. | 758 | 778 >gi\|85567019\|gb\|BC112140.1\| Homo sapiens histone cluster 1; H1a; mRNA (cDNA clone MGC:138345 IMAGE:8327608) |
| 525. | 520 | 540 >gi\|85567358\|gb\|BC112072.1\| Homo sapiens histone cluster 1; H2al; mRNA (cDNA clone MGC:138277 IMAGE:8327540) |
| 526. | 511 | 531 >gi\|106775677\|ref\|NM_001040874.1\| Homo sapiens histone cluster 2; H2aa4 (HIST2H2AA4); mRNA |
| 527. | 484 | 504 >gi\|106775679\|ref\|NM_001005464.2\| Homo sapiens histone cluster 2; H3a (HIST2H3A); mRNA |
| 528. | 415 | 435 >gi\|109730017\|gb\|BC096122.3\| Homo sapiens histone cluster 1; H2bd; mRNA (cDNA clone MGC:116768 IMAGE:40002354) |
| 529. | 440 | 460 >gi\|109730018\|gb\|BC096130.3\| Homo sapiens histone cluster 1; H3h; mRNA (cDNA clone MGC:116776 IMAGE:40002510) |
| 530. | 440 | 460 >gi\|109730069\|gb\|BC096129.3\| Homo sapiens histone cluster 1; H3h; mRNA (cDNA clone MGC:116775 IMAGE:40002509) |
| 531. | 332 | 352 >gi\|109730246\|gb\|BC111434.1\| Homo sapiens histone cluster 4; H4; mRNA (cDNA clone MGC:133360 IMAGE:40069044) |
| 532. | 332 | 352 >gi\|109730274\|gb\|BC111093.1\| Homo sapiens histone cluster 4; H4; mRNA (cDNA clone MGC:133359 IMAGE:40069039) |

Figure 11Y

| | | |
|---|---|---|
| 533. | 402 | 422 >gi\|109731517\|gb\|BC096116.3\| Homo sapiens histone cluster 1; H2bh; mRNA (cDNA clone MGC:116762 IMAGE:40002316) |
| 534. | 435 | 455 >gi\|109731518\|gb\|BC096121.2\| Homo sapiens histone cluster 2; H2be; mRNA (cDNA clone MGC:116767 IMAGE:40002353) |
| 535. | 440 | 460 >gi\|109731519\|gb\|BC096128.3\| Homo sapiens histone cluster 1; H3h; mRNA (cDNA clone MGC:116774 IMAGE:40002508) |
| 536. | 443 | 463 >gi\|109731520\|gb\|BC096131.2\| Homo sapiens histone cluster 1; H3f; mRNA (cDNA clone MGC:116777 IMAGE:40002512) |
| 537. | 351 | 371 >gi\|115528447\|gb\|BC120939.2\| Homo sapiens histone cluster 1; H4h; mRNA (cDNA clone MGC:149417 IMAGE:40115073) |
| 538. | 332 | 352 >gi\|115528473\|gb\|BC120940.2\| Homo sapiens histone cluster 1; H4h; mRNA (cDNA clone MGC:149418 IMAGE:40115074) |
| 539. | 758 | 778 >gi\|116256359\|ref\|NM_005325.3\| Homo sapiens histone cluster 1; H1a (HIST1H1A); mRNA |
| 540. | 436 | 456 >gi\|118341330\|gb\|BC127610.1\| Homo sapiens histone cluster 1; H3c; mRNA (cDNA clone MGC:156109 IMAGE:40002514) |
| 541. | 437 | 457 >gi\|118341613\|gb\|BC128035.1\| Homo sapiens histone cluster 1; H2ad; mRNA (cDNA clone MGC:158906 IMAGE:40021702) |
| 542. | 415 | 435 >gi\|126632042\|gb\|BC134366.1\| Homo sapiens histone cluster 1; H2ah; mRNA (cDNA clone MGC:158907 IMAGE:40021708) |
| 543. | 440 | 460 >gi\|148744623\|gb\|BC143046.1\| Homo sapiens histone cluster 1; H3h; mRNA (cDNA clone MGC:165323 IMAGE:40112088) |
| 544. | 440 | 460 >gi\|156139005\|gb\|BC148250.1\| Homo sapiens histone cluster 1; H3h; mRNA (cDNA clone MGC:165298 IMAGE:40002516) |
| 545. | 440 | 460 >gi\|156139037\|gb\|BC148243.1\| Homo sapiens histone cluster 1; H3h; mRNA (cDNA clone MGC:165244 IMAGE:40082529) |
| 546. | 709 | 729 >gi\|158255329\|dbj\|AK290947.1\| Homo sapiens cDNA FLJ76039 complete cds; highly similar to Homo sapiens histone 1; H1c (HIST1H1C); mRNA |
| 547. | 472 | 492 >gi\|158257555\|dbj\|AK292062.1\| Homo sapiens cDNA FLJ77691 complete cds; highly similar to Homo sapiens histone 1; H2bk (HIST1H2BK); mRNA |
| 548. | 468 | 488 >gi\|158260350\|dbj\|AK289664.1\| Homo sapiens cDNA FLJ77920 complete cds; highly similar to Homo sapiens histone 1; H2bh (HIST1H2BH); mRNA |
| 549. | 835 | 855 >gi\|158260472\|dbj\|AK289725.1\| Homo sapiens cDNA FLJ77860 complete cds; highly similar to Homo sapiens histone 2; H2be (HIST2H2BE); mRNA |
| 550. | 415 | 435 >gi\|159155510\|gb\|BC148293.2\| Homo sapiens histone cluster 1; H2ah; mRNA (cDNA clone MGC:171151 IMAGE:40021709) |
| 551. | 767 | 787 >gi\|73955041\|ref\|XM_848163.1\| PREDICTED: Canis familiaris similar to Histone H2A.x (H2a/x) (LOC489372); mRNA |
| 552. | 421 | 441 >gi\|73975427\|ref\|XM_539321.2\| PREDICTED: Canis familiaris similar to histone 3; H2ba (LOC482202); mRNA |
| 553. | 479 | 499 >gi\|73981237\|ref\|XM_540288.2\| PREDICTED: Canis familiaris similar to H2B histone family; member F; transcript variant 4 (LOC483170); mRNA |
| 554. | 479 | 499 >gi\|73981240\|ref\|XM_844635.1\| PREDICTED: Canis familiaris similar to H2B histone family; member F; transcript variant 2 (LOC483169); mRNA |

Figure 11Z

| 555. | 442 | 462 | >gi\|73981509\|ref\|XM_540282.2\| PREDICTED: Canis familiaris similar to Histone H2B 291B (LOC483164); mRNA |
|---|---|---|---|
| 556. | 486 | 506 | >gi\|73981515\|ref\|XM_540286.2\| PREDICTED: Canis familiaris similar to Histone H2A.o (H2A/o) (H2A.2) (H2a-615) (LOC483168); mRNA |
| 557. | 486 | 506 | >gi\|73981523\|ref\|XM_845715.1\| PREDICTED: Canis familiaris similar to Histone H2A.o (H2A/o) (H2A.2) (H2a-615) (LOC608631); mRNA |
| 558. | 447 | 467 | >gi\|73981531\|ref\|XM_540291.2\| PREDICTED: Canis familiaris similar to H2B histone family; member F (LOC483173); mRNA |
| 559. | 438 | 458 | >gi\|74003972\|ref\|XM_854116.1\| PREDICTED: Canis familiaris similar to histone 1; H2ai (predicted); transcript variant 2 (LOC480760); mRNA |
| 560. | 813 | 833 | >gi\|74003974\|ref\|XM_854155.1\| PREDICTED: Canis familiaris similar to histone 1; H2ai (predicted); transcript variant 3 (LOC480760); mRNA |
| 561. | 673 | 693 | >gi\|74003978\|ref\|XM_545386.2\| PREDICTED: Canis familiaris similar to Histone H1.2 (H1d) (LOC488264); mRNA |
| 562. | 402 | 422 | >gi\|74004198\|ref\|XM_848802.1\| PREDICTED: Canis familiaris similar to H2B histone family; member T (LOC611158); mRNA |
| 563. | 438 | 458 | >gi\|74009671\|ref\|XM_843136.1\| PREDICTED: Canis familiaris similar to Histone H2B 291B; transcript variant 2 (LOC478743); mRNA |
| 564. | 407 | 427 | >gi\|74012716\|ref\|XM_545431.2\| PREDICTED: Canis familiaris similar to Histone H2B 291B (LOC488309); partial mRNA |
| 565. | 464 | 484 | >gi\|149731869\|ref\|XM_001497420.1\| PREDICTED: Equus caballus similar to histone cluster 1; H2bd (LOC100053645); mRNA |
| 566. | 451 | 471 | >gi\|149731901\|ref\|XM_001498344.1\| PREDICTED: Equus caballus similar to histone 1; H2bn (predicted) (LOC100054473); mRNA |
| 567. | 458 | 478 | >gi\|149751186\|ref\|XM_001488154.1\| PREDICTED: Equus caballus similar to histone cluster 2; H2aa4 (LOC100054058); mRNA |
| 568. | 467 | 487 | >gi\|149751191\|ref\|XM_001488491.1\| PREDICTED: Equus caballus similar to histone cluster 1; H2bb (LOC100054211); mRNA |
| 569. | 426 | 446 | >gi\|149751193\|ref\|XM_001488506.1\| PREDICTED: Equus caballus similar to histone cluster 2; H2ab (LOC100054253); mRNA |
| 570. | 417 | 437 | >gi\|149754735\|ref\|XM_001505029.1\| PREDICTED: Equus caballus similar to histone cluster 1; H2bb (LOC100052568); mRNA |
| 571. | 426 | 446 | >gi\|149754747\|ref\|XM_001505035.1\| PREDICTED: Equus caballus similar to histone cluster 1; H2bd (LOC100052889); mRNA |
| 572. | 433 | 453 | >gi\|194210865\|ref\|XM_001917283.1\| PREDICTED: Equus caballus similar to histone H2a(A)-613 (LOC100058587); mRNA |
| 573. | 741 | 761 | >gi\|194210871\|ref\|XM_001491422.2\| PREDICTED: Equus caballus similar to histone H3.2 (LOC100058466); mRNA |
| 574. | 431 | 451 | >gi\|194210873\|ref\|XM_001917309.1\| PREDICTED: Equus caballus similar to histone cluster 1; H2bb (LOC100053968); mRNA |
| 575. | 458 | 478 | >gi\|194210875\|ref\|XM_001917311.1\| PREDICTED: Equus caballus similar to histone cluster 2; H2aa4 (LOC100054113); mRNA |
| 576. | 741 | 761 | >gi\|194210877\|ref\|XM_001491369.2\| PREDICTED: Equus caballus similar to histone H3.2 (LOC100058378); mRNA |

Figure 11AA

| 577. | 410 | 430 | >gi\|194220197\|ref\|XM_001918356.1\| PREDICTED: Equus caballus similar to histone cluster 3; H2bb (LOC100060980); mRNA |
|---|---|---|---|
| 578. | 1168 | 1188 | >gi\|194220199\|ref\|XM_001918289.1\| PREDICTED: Equus caballus similar to histone cluster 3; H2bb (LOC100061573); mRNA |
| 579. | 417 | 437 | >gi\|194223077\|ref\|XM_001497402.2\| PREDICTED: Equus caballus similar to histone cluster 1; H2bd (LOC100053499); mRNA |
| 580. | 435 | 455 | >gi\|194223078\|ref\|XM_001497311.2\| PREDICTED: Equus caballus similar to Histone H2A type 1-C (H2A/l) (LOC100053545); mRNA |
| 581. | 415 | 435 | >gi\|194223081\|ref\|XM_001497558.2\| PREDICTED: Equus caballus similar to histone cluster 1; H2bd (LOC100053695); mRNA |
| 582. | 419 | 439 | >gi\|194223086\|ref\|XM_001497804.2\| PREDICTED: Equus caballus similar to histone cluster 1; H2bd (LOC100053847); mRNA |
| 583. | 415 | 435 | >gi\|194223109\|ref\|XM_001505043.2\| PREDICTED: Equus caballus similar to histone cluster 1; H2bj (LOC100053472); mRNA |
| 584. | 427 | 447 | >gi\|194223111\|ref\|XM_001505039.2\| PREDICTED: Equus caballus similar to histone cluster 1; H2bk (LOC100053279); mRNA |
| 585. | 439 | 459 | >gi\|194223121\|ref\|XM_001916393.1\| PREDICTED: Equus caballus similar to histone cluster 1; H2ag (LOC100147394); mRNA |
| 586. | 426 | 446 | >gi\|194223126\|ref\|XM_001505033.2\| PREDICTED: Equus caballus similar to histone cluster 1; H2ag (LOC100052837); mRNA |
| 587. | 428 | 448 | >gi\|194223127\|ref\|XM_001505026.2\| PREDICTED: Equus caballus similar to histone cluster 1; H2ag (LOC100052624); mRNA |
| 588. | 423 | 443 | >gi\|194036301\|ref\|XM_001926669.1\| PREDICTED: Sus scrofa similar to histone cluster 2; H2ab (LOC100154181); mRNA |
| 589. | 457 | 477 | >gi\|194036303\|ref\|XM_001926706.1\| PREDICTED: Sus scrofa similar to His3:CG31613 CG31613-PA (LOC100155404); mRNA |
| 590. | 459 | 479 | >gi\|194036305\|ref\|XM_001927015.1\| PREDICTED: Sus scrofa similar to histone cluster 1; H2bd (LOC100158169); mRNA |
| 591. | 472 | 492 | >gi\|194039767\|ref\|XM_001926284.1\| PREDICTED: Sus scrofa similar to histone cluster 1; H3f (LOC100154918); mRNA |
| 592. | 464 | 484 | >gi\|194039771\|ref\|XM_001926427.1\| PREDICTED: Sus scrofa similar to histone cluster 1; H2bb (LOC100152507); mRNA |
| 593. | 446 | 466 | >gi\|194039781\|ref\|XM_001926981.1\| PREDICTED: Sus scrofa similar to histone cluster 1; H2bd (LOC100156957); mRNA |
| 594. | 481 | 501 | >gi\|194039783\|ref\|XM_001927079.1\| PREDICTED: Sus scrofa similar to Histone H2A type 1-C (H2A/l) (LOC100155761); mRNA |
| 595. | 450 | 470 | >gi\|194039789\|ref\|XM_001927484.1\| PREDICTED: Sus scrofa similar to histone cluster 1; H2bd (LOC100152133); mRNA |
| 596. | 482 | 502 | >gi\|194039801\|ref\|XM_001927575.1\| PREDICTED: Sus scrofa similar to histone cluster 1; H3f (LOC100152532); mRNA |
| 597. | 464 | 484 | >gi\|194039805\|ref\|XM_001927624.1\| PREDICTED: Sus scrofa similar to histone cluster 1; H2bb (LOC100156495); mRNA |
| 598. | 708 | 728 | >gi\|194039809\|ref\|XM_001927686.1\| PREDICTED: Sus scrofa similar to histone H1.3-like protein (LOC100152876); mRNA |

Figure 11BB

| 599. | 413 | 433 | >gi\|194039813\|ref\|XM_001927717.1\| PREDICTED: Sus scrofa similar to histone cluster 1; H2bd (LOC100156937); mRNA |
|---|---|---|---|
| 600. | 477 | 497 | >gi\|194039815\|ref\|XM_001927727.1\| PREDICTED: Sus scrofa similar to histone 2a (LOC100155734); mRNA |
| 601. | 464 | 484 | >gi\|194039817\|ref\|XM_001927766.1\| PREDICTED: Sus scrofa similar to histone cluster 1; H3f (LOC100154511); mRNA |
| 602. | 1052 | 1072 | >gi\|194039819\|ref\|XM_001927879.1\| PREDICTED: Sus scrofa similar to histone cluster 1; H2bd (LOC100157327); mRNA |
| 603. | 408 | 428 | >gi\|194039821\|ref\|XM_001927939.1\| PREDICTED: Sus scrofa similar to histone cluster 1; H2bd (LOC100156127); mRNA |
| 604. | 446 | 466 | >gi\|194039831\|ref\|XM_001928089.1\| PREDICTED: Sus scrofa similar to histone cluster 1; H2bd (LOC100156527); mRNA |
| 605. | 485 | 505 | >gi\|194039833\|ref\|XM_001928124.1\| PREDICTED: Sus scrofa similar to Histone H2A type 1-C (H2A/l) (LOC100155325); mRNA |
| 606. | 435 | 455 | >gi\|194039883\|ref\|XM_001928557.1\| PREDICTED: Sus scrofa similar to histone cluster 1; H2ag (LOC100157763); mRNA |
| 607. | 343 | 363 | >gi\|194039887\|ref\|XM_001928607.1\| PREDICTED: Sus scrofa similar to Histone H4 replacement CG3379-PC (LOC100155354); mRNA |
| 608. | 415 | 435 | >gi\|194039891\|ref\|XM_001928621.1\| PREDICTED: Sus scrofa similar to histone cluster 1; H2bd (LOC100155732); mRNA |
| 609. | 343 | 363 | >gi\|194039895\|ref\|XM_001928644.1\| PREDICTED: Sus scrofa similar to Histone H4 replacement CG3379-PC (LOC100152869); mRNA |
| 610. | 482 | 502 | >gi\|194039899\|ref\|XM_001928617.1\| PREDICTED: Sus scrofa similar to histone cluster 1; H2bd (LOC100156932); mRNA |
| 611. | 437 | 457 | >gi\|81294306\|gb\|BC108143.1\| Bos taurus histone H2B-like; mRNA (cDNA clone MGC:133641 IMAGE:8049327) |
| 612. | 463 | 483 | >gi\|85057062\|gb\|BC111653.1\| Bos taurus H2B histone family; member T; mRNA (cDNA clone MGC:137516 IMAGE:8026091) |
| 613. | 553 | 573 | >gi\|109659378\|gb\|BC118370.1\| Bos taurus H2A histone family; member X; mRNA (cDNA clone MGC:140578 IMAGE:8272088) |
| 614. | 463 | 483 | >gi\|118151207\|ref\|NM_001078063.1\| Bos taurus H2B histone family; member T (HIST1H2BK); mRNA |
| 615. | 553 | 573 | >gi\|119331191\|ref\|NM_001079780.1\| Bos taurus H2A histone family; member X (H2AFX); mRNA |
| 616. | 426 | 446 | >gi\|119889439\|ref\|XM_866640.2\| PREDICTED: Bos taurus histone cluster 2; H2ab (HIST2H2AB); mRNA |
| 617. | 348 | 368 | >gi\|119893876\|ref\|XM_001249844.1\| PREDICTED: Bos taurus similar to Hist1h4c protein (LOC781223); mRNA |
| 618. | 436 | 456 | >gi\|119915557\|ref\|XM_868991.2\| PREDICTED: Bos taurus similar to histone cluster 1; H2bd (LOC616868); mRNA |
| 619. | 467 | 487 | >gi\|119915567\|ref\|XM_865976.2\| PREDICTED: Bos taurus similar to histone cluster 1; H2ad (LOC614970); mRNA |
| 620. | 654 | 674 | >gi\|119915729\|ref\|XM_601510.3\| PREDICTED: Bos taurus similar to histone cluster 1; H3f (LOC523214); mRNA |

Figure 11CC

| | | |
|---|---|---|
| 621. | 441 | 461 >gi|119915734|ref|XM_591827.3| PREDICTED: Bos taurus similar to histone cluster 1; H3f (LOC540148); mRNA |
| 622. | 434 | 454 >gi|119915760|ref|XM_603864.3| PREDICTED: Bos taurus similar to histone cluster 1; H3f (LOC525511); mRNA |
| 623. | 470 | 490 >gi|119936490|gb|BT029886.1| Bos taurus histone 1; H2bc (HIST1H2BC); mRNA |
| 624. | 470 | 490 >gi|120474977|ref|NM_001037469.2| Bos taurus histone H2B-like (H2B); mRNA |
| 625. | 719 | 739 >gi|126717466|gb|BC133454.1| Bos taurus histone cluster 1; H1c; mRNA (cDNA clone MGC:148836 IMAGE:8255450) |
| 626. | 719 | 739 >gi|134085670|ref|NM_001083425.1| Bos taurus histone cluster 1; H1c (HIST1H1C); mRNA |
| 627. | 469 | 489 >gi|146186573|gb|BC140622.1| Bos taurus histone cluster 2; H2be; mRNA (cDNA clone MGC:148667 IMAGE:8132885) |
| 628. | 715 | 735 >gi|148744065|gb|BC142322.1| Bos taurus histone cluster 1; H1e; mRNA (cDNA clone MGC:157184 IMAGE:8449066) |
| 629. | 378 | 398 >gi|148744131|gb|BC141999.1| Bos taurus histone H4-like; mRNA (cDNA clone MGC:159482 IMAGE:8402748) |
| 630. | 467 | 487 >gi|148745283|gb|BC142109.1| Bos taurus histone cluster 1; H2ag; mRNA (cDNA clone MGC:152619 IMAGE:8435097) |
| 631. | 493 | 513 >gi|148745473|gb|BC142102.1| Bos taurus histone H2B-like; mRNA (cDNA clone MGC:152559 IMAGE:8430003) |
| 632. | 386 | 406 >gi|148745522|gb|BC142359.1| Bos taurus histone H4; mRNA (cDNA clone MGC:159383 IMAGE:7957203) |
| 633. | 469 | 489 >gi|150247078|ref|NM_001099384.1| Bos taurus histone cluster 2; H2be (HIST2H2BE); mRNA |
| 634. | 378 | 398 >gi|153791427|ref|NM_001099724.1| Bos taurus histone H4-like (LOC617875); mRNA |
| 635. | 758 | 778 >gi|154426099|gb|BC151257.1| Bos taurus histone cluster 1; H1d; mRNA (cDNA clone MGC:159497 IMAGE:8406138) |
| 636. | 715 | 735 >gi|154707859|ref|NM_001098989.1| Bos taurus histone cluster 1; H1c (HIST1H1E); mRNA |
| 637. | 758 | 778 >gi|155371862|ref|NM_001101066.1| Bos taurus histone cluster 1; H1d (HIST1H1D); mRNA |
| 638. | 477 | 497 >gi|194665129|ref|XM_871460.3| PREDICTED: Bos taurus similar to His3:CG31613 CG31613-PA (LOC619141); mRNA |
| 639. | 536 | 556 >gi|194665130|ref|XM_001788780.1| PREDICTED: Bos taurus similar to histone cluster 1; H2bd (LOC506306); partial mRNA |
| 640. | 399 | 419 >gi|194665132|ref|XM_001788784.1| PREDICTED: Bos taurus similar to Hist1h3e protein (LOC788077); partial mRNA |
| 641. | 349 | 369 >gi|194665134|ref|XM_594900.4| PREDICTED: Bos taurus similar to Histone H4 replacement CG3379-PC (LOC516742); mRNA |
| 642. | 379 | 399 >gi|194666723|ref|XM_609250.4| PREDICTED: Bos taurus similar to Histone H4 replacement CG3379-PC (LOC530773); mRNA |
| 643. | 467 | 487 >gi|194672626|ref|XM_602496.4| PREDICTED: Bos taurus similar to histone cluster 1; H2ag (LOC524176); mRNA |

Figure 11DD

| | | |
|---|---|---|
| 644. | 471 | 491 >gi|194674383|ref|XM_866523.3| PREDICTED: Bos taurus similar to histone; H2A (LOC614881); mRNA |
| 645. | 410 | 430 >gi|194677786|ref|XM_868885.3| PREDICTED: Bos taurus similar to histone cluster 1; H2bd (LOC616776); mRNA |
| 646. | 422 | 442 >gi|194677788|ref|XM_607721.4| PREDICTED: Bos taurus similar to histone cluster 1; H2ag (LOC529277); mRNA |
| 647. | 466 | 486 >gi|194677794|ref|XM_869001.3| PREDICTED: Bos taurus similar to histone cluster 1; H2ag (LOC616875); mRNA |
| 648. | 714 | 734 >gi|194677801|ref|XM_001253575.2| PREDICTED: Bos taurus hypothetical LOC787509 (LOC787509); mRNA |
| 649. | 446 | 466 >gi|194677815|ref|XM_608099.4| PREDICTED: Bos taurus similar to histone cluster 1; H2bd (LOC529646); mRNA |
| 650. | 377 | 397 >gi|194677822|ref|XM_001253548.2| PREDICTED: Bos taurus similar to Histone H4 replacement CG3379-PC (LOC787485); mRNA |
| 651. | 472 | 492 >gi|194677825|ref|XM_583411.4| PREDICTED: Bos taurus histone H2A.l (H2A/l); transcript variant 1 (LOC506900); mRNA |
| 652. | 438 | 458 >gi|194677826|ref|XM_001253339.2| PREDICTED: Bos taurus similar to histone cluster 1; H2bd (LOC787269); mRNA |
| 653. | 690 | 710 >gi|194677829|ref|XM_870488.2| PREDICTED: Bos taurus similar to Histone H1.1 (LOC618164); mRNA |
| 654. | 422 | 442 >gi|194687901|ref|XM_001250730.2| PREDICTED: Bos taurus histone H2A type 1 (LOC786163); mRNA |
| 655. | 467 | 487 >gi|198282090|ref|NM_001098720.1| Bos taurus histone cluster 1; H2ag (HIST1H2AG); mRNA |
| 656. | 527 | 547 >gi|51141|emb|X58069.1| Mouse mRNA for Histone H2A.X |
| 657. | 27 | 47 >gi|193863|gb|M15434.1|MUSHISH3A Mouse histone H3.21 mRNA; 3' flank |
| 658. | 703 | 723 >gi|9845256|ref|NM_015786.1| Mus musculus histone cluster 1; H1c (Hist1h1c); mRNA |
| 659. | 493 | 513 >gi|12832916|dbj|AK002725.1| Mus musculus adult male kidney cDNA; RIKEN full-length enriched library; clone:0610031H01 product:histone gene complex 2; full insert sequence |
| 660. | 745 | 765 >gi|12838849|dbj|AK005982.1| Mus musculus adult male testis cDNA; RIKEN full-length enriched library; clone:1700014N06 product:HISTONE H2B; full insert sequence |
| 661. | 841 | 861 >gi|12838849|dbj|AK005982.1| Mus musculus adult male testis cDNA; RIKEN full-length enriched library; clone:1700014N06 product:HISTONE H2B; full insert sequence |
| 662. | 492 | 512 >gi|12839958|dbj|AK006728.1| Mus musculus adult male testis cDNA; RIKEN full-length enriched library; clone:1700048I17 product:histone gene complex 2; full insert sequence |
| 663. | 459 | 479 >gi|12839977|dbj|AK006742.1| Mus musculus adult male testis cDNA; RIKEN full-length enriched library; clone:1700049H14 product:H3 HISTONE homolog [Rattus norvegicus]; full insert sequence |

Figure 11EE

| | | |
|---|---|---|
| 664. | 543 | 563 >gi\|12842115\|dbj\|AK008124.1\| Mus musculus adult male small intestine cDNA; RIKEN full-length enriched library; clone:2010005I09 product:H2A histone family; member X; full insert sequence |
| 665. | 375 | 395 >gi\|12845284\|dbj\|AK010085.1\| Mus musculus adult male tongue cDNA; RIKEN full-length enriched library; clone:2310067E17 product:histone 4 protein; full insert sequence |
| 666. | 467 | 487 >gi\|12845342\|dbj\|AK010121.1\| Mus musculus adult male tongue cDNA; RIKEN full-length enriched library; clone:2310069A13 product:HISTONE H3-VI homolog [Gallus gallus]; full insert sequence |
| 667. | 380 | 400 >gi\|12847762\|dbj\|AK011560.1\| Mus musculus 10 days embryo whole body cDNA; RIKEN full-length enriched library; clone:2610027B07 product:histone 4 protein; full insert sequence |
| 668. | 437 | 457 >gi\|12858647\|dbj\|AK018765.1\| Mus musculus adult male cerebellum cDNA; RIKEN full-length enriched library; clone:1500011O09 product:HISTONE H2B; full insert sequence |
| 669. | 480 | 500 >gi\|12858929\|dbj\|AK018952.1\| Mus musculus adult male testis cDNA; RIKEN full-length enriched library; clone:1700111A06 product:H3 HISTONE homolog [Rattus norvegicus]; full insert sequence |
| 670. | 480 | 500 >gi\|12861000\|dbj\|AK020421.1\| Mus musculus 12 days embryo embryonic body between diaphragm region and neck cDNA; RIKEN full-length enriched library; clone:9430017D03 product:histone 2; H3c2; full insert sequence |
| 671. | 517 | 537 >gi\|13529487\|gb\|BC005468.1\| Mus musculus H2A histone family; member X; mRNA (cDNA clone MGC:6616 IMAGE:3490058) |
| 672. | 476 | 496 >gi\|14714826\|gb\|BC010564.1\| Mus musculus histone cluster 2; H2aa2; mRNA (cDNA clone MGC:5956 IMAGE:3582122) |
| 673. | 625 | 645 >gi\|15929685\|gb\|BC015270.1\| Mus musculus histone cluster 2; H3c2; mRNA (cDNA clone MGC:18559 IMAGE:4240748) |
| 674. | 523 | 543 >gi\|16307579\|gb\|BC010336.1\| Mus musculus H2A histone family; member X; mRNA (cDNA clone MGC:11561 IMAGE:3156946) |
| 675. | 369 | 389 >gi\|18043917\|gb\|BC019757.1\| Mus musculus histone cluster 1; H4i; mRNA (cDNA clone IMAGE:4205460); with apparent retained intron |
| 676. | 492 | 512 >gi\|20799906\|ref\|NM_013549.1\| Mus musculus histone cluster 2; H2aa1 (Hist2h2aa1); mRNA |
| 677. | 379 | 399 >gi\|21361208\|ref\|NM_033596.1\| Mus musculus histone cluster 2; H4 (Hist2h4); mRNA |
| 678. | 718 | 738 >gi\|21426822\|ref\|NM_030609.1\| Mus musculus histone cluster 1; H1a (Hist1h1a); mRNA |
| 679. | 412 | 432 >gi\|26090763\|dbj\|AK045187.1\| Mus musculus 9.5 days embryo parthenogenote cDNA; RIKEN full-length enriched library; clone:B130044J01 product:H4 HISTONE homolog [Homo sapiens]; full insert sequence |
| 680. | 489 | 509 >gi\|26100400\|dbj\|AK082083.1\| Mus musculus 0 day neonate cerebellum cDNA; RIKEN full-length enriched library; clone:C230003M12 product:H2A HISTONE FAMILY; MEMBER L homolog [Homo sapiens]; full insert sequence |

Figure 11FF

| 681. | 546 | 566 | >gi\|26104653\|dbj\|AK088040.1\| Mus musculus 2 days neonate thymus thymic cells cDNA; RIKEN full-length enriched library; clone:E430002L09 product:H2A histone family; member X; full insert sequence |
|---|---|---|---|
| 682. | 629 | 649 | >gi\|26326540\|dbj\|AK030546.1\| Mus musculus adult male pituitary gland cDNA; RIKEN full-length enriched library; clone:5330429M17 product:H2B histone family; member S; full insert sequence |
| 683. | 467 | 487 | >gi\|26329196\|dbj\|AK033518.1\| Mus musculus adult male colon cDNA; RIKEN full-length enriched library; clone:9030420B16 product:histone 1; H2ac; full insert sequence |
| 684. | 602 | 622 | >gi\|26340675\|dbj\|AK049948.1\| Mus musculus adult male hippocampus cDNA; RIKEN full-length enriched library; clone:C630013P15 product:H2B histone family; member S; full insert sequence |
| 685. | 486 | 506 | >gi\|26341961\|dbj\|AK051448.1\| Mus musculus 12 days embryo spinal ganglion cDNA; RIKEN full-length enriched library; clone:D130049H21 product:H2A HISTONE FAMILY; MEMBER L homolog [Homo sapiens]; full insert sequence |
| 686. | 751 | 771 | >gi\|26344108\|dbj\|AK054269.1\| Mus musculus 2 days pregnant adult female ovary cDNA; RIKEN full-length enriched library; clone:E330008J23 product:histone H1; full insert sequence |
| 687. | 486 | 506 | >gi\|26346433\|dbj\|AK077568.1\| Mus musculus 8 days embryo whole body cDNA; RIKEN full-length enriched library; clone:5730450G06 product:H2A HISTONE FAMILY; MEMBER L homolog [Homo sapiens]; full insert sequence |
| 688. | 486 | 506 | >gi\|26350292\|dbj\|AK083155.1\| Mus musculus adult male hippocampus cDNA; RIKEN full-length enriched library; clone:C630019H19 product:H2A HISTONE FAMILY; MEMBER L homolog [Homo sapiens]; RING finger protein TERF; full insert sequence |
| 689. | 487 | 507 | >gi\|26352573\|dbj\|AK087537.1\| Mus musculus 0 day neonate eyeball cDNA; RIKEN full-length enriched library; clone:E130315C04 product:H2A HISTONE FAMILY; MEMBER L homolog [Homo sapiens]; full insert sequence |
| 690. | 457 | 477 | >gi\|30089711\|ref\|NM_175653.1\| Mus musculus histone cluster 1; H3c (Hist1h3c); mRNA |
| 691. | 427 | 447 | >gi\|30704882\|gb\|BC051921.1\| Mus musculus histone cluster 3; H2ba; mRNA (cDNA clone MGC:62161 IMAGE:5684450) |
| 692. | 352 | 372 | >gi\|30705054\|gb\|BC052219.1\| Mus musculus histone cluster 1; H4i; mRNA (cDNA clone IMAGE:30017176) |
| 693. | 523 | 543 | >gi\|31981698\|ref\|NM_010436.2\| Mus musculus H2A histone family; member X (H2afx); mRNA |
| 694. | 485 | 505 | >gi\|32172801\|gb\|BC053966.1\| Mus musculus histone cluster 2; H2aa1; mRNA (cDNA clone IMAGE:1349026) |
| 695. | 625 | 645 | >gi\|34328342\|ref\|NM_054045.2\| Mus musculus histone cluster 2; H3c2 (Hist2h3c2); mRNA |
| 696. | 751 | 771 | >gi\|34328364\|ref\|NM_145713.2\| Mus musculus histone cluster 1; H1d (Hist1h1d); mRNA |
| 697. | 458 | 478 | >gi\|37046860\|gb\|BC058119.1\| Mus musculus histone cluster 3; H2a; mRNA (cDNA clone MGC:69670 IMAGE:6819179) |

Figure 11GG

| | | |
|---|---|---|
| 698. | 355 | 375 >gi\|37046893\|gb\|BC057955.1\| Mus musculus histone cluster 2; H4; mRNA (cDNA clone MGC:65490 IMAGE:5359141) |
| 699. | 468 | 488 >gi\|37805223\|gb\|BC060304.1\| Mus musculus histone cluster 1; H2bg; mRNA (cDNA clone MGC:70229 IMAGE:4217587) |
| 700. | 476 | 496 >gi\|38566129\|gb\|BC062255.1\| Mus musculus histone cluster 2; H2aa2; mRNA (cDNA clone MGC:73680 IMAGE:1448126) |
| 701. | 452 | 472 >gi\|39795284\|gb\|BC063781.1\| Mus musculus histone cluster 3; H2a; mRNA (cDNA clone MGC:70265 IMAGE:6493838) |
| 702. | 449 | 469 >gi\|41388974\|gb\|BC065803.1\| Mus musculus histone cluster 1; H2ag; mRNA (cDNA clone MGC:73771 IMAGE:1263745) |
| 703. | 415 | 435 >gi\|47682211\|gb\|BC069889.1\| Mus musculus histone cluster 1; H2be; mRNA (cDNA clone MGC:78105 IMAGE:4217814) |
| 704. | 476 | 496 >gi\|51873924\|gb\|BC080809.1\| Mus musculus histone cluster 2; H3c1; mRNA (cDNA clone IMAGE:6466339) |
| 705. | 1771 | 1791 >gi\|51873924\|gb\|BC080809.1\| Mus musculus histone cluster 2; H3c1; mRNA (cDNA clone IMAGE:6466339) |
| 706. | 533 | 553 >gi\|58477285\|gb\|BC089519.1\| Mus musculus histone cluster 2; H2aa2; mRNA (cDNA clone MGC:107211 IMAGE:6771160) |
| 707. | 703 | 723 >gi\|59808086\|gb\|BC089604.1\| Mus musculus histone cluster 1; H1c; mRNA (cDNA clone MGC:107646 IMAGE:6763721) |
| 708. | 759 | 779 >gi\|59809089\|gb\|BC089600.1\| Mus musculus histone cluster 1; H1e; mRNA (cDNA clone MGC:107634 IMAGE:6745595) |
| 709. | 759 | 779 >gi\|60097927\|ref\|NM_015787.2\| Mus musculus histone cluster 1; H1e (Hist1h1e); mRNA |
| 710. | 414 | 434 >gi\|62025334\|gb\|BC092138.1\| Mus musculus histone cluster 1; H2bh; mRNA (cDNA clone MGC:106612 IMAGE:30613720) |
| 711. | 369 | 389 >gi\|62027482\|gb\|BC092144.1\| Mus musculus histone cluster 1; H4i; mRNA (cDNA clone MGC:106611 IMAGE:30612926) |
| 712. | 640 | 660 >gi\|62739243\|gb\|BC094041.1\| Mus musculus histone cluster 2; H3c1; mRNA (cDNA clone MGC:102454 IMAGE:5099464) |
| 713. | 353 | 373 >gi\|67677829\|gb\|BC096767.1\| Mus musculus histone 2; H4; mRNA (cDNA clone IMAGE:30094179) |
| 714. | 449 | 469 >gi\|67972648\|ref\|NM_178186.2\| Mus musculus histone cluster 1; H2ag (Hist1h2ag); mRNA |
| 715. | 369 | 389 >gi\|67972651\|ref\|NM_175656.2\| Mus musculus histone cluster 1; H4i (Hist1h4i); mRNA |
| 716. | 469 | 489 >gi\|68226432\|ref\|NM_175666.2\| Mus musculus histone cluster 2; H2bb (Hist2h2bb); mRNA |
| 717. | 425 | 445 >gi\|71050985\|gb\|BC099406.1\| Mus musculus histone cluster 1; H2ai; mRNA (cDNA clone MGC:117571 IMAGE:30789778) |
| 718. | 878 | 898 >gi\|73695351\|gb\|BC103549.1\| Mus musculus histone cluster 1; H3f; mRNA (cDNA clone MGC:123925 IMAGE:40044771) |
| 719. | 373 | 393 >gi\|74137714\|dbj\|AK139521.1\| Mus musculus 2 cells egg cDNA; RIKEN full-length enriched library; clone:B020002O07 product:histone 1; H4j; full insert sequence |

Figure 11HH

| | | | |
|---|---|---|---|
| 720. | 448 | 468 | >gi\|74152995\|dbj\|AK158416.1\| Mus musculus adult inner ear cDNA; RIKEN full-length enriched library; clone:F930115B13 product:histone 1; H2bh; full insert sequence |
| 721. | 435 | 455 | >gi\|74187134\|dbj\|AK135614.1\| Mus musculus adult male adrenal gland cDNA; RIKEN full-length enriched library; clone:7330411A02 product:histone 1; H1c; full insert sequence |
| 722. | 753 | 773 | >gi\|74206881\|dbj\|AK155411.1\| Mus musculus NOD-derived CD11c +ve dendritic cells cDNA; RIKEN full-length enriched library; clone:F630225J18 product:Histone H1.3 (H1 VAR.4) (H1D); full insert sequence |
| 723. | 704 | 724 | >gi\|74207016\|dbj\|AK155502.1\| Mus musculus NOD-derived CD11c +ve dendritic cells cDNA; RIKEN full-length enriched library; clone:F630308G16 product:histone 1; H1c; full insert sequence |
| 724. | 461 | 481 | >gi\|74212912\|dbj\|AK155722.1\| Mus musculus B6-derived CD11 +ve dendritic cells cDNA; RIKEN full-length enriched library; clone:F730210F11 product:histone 1; H3h; full insert sequence |
| 725. | 878 | 898 | >gi\|74353627\|gb\|BC101955.1\| Mus musculus histone cluster 1; H3f; mRNA (cDNA clone MGC:123923 IMAGE:40044769) |
| 726. | 878 | 898 | >gi\|74353629\|gb\|BC101954.1\| Mus musculus histone cluster 1; H3f; mRNA (cDNA clone MGC:123924 IMAGE:40044770) |
| 727. | 878 | 898 | >gi\|74353814\|gb\|BC101956.1\| Mus musculus histone cluster 1; H3f; mRNA (cDNA clone MGC:123922 IMAGE:40044765) |
| 728. | 469 | 489 | >gi\|75991703\|ref\|NM_145073.2\| Mus musculus histone cluster 1; H3g (Hist1h3g); mRNA |
| 729. | 460 | 480 | >gi\|75991704\|ref\|NM_178207.2\| Mus musculus histone cluster 1; H3i (Hist1h3i); mRNA |
| 730. | 465 | 485 | >gi\|75991705\|ref\|NM_178206.2\| Mus musculus histone cluster 1; H3h (Hist1h3h); mRNA |
| 731. | 482 | 502 | >gi\|87299610\|ref\|NM_175660.2\| Mus musculus histone cluster 1; H2ab (Hist1h2ab); mRNA |
| 732. | 529 | 549 | >gi\|94378250\|ref\|XM_976380.1\| PREDICTED: Mus musculus similar to histone H4 (LOC674678); mRNA |
| 733. | 744 | 764 | >gi\|94408203\|ref\|XM_906752.2\| PREDICTED: Mus musculus RIKEN cDNA 1700014N06 gene (1700014N06Rik); mRNA |
| 734. | 840 | 860 | >gi\|94408203\|ref\|XM_906752.2\| PREDICTED: Mus musculus RIKEN cDNA 1700014N06 gene (1700014N06Rik); mRNA |
| 735. | 744 | 764 | >gi\|94408273\|ref\|XM_486774.3\| PREDICTED: Mus musculus RIKEN cDNA 1700014N06 gene (1700014N06Rik); mRNA |
| 736. | 840 | 860 | >gi\|94408273\|ref\|XM_486774.3\| PREDICTED: Mus musculus RIKEN cDNA 1700014N06 gene (1700014N06Rik); mRNA |
| 737. | 386 | 406 | >gi\|109733152\|gb\|BC117012.1\| Mus musculus histone cluster 1; H4k; mRNA (cDNA clone MGC:151389 IMAGE:40126331) |
| 738. | 735 | 755 | >gi\|109733194\|gb\|BC117076.1\| Mus musculus RIKEN cDNA 1700014N06 gene; mRNA (cDNA clone MGC:151453 IMAGE:40126395) |
| 739. | 831 | 851 | >gi\|109733194\|gb\|BC117076.1\| Mus musculus RIKEN cDNA 1700014N06 gene; mRNA (cDNA clone MGC:151453 IMAGE:40126395) |

Figure 11II

| 740. | 445 | 465 | >gi|109733210|gb|BC117094.1| Mus musculus histone cluster 2; H2ac; mRNA (cDNA clone MGC:151471 IMAGE:40126413) |
|---|---|---|---|
| 741. | 445 | 465 | >gi|109733213|gb|BC117096.1| Mus musculus histone cluster 2; H2ac; mRNA (cDNA clone MGC:151473 IMAGE:40126415) |
| 742. | 735 | 755 | >gi|109733658|gb|BC117080.1| Mus musculus RIKEN cDNA 1700014N06 gene; mRNA (cDNA clone MGC:151457 IMAGE:40126399) |
| 743. | 831 | 851 | >gi|109733658|gb|BC117080.1| Mus musculus RIKEN cDNA 1700014N06 gene; mRNA (cDNA clone MGC:151457 IMAGE:40126399) |
| 744. | 750 | 770 | >gi|109733953|gb|BC117045.1| Mus musculus histone cluster 1; H1d; mRNA (cDNA clone MGC:151422 IMAGE:40126364) |
| 745. | 386 | 406 | >gi|109734253|gb|BC117010.1| Mus musculus histone cluster 1; H4k; mRNA (cDNA clone MGC:151387 IMAGE:40126329) |
| 746. | 538 | 558 | >gi|111306830|gb|BC120802.1| Mus musculus histone cluster 1; H3c; mRNA (cDNA clone MGC:156039 IMAGE:40129725) |
| 747. | 538 | 558 | >gi|111308365|gb|BC120800.1| Mus musculus histone cluster 1; H3c; mRNA (cDNA clone MGC:156037 IMAGE:40129723) |
| 748. | 476 | 496 | >gi|111599447|gb|BC115816.1| Mus musculus histone cluster 1; H3a; mRNA (cDNA clone MGC:144700 IMAGE:40105082) |
| 749. | 750 | 770 | >gi|111600701|gb|BC119173.1| Mus musculus histone cluster 1; H1d; mRNA (cDNA clone MGC:155489 IMAGE:8733922) |
| 750. | 712 | 732 | >gi|112807206|ref|NM_010377.2| Mus musculus histone cluster 1; H1t (Hist1h1t); mRNA |
| 751. | 465 | 485 | >gi|116138253|gb|BC125355.1| Mus musculus histone cluster 1; H3g; mRNA (cDNA clone MGC:159058 IMAGE:40129870) |
| 752. | 465 | 485 | >gi|116138650|gb|BC125357.1| Mus musculus histone cluster 1; H3g; mRNA (cDNA clone MGC:159060 IMAGE:40129872) |
| 753. | 363 | 383 | >gi|116138763|gb|BC125598.1| Mus musculus histone cluster 1; H4i; mRNA (cDNA clone MGC:159301 IMAGE:40130113) |
| 754. | 363 | 383 | >gi|116138929|gb|BC125600.1| Mus musculus histone cluster 1; H4i; mRNA (cDNA clone MGC:159303 IMAGE:40130115) |
| 755. | 427 | 447 | >gi|124297397|gb|BC132186.1| Mus musculus histone cluster 1; H4b; mRNA (cDNA clone MGC:163817 IMAGE:40130463) |
| 756. | 427 | 447 | >gi|124297654|gb|BC132212.1| Mus musculus histone cluster 1; H4b; mRNA (cDNA clone MGC:163843 IMAGE:40130489) |
| 757. | 436 | 456 | >gi|142347259|ref|NM_030082.2| Mus musculus histone cluster 3; H2ba (Hist3h2ba); mRNA |
| 758. | 479 | 499 | >gi|142374465|ref|NM_013550.4| Mus musculus histone cluster 1; H3a (Hist1h3a); mRNA |
| 759. | 485 | 505 | >gi|142376228|ref|NM_178218.3| Mus musculus histone cluster 3; H2a (Hist3h2a); mRNA |
| 760. | 627 | 647 | >gi|142377782|ref|NM_178194.3| Mus musculus histone cluster 1; H2bc (Hist1h2be); mRNA |
| 761. | 465 | 485 | >gi|142381322|ref|NM_178189.3| Mus musculus histone cluster 1; H2ac (Hist1h2ac); mRNA |

Figure 11JJ

| | | |
|---|---|---|
| 762. | 499 | 519 >gi\|148878396\|gb\|BC146008.1\| Mus musculus histone cluster 1; H2ah; mRNA (cDNA clone MGC:175895 IMAGE:40131311) |
| 763. | 438 | 458 >gi\|149264031\|ref\|XM_001475900.1\| PREDICTED: Mus musculus similar to Hist1h2bj protein (LOC100046213); mRNA |
| 764. | 878 | 898 >gi\|187281357\|ref\|NM_013548.3\| Mus musculus histone cluster 1; H3f (Hist1h3f); mRNA |
| 765. | 460 | 480 >gi\|187951426\|gb\|BC139381.1\| Mus musculus histone cluster 1; H2bm; mRNA (cDNA clone MGC:171008 IMAGE:8862403) |
| 766. | 401 | 421 >gi\|187952224\|gb\|BC139425.1\| Mus musculus histone cluster 2; H4; mRNA (cDNA clone MGC:171052 IMAGE:8862447) |
| 767. | 401 | 421 >gi\|187952226\|gb\|BC139437.1\| Mus musculus histone cluster 2; H4; mRNA (cDNA clone MGC:171064 IMAGE:8862459) |
| 768. | 499 | 519 >gi\|187953206\|gb\|BC139479.1\| Mus musculus histone cluster 1; H2ah; mRNA (cDNA clone MGC:171106 IMAGE:8862501) |
| 769. | 460 | 480 >gi\|187954288\|gb\|BC139382.1\| Mus musculus histone cluster 1; H2bm; mRNA (cDNA clone MGC:171009 IMAGE:8862404) |
| 770. | 441 | 461 >gi\|218505701\|ref\|NM_178196.3\| Mus musculus histone cluster 1; H2bg (Hist1h2bg); mRNA |
| 771. | 471 | 491 >gi\|496635\|emb\|Z30940.1\| M.domesticus (CD-1) mRNA for histone H2A (partial) |
| 772. | 206 | 226 >gi\|496636\|emb\|Z30939.1\| Mus domesticus partial mRNA for histone H3; CD-1 |
| 773. | 450 | 470 >gi\|204602\|gb\|M18045.1\|RATHISTS Rat testis-specific histone TH2B mRNA |
| 774. | 450 | 470 >gi\|204604\|gb\|M18046.1\|RATHISTSA Rat testis-specific histone H2B mRNA |
| 775. | 723 | 743 >gi\|6981005\|ref\|NM_012579.1\| Rattus norvegicus histone cluster 1; H1t (Hist1h1t); mRNA |
| 776. | 450 | 470 >gi\|12025523\|ref\|NM_022643.1\| Rattus norvegicus histone cluster 1; H2ba (Hist1h2ba); mRNA |
| 777. | 435 | 455 >gi\|71051165\|gb\|BC099140.1\| Rattus norvegicus histone cluster 3; H2a; mRNA (cDNA clone MGC:116285 IMAGE:7457173) |
| 778. | 435 | 455 >gi\|75832134\|ref\|NM_021840.2\| Rattus norvegicus histone cluster 3; H2a (Hist3h2a); mRNA |
| 779. | 469 | 489 >gi\|109465237\|ref\|XM_227463.2\| PREDICTED: Rattus norvegicus similar to histone H2b-616 (predicted); transcript variant 2 (RGD1561543_predicted); mRNA |
| 780. | 1127 | 1147 >gi\|109465262\|ref\|XM_001073395.1\| PREDICTED: Rattus norvegicus similar to H2A histone family; member O (LOC690131); mRNA |
| 781. | 547 | 567 >gi\|109465264\|ref\|XM_345255.3\| PREDICTED: Rattus norvegicus histone 2; H2aa (predicted) (Hist2h2aa_predicted); mRNA |
| 782. | 469 | 489 >gi\|109467200\|ref\|XM_001059351.1\| PREDICTED: Rattus norvegicus similar to histone H2b-616 (predicted); transcript variant 2 (RGD1561543_predicted); mRNA |
| 783. | 1124 | 1144 >gi\|109467215\|ref\|XM_001062026.1\| PREDICTED: Rattus norvegicus similar to H2A histone family; member O (LOC682560); mRNA |
| 784. | 547 | 567 >gi\|109467217\|ref\|XM_001062079.1\| PREDICTED: Rattus norvegicus histone 2; H2aa (predicted) (Hist2h2aa_predicted); mRNA |

Figure 11KK

| 785. | 581 | 601 | >gi|109467219|ref|XR_007982.1| PREDICTED: Rattus norvegicus similar to histone protein Hist2h3c1 (predicted) (RGD1563516_predicted); mRNA |
|---|---|---|---|
| 786. | 378 | 398 | >gi|109472789|ref|XM_575704.2| PREDICTED: Rattus norvegicus histone H4 variant H4-v.1 (predicted) (RGD1562378_predicted); mRNA |
| 787. | 365 | 385 | >gi|109472794|ref|XM_578415.2| PREDICTED: Rattus norvegicus similar to germinal histone H4 gene (predicted) (RGD1565073_predicted); mRNA |
| 788. | 378 | 398 | >gi|109474408|ref|XM_001072344.1| PREDICTED: Rattus norvegicus histone H4 variant H4-v.1 (predicted) (RGD1562378_predicted); mRNA |
| 789. | 365 | 385 | >gi|109474414|ref|XM_001072499.1| PREDICTED: Rattus norvegicus similar to germinal histone H4 gene (predicted) (RGD1565073_predicted); mRNA |
| 790. | 435 | 455 | >gi|109487823|ref|XM_001053023.1| PREDICTED: Rattus norvegicus histone 2a (H2a); mRNA |
| 791. | 444 | 464 | >gi|109490812|ref|XM_001076753.1| PREDICTED: Rattus norvegicus similar to histone 3; H2ba (LOC687018); mRNA |
| 792. | 491 | 511 | >gi|109490814|ref|XM_001076772.1| PREDICTED: Rattus norvegicus similar to histone 3; H2bb (LOC687023); mRNA |
| 793. | 354 | 374 | >gi|109504920|ref|XM_001054684.1| PREDICTED: Rattus norvegicus similar to germinal histone H4 gene (LOC679840); mRNA |
| 794. | 406 | 426 | >gi|109504923|ref|XM_001054927.1| PREDICTED: Rattus norvegicus similar to Histone H2B 291B (LOC679910); mRNA |
| 795. | 456 | 476 | >gi|109504925|ref|XM_001055051.1| PREDICTED: Rattus norvegicus similar to CG31613-PA (LOC679950); mRNA |
| 796. | 459 | 479 | >gi|109504930|ref|XM_001055231.1| PREDICTED: Rattus norvegicus similar to histone 1; H2ai (predicted) (LOC679994); mRNA |
| 797. | 452 | 472 | >gi|109504947|ref|XM_225372.3| PREDICTED: Rattus norvegicus similar to histone 2a (LOC306962); mRNA |
| 798. | 436 | 456 | >gi|109504959|ref|XM_001057044.1| PREDICTED: Rattus norvegicus similar to Histone H2B 291B (LOC680403); mRNA |
| 799. | 354 | 374 | >gi|109504962|ref|XM_001057149.1| PREDICTED: Rattus norvegicus similar to germinal histone H4 gene (LOC680430); mRNA |
| 800. | 423 | 443 | >gi|109504966|ref|XM_225384.2| PREDICTED: Rattus norvegicus histone 1; H2bp (predicted) (Hist1h2bp_predicted); mRNA |
| 801. | 456 | 476 | >gi|109504971|ref|XM_001057500.1| PREDICTED: Rattus norvegicus similar to histone 1; H2ai (predicted) (LOC680511); mRNA |
| 802. | 443 | 463 | >gi|109504975|ref|XM_577577.2| PREDICTED: Rattus norvegicus similar to Histone H2A.1 (predicted) (RGD1562827_predicted); mRNA |
| 803. | 459 | 479 | >gi|109505787|ref|XM_001071228.1| PREDICTED: Rattus norvegicus similar to histone 1; H2ai (predicted) (LOC684610); mRNA |
| 804. | 456 | 476 | >gi|109505792|ref|XM_001071342.1| PREDICTED: Rattus norvegicus similar to CG31613-PA (LOC684633); mRNA |
| 805. | 406 | 426 | >gi|109505794|ref|XM_001071428.1| PREDICTED: Rattus norvegicus similar to Histone H2B 291B (LOC684647); mRNA |
| 806. | 435 | 455 | >gi|109505798|ref|XM_001071516.1| PREDICTED: Rattus norvegicus histone 1; H4a (predicted) (Hist1h4a_predicted); mRNA |

Figure 11LL

| 807. | 978 | 998 | >gi|109505800|ref|XM_001071565.1| PREDICTED: Rattus norvegicus similar to Histone H1.2 (H1 VAR.1) (H1c) (LOC684681); mRNA |
|---|---|---|---|
| 808. | 351 | 371 | >gi|109505802|ref|XM_001071605.1| PREDICTED: Rattus norvegicus similar to germinal histone H4 gene (LOC684686); mRNA |
| 809. | 428 | 448 | >gi|109505810|ref|XM_001071887.1| PREDICTED: Rattus norvegicus similar to histone 2a (LOC684773); mRNA |
| 810. | 417 | 437 | >gi|109505812|ref|XM_001071972.1| PREDICTED: Rattus norvegicus similar to Histone H2B 291B (LOC684797); mRNA |
| 811. | 746 | 766 | >gi|109505818|ref|XM_001072089.1| PREDICTED: Rattus norvegicus similar to Histone H1.2 (H1 VAR.1) (H1c) (LOC684828); mRNA |
| 812. | 445 | 465 | >gi|109505820|ref|XM_001072155.1| PREDICTED: Rattus norvegicus similar to CG31613-PA (LOC684841); mRNA |
| 813. | 406 | 426 | >gi|109505956|ref|XM_001061167.1| PREDICTED: Rattus norvegicus similar to Histone H2B 291B (LOC682355); mRNA |
| 814. | 443 | 463 | >gi|109505958|ref|XM_001061350.1| PREDICTED: Rattus norvegicus similar to Histone H2A.1 (predicted) (RGD1562827_predicted); mRNA |
| 815. | 456 | 476 | >gi|109505964|ref|XM_001061523.1| PREDICTED: Rattus norvegicus similar to histone 1; H2ai (predicted) (LOC682439); mRNA |
| 816. | 434 | 454 | >gi|109505970|ref|XM_001061682.1| PREDICTED: Rattus norvegicus histone 1; H2bp (predicted) (Hist1h2bp_predicted); mRNA |
| 817. | 354 | 374 | >gi|109505974|ref|XM_001061844.1| PREDICTED: Rattus norvegicus similar to germinal histone H4 gene (LOC682518); mRNA |
| 818. | 436 | 456 | >gi|109505980|ref|XM_001062018.1| PREDICTED: Rattus norvegicus similar to Histone H2B 291B (LOC682558); mRNA |
| 819. | 404 | 424 | >gi|109505990|ref|XM_001062548.1| PREDICTED: Rattus norvegicus similar to H2B histone family; member T (LOC682665); mRNA |
| 820. | 452 | 472 | >gi|109505992|ref|XM_001062714.1| PREDICTED: Rattus norvegicus similar to histone 2a (LOC306962); mRNA |
| 821. | 719 | 739 | >gi|157817074|ref|NM_001106113.1| Rattus norvegicus histone cluster 1; H1a (Hist1h1a); mRNA |
| 822. | 523 | 543 | >gi|157817663|ref|NM_001109291.1| Rattus norvegicus H2A histone family; member X (H2afx); mRNA |
| 823. | 491 | 511 | >gi|157820456|ref|NM_001109641.1| Rattus norvegicus histone cluster 3; H2bb (Hist3h2bb); mRNA |
| 824. | 437 | 457 | >gi|162138977|ref|NM_001111127.1| Rattus norvegicus histone cluster 3; H2ba (Hist3h2ba); mRNA |
| 825. | 375 | 395 | >gi|183986772|ref|NM_001123469.1| Rattus norvegicus histone cluster 2; H4 (Hist2h4); mRNA |
| 826. | 463 | 483 | >gi|196012823|ref|XM_002116238.1| Trichoplax adhaerens conserved hypothetical protein; mRNA |
| 827. | 402 | 422 | >gi|26800913|emb|AJ494853.1| Oikopleura dioica mRNA for histone H2A.1a (H2A.1a gene) |
| 828. | 376 | 396 | >gi|26800915|emb|AJ494854.1| Oikopleura dioica partial mRNA for histone h2A.1b (H2a.1b gene) |

Figure 11MM

| | | | |
|---|---|---|---|
| 829. | 347 | 367 | >gi\|26800917\|emb\|AJ494855.1\| Oikopleura dioica partial mRNA for histone h4 (H4 gene) |
| 830. | 262 | 282 | >gi\|222804053\|gb\|EZ032441.1\| TSA: Acropora millepora SeqIndex6010; mRNA sequence |
| 831. | 262 | 282 | >gi\|222804061\|gb\|EZ032449.1\| TSA: Acropora millepora SeqIndex6011; mRNA sequence |
| 832. | 485 | 505 | >gi\|156321366\|ref\|XM_001618210.1\| Nematostella vectensis predicted protein (NEMVEDRAFT_v1g196043) partial mRNA |
| 833. | 485 | 505 | >gi\|156330407\|ref\|XM_001619062.1\| Nematostella vectensis predicted protein (NEMVEDRAFT_v1g196006) partial mRNA |
| 834. | 391 | 411 | >gi\|76153607\|gb\|DQ213262.1\| Taeniopygia guttata clone 0061P0011F09 putative histone 1 H4h variant 1 mRNA |
| 835. | 735 | 755 | >gi\|76156518\|gb\|DQ213950.1\| Taeniopygia guttata clone 0061P0024E05 putative histone H1.10 mRNA |
| 836. | 717 | 737 | >gi\|76156521\|gb\|DQ213951.1\| Taeniopygia guttata clone 0063P0014G11 putative histone H1.10 mRNA |
| 837. | 495 | 515 | >gi\|76157207\|gb\|DQ214187.1\| Taeniopygia guttata clone 0058P0044E04 putative histone 1 H2ai mRNA |
| 838. | 495 | 515 | >gi\|76157210\|gb\|DQ214188.1\| Taeniopygia guttata clone 0058P0024E05 putative histone 1 H2ai mRNA |
| 839. | 465 | 485 | >gi\|76158668\|gb\|DQ215263.1\| Taeniopygia guttata clone 0058P0013D11 histone 1 H2be -like mRNA; complete sequence |
| 840. | 390 | 410 | >gi\|120431858\|gb\|EF191850.1\| Taeniopygia guttata clone 0069P0006C11 putative histone 1 H4h variant 2 mRNA |
| 841. | 438 | 458 | >gi\|224094528\|ref\|XM_002192776.1\| PREDICTED: Taeniopygia guttata similar to Histone H2A (LOC100224417); mRNA |
| 842. | 428 | 448 | >gi\|224094534\|ref\|XM_002192929.1\| PREDICTED: Taeniopygia guttata similar to histone 1; H2bn (predicted) (LOC100221480); mRNA |
| 843. | 422 | 442 | >gi\|224094538\|ref\|XM_002193157.1\| PREDICTED: Taeniopygia guttata similar to histone 1; H2bn (predicted) (LOC100218635); mRNA |
| 844. | 420 | 440 | >gi\|224094547\|ref\|XM_002193367.1\| PREDICTED: Taeniopygia guttata similar to histone 1; H2bn (predicted) (LOC100225375); mRNA |
| 845. | 497 | 517 | >gi\|224094549\|ref\|XM_002193400.1\| PREDICTED: Taeniopygia guttata similar to histone cluster 2; H2ac (LOC100222481); mRNA |
| 846. | 444 | 464 | >gi\|224094553\|ref\|XM_002193592.1\| PREDICTED: Taeniopygia guttata H3 histone; family 3A (LOC100219617); mRNA |
| 847. | 443 | 463 | >gi\|224094555\|ref\|XM_002193640.1\| PREDICTED: Taeniopygia guttata H3 histone; family 3A (LOC100232119); mRNA |
| 848. | 473 | 493 | >gi\|224094561\|ref\|XM_002193813.1\| PREDICTED: Taeniopygia guttata similar to histone H2A (LOC100226365); mRNA |
| 849. | 421 | 441 | >gi\|224094565\|ref\|XM_002193862.1\| PREDICTED: Taeniopygia guttata similar to histone 1; H2bn (predicted) (LOC100223493); mRNA |
| 850. | 734 | 754 | >gi\|224094567\|ref\|XM_002193962.1\| PREDICTED: Taeniopygia guttata similar to Histone H1.2 (H1d) (LOC100220586); mRNA |

Figure 11NN

| 851. | 454 | 474 | >gi|224094577|ref|XM_002194105.1| PREDICTED: Taeniopygia guttata H3 histone; family 3A (LOC100227232); mRNA |
| --- | --- | --- | --- |
| 852. | 452 | 472 | >gi|224094585|ref|XM_002194248.1| PREDICTED: Taeniopygia guttata H3 histone; family 3A (LOC100218576); mRNA |
| 853. | 444 | 464 | >gi|224094589|ref|XM_002194328.1| PREDICTED: Taeniopygia guttata similar to Histone H2A (LOC100231060); mRNA |
| 854. | 725 | 745 | >gi|224094595|ref|XM_002194486.1| PREDICTED: Taeniopygia guttata similar to Histone H1.2 (H1d) (LOC100225322); mRNA |
| 855. | 487 | 507 | >gi|224094599|ref|XM_002194574.1| PREDICTED: Taeniopygia guttata similar to histone cluster 2; H2ac (LOC100222423); mRNA |
| 856. | 448 | 468 | >gi|224094603|ref|XM_002194623.1| PREDICTED: Taeniopygia guttata similar to histone 1; H2bn (predicted) (LOC100219559); mRNA |
| 857. | 474 | 494 | >gi|224094605|ref|XM_002194862.1| PREDICTED: Taeniopygia guttata similar to histone cluster 2; H2ac (LOC100223439); mRNA |
| 858. | 464 | 484 | >gi|224094607|ref|XM_002194693.1| PREDICTED: Taeniopygia guttata similar to histone 1; H2bn (predicted) (LOC100220543); mRNA |
| 859. | 468 | 488 | >gi|224094613|ref|XM_002191393.1| PREDICTED: Taeniopygia guttata H3 histone; family 3A (LOC100221418); partial mRNA |
| 860. | 469 | 489 | >gi|224094617|ref|XM_002194670.1| PREDICTED: Taeniopygia guttata similar to histone cluster 2; H2ac (LOC100226305); mRNA |
| 861. | 438 | 458 | >gi|224094631|ref|XM_002195263.1| PREDICTED: Taeniopygia guttata similar to histone 1; H2bn (predicted) (LOC100227296); mRNA |
| 862. | 444 | 464 | >gi|224094633|ref|XM_002195287.1| PREDICTED: Taeniopygia guttata similar to histone cluster 2; H2ac (LOC100224416); mRNA |
| 863. | 464 | 484 | >gi|224164721|ref|XM_002188885.1| PREDICTED: Taeniopygia guttata similar to histone 1; H2bn (predicted) (LOC100221533); mRNA |
| 864. | 471 | 491 | >gi|224164723|ref|XM_002188918.1| PREDICTED: Taeniopygia guttata similar to histone cluster 2; H2ac (LOC100218691); mRNA |
| 865. | 448 | 468 | >gi|224165476|ref|XM_002194933.1| PREDICTED: Taeniopygia guttata similar to histone 1; H2bn (predicted) (LOC100232209); mRNA |
| 866. | 455 | 475 | >gi|145652157|gb|EF526308.1| Bubalus bubalis histone 2B (H2B) mRNA |
| 867. | 514 | 534 | >gi|194719518|gb|EU734830.1| Carassius auratus gibelio H2A mRNA |

Figure 13
A.
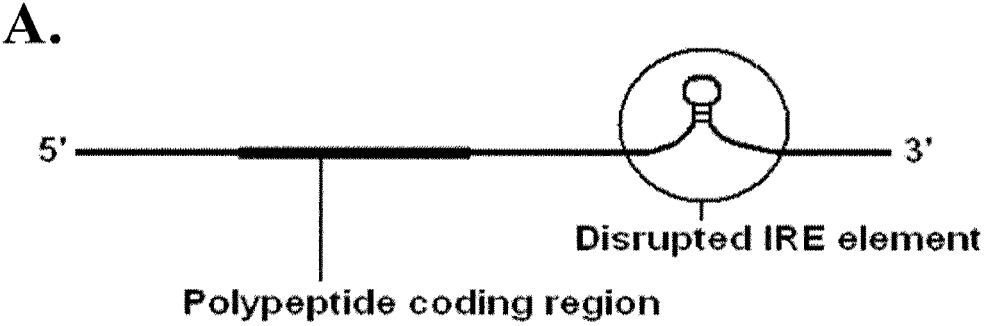
B.
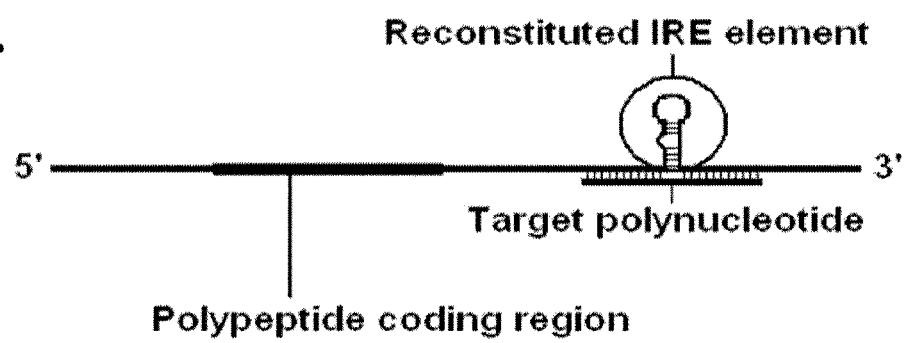

| | start | end | origin |
|---|---|---|---|
| 1. | 1488 | 1510 | >gi|58339282|gb|AY738114.1| Triticum aestivum leucine zipper protein zip1 (zip1) mRNA; |
| 2. | 1461 | 1483 | >gi|62736387|gb|AY914051.1| Triticum aestivum putative leucine zipper protein (zip1) mRNA; |
| 3. | 22 | 44 | >gi|9649|emb|X56778.1| L.stagnalis L. mRNA for som_fer gene |
| 4. | 63 | 83 | >gi|118428733|gb|DQ983429.1| Daphnia pulex clone Contig_138 ferritin 3-like protein mRNA; |
| 5. | 14 | 34 | >gi|118428740|gb|DQ983433.1| Daphnia pulex clone 1798340:4 ferritin 3-like protein C mRNA; |
| 6. | 686 | 706 | >gi|118428740|gb|DQ983433.1| Daphnia pulex clone 1798340:4 ferritin 3-like protein C mRNA; |
| 7. | 48 | 78 | >gi|56684768|gb|AY691510.1| Carcinoscorpius rotundicauda ferritin heavy chain-1b mRNA; |
| 8. | 7 | 31 | >gi|29140534|gb|AF068225.2| Ornithodoros moubata ferritin (Fer) mRNA; |
| 9. | 3 | 27 | >gi|32187063|gb|AY307447.1| Boophilus microplus ferritin mRNA; |
| 10. | 20 | 40 | >gi|33772680|gb|AY277902.1| Boophilus microplus ferritin (Fer) mRNA; |
| 11. | 20 | 40 | >gi|33772676|gb|AY277900.1| Amblyomma americanum ferritin (Fer) mRNA; |
| 12. | 18 | 42 | >gi|33772688|gb|AY277906.1| Ixodes scapularis ferritin (Fer) mRNA; |
| 13. | 83 | 107 | >gi|189234640|ref|XM_961965.2| PREDICTED: Tribolium castaneum similar to ferritin (LOC655420); mRNA |
| 14. | 111 | 137 | >gi|94451507|gb|DQ483055.1| Bombyx mori ferritin subunit mRNA; |
| 15. | 125 | 151 | >gi|95102693|gb|DQ443196.1| Bombyx mori ferritin mRNA; |
| 16. | 107 | 133 | >gi|95102795|gb|DQ443250.1| Bombyx mori ferritin isoform 1 mRNA; |
| 17. | 107 | 133 | >gi|95102797|gb|DQ443251.1| Bombyx mori ferritin isoform 2 mRNA; |
| 18. | 98 | 124 | >gi|110559583|gb|DQ683021.1| Bombyx mori iron storage protein mRNA; |
| 19. | 98 | 124 | >gi|112982959|ref|NM_001044119.1| Bombyx mori ferritin (LOC732949); mRNA |
| 20. | 106 | 132 | >gi|148224250|ref|NM_001044115.3| Bombyx mori ferritin (LOC732916); mRNA |
| 21. | 21 | 47 | >gi|110559585|gb|DQ683022.1| Bombyx mandarina iron storage protein mRNA; |
| 22. | 42 | 68 | >gi|7272335|gb|L47123.1| Manduca sexta ferritin mRNA; |
| 23. | 115 | 141 | >gi|9802371|gb|AF270492.1| Manduca sexta midgut-secreted ferritin mRNA; partial cds |
| 24. | 110 | 136 | >gi|18031706|gb|AY032659.1| Manduca sexta ferritin heavy chain-like protein precursor; mRNA; |
| 25. | 63 | 89 | >gi|11890403|gb|AF142340.1|AF142340 Galleria mellonella 26kDa ferritin subunit mRNA; |
| 26. | 4 | 30 | >gi|17901817|gb|AF329683.1| Galleria mellonella 32 kDa ferritin subunit mRNA; |

Figure 14B

| | start | end | origin |
|---|---|---|---|
| 27. | 85 | 111 | >gi|559066|gb|L37082.1|MQSFERRSUB Aedes aegypti ferritin subunit mRNA; |
| 28. | 86 | 112 | >gi|42762741|gb|AY433539.1| Aedes aegypti ASAP ID: 42839 ferritin subunit mRNA sequence |
| 29. | 86 | 112 | >gi|157115952|ref|XM_001652681.1| Aedes aegypti ferritin subunit 1 partial mRNA |
| 30. | 146 | 170 | >gi|151194065|gb|EF472236.1| Anopheles gambiae ferritin heavy chain-like protein precursor (HCH) mRNA; |
| 31. | 107 | 131 | >gi|157674422|gb|EU124589.1| Lutzomyia longipalpis putative ferritin heavy-chain subunit (FHC) mRNA; |
| 32. | 149 | 175 | >gi|2231677|gb|U91524.1|DMU91524 Drosophila melanogaster ferritin subunit 1 (Fer1) mRNA; |
| 33. | 151 | 177 | >gi|3559829|emb|Y15629.1| Drosophila melanogaster mRNA for ferritin subunit 1 |
| 34. | 105 | 131 | >gi|3559837|emb|Y15630.1| Drosophila melanogaster ferritin subunit 1 5'UTR; clone cDNA1 |
| 35. | 422 | 448 | >gi|16902029|gb|AY061831.1| Drosophila melanogaster LD25232 full length cDNA |
| 36. | 78 | 106 | >gi|21430209|gb|AY118923.1| Drosophila melanogaster LD23740 full insert cDNA |
| 37. | 96 | 124 | >gi|24586080|ref|NM_057753.3| Drosophila melanogaster succinate dehydrogenase B (SdhB); mRNA |
| 38. | 422 | 448 | >gi|24651354|ref|NM_080134.2| Drosophila melanogaster ferritin 1 heavy chain homologue (Fer1HCH); transcript variant A; mRNA |
| 39. | 844 | 864 | >gi|195175071|ref|XM_002028251.1| Drosophila persimilis GL16733 (Dper\GL16733); mRNA |
| 40. | 237 | 267 | >gi|156546547|ref|XM_001607310.1| PREDICTED: Nasonia vitripennis similar to ferritin (LOC100116376); mRNA |
| 41. | 115 | 147 | >gi|110762640|ref|XM_624041.2| PREDICTED: Apis mellifera similar to Ferritin 1 heavy chain homologue CG2216-PE; isoform E (LOC551651); mRNA |
| 42. | 75 | 95 | >gi|198436810|ref|XM_002126984.1| PREDICTED: Ciona intestinalis similar to Sdhb-prov protein (LOC100181830); mRNA |
| 43. | 9 | 29 | >gi|219498211|ref|XM_002245612.1| Branchiostoma floridae hypothetical protein (BRAFLDRAFT_272879) mRNA; |
| 44. | 73 | 99 | >gi|219502517|ref|XM_002247552.1| Branchiostoma floridae hypothetical protein (BRAFLDRAFT_273662) mRNA; |
| 45. | 6 | 26 | >gi|26324279|gb|AY157150.1| Branchiostoma belcheri ferritin mRNA; |
| 46. | 82 | 108 | >gi|7109244|gb|AF226612.1| Danio rerio ferroportin1 (fpn1) mRNA; |
| 47. | 10 | 32 | >gi|11545422|gb|AF295373.1|AF295373 Danio rerio ferritin heavy chain (fth1) mRNA; |
| 48. | 10 | 32 | >gi|18858718|ref|NM_131585.1| Danio rerio ferritin; heavy polypeptide 1 (fth1); mRNA |

Figure 14C

| | start | end | origin |
|---|---|---|---|
| 49. | 82 | 108 | >gi|18859378|ref|NM_131629.1| Danio rerio solute carrier family 40 (iron-regulated transporter); member 1 (slc40a1); mRNA |
| 50. | 43 | 65 | >gi|28278804|gb|BC045278.1| Danio rerio ferritin; heavy polypeptide 1; mRNA (cDNA clone MGC:55220 IMAGE:3815619); |
| 51. | 20 | 42 | >gi|49902698|gb|BC075879.1| Danio rerio zgc:92066; mRNA (cDNA clone MGC:92066 IMAGE:7046348); |
| 52. | 20 | 42 | >gi|50539815|ref|NM_001002378.1| Danio rerio zgc:92066 (zgc:92066); mRNA |
| 53. | 33 | 55 | >gi|63102343|gb|BC095061.1| Danio rerio zgc:109934; mRNA (cDNA clone MGC:109934 IMAGE:7252599); |
| 54. | 33 | 55 | >gi|66472683|ref|NM_001020531.1| Danio rerio zgc:109934 (zgc:109934); mRNA |
| 55. | 2923 | 2949 | >gi|82524362|ref|NM_001009918.2| Danio rerio transferrin receptor 1b (tfr1b); mRNA |
| 56. | 2966 | 2996 | >gi|82524362|ref|NM_001009918.2| Danio rerio transferrin receptor 1b (tfr1b); mRNA |
| 57. | 29 | 51 | >gi|156914785|gb|BC152596.1| Danio rerio zgc:173594; mRNA (cDNA clone MGC:173594 IMAGE:8151242); |
| 58. | 29 | 51 | >gi|157954495|ref|NM_001109854.1| Danio rerio zgc:173594 (zgc:173594); mRNA |
| 59. | 29 | 51 | >gi|158253855|gb|BC154146.1| Danio rerio zgc:109934; mRNA (cDNA clone MGC:173595 IMAGE:8154848); |
| 60. | 33 | 55 | >gi|159155701|gb|BC154746.1| Danio rerio wu:fj24c01; mRNA (cDNA clone MGC:173592 IMAGE:7407378); |
| 61. | 33 | 55 | >gi|165972410|ref|NM_001113659.1| Danio rerio wu:fj24c01 (wu:fj24c01); mRNA |
| 62. | 17 | 39 | >gi|189517135|ref|XM_001921696.1| PREDICTED: Danio rerio similar to Ferritin heavy chain (Ferritin H subunit) (Cell proliferation-inducing gene 15 protein) (LOC100006428); mRNA |
| 63. | 12 | 34 | >gi|190338087|gb|BC162709.1| Danio rerio zgc:194125; mRNA (cDNA clone MGC:194125 IMAGE:9038211); |
| 64. | 12 | 34 | >gi|190339495|gb|BC162683.1| Danio rerio zgc:194125; mRNA (cDNA clone MGC:194099 IMAGE:9038213); |
| 65. | 12 | 34 | >gi|194578824|ref|NM_001130667.1| Danio rerio zgc:194125 (zgc:194125); mRNA |
| 66. | 20 | 42 | >gi|68161034|gb|DQ086166.1| Ictalurus punctatus ferritin heavy subunit mRNA; |
| 67. | 15 | 37 | >gi|68161040|gb|DQ086169.1| Ictalurus punctatus ferritin H-3 mRNA; partial cds |
| 68. | 6 | 28 | >gi|1752749|dbj|D86626.1| Oncorhynchus mykiss mRNA for ferritin H-2; |
| 69. | 6 | 28 | >gi|185133948|ref|NM_001124548.1| Oncorhynchus mykiss ferritin H-2 (LOC100136294); mRNA |
| 70. | 15 | 37 | >gi|12802902|gb|AF338763.1|AF338763 Oncorhynchus nerka ferritin-H |

Figure 14D

| | start | end | origin |
|---|---|---|---|
| | | | subunit mRNA; |
| 71. | 32 | 54 | >gi|999126|gb|S77386.1| ferritin middle subunit [Salmo salar=Atlantic salmon; liver; mRNA; 1010 nt] |
| 72. | 32 | 54 | >gi|185132427|ref|NM_001123658.1| Salmo salar ferritin middle subunit (LOC100136565); mRNA |
| 73. | 12 | 34 | >gi|197632418|gb|BT043818.1| Salmo salar clone HM4_1383 ferritin; heavy polypeptide 1-1 mRNA; |
| 74. | 5 | 27 | >gi|197632420|gb|BT043819.1| Salmo salar clone HM5_2952 ferritin; heavy polypeptide 1-2 mRNA; |
| 75. | 16 | 38 | >gi|209154679|gb|BT045310.1| Salmo salar clone ssal-rgf-518-052 Ferritin; middle subunit putative mRNA; |
| 76. | 10 | 32 | >gi|209154795|gb|BT045368.1| Salmo salar clone ssal-rgf-519-193 Ferritin; heavy subunit putative mRNA; |
| 77. | 41 | 63 | >gi|209730473|gb|BT046305.1| Salmo salar clone ssal-eve-567-231 Ferritin; middle subunit putative mRNA; |
| 78. | 19 | 41 | >gi|209730753|gb|BT046445.1| Salmo salar clone ssal-eve-573-257 Ferritin; middle subunit putative mRNA; |
| 79. | 17 | 39 | >gi|209731389|gb|BT046763.1| Salmo salar clone ssal-rgb2-565-077 Ferritin; middle subunit putative mRNA; |
| 80. | 16 | 38 | >gi|209731495|gb|BT046816.1| Salmo salar clone ssal-rgb2-570-157 Ferritin; middle subunit putative mRNA; |
| 81. | 42 | 64 | >gi|209731581|gb|BT046859.1| Salmo salar clone ssal-eve-544-067 Ferritin; middle subunit putative mRNA; |
| 82. | 20 | 42 | >gi|209732295|gb|BT047216.1| Salmo salar clone ssal-rgb2-567-134 Ferritin; middle subunit putative mRNA; |
| 83. | 13 | 35 | >gi|209733107|gb|BT047622.1| Salmo salar clone ssal-plnb-510-341 Ferritin; middle subunit putative mRNA; |
| 84. | 34 | 56 | >gi|209733689|gb|BT047913.1| Salmo salar clone ssal-eve-006-108 Ferritin; middle subunit putative mRNA; |
| 85. | 9 | 31 | >gi|209733751|gb|BT047944.1| Salmo salar clone ssal-plnb-512-029 Ferritin; middle subunit putative mRNA; |
| 86. | 40 | 62 | >gi|209734161|gb|BT048149.1| Salmo salar clone ssal-cvf-549-063 Ferritin; heavy subunit putative mRNA; |
| 87. | 11 | 33 | >gi|209734739|gb|BT048438.1| Salmo salar clone ssal-rgb2-580-054 Ferritin; heavy subunit putative mRNA; |
| 88. | 60 | 82 | >gi|209735029|gb|BT048583.1| Salmo salar clone ssal-cvd-531-097 Ferritin; middle subunit putative mRNA; |
| 89. | 111 | 133 | >gi|209735539|gb|BT048838.1| Salmo salar clone ssal-evd-563-175 Ferritin; middle subunit putative mRNA; |
| 90. | 16 | 38 | >gi|209735939|gb|BT049038.1| Salmo salar clone ssal-rgb2-509-101 Ferritin; middle subunit putative mRNA; |
| 91. | 20 | 42 | >gi|209736165|gb|BT049151.1| Salmo salar clone ssal-evd-504-104 Ferritin; middle subunit putative mRNA; |

Figure 14E

| | start | end | origin |
|---|---|---|---|
| 92. | 16 | 38 | >gi|209736347|gb|BT049242.1| Salmo salar clone ssal-plnb-014-075 Ferritin; middle subunit putative mRNA; |
| 93. | 15 | 37 | >gi|209736357|gb|BT049247.1| Salmo salar clone ssal-evf-520-218 Ferritin; middle subunit putative mRNA; |
| 94. | 17 | 39 | >gi|209737099|gb|BT049618.1| Salmo salar clone ssal-rgb2-507-351 Ferritin; middle subunit putative mRNA; |
| 95. | 16 | 38 | >gi|209737211|gb|BT049674.1| Salmo salar clone ssal-evd-520-065 Ferritin; middle subunit putative mRNA; |
| 96. | 34 | 56 | >gi|209737541|gb|BT049839.1| Salmo salar clone ssal-evd-520-176 Ferritin; middle subunit putative mRNA; |
| 97. | 14 | 36 | >gi|209737929|gb|BT050033.1| Salmo salar clone ssal-rgb2-616-306 Ferritin; middle subunit putative mRNA; |
| 98. | 12 | 34 | >gi|213513867|ref|NM_001139722.1| Salmo salar ferritin; heavy polypeptide 1-1 (LOC100194637); mRNA |
| 99. | 3919 | 3939 | >gi|14905702|gb|AY034103.1| Poecilia reticulata xanthine dehydrogenase mRNA; |
| 100. | 6 | 28 | >gi|30349211|gb|AY260753.1| Oreochromis mossambicus ferritin heavy subunit mRNA; partial cds |
| 101. | 33 | 55 | >gi|62079569|gb|AY737021.1| Oreochromis mossambicus clone Contig24 ferritin middle subunit mRNA; partial cds |
| 102. | 18 | 40 | >gi|10121670|gb|AF266195.1|AF266195 Gillichthys mirabilis ferritin middle subunit mRNA; |
| 103. | 171 | 193 | >gi|64690|emb|X51395.1| Xenopus laevis mRNA for ferritin |
| 104. | 11 | 33 | >gi|214135|gb|M55010.1|XELFERHSU Xenopus laevis ferritin H subunit mRNA; |
| 105. | 506 | 528 | >gi|238858|gb|S64727.1| ferritin [Xenopus laevis; XL2 cells; mRNA; 1388 nt] |
| 106. | 31 | 53 | >gi|27882414|gb|BC044685.1| Xenopus laevis Ferritin heavy chain; oocyte isoform; mRNA (cDNA clone MGC:53349 IMAGE:5571031); |
| 107. | 18 | 40 | >gi|27924171|gb|BC044961.1| Xenopus laevis ferritin heavy chain; mRNA (cDNA clone MGC:52598 IMAGE:5543148); |
| 108. | 12 | 34 | >gi|28302245|gb|BC046680.1| Xenopus laevis hypothetical protein MGC53066; mRNA (cDNA clone MGC:53066 IMAGE:5541973); |
| 109. | 29 | 51 | >gi|33331484|gb|AF538970.1| Xenopus laevis ferritin heavy chain mRNA; |
| 110. | 17 | 39 | >gi|33331486|gb|AF538971.1| Xenopus laevis ferritin light chain mRNA; |
| 111. | 707 | 729 | >gi|34784901|gb|BC056858.1| Xenopus laevis Ferritin heavy chain; oocyte isoform; mRNA (cDNA clone MGC:64558 IMAGE:6880106); |
| 112. | 21 | 43 | >gi|34785676|gb|BC057216.1| Xenopus laevis Ferritin light chain; oocyte isoform; mRNA (cDNA clone MGC:68606 IMAGE:4031959); |
| 113. | 18 | 40 | >gi|38014726|gb|BC060381.1| Xenopus laevis ferritin; heavy polypeptide 1; mRNA (cDNA clone MGC:68515 IMAGE:4030710); |
| 114. | 8 | 30 | >gi|118835678|gb|BC128943.1| Xenopus laevis hypothetical protein LOC100036818; mRNA (cDNA clone MGC:160341 IMAGE:8539473); |

Figure 14F

| | start | end | origin |
|---|---|---|---|
| 115. | 8 | 30 | >gi|147898654|ref|NM_001097109.1| Xenopus laevis hypothetical protein LOC100036818 (LOC100036818); mRNA |
| 116. | 18 | 40 | >gi|148224145|ref|NM_001096738.1| Xenopus laevis ferritin; heavy polypeptide 1 (fth1); mRNA |
| 117. | 98 | 124 | >gi|148224727|ref|NM_001093357.1| Xenopus laevis solute carrier family 40 (iron-regulated transporter); member 1 (slc40a1); mRNA |
| 118. | 506 | 528 | >gi|148226275|ref|NM_001090588.1| Xenopus laevis ferritin protein (ferritin); mRNA |
| 119. | 12 | 34 | >gi|148232660|ref|NM_001086183.1| Xenopus laevis hypothetical protein MGC53066 (MGC53066); mRNA |
| 120. | 18 | 40 | >gi|148234982|ref|NM_001086111.1| Xenopus laevis ferritin heavy chain (MGC52598); mRNA |
| 121. | 21 | 43 | >gi|148236188|ref|NM_001086458.1| Xenopus laevis Ferritin light chain; oocyte isoform (MGC68606); mRNA |
| 122. | 707 | 729 | >gi|148236234|ref|NM_001089603.1| Xenopus laevis Ferritin heavy chain; oocyte isoform (MGC64558); mRNA |
| 123. | 34 | 56 | >gi|38648960|gb|BC063337.1| Xenopus tropicalis hypothetical protein MGC75752; mRNA (cDNA clone MGC:75752 IMAGE:5381534); |
| 124. | 34 | 56 | >gi|45361268|ref|NM_203881.1| Xenopus (Silurana) tropicalis hypothetical protein MGC75752 (MGC75752); mRNA |
| 125. | 8 | 30 | >gi|49898968|gb|BC076689.1| Xenopus tropicalis MGC79725 protein; mRNA (cDNA clone MGC:79725 IMAGE:6982176); |
| 126. | 47 | 69 | >gi|50416661|gb|BC077674.1| Xenopus tropicalis MGC89846 protein; mRNA (cDNA clone MGC:89846 IMAGE:7028826); |
| 127. | 8 | 30 | >gi|52345939|ref|NM_001005018.1| Xenopus (Silurana) tropicalis MGC79725 protein (MGC79725); mRNA |
| 128. | 47 | 69 | >gi|52346185|ref|NM_001005135.1| Xenopus (Silurana) tropicalis MGC89846 protein (MGC89846); mRNA |
| 129. | 13 | 35 | >gi|77626900|emb|CR760872.2| Xenopus tropicalis finished cDNA; clone TTpA007g24 |
| 130. | 29 | 51 | >gi|170285169|gb|BC160952.1| Xenopus tropicalis hypothetical protein LOC100145388; mRNA (cDNA clone MGC:180954 IMAGE:8856335); |
| 131. | 29 | 51 | >gi|187607887|ref|NM_001126853.1| Xenopus (Silurana) tropicalis hypothetical protein LOC100145388 (LOC100145388); mRNA |
| 132. | 29 | 51 | >gi|189441768|gb|BC167527.1| Xenopus tropicalis hypothetical protein LOC100170515; mRNA (cDNA clone MGC:180940 IMAGE:8854073); |
| 133. | 29 | 51 | >gi|194332553|ref|NM_001130294.1| Xenopus (Silurana) tropicalis hypothetical protein LOC100170515 (LOC100170515); mRNA |
| 134. | 28 | 50 | >gi|213672|gb|M15655.1|RANFERH Frog (Rana catesbeiana) apoferritin higher subunit; mRNA; |
| 135. | 28 | 50 | >gi|213691|gb|M12120.1|RANRCFA Bull frog (R.catesbeiana) tadpole red cell ferritin mRNA; |
| 136. | 103 | 135 | >gi|61098365|ref|NM_001012913.1| Gallus gallus solute carrier family 40 |

Figure 14G

| | start | end | origin |
|---|---|---|---|
| | | | (iron-regulated transporter); member 1 (SLC40A1); mRNA |
| 137. | 54 | 76 | >gi|149463000|ref|XM_001513998.1| PREDICTED: Ornithorhynchus anatinus similar to iron storage protein H-ferritin (LOC100090297); mRNA |
| 138. | 44 | 66 | >gi|90075727|dbj|AB170481.1| Macaca fascicularis brain cDNA clone: QmoA-11095; similar to human ferritin; light polypeptide (FTL); mRNA; RefSeq: NM_000146.2 |
| 139. | 34 | 56 | >gi|90075885|dbj|AB170560.1| Macaca fascicularis brain cDNA clone: QmoA-11465; similar to human ferritin; heavy polypeptide 1 (FTH1); mRNA; RefSeq: NM_002032.1 |
| 140. | 32 | 54 | >gi|109085790|ref|XM_001104405.1| PREDICTED: Macaca mulatta similar to Ferritin heavy chain (Ferritin H subunit) (Proliferation-inducing gene 15 protein) (FTH1); mRNA |
| 141. | 33 | 55 | >gi|109095940|ref|XM_001099912.1| PREDICTED: Macaca mulatta similar to Ferritin heavy chain (Ferritin H subunit) (Proliferation-inducing gene 15 protein) (FTH1); mRNA |
| 142. | 56 | 78 | >gi|109133920|ref|XM_001119579.1| PREDICTED: Macaca mulatta similar to Ferritin light chain (Ferritin L subunit) (FTL); partial mRNA |
| 143. | 148 | 170 | >gi|114637917|ref|XM_001140124.1| PREDICTED: Pan troglodytes similar to Ferritin heavy chain (Ferritin H subunit) (Proliferation-inducing gene 15 protein) (LOC738986); mRNA |
| 144. | 11 | 33 | >gi|114639491|ref|XM_001175066.1| PREDICTED: Pan troglodytes ferritin; heavy polypeptide 1 (FTH1); mRNA |
| 145. | 194 | 216 | >gi|114649148|ref|XM_509574.2| PREDICTED: Pan troglodytes similar to FTH1 protein (LOC452477); mRNA |
| 146. | 131 | 153 | >gi|114678175|ref|XM_001155938.1| PREDICTED: Pan troglodytes hypothetical protein LOC747113 (LOC747113); mRNA |
| 147. | 89 | 111 | >gi|114681008|ref|XM_514491.2| PREDICTED: Pan troglodytes hypothetical LOC458071 (LOC458071); mRNA |
| 148. | 112 | 138 | >gi|55728696|emb|CR858889.1| Pongo abelii mRNA; cDNA DKFZp459N191 (from clone DKFZp459N191) |
| 149. | 33 | 55 | >gi|55730381|emb|CR859755.1| Pongo abelii mRNA; cDNA DKFZp469N1034 (from clone DKFZp469N1034) |
| 150. | 30 | 52 | >gi|55732870|emb|CR861037.1| Pongo abelii mRNA; cDNA DKFZp470G1212 (from clone DKFZp470G1212) |
| 151. | 112 | 138 | >gi|197099267|ref|NM_001132161.1| Pongo abelii solute carrier family 40 (iron-regulated transporter); member 1 (SLC40A1); mRNA |
| 152. | 33 | 55 | >gi|197099311|ref|NM_001132636.1| Pongo abelii ferritin; heavy polypeptide 1 (FTH1); mRNA |
| 153. | 30 | 52 | >gi|197101170|ref|NM_001133378.1| Pongo abelii ferritin; light polypeptide (FTL); mRNA |
| 154. | 13 | 35 | >gi|28587|emb|X60364.1| Human ALAS mRNA for 5-aminolevulinate synthase precursor |
| 155. | 34 | 56 | >gi|507251|gb|L20941.1|HUMFERRITH Human ferritin heavy chain |

Figure 14H

| | start | end | origin |
|---|---|---|---|
| | | | mRNA; |
| 156. | 8 | 30 | >gi\|2230868\|emb\|Y09188.1\| H.sapiens mRNA for ferritin L-chain |
| 157. | 77 | 103 | >gi\|7109248\|gb\|AF226614.1\|AF226614 Homo sapiens ferroportin1 (FPN1) mRNA; |
| 158. | 77 | 103 | >gi\|7264728\|gb\|AF231121.1\|AF231121 Homo sapiens iron-regulated transporter IREG1 (IREG1) mRNA; |
| 159. | 77 | 103 | >gi\|8895484\|gb\|AF215636.1\|AF215636 Homo sapiens SLC11A3 iron transporter mRNA; |
| 160. | 21 | 43 | >gi\|12654092\|gb\|BC000857.1\| Homo sapiens ferritin; heavy polypeptide 1; mRNA (cDNA clone MGC:5580 IMAGE:3459353); |
| 161. | 19 | 41 | >gi\|13279004\|gb\|BC004245.1\| Homo sapiens ferritin; light polypeptide; mRNA (cDNA clone MGC:10465 IMAGE:3615360); |
| 162. | 30 | 52 | >gi\|14250068\|gb\|BC008439.1\| Homo sapiens ferritin; light polypeptide; mRNA (cDNA clone MGC:14642 IMAGE:4093482); |
| 163. | 34 | 56 | >gi\|15530276\|gb\|BC013928.1\| Homo sapiens ferritin; light polypeptide; mRNA (cDNA clone MGC:24228 IMAGE:3839120); |
| 164. | 37 | 59 | >gi\|16359090\|gb\|BC016009.1\| Homo sapiens ferritin; heavy polypeptide 1; mRNA (cDNA clone MGC:27328 IMAGE:4666545); |
| 165. | 1281 | 1303 | >gi\|16549428\|dbj\|AK054816.1\| Homo sapiens cDNA FLJ30254 fis; clone BRACE2002441; highly similar to Ferritin heavy chain (EC 1.16.3.1) |
| 166. | 34 | 56 | >gi\|16740988\|gb\|BC016346.1\| Homo sapiens ferritin; light polypeptide; mRNA (cDNA clone MGC:24392 IMAGE:4066010); |
| 167. | 34 | 56 | >gi\|16741008\|gb\|BC016354.1\| Homo sapiens ferritin; light polypeptide; mRNA (cDNA clone MGC:24480 IMAGE:4092360); |
| 168. | 34 | 56 | >gi\|16876868\|gb\|BC016715.1\| Homo sapiens ferritin; light polypeptide; mRNA (cDNA clone MGC:24401 IMAGE:4067055); |
| 169. | 33 | 55 | >gi\|18203881\|gb\|BC021670.1\| Homo sapiens ferritin; light polypeptide; mRNA (cDNA clone MGC:22710 IMAGE:4051089); |
| 170. | 15 | 37 | >gi\|21104437\|dbj\|AB062402.1\| Homo sapiens OK/SW-cl.84 mRNA for ferritin-heavy polypeptide 1; |
| 171. | 34 | 56 | >gi\|28894134\|gb\|AY207005.1\| Homo sapiens ferritin-like protein mRNA; |
| 172. | 29 | 51 | >gi\|33096740\|emb\|BX571748.1\| Homo sapiens mRNA; cDNA DKFZp686L19147 (from clone DKFZp686L19147); |
| 173. | 2 | 24 | >gi\|33873848\|gb\|BC018990.2\| Homo sapiens ferritin; light polypeptide; mRNA (cDNA clone MGC:20176 IMAGE:3503710); |
| 174. | 12 | 34 | >gi\|34189606\|gb\|BC011359.2\| Homo sapiens ferritin; heavy polypeptide 1; mRNA (cDNA clone MGC:18238 IMAGE:4157296); |
| 175. | 15 | 37 | >gi\|34190319\|gb\|BC013724.2\| Homo sapiens ferritin; heavy polypeptide 1; mRNA (cDNA clone MGC:17255 IMAGE:3857790); |
| 176. | 34 | 56 | >gi\|37573984\|gb\|BC058820.1\| Homo sapiens ferritin; light polypeptide; mRNA (cDNA clone MGC:61835 IMAGE:4049525); |
| 177. | 33 | 55 | >gi\|38541892\|gb\|BC062708.1\| Homo sapiens ferritin; light polypeptide; mRNA (cDNA clone MGC:71996 IMAGE:4774403); |

Figure 14I

| | start | end | origin |
|---|---|---|---|
| 178. | 4 | 26 | >gi\|39645111\|gb\|BC063514.1\| Homo sapiens ferritin; heavy polypeptide 1; mRNA (cDNA clone MGC:70834 IMAGE:3882345); |
| 179. | 33 | 55 | >gi\|42490865\|gb\|BC066341.1\| Homo sapiens ferritin; heavy polypeptide 1; mRNA (cDNA clone MGC:87457 IMAGE:5288688); |
| 180. | 35 | 57 | >gi\|44890439\|gb\|BC066961.1\| Homo sapiens ferritin; heavy polypeptide 1; mRNA (cDNA clone MGC:87456 IMAGE:4796312); |
| 181. | 2 | 26 | >gi\|46411160\|ref\|NM_001098.2\| Homo sapiens aconitase 2; mitochondrial (ACO2); nuclear gene encoding mitochondrial protein; mRNA |
| 182. | 13 | 35 | >gi\|47125325\|gb\|BC070494.1\| Homo sapiens ferritin; heavy polypeptide 1; mRNA (cDNA clone IMAGE:6009374); partial cds |
| 183. | 19 | 41 | >gi\|49256418\|gb\|BC073750.1\| Homo sapiens ferritin; heavy polypeptide 1; mRNA (cDNA clone MGC:88754 IMAGE:6256153); |
| 184. | 62 | 84 | >gi\|56682958\|ref\|NM_002032.2\| Homo sapiens ferritin; heavy polypeptide 1 (FTH1); mRNA |
| 185. | 30 | 52 | >gi\|56682960\|ref\|NM_000146.3\| Homo sapiens ferritin; light polypeptide (FTL); mRNA |
| 186. | 124 | 150 | >gi\|67633295\|gb\|DQ065759.1\| Homo sapiens ferroportin 1 variant I (SLC40A1) mRNA; partial cds |
| 187. | 37 | 59 | >gi\|74356467\|gb\|BC104643.1\| Homo sapiens ferritin; heavy polypeptide 1; mRNA (cDNA clone MGC:104426 IMAGE:4043391); |
| 188. | 37 | 59 | >gi\|76779198\|gb\|BC105802.1\| Homo sapiens ferritin; heavy polypeptide 1; mRNA (cDNA clone IMAGE:4717046); partial cds |
| 189. | 6892 | 6914 | >gi\|113204433\|ref\|NM_003607.3\| Homo sapiens CDC42 binding protein kinase alpha (DMPK-like) (CDC42BPA); transcript variant B; mRNA |
| 190. | 6649 | 6671 | >gi\|113204434\|ref\|NM_014826.4\| Homo sapiens CDC42 binding protein kinase alpha (DMPK-like) (CDC42BPA); transcript variant A; mRNA |
| 191. | 99 | 125 | >gi\|158257723\|dbj\|AK292146.1\| Homo sapiens cDNA FLJ78004 ; highly similar to Homo sapiens solute carrier family 40 (iron-regulated transporter); member 1; mRNA |
| 192. | 30 | 52 | >gi\|164697506\|dbj\|AK311773.1\| Homo sapiens cDNA; FLJ92034; highly similar to Homo sapiens ferritin; light polypeptide (FTL); mRNA |
| 193. | 106 | 128 | >gi\|169160875\|ref\|XM_001722297.1\| PREDICTED: Homo sapiens similar to hCG1648021 (LOC642337); mRNA |
| 194. | 124 | 150 | >gi\|187607385\|ref\|NM_014585.5\| Homo sapiens solute carrier family 40 (iron-regulated transporter); member 1 (SLC40A1); mRNA |
| 195. | 99 | 121 | >gi\|195539357\|ref\|NM_000032.4\| Homo sapiens aminolevulinate; delta-; synthase 2 (ALAS2); nuclear gene encoding mitochondrial protein; transcript variant 1; mRNA |
| 196. | 99 | 121 | >gi\|195539358\|ref\|NM_001037967.3\| Homo sapiens aminolevulinate; delta-; synthase 2 (ALAS2); nuclear gene encoding mitochondrial protein; transcript variant 2; mRNA |
| 197. | 99 | 121 | >gi\|195539359\|ref\|NM_001037968.3\| Homo sapiens aminolevulinate; delta-; synthase 2 (ALAS2); nuclear gene encoding mitochondrial protein; |

Figure 14J

| | start | end | origin |
|---|---|---|---|
| | | | transcript variant 3; mRNA |
| 198. | 7 | 29 | >gi|15076950|gb|AF285177.1|AF285177 Canis familiaris ferritin mRNA; |
| 199. | 7 | 29 | >gi|50978755|ref|NM_001003080.1| Canis lupus familiaris ferritin; heavy polypeptide 1 (FTH1); mRNA |
| 200. | 67 | 89 | >gi|73958100|ref|XM_536874.2| PREDICTED: Canis familiaris similar to Ferritin light chain 2 (Ferritin L subunit 2) (Ferritin subunit LG) (LOC479746); mRNA |
| 201. | 23 | 45 | >gi|73970829|ref|XM_845705.1| PREDICTED: Canis familiaris similar to ferritin light chain 1 (LOC608625); mRNA |
| 202. | 318 | 340 | >gi|73977528|ref|XM_847150.1| PREDICTED: Canis familiaris similar to Ferritin light chain 1 (Ferritin L subunit 1) (LOC609811); mRNA |
| 203. | 17 | 39 | >gi|73998112|ref|XM_534978.2| PREDICTED: Canis familiaris similar to ferritin light chain 1 (LOC477783); mRNA |
| 204. | 4 | 26 | >gi|5281115|gb|AF086786.1|AF086786 Delphinapterus leucas erythroid-specific 5-aminolevulinic acid synthase (ALS2) mRNA; |
| 205. | 16 | 38 | >gi|21435815|gb|AY112742.1| Equus caballus ferritin heavy chain mRNA; |
| 206. | 16 | 38 | >gi|154350229|ref|NM_001100413.1| Equus caballus ferritin heavy chain (FT); mRNA |
| 207. | 33 | 55 | >gi|194224682|ref|XM_001495020.2| PREDICTED: Equus caballus similar to ferritin heavy chain (LOC100062546); mRNA |
| 208. | 3 | 25 | >gi|194227936|ref|XM_001914641.1| PREDICTED: Equus caballus hypothetical protein LOC100146482 (LOC100146482); mRNA |
| 209. | 17 | 39 | >gi|286151|dbj|D15071.1|PIGFE Sus scrofa mRNA for ferritin heavy-chain; |
| 210. | 17 | 39 | >gi|47522775|ref|NM_213975.1| Sus scrofa ferritin; heavy polypeptide 1 (FTH1); mRNA |
| 211. | 13 | 35 | >gi|194043882|ref|XM_001924122.1| PREDICTED: Sus scrofa hypothetical protein LOC100153286 (LOC100153286); mRNA |
| 212. | 19 | 41 | >gi|28189736|dbj|AB098993.1| Bos taurus mRNA for similar to ferritin H subunit; partial cds; clone: ORCS11746 |
| 213. | 31 | 53 | >gi|28189936|dbj|AB099093.1| Bos taurus mRNA for similar to ferritin L subunit; partial cds; clone: ORCS13934 |
| 214. | 22 | 44 | >gi|42564198|gb|AY528246.1| Bos taurus ferritin light polypeptide (FTL) mRNA; |
| 215. | 22 | 44 | >gi|54262148|ref|NM_174792.3| Bos taurus ferritin; light polypeptide (FTL); mRNA |
| 216. | 34 | 56 | >gi|57864498|dbj|AB099065.2| Bos taurus mRNA for similar to ferritin H subunit; partial cds; clone: ORCS13217 |
| 217. | 31 | 53 | >gi|58760373|gb|AY911329.1| Bos taurus clone IMAGE:7961468 ferritin heavy polypeptide 1 mRNA; |
| 218. | 35 | 57 | >gi|73586641|gb|BC103021.1| Bos taurus ferritin; light polypeptide; mRNA (cDNA clone MGC:128093 IMAGE:7954568); |
| 219. | 32 | 54 | >gi|86827677|gb|BC105376.1| Bos taurus ferritin; heavy polypeptide 1; mRNA (cDNA clone MGC:128102 IMAGE:7942224); |

Figure 14K

| | start | end | origin |
|---|---|---|---|
| 220. | 32 | 54 | >gi|88319924|ref|NM_174062.3| Bos taurus ferritin; heavy polypeptide 1 (FTH1); mRNA |
| 221. | 1052 | 1074 | >gi|126010816|gb|BC133520.1| Bos taurus fatty acid desaturase domain family; member 6; mRNA (cDNA clone MGC:151555 IMAGE:8281070); |
| 222. | 1052 | 1074 | >gi|126165302|ref|NM_001081722.1| Bos taurus fatty acid desaturase domain family; member 6 (FADS6); mRNA |
| 223. | 32 | 54 | >gi|154426177|gb|BC151549.1| Bos taurus ferritin; heavy polypeptide 1; mRNA (cDNA clone MGC:179308 IMAGE:7342905); |
| 224. | 48 | 70 | >gi|194663447|ref|XM_001251063.2| PREDICTED: Bos taurus similar to ferritin L subunit (LOC782921); mRNA |
| 225. | 42 | 64 | >gi|194667562|ref|XM_591595.4| PREDICTED: Bos taurus similar to Ferritin; heavy polypeptide 1; transcript variant 1 (LOC513842); mRNA |
| 226. | 38 | 60 | >gi|194668159|ref|XM_001251437.2| PREDICTED: Bos taurus similar to ferritin L subunit (LOC784025); mRNA |
| 227. | 39 | 61 | >gi|194673278|ref|XM_001250935.2| PREDICTED: Bos taurus similar to Ferritin; heavy polypeptide 1 (LOC782705); mRNA |
| 228. | 48 | 70 | >gi|194677015|ref|XM_001251302.2| PREDICTED: Bos taurus similar to ferritin L subunit (LOC783220); mRNA |
| 229. | 33 | 55 | >gi|194677850|ref|XM_001254819.2| PREDICTED: Bos taurus similar to ferritin L subunit (LOC788801); mRNA |
| 230. | 40 | 62 | >gi|194678436|ref|XM_001250276.2| PREDICTED: Bos taurus similar to ferritin L subunit (LOC785297); mRNA |
| 231. | 35 | 57 | >gi|1560|emb|X14578.1| Rabbit mRNA for ferritin light chain subunit 5'end |
| 232. | 11 | 33 | >gi|191071|gb|M99692.1|CRUFERR Hamster iron binding protein (ferretin) mRNA |
| 233. | 2 | 24 | >gi|193268|gb|J04716.1|MUSFERLA Mouse ferritin light chain; |
| 234. | 15 | 37 | >gi|1220399|gb|M63244.1|MUSALASE Mus musculus amino levulinate synthase mRNA; |
| 235. | 33 | 55 | >gi|6753911|ref|NM_010239.1| Mus musculus ferritin heavy chain 1 (Fth1); mRNA |
| 236. | 69 | 95 | >gi|7109246|gb|AF226613.1|AF226613 Mus musculus ferroportin1 (Fpn1) mRNA; |
| 237. | 42 | 68 | >gi|7264726|gb|AF231120.1|AF231120 Mus musculus iron-regulated transporter IREG1 (Ireg1) mRNA; |
| 238. | 56 | 82 | >gi|8895486|gb|AF215637.1|AF215637 Mus musculus SLC11A3 iron transporter mRNA; |
| 239. | 37 | 59 | >gi|12832084|dbj|AK002242.1| Mus musculus adult male kidney cDNA; RIKEN full-length enriched library; clone:0610006G13 product:ferritin light chain 1; full insert sequence |
| 240. | 35 | 57 | >gi|12832103|dbj|AK002253.1| Mus musculus adult male kidney cDNA; RIKEN full-length enriched library; clone:0610006K08 product:ferritin light chain 1; full insert sequence |
| 241. | 35 | 57 | >gi|12832607|dbj|AK002547.1| Mus musculus adult male kidney cDNA; |

Figure 14L

| | start | end | origin |
|---|---|---|---|
| | | | RIKEN full-length enriched library; clone:0610011I07 product:ferritin light chain 1; full insert sequence |
| 242. | 36 | 58 | >gi|12846842|dbj|AK011009.1| Mus musculus 13 days embryo liver cDNA; RIKEN full-length enriched library; clone:2510027K02 product:ferritin light chain 1; full insert sequence |
| 243. | 35 | 57 | >gi|12846879|dbj|AK011029.1| Mus musculus 13 days embryo liver cDNA; RIKEN full-length enriched library; clone:2510030C10 product:ferritin light chain 1; full insert sequence |
| 244. | 37 | 59 | >gi|12847239|dbj|AK011244.1| Mus musculus 10 days embryo whole body cDNA; RIKEN full-length enriched library; clone:2600017I12 product:ferritin light chain 1; full insert sequence |
| 245. | 11 | 33 | >gi|15126787|gb|BC012314.1| Mus musculus ferritin heavy chain 1; mRNA (cDNA clone MGC:19422 IMAGE:3488821); |
| 246. | 15 | 37 | >gi|18044715|gb|BC019840.1| Mus musculus ferritin light chain 1; mRNA (cDNA clone MGC:29974 IMAGE:5123770); |
| 247. | 119 | 145 | >gi|26083702|dbj|AK033987.1| Mus musculus adult male diencephalon cDNA; RIKEN full-length enriched library; clone:9330134D20 product:solute carrier family 39 (iron-regulated transporter); member 1; full insert sequence |
| 248. | 41 | 63 | >gi|26353689|dbj|AK088647.1| Mus musculus 2 days neonate thymus thymic cells cDNA; RIKEN full-length enriched library; clone:E430022I20 product:ferritin light chain 1; full insert sequence |
| 249. | 33 | 55 | >gi|26389189|dbj|AK027998.1| Mus musculus 18-day embryo whole body cDNA; RIKEN full-length enriched library; clone:1110070P14 product:ferritin heavy chain; full insert sequence |
| 250. | 1731 | 1751 | >gi|31543965|ref|NM_025830.3| Mus musculus WW domain containing E3 ubiquitin protein ligase 2 (Wwp2); mRNA |
| 251. | 3163 | 3195 | >gi|34328492|ref|NM_011638.3| Mus musculus transferrin receptor (Tfrc); mRNA |
| 252. | 3222 | 3254 | >gi|34328492|ref|NM_011638.3| Mus musculus transferrin receptor (Tfrc); mRNA |
| 253. | 3603 | 3631 | >gi|34328492|ref|NM_011638.3| Mus musculus transferrin receptor (Tfrc); mRNA |
| 254. | 3669 | 3695 | >gi|34328492|ref|NM_011638.3| Mus musculus transferrin receptor (Tfrc); mRNA |
| 255. | 3715 | 3743 | >gi|34328492|ref|NM_011638.3| Mus musculus transferrin receptor (Tfrc); mRNA |
| 256. | 2 | 24 | >gi|51858896|gb|BC081462.1| Mus musculus ferritin light chain 1; mRNA (cDNA clone MGC:102130 IMAGE:6823712); |
| 257. | 13 | 35 | >gi|53734661|gb|BC083350.1| Mus musculus ferritin light chain 1; mRNA (cDNA clone MGC:102131 IMAGE:6824407); |
| 258. | 15 | 37 | >gi|55154578|gb|BC085309.1| Mus musculus ferritin light chain 1; mRNA (cDNA clone MGC:103171 IMAGE:6489467); |

Figure 14M

| | start | end | origin |
|---|---|---|---|
| 259. | 4 | 26 | >gi\|62185706\|gb\|BC092259.1\| Mus musculus ferritin light chain 1; mRNA (cDNA clone MGC:103170 IMAGE:5125514); |
| 260. | 30 | 54 | >gi\|74024910\|ref\|NM_080633.2\| Mus musculus aconitase 2; mitochondrial (Aco2); nuclear gene encoding mitochondrial protein; mRNA |
| 261. | 33 | 55 | >gi\|74137852\|dbj\|AK139622.1\| Mus musculus 2 cells egg cDNA; RIKEN full-length enriched library; clone:B020006O06 product:ferritin heavy chain; full insert sequence |
| 262. | 33 | 55 | >gi\|74139311\|dbj\|AK169004.1\| Mus musculus 17 days pregnant adult female amnion cDNA; RIKEN full-length enriched library; clone:I920073F02 product:ferritin heavy chain; full insert sequence |
| 263. | 36 | 58 | >gi\|74139487\|dbj\|AK169100.1\| Mus musculus 17 days pregnant adult female amnion cDNA; RIKEN full-length enriched library; clone:I920080A13 product:ferritin light chain 1; full insert sequence |
| 264. | 37 | 59 | >gi\|74139601\|dbj\|AK169159.1\| Mus musculus 17 days pregnant adult female amnion cDNA; RIKEN full-length enriched library; clone:I920086H18 product:ferritin light chain 1; full insert sequence |
| 265. | 36 | 58 | >gi\|74139912\|dbj\|AK153195.1\| Mus musculus bone marrow macrophage cDNA; RIKEN full-length enriched library; clone:I830127C18 product:ferritin heavy chain; full insert sequence |
| 266. | 36 | 58 | >gi\|74139920\|dbj\|AK153199.1\| Mus musculus bone marrow macrophage cDNA; RIKEN full-length enriched library; clone:I830127D09 product:ferritin heavy chain; full insert sequence |
| 267. | 36 | 58 | >gi\|74151068\|dbj\|AK147082.1\| Mus musculus 17 days embryo heart cDNA; RIKEN full-length enriched library; clone:I920099K06 product:ferritin heavy chain; full insert sequence |
| 268. | 89 | 115 | >gi\|74151168\|dbj\|AK147137.1\| Mus musculus cDNA; RIKEN full-length enriched library; clone:I920184L03 product:solute carrier family 40 (iron-regulated transporter); member 1; full insert sequence |
| 269. | 33 | 55 | >gi\|74151861\|dbj\|AK150628.1\| Mus musculus bone marrow macrophage cDNA; RIKEN full-length enriched library; clone:I830012O08 product:ferritin heavy chain; full insert sequence |
| 270. | 36 | 58 | >gi\|74177921\|dbj\|AK150679.1\| Mus musculus bone marrow macrophage cDNA; RIKEN full-length enriched library; clone:I830013J05 product:ferritin heavy chain; full insert sequence |
| 271. | 33 | 55 | >gi\|74177953\|dbj\|AK150693.1\| Mus musculus bone marrow macrophage cDNA; RIKEN full-length enriched library; clone:I830013M05 product:ferritin heavy chain; full insert sequence |
| 272. | 33 | 55 | >gi\|74185436\|dbj\|AK151192.1\| Mus musculus bone marrow macrophage cDNA; RIKEN full-length enriched library; clone:I830026K07 product:ferritin heavy chain; full insert sequence |
| 273. | 36 | 58 | >gi\|74185529\|dbj\|AK151241.1\| Mus musculus bone marrow macrophage cDNA; RIKEN full-length enriched library; clone:I830027C06 product:ferritin heavy chain; full insert sequence |

Figure 14N

| | start | end | origin |
|---|---|---|---|
| 274. | 37 | 59 | >gi|74185554|dbj|AK151255.1| Mus musculus bone marrow macrophage cDNA; RIKEN full-length enriched library; clone:I830027E10 product:ferritin light chain 1; full insert sequence |
| 275. | 19 | 41 | >gi|74191587|dbj|AK151399.1| Mus musculus bone marrow macrophage cDNA; RIKEN full-length enriched library; clone:I830029C02 product:ferritin heavy chain; full insert sequence |
| 276. | 33 | 55 | >gi|74192829|dbj|AK159243.1| Mus musculus osteoclast-like cell cDNA; RIKEN full-length enriched library; clone:I420011I19 product:ferritin heavy chain; full insert sequence |
| 277. | 92 | 118 | >gi|74192924|dbj|AK159294.1| Mus musculus osteoclast-like cell cDNA; RIKEN full-length enriched library; clone:I420015B21 product:solute carrier family 40 (iron-regulated transporter); member 1; full insert sequence |
| 278. | 89 | 115 | >gi|74194988|dbj|AK144780.1| Mus musculus lung RCB-0558 LLC cDNA; RIKEN full-length enriched library; clone:G730032N16 product:solute carrier family 40 (iron-regulated transporter); member 1; full insert sequence |
| 279. | 34 | 56 | >gi|74195356|dbj|AK167410.1| Mus musculus 14 days embryo liver cDNA; RIKEN full-length enriched library; clone:I530012G11 product:ferritin light chain 1; full insert sequence |
| 280. | 33 | 55 | >gi|74195980|dbj|AK151609.1| Mus musculus bone marrow macrophage cDNA; RIKEN full-length enriched library; clone:I830032D05 product:ferritin heavy chain; full insert sequence |
| 281. | 37 | 59 | >gi|74198028|dbj|AK159574.1| Mus musculus osteoclast-like cell cDNA; RIKEN full-length enriched library; clone:I420024L05 product:ferritin light chain 1; full insert sequence |
| 282. | 92 | 118 | >gi|74198352|dbj|AK167608.1| Mus musculus 14 days embryo liver cDNA; RIKEN full-length enriched library; clone:I530025A06 product:solute carrier family 40 (iron-regulated transporter); member 1; full insert sequence |
| 283. | 33 | 55 | >gi|74198737|dbj|AK151675.1| Mus musculus bone marrow macrophage cDNA; RIKEN full-length enriched library; clone:I830033H17 product:ferritin heavy chain; full insert sequence |
| 284. | 89 | 115 | >gi|74204726|dbj|AK159855.1| Mus musculus osteoclast-like cell cDNA; RIKEN full-length enriched library; clone:I420034H23 product:solute carrier family 40 (iron-regulated transporter); member 1; full insert sequence |
| 285. | 36 | 58 | >gi|74207417|dbj|AK152030.1| Mus musculus bone marrow macrophage cDNA; RIKEN full-length enriched library; clone:I830045K08 product:ferritin light chain 1; full insert sequence |
| 286. | 36 | 58 | >gi|74208246|dbj|AK145265.1| Mus musculus mammary gland RCB-0527 Jyg-MC(B) cDNA; RIKEN full-length enriched library; clone:G930030L06 product:ferritin light chain 1; full insert sequence |

Figure 14O

| | start | end | origin |
|---|---|---|---|
| 287. | 36 | 58 | >gi|74212180|dbj|AK168310.1| Mus musculus CRL-1722 L5178Y-R cDNA; RIKEN full-length enriched library; clone:I730089E24 product:ferritin light chain 1; full insert sequence |
| 288. | 33 | 55 | >gi|74212345|dbj|AK152071.1| Mus musculus bone marrow macrophage cDNA; RIKEN full-length enriched library; clone:I830047B18 product:ferritin heavy chain; full insert sequence |
| 289. | 33 | 55 | >gi|74214002|dbj|AK150262.1| Mus musculus bone marrow macrophage cDNA; RIKEN full-length enriched library; clone:G530150D16 product:ferritin heavy chain; full insert sequence |
| 290. | 32 | 54 | >gi|74214666|dbj|AK152385.1| Mus musculus bone marrow macrophage cDNA; RIKEN full-length enriched library; clone:I830067K24 product:ferritin light chain 1; full insert sequence |
| 291. | 34 | 56 | >gi|74214682|dbj|AK152393.1| Mus musculus bone marrow macrophage cDNA; RIKEN full-length enriched library; clone:I830067O04 product:ferritin light chain 1; full insert sequence |
| 292. | 36 | 58 | >gi|74216902|dbj|AK145658.1| Mus musculus blastocyst blastocyst cDNA; RIKEN full-length enriched library; clone:I1C0026K01 product:ferritin light chain 1; full insert sequence |
| 293. | 36 | 58 | >gi|74219657|dbj|AK150480.1| Mus musculus bone marrow macrophage cDNA; RIKEN full-length enriched library; clone:I830008E24 product:ferritin light chain 1; full insert sequence |
| 294. | 32 | 54 | >gi|74219659|dbj|AK150481.1| Mus musculus bone marrow macrophage cDNA; RIKEN full-length enriched library; clone:I830008F04 product:ferritin light chain 1; full insert sequence |
| 295. | 33 | 55 | >gi|74219710|dbj|AK150508.1| Mus musculus bone marrow macrophage cDNA; RIKEN full-length enriched library; clone:I830008M07 product:ferritin heavy chain; full insert sequence |
| 296. | 33 | 55 | >gi|74219750|dbj|AK168601.1| Mus musculus 17 days embryo kidney cDNA; RIKEN full-length enriched library; clone:I920037M17 product:ferritin heavy chain; full insert sequence |
| 297. | 36 | 58 | >gi|74219992|dbj|AK168735.1| Mus musculus 17 days pregnant adult female amnion cDNA; RIKEN full-length enriched library; clone:I920048K01 product:ferritin light chain 1; full insert sequence |
| 298. | 36 | 58 | >gi|74220235|dbj|AK152542.1| Mus musculus bone marrow macrophage cDNA; RIKEN full-length enriched library; clone:I830078K18 product:ferritin heavy chain; full insert sequence |
| 299. | 36 | 58 | >gi|74220277|dbj|AK152564.1| Mus musculus bone marrow macrophage cDNA; RIKEN full-length enriched library; clone:I830079H19 product:ferritin light chain 1; full insert sequence |
| 300. | 661 | 683 | >gi|74220413|dbj|AK152702.1| Mus musculus bone marrow macrophage cDNA; RIKEN full-length enriched library; clone:I830082N06 product:ferritin heavy chain; full insert sequence |
| 301. | 36 | 58 | >gi|74220773|dbj|AK152612.1| Mus musculus bone marrow macrophage |

Figure 14P

| | start | end | origin |
|---|---|---|---|
| | | | cDNA; RIKEN full-length enriched library; clone:I830081C12 product:ferritin light chain 1; full insert sequence |
| 302. | 37 | 59 | >gi\|74223082\|dbj\|AK168862.1\| Mus musculus 17 days pregnant adult female amnion cDNA; RIKEN full-length enriched library; clone:I920061K21 product:ferritin light chain 1; full insert sequence |
| 303. | 36 | 58 | >gi\|74223090\|dbj\|AK168866.1\| Mus musculus 17 days embryo kidney cDNA; RIKEN full-length enriched library; clone:I920061M18 product:ferritin light chain 1; full insert sequence |
| 304. | 33 | 55 | >gi\|74225482\|dbj\|AK153017.1\| Mus musculus bone marrow macrophage cDNA; RIKEN full-length enriched library; clone:I830119B06 product:ferritin heavy chain; full insert sequence |
| 305. | 2 | 24 | >gi\|76779286\|gb\|BC106145.1\| Mus musculus ferritin light chain 1; mRNA (cDNA clone MGC:118079 IMAGE:5068947); |
| 306. | 15 | 37 | >gi\|76780238\|gb\|BC106146.1\| Mus musculus ferritin light chain 1; mRNA (cDNA clone MGC:118080 IMAGE:6476394); |
| 307. | 31 | 53 | >gi\|94401564\|ref\|XM_973894.1\| PREDICTED: Mus musculus similar to ferritin light chain 1; transcript variant 2 (LOC634386); mRNA |
| 308. | 43 | 65 | >gi\|94401566\|ref\|XM_909091.2\| PREDICTED: Mus musculus similar to ferritin light chain 1; transcript variant 1 (LOC634386); mRNA |
| 309. | 83 | 105 | >gi\|114326465\|ref\|NM_010240.2\| Mus musculus ferritin light chain 1 (Ftl1); mRNA |
| 310. | 635 | 657 | >gi\|121247409\|ref\|NM_025576.2\| Mus musculus protein tyrosine phosphatase; mitochondrial 1 (Ptpmt1); nuclear gene encoding mitochondrial protein; mRNA |
| 311. | 103 | 129 | >gi\|124248584\|ref\|NM_016917.2\| Mus musculus solute carrier family 40 (iron-regulated transporter); member 1 (Slc40a1); mRNA |
| 312. | 71 | 93 | >gi\|130485276\|ref\|NM_008049.2\| Mus musculus ferritin light chain 2 (Ftl2); mRNA |
| 313. | 51 | 71 | >gi\|149261588\|ref\|XM_486478.5\| PREDICTED: Mus musculus similar to ferritin light chain 2 (LOC434624); mRNA |
| 314. | 95 | 117 | >gi\|149264342\|ref\|XM_001478411.1\| PREDICTED: Mus musculus similar to ferritin light chain 1 (LOC634386); mRNA |
| 315. | 70 | 92 | >gi\|149264481\|ref\|XM_001471608.1\| PREDICTED: Mus musculus predicted gene; EG665937 (EG665937); mRNA |
| 316. | 24 | 46 | >gi\|204136\|gb\|M18812.1\|RATFERUTR Rat ferritin light subunit 5' untranslated region (UTR) |
| 317. | 2816 | 2848 | >gi\|207463\|gb\|M58040.1\|RATTRFR Rat transferrin receptor mRNA; 3' end |
| 318. | 2866 | 2898 | >gi\|207463\|gb\|M58040.1\|RATTRFR Rat transferrin receptor mRNA; 3' end |
| 319. | 3242 | 3272 | >gi\|207463\|gb\|M58040.1\|RATTRFR Rat transferrin receptor mRNA; 3' end |
| 320. | 3355 | 3383 | >gi\|207463\|gb\|M58040.1\|RATTRFR Rat transferrin receptor mRNA; 3' end |
| 321. | 3925 | 3947 | >gi\|6981287\|ref\|NM_013173.1\| Rattus norvegicus solute carrier family 11 (proton-coupled divalent metal ion transporters); member 2 (Slc11a2); mRNA |

Figure 14Q

| | start | end | origin |
|---|---|---|---|
| 322. | 19 | 41 | >gi|10441418|gb|AF186775.1|AF186775 Rattus norvegicus 5-aminolevulinate synthase (ALS2) mRNA; partial cds |
| 323. | 10 | 36 | >gi|18846873|gb|AF394785.3| Rattus norvegicus ferroportin 1 mRNA; |
| 324. | 36 | 58 | >gi|38014710|gb|BC060581.1| Rattus norvegicus ferritin heavy chain 1; mRNA (cDNA clone IMAGE:6922002); partial cds |
| 325. | 39 | 61 | >gi|38181802|gb|BC061525.1| Rattus norvegicus ferritin light chain 1; mRNA (cDNA clone MGC:72644 IMAGE:6921603); |
| 326. | 9 | 31 | >gi|50927648|gb|BC078892.1| Rattus norvegicus ferritin heavy chain 1; mRNA (cDNA clone IMAGE:7189574); partial cds |
| 327. | 16 | 38 | >gi|55778686|gb|BC086583.1| Rattus norvegicus ferritin light chain 1; mRNA (cDNA clone MGC:105275 IMAGE:7307718); |
| 328. | 16 | 38 | >gi|56788989|gb|BC088756.1| Rattus norvegicus ferritin light chain 1; mRNA (cDNA clone MGC:105276 IMAGE:7307747); |
| 329. | 23 | 45 | >gi|58477731|gb|BC089817.1| Rattus norvegicus ferritin heavy chain 1; mRNA (cDNA clone IMAGE:7124353); partial cds |
| 330. | 23 | 45 | >gi|66911978|gb|BC097341.1| Rattus norvegicus ferritin heavy chain 1; mRNA (cDNA clone IMAGE:7446591); partial cds |
| 331. | 17 | 39 | >gi|83404986|gb|BC111078.1| Rattus norvegicus ferritin heavy chain 1; mRNA (cDNA clone IMAGE:7387633); partial cds |
| 332. | 39 | 61 | >gi|84000578|ref|NM_022500.3| Rattus norvegicus ferritin; light polypeptide (Ftl); mRNA |
| 333. | 34 | 56 | >gi|109459039|ref|XM_001056161.1| PREDICTED: Rattus norvegicus similar to Ferritin light chain 2 (Ferritin L subunit 2) (Ferritin subunit LG) (LOC680217); mRNA |
| 334. | 40 | 62 | >gi|109459270|ref|XM_574537.2| PREDICTED: Rattus norvegicus similar to ferritin light chain (predicted) (RGD1566189_predicted); mRNA |
| 335. | 34 | 56 | >gi|109462410|ref|XM_001061623.1| PREDICTED: Rattus norvegicus similar to Ferritin light chain 2 (Ferritin L subunit 2) (Ferritin subunit LG) (LOC682465); mRNA |
| 336. | 40 | 62 | >gi|109462698|ref|XM_001077872.1| PREDICTED: Rattus norvegicus similar to ferritin light chain (predicted) (RGD1566189_predicted); mRNA |
| 337. | 42 | 64 | >gi|109511223|ref|XM_577041.2| PREDICTED: Rattus norvegicus similar to Ferritin light chain 2 (Ferritin L subunit 2) (Ferritin subunit LG) (predicted) (RGD1561055_predicted); mRNA |
| 338. | 42 | 64 | >gi|109512652|ref|XM_001070733.1| PREDICTED: Rattus norvegicus similar to Ferritin light chain 2 (Ferritin L subunit 2) (Ferritin subunit LG) (predicted) (RGD1561055_predicted); mRNA |
| 339. | 2 | 24 | >gi|117558588|gb|BC127507.1| Rattus norvegicus ferritin heavy chain 1; mRNA (cDNA clone IMAGE:7445527); partial cds |
| 340. | 65 | 91 | >gi|158635997|ref|NM_133315.2| Rattus norvegicus solute carrier family 39 (iron-regulated transporter); member 1 (Slc40a1); mRNA |
| 341. | 9 | 31 | >gi|16416388|dbj|AB073371.1| Cavia porcellus mRNA for ferritin heavy chain; |

Figure 14R

| | start | end | origin |
|---|---|---|---|
| 342. | 44 | 66 | >gi|67043813|gb|AY998625.1| Pelodiscus sinensis ferritin heavy chain mRNA; partial cds |
| 343. | 60 | 84 | >gi|157361558|gb|EU045340.1| Phlebotomus papatasi ferritin heavy chain-like protein (FHC) mRNA; |
| 344. | 10 | 32 | >gi|32479248|gb|AY321299.1| Crassostrea gigas ferritin GF1 (GF1) mRNA; |
| 345. | 3 | 27 | >gi|32479250|gb|AY321300.1| Crassostrea gigas ferritin GF2 (GF2) mRNA; |
| 346. | 31 | 53 | >gi|89515093|gb|DQ437112.1| Bufo gargarizans ferritin H mRNA; |
| 347. | 20 | 40 | >gi|33772678|gb|AY277901.1| Amblyomma maculatum ferritin (Fer) mRNA; |
| 348. | 2 | 26 | >gi|3192912|gb|AF068224.1| Ixodes ricinus ferritin (Fer) mRNA; |
| 349. | 19 | 39 | >gi|38489894|gb|AY456681.1| Dermacentor andersoni ferritin heavy chain-like protein mRNA; |
| 350. | 20 | 40 | >gi|33772684|gb|AY277904.1| Dermacentor variabilis ferritin (Fer) mRNA; |
| 351. | 19 | 39 | >gi|38155603|gb|AF467696.2| Dermacentor variabilis ferritin mRNA; |
| 352. | 20 | 40 | >gi|33772690|gb|AY277907.1| Rhipicephalus sanguineus ferritin (Fer) mRNA; |
| 353. | 19 | 41 | >gi|150036369|emb|AM419433.1| Chionodraco rastrospinosus mRNA for ferritin heavy chain (ftH gene) |
| 354. | 164 | 190 | >gi|83944689|gb|DQ294233.1| Glossina morsitans morsitans TC38 ferritin heavy chain-like mRNA; |
| 355. | 20 | 40 | >gi|33772686|gb|AY277905.1| Haemaphysalis longicornis ferritin (Fer) mRNA; |
| 356. | 843 | 863 | >gi|198465487|ref|XM_001353615.2| Drosophila pseudoobscura pseudoobscura GA17248 (Dpse\GA17248); mRNA |
| 357. | 8 | 34 | >gi|33333948|gb|AF547223.1| Pinctada fucata ferritin-like protein mRNA; |
| 358. | 20 | 40 | >gi|33772682|gb|AY277903.1| Dermacentor albipictus ferritin (Fer) mRNA; |
| 359. | 100 | 126 | >gi|124245060|gb|EF032586.1| Pieris rapae ferritin LCH mRNA; |
| 360. | 96 | 126 | >gi|5738075|gb|AF161707.1|AF161707 Calpodes ethlius fat body secreted ferritin S subunit precursor (FER) mRNA; |
| 361. | 96 | 126 | >gi|5738077|gb|AF161708.1|AF161708 Calpodes ethlius midgut secreted ferritin S subunit precursor (FER) mRNA; |
| 362. | 103 | 129 | >gi|5738079|gb|AF161709.1|AF161709 Calpodes ethlius fat body secreted ferritin G subunit precursor (FER2) mRNA; |
| 363. | 103 | 129 | >gi|5738081|gb|AF161710.1|AF161710 Calpodes ethlius midgut secreted ferritin G subunit precursor (FER2) mRNA; |
| 364. | 50 | 72 | >gi|157284013|gb|EF628371.1| Pimephales promelas ferritin heavy chain mRNA; |
| 365. | 34 | 58 | >gi|110734441|gb|DQ821494.1| Haliotis discus discus ferritin subunit 2 mRNA; |
| 366. | 5 | 27 | >gi|197725772|gb|EU714166.1| Epinephelus coioides ferritin heavy subunit mRNA; |

Figure 14S

| | start | end | origin |
|---|---|---|---|
| 367. | 136 | 162 | >gi|6688880|emb|AJ251148.1| Nilaparvata lugens mRNA for ferritin subunit (non-glycosylated); (fersub1 gene) |
| 368. | 38 | 60 | >gi|67772035|gb|AY909464.1| Siniperca chuatsi clone C132 ferritin middle subunit mRNA; partial cds |
| 369. | 3 | 35 | >gi|157704372|gb|EU144232.1| Bombus ignitus ferritin mRNA; |
| 370. | 36 | 58 | >gi|37779021|gb|AY190695.1| Pagrus major ferritin heavy chain mRNA; partial cds |
| 371. | 37 | 59 | >gi|115344219|gb|DQ915952.1| Epinephelus awoara ferritin heavy subunit mRNA; |
| 372. | 4 | 24 | >gi|27728699|gb|AY175376.1| Branchiostoma belcheri tsingtaunese ferritin mRNA; |
| 373. | 19 | 39 | >gi|33520123|gb|AY277909.1| Branchiostoma belcheri tsingtaunese ferritin mRNA; |
| 374. | 37 | 59 | >gi|162949441|gb|EU302524.1| Oncorhynchus masou formosanus ferritin-H subunit (ftH) mRNA; |
| 375. | 141 | 165 | >gi|158290946|ref|XM_312474.4| Anopheles gambiae str. PEST AGAP002465-PA (AgaP_AGAP002465) mRNA; |
| 376. | 52 | 74 | >gi|23956478|gb|AY120878.1| Araneus ventricosus ferritin mRNA; |
| 377. | 3 | 27 | >gi|37683082|gb|AY422797.1| Rhipicephalus haemaphysaloides haemaphysaloides ferritin mRNA; |
| 378. | 5 | 29 | >gi|45479210|gb|AY550979.1| Hyalomma asiaticum asiaticum ferritin mRNA; |
| 379. | 16 | 40 | >gi|71044432|gb|DQ069277.1| Meretrix meretrix ferritin subunit mRNA; |
| 380. | 1428 | 1448 | >gi|118352980|ref|XM_001009761.1| Tetrahymena thermophila SB210 cyclic nucleotide-binding domain containing protein (TTHERM_00158330) partial mRNA |
| 381. | 3146 | 3168 | >gi|118361198|ref|XM_001013830.1| Tetrahymena thermophila SB210 cation channel family protein (TTHERM_00427510) partial mRNA |

Figure 15A

|     | start | end  | origin |
| --- | ----- | ---- | ------ |
| 1.  | 10    | 39   | >gi\|83595142\|gb\|DQ286043.1\| Hydra vulgaris ferritin mRNA |
| 2.  | 18    | 47   | >gi\|9649\|emb\|X56778.1\| L.stagnalis L. mRNA for som fer gene |
| 3.  | 55    | 90   | >gi\|118428733\|gb\|DQ983429.1\| Daphnia pulex clone Contig_138 ferritin 3-like protein mRNA |
| 4.  | 6     | 41   | >gi\|118428740\|gb\|DQ983433.1\| Daphnia pulex clone 1798340:4 ferritin 3-like protein C mRNA |
| 5.  | 6     | 39   | >gi\|118428742\|gb\|DQ983434.1\| Daphnia pulex clone 1801185:6 ferritin 3-like protein mRNA |
| 6.  | 1     | 36   | >gi\|29140534\|gb\|AF068225.2\| Ornithodoros moubata ferritin (Fer) mRNA |
| 7.  | 1     | 28   | >gi\|32187063\|gb\|AY307447.1\| Boophilus microplus ferritin mRNA |
| 8.  | 12    | 47   | >gi\|33772688\|gb\|AY277906.1\| Ixodes scapularis ferritin (Fer) mRNA |
| 9.  | 409   | 436  | >gi\|115764817\|ref\|XM_001197262.1\| PREDICTED: Strongylocentrotus purpuratus similar to ENSANGP00000009272 (LOC757031); mRNA |
| 10. | 3422  | 3449 | >gi\|115966283\|ref\|XM_001198093.1\| PREDICTED: Strongylocentrotus purpuratus similar to ENSANGP00000009272 (LOC578213); mRNA |
| 11. | 142   | 169  | >gi\|115968537\|ref\|XM_001184706.1\| PREDICTED: Strongylocentrotus purpuratus similar to ferritin (LOC587996); mRNA |
| 12. | 70    | 99   | >gi\|198436810\|ref\|XM_002126984.1\| PREDICTED: Ciona intestinalis similar to Sdhb-prov protein (LOC100181830); mRNA |
| 13. | 1     | 36   | >gi\|219498211\|ref\|XM_002245612.1\| Branchiostoma floridae hypothetical protein (BRAFLDRAFT_272879) mRNA |
| 14. | 1     | 30   | >gi\|26324279\|gb\|AY157150.1\| Branchiostoma belcheri ferritin mRNA |
| 15. | 9     | 32   | >gi\|11545422\|gb\|AF295373.1\|AF295373 Danio rerio ferritin heavy chain (fth1) mRNA |
| 16. | 9     | 32   | >gi\|18858718\|ref\|NM_131585.1\| Danio rerio ferritin; heavy polypeptide 1 (fth1); mRNA |
| 17. | 42    | 65   | >gi\|28278804\|gb\|BC045278.1\| Danio rerio ferritin; heavy polypeptide 1; mRNA (cDNA clone MGC:55220 IMAGE:3815619) |
| 18. | 13    | 48   | >gi\|49902698\|gb\|BC075879.1\| Danio rerio zgc:92066; mRNA (cDNA clone MGC:92066 IMAGE:7046348) |
| 19. | 13    | 48   | >gi\|50539815\|ref\|NM_001002378.1\| Danio rerio zgc:92066 (zgc:92066); mRNA |
| 20. | 26    | 61   | >gi\|63102343\|gb\|BC095061.1\| Danio rerio zgc:109934; mRNA (cDNA clone MGC:109934 IMAGE:7252599) |
| 21. | 26    | 61   | >gi\|66472683\|ref\|NM_001020531.1\| Danio rerio zgc:109934 (zgc:109934); mRNA |
| 22. | 22    | 57   | >gi\|156914785\|gb\|BC152596.1\| Danio rerio zgc:173594; mRNA (cDNA clone MGC:173594 IMAGE:8151242); |
| 23. | 22    | 57   | >gi\|157954495\|ref\|NM_001109854.1\| Danio rerio zgc:173594 (zgc:173594); mRNA |
| 24. | 22    | 57   | >gi\|158253855\|gb\|BC154146.1\| Danio rerio zgc:109934; mRNA (cDNA clone MGC:173595 IMAGE:8154848) |
| 25. | 26    | 61   | >gi\|159155701\|gb\|BC154746.1\| Danio rerio wu:fj24c01; mRNA (cDNA clone MGC:173592 IMAGE:7407378) |
| 26. | 26    | 61   | >gi\|165972410\|ref\|NM_001113659.1\| Danio rerio wu:fj24c01 (wu:fj24c01); mRNA |

Figure 15B

| | start | end | origin |
|---|---|---|---|
| 27. | 10 | 45 | >gi|189517135|ref|XM_001921696.1| PREDICTED: Danio rerio similar to Ferritin heavy chain (Ferritin H subunit) (Cell proliferation-inducing gene 15 protein) (LOC100006428); mRNA |
| 28. | 5 | 40 | >gi|190338087|gb|BC162709.1| Danio rerio zgc:194125; mRNA (cDNA clone MGC:194125 IMAGE:9038211) |
| 29. | 5 | 40 | >gi|190339495|gb|BC162683.1| Danio rerio zgc:194125; mRNA (cDNA clone MGC:194099 IMAGE:9038213) |
| 30. | 5 | 40 | >gi|194578824|ref|NM_001130667.1| Danio rerio zgc:194125 (zgc:194125); mRNA |
| 31. | 19 | 42 | >gi|68161034|gb|DQ086166.1| Ictalurus punctatus ferritin heavy subunit mRNA |
| 32. | 11 | 40 | >gi|68161040|gb|DQ086169.1| Ictalurus punctatus ferritin H-3 mRNA partial cds |
| 33. | 14 | 37 | >gi|12802902|gb|AF338763.1|AF338763 Oncorhynchus nerka ferritin-H subunit mRNA |
| 34. | 27 | 58 | >gi|999126|gb|S77386.1| ferritin middle subunit [Salmo salar=Atlantic salmon; liver; mRNA 1010 nt] |
| 35. | 27 | 58 | >gi|185132427|ref|NM_001123658.1| Salmo salar ferritin middle subunit (LOC100136565); mRNA |
| 36. | 11 | 34 | >gi|197632418|gb|BT043818.1| Salmo salar clone HM4_1383 ferritin; heavy polypeptide 1-1 mRNA |
| 37. | 4 | 27 | >gi|197632420|gb|BT043819.1| Salmo salar clone HM5_2952 ferritin; heavy polypeptide 1-2 mRNA |
| 38. | 11 | 42 | >gi|209154679|gb|BT045310.1| Salmo salar clone ssal-rgf-518-052 Ferritin; middle subunit putative mRNA |
| 39. | 9 | 32 | >gi|209154795|gb|BT045368.1| Salmo salar clone ssal-rgf-519-193 Ferritin; heavy subunit putative mRNA |
| 40. | 36 | 67 | >gi|209730473|gb|BT046305.1| Salmo salar clone ssal-eve-567-231 Ferritin; middle subunit putative mRNA |
| 41. | 14 | 45 | >gi|209730753|gb|BT046445.1| Salmo salar clone ssal-eve-573-257 Ferritin; middle subunit putative mRNA |
| 42. | 12 | 43 | >gi|209731389|gb|BT046763.1| Salmo salar clone ssal-rgb2-565-077 Ferritin; middle subunit putative mRNA |
| 43. | 11 | 42 | >gi|209731495|gb|BT046816.1| Salmo salar clone ssal-rgb2-570-157 Ferritin; middle subunit putative mRNA |
| 44. | 37 | 68 | >gi|209731581|gb|BT046859.1| Salmo salar clone ssal-eve-544-067 Ferritin; middle subunit putative mRNA |
| 45. | 15 | 46 | >gi|209732295|gb|BT047216.1| Salmo salar clone ssal-rgb2-567-134 Ferritin; middle subunit putative mRNA |
| 46. | 7 | 40 | >gi|209733107|gb|BT047622.1| Salmo salar clone ssal-plnb-510-341 Ferritin; middle subunit putative mRNA |
| 47. | 29 | 60 | >gi|209733689|gb|BT047913.1| Salmo salar clone ssal-eve-006-108 Ferritin; middle subunit putative mRNA |
| 48. | 4 | 35 | >gi|209733751|gb|BT047944.1| Salmo salar clone ssal-plnb-512-029 Ferritin; middle subunit putative mRNA |
| 49. | 39 | 62 | >gi|209734161|gb|BT048149.1| Salmo salar clone ssal-cvf-549-063 Ferritin; heavy subunit putative mRNA |

Figure 15C

| | start | end | origin |
|---|---|---|---|
| 50. | 10 | 33 | >gi\|209734739\|gb\|BT048438.1\| Salmo salar clone ssal-rgb2-580-054 Ferritin; heavy subunit putative mRNA |
| 51. | 55 | 86 | >gi\|209735029\|gb\|BT048583.1\| Salmo salar clone ssal-evd-531-097 Ferritin; middle subunit putative mRNA |
| 52. | 106 | 137 | >gi\|209735539\|gb\|BT048838.1\| Salmo salar clone ssal-evd-563-175 Ferritin; middle subunit putative mRNA |
| 53. | 11 | 42 | >gi\|209735939\|gb\|BT049038.1\| Salmo salar clone ssal-rgb2-509-101 Ferritin; middle subunit putative mRNA |
| 54. | 18 | 43 | >gi\|209736165\|gb\|BT049151.1\| Salmo salar clone ssal-evd-504-104 Ferritin; middle subunit putative mRNA |
| 55. | 11 | 42 | >gi\|209736347\|gb\|BT049242.1\| Salmo salar clone ssal-plnb-014-075 Ferritin; middle subunit putative mRNA |
| 56. | 10 | 41 | >gi\|209736357\|gb\|BT049247.1\| Salmo salar clone ssal-cvf-520-218 Ferritin; middle subunit putative mRNA |
| 57. | 12 | 43 | >gi\|209737099\|gb\|BT049618.1\| Salmo salar clone ssal-rgb2-507-351 Ferritin; middle subunit putative mRNA |
| 58. | 11 | 42 | >gi\|209737211\|gb\|BT049674.1\| Salmo salar clone ssal-evd-520-065 Ferritin; middle subunit putative mRNA |
| 59. | 29 | 60 | >gi\|209737541\|gb\|BT049839.1\| Salmo salar clone ssal-evd-520-176 Ferritin; middle subunit putative mRNA |
| 60. | 9 | 40 | >gi\|209737929\|gb\|BT050033.1\| Salmo salar clone ssal-rgb2-616-306 Ferritin; middle subunit putative mRNA |
| 61. | 11 | 34 | >gi\|213513867\|ref\|NM_001139722.1\| Salmo salar ferritin; heavy polypeptide 1-1 (LOC100194637); mRNA |
| 62. | 1778 | 1803 | >gi\|11877337\|emb\|AJ300650.1\| Melanogrammus aeglefinus partial mRNA for Transferrin (tf gene) |
| 63. | 5 | 28 | >gi\|30349211\|gb\|AY260753.1\| Oreochromis mossambicus ferritin heavy subunit mRNA partial cds |
| 64. | 26 | 61 | >gi\|62079569\|gb\|AY737021.1\| Oreochromis mossambicus clone Contig24 ferritin middle subunit mRNA partial cds |
| 65. | 11 | 46 | >gi\|10121670\|gb\|AF266195.1\|AF266195 Gillichthys mirabilis ferritin middle subunit mRNA |
| 66. | 167 | 196 | >gi\|64690\|emb\|X51395.1\| Xenopus laevis mRNA for ferritin |
| 67. | 7 | 36 | >gi\|214135\|gb\|M55010.1\|XELFERHSU Xenopus laevis ferritin H subunit mRNA |
| 68. | 502 | 531 | >gi\|238858\|gb\|S64727.1\| ferritin [Xenopus laevis; XL2 cells; mRNA 1388 nt] |
| 69. | 26 | 57 | >gi\|27882414\|gb\|BC044685.1\| Xenopus laevis Ferritin heavy chain; oocyte isoform; mRNA (cDNA clone MGC:53349 IMAGE:5571031); |
| 70. | 14 | 43 | >gi\|27924171\|gb\|BC044961.1\| Xenopus laevis ferritin heavy chain; mRNA (cDNA clone MGC:52598 IMAGE:5543148); |
| 71. | 7 | 38 | >gi\|28302245\|gb\|BC046680.1\| Xenopus laevis hypothetical protein MGC53066; mRNA (cDNA clone MGC:53066 IMAGE:5541973); |
| 72. | 24 | 55 | >gi\|33331484\|gb\|AF538970.1\| Xenopus laevis ferritin heavy chain mRNA |
| 73. | 12 | 43 | >gi\|33331486\|gb\|AF538971.1\| Xenopus laevis ferritin light chain mRNA |

Figure 15D

| | start | end | origin |
|---|---|---|---|
| 74. | 702 | 733 | >gi|34784901|gb|BC056858.1| Xenopus laevis Ferritin heavy chain; oocyte isoform; mRNA (cDNA clone MGC:64558 IMAGE:6880106); |
| 75. | 16 | 47 | >gi|34785676|gb|BC057216.1| Xenopus laevis Ferritin light chain; oocyte isoform; mRNA (cDNA clone MGC:68606 IMAGE:4031959); |
| 76. | 14 | 43 | >gi|38014726|gb|BC060381.1| Xenopus laevis ferritin; heavy polypeptide 1; mRNA (cDNA clone MGC:68515 IMAGE:4030710); |
| 77. | 4 | 33 | >gi|118835678|gb|BC128943.1| Xenopus laevis hypothetical protein LOC100036818; mRNA (cDNA clone MGC:160341 IMAGE:8539473); |
| 78. | 4 | 33 | >gi|147898654|ref|NM_001097109.1| Xenopus laevis hypothetical protein LOC100036818 (LOC100036818); mRNA |
| 79. | 14 | 43 | >gi|148224145|ref|NM_001096738.1| Xenopus laevis ferritin; heavy polypeptide 1 (fth1); mRNA |
| 80. | 502 | 531 | >gi|148226275|ref|NM_001090588.1| Xenopus laevis ferritin protein (ferritin); mRNA |
| 81. | 7 | 38 | >gi|148232660|ref|NM_001086183.1| Xenopus laevis hypothetical protein MGC53066 (MGC53066); mRNA |
| 82. | 14 | 43 | >gi|148234982|ref|NM_001086111.1| Xenopus laevis ferritin heavy chain (MGC52598); mRNA |
| 83. | 16 | 47 | >gi|148236188|ref|NM_001086458.1| Xenopus laevis Ferritin light chain; oocyte isoform (MGC68606); mRNA |
| 84. | 702 | 733 | >gi|148236234|ref|NM_001089603.1| Xenopus laevis Ferritin heavy chain; oocyte isoform (MGC64558); mRNA |
| 85. | 29 | 60 | >gi|38648960|gb|BC063337.1| Xenopus tropicalis hypothetical protein MGC75752; mRNA (cDNA clone MGC:75752 IMAGE:5381534); |
| 86. | 29 | 60 | >gi|45361268|ref|NM_203881.1| Xenopus (Silurana) tropicalis hypothetical protein MGC75752 (MGC75752); mRNA |
| 87. | 4 | 33 | >gi|49898968|gb|BC076689.1| Xenopus tropicalis MGC79725 protein; mRNA (cDNA clone MGC:79725 IMAGE:6982176); |
| 88. | 42 | 73 | >gi|50416661|gb|BC077674.1| Xenopus tropicalis MGC89846 protein; mRNA (cDNA clone MGC:89846 IMAGE:7028826); |
| 89. | 4 | 33 | >gi|52345939|ref|NM_001005018.1| Xenopus (Silurana) tropicalis MGC79725 protein (MGC79725); mRNA |
| 90. | 42 | 73 | >gi|52346185|ref|NM_001005135.1| Xenopus (Silurana) tropicalis MGC89846 protein (MGC89846); mRNA |
| 91. | 8 | 39 | >gi|77626900|emb|CR760872.2| Xenopus tropicalis finished cDNA; clone TTpA007g24 |
| 92. | 22 | 57 | >gi|170285169|gb|BC160952.1| Xenopus tropicalis hypothetical protein LOC100145388; mRNA (cDNA clone MGC:180954 IMAGE:8856335); |
| 93. | 22 | 57 | >gi|187607887|ref|NM_001126853.1| Xenopus (Silurana) tropicalis hypothetical protein LOC100145388 (LOC100145388); mRNA |
| 94. | 22 | 57 | >gi|189441768|gb|BC167527.1| Xenopus tropicalis hypothetical protein LOC100170515; mRNA (cDNA clone MGC:180940 IMAGE:8854073); |
| 95. | 22 | 57 | >gi|194332553|ref|NM_001130294.1| Xenopus (Silurana) tropicalis hypothetical protein LOC100170515 (LOC100170515); mRNA |

Figure 15E

| | start | end | origin |
|---|---|---|---|
| 96. | 24 | 53 | >gi|213672|gb|M15655.1|RANFERH Frog (Rana catesbeiana) apoferritin higher subunit; mRNA |
| 97. | 24 | 53 | >gi|213691|gb|M12120.1|RANRCFA Bull frog (R.catesbeiana) tadpole red cell ferritin mRNA |
| 98. | 47 | 82 | >gi|149463000|ref|XM_001513998.1| PREDICTED: Ornithorhynchus anatinus similar to iron storage protein H-ferritin (LOC100090297); mRNA |
| 99. | 42 | 67 | >gi|90075727|dbj|AB170481.1| Macaca fascicularis brain cDNA clone: QmoA-11095; similar to human ferritin; light polypeptide (FTL); mRNA RefSeq: NM_000146.2 |
| 100. | 31 | 58 | >gi|90075885|dbj|AB170560.1| Macaca fascicularis brain cDNA clone: QmoA-11465; similar to human ferritin; heavy polypeptide 1 (FTH1); mRNA RefSeq: NM_002032.1 |
| 101. | 29 | 56 | >gi|109085790|ref|XM_001104405.1| PREDICTED: Macaca mulatta similar to Ferritin heavy chain (Ferritin H subunit) (Proliferation-inducing gene 15 protein) (FTH1); mRNA |
| 102. | 30 | 57 | >gi|109095940|ref|XM_001099912.1| PREDICTED: Macaca mulatta similar to Ferritin heavy chain (Ferritin H subunit) (Proliferation-inducing gene 15 protein) (FTH1); mRNA |
| 103. | 54 | 79 | >gi|109133920|ref|XM_001119579.1| PREDICTED: Macaca mulatta similar to Ferritin light chain (Ferritin L subunit) (FTL); partial mRNA |
| 104. | 145 | 172 | >gi|114637917|ref|XM_001140124.1| PREDICTED: Pan troglodytes similar to Ferritin heavy chain (Ferritin H subunit) (Proliferation-inducing gene 15 protein) (LOC738986); mRNA |
| 105. | 8 | 35 | >gi|114639491|ref|XM_001175066.1| PREDICTED: Pan troglodytes ferritin; heavy polypeptide 1 (FTH1); mRNA |
| 106. | 191 | 218 | >gi|114649148|ref|XM_509574.2| PREDICTED: Pan troglodytes similar to FTH1 protein (LOC452477); mRNA |
| 107. | 129 | 154 | >gi|114678175|ref|XM_001155938.1| PREDICTED: Pan troglodytes hypothetical protein LOC747113 (LOC747113); mRNA |
| 108. | 87 | 112 | >gi|114681008|ref|XM_514491.2| PREDICTED: Pan troglodytes hypothetical LOC458071 (LOC458071); mRNA |
| 109. | 30 | 57 | >gi|55730381|emb|CR859755.1| Pongo abelii mRNA cDNA DKFZp469N1034 (from clone DKFZp469N1034) |
| 110. | 28 | 53 | >gi|55732870|emb|CR861037.1| Pongo abelii mRNA cDNA DKFZp470G1212 (from clone DKFZp470G1212) |
| 111. | 30 | 57 | >gi|197099311|ref|NM_001132636.1| Pongo abelii ferritin; heavy polypeptide 1 (FTH1); mRNA |
| 112. | 28 | 53 | >gi|197101170|ref|NM_001133378.1| Pongo abelii ferritin; light polypeptide (FTL); mRNA |
| 113. | 31 | 58 | >gi|507251|gb|L20941.1|HUMFERRITH Human ferritin heavy chain mRNA |
| 114. | 6 | 31 | >gi|2230868|emb|Y09188.1| H.sapiens mRNA for ferritin L-chain |
| 115. | 18 | 45 | >gi|12654092|gb|BC000857.1| Homo sapiens ferritin; heavy polypeptide 1; mRNA (cDNA clone MGC:5580 IMAGE:3459353); |
| 116. | 17 | 42 | >gi|13279004|gb|BC004245.1| Homo sapiens ferritin; light polypeptide; mRNA (cDNA clone MGC:10465 IMAGE:3615360); |

Figure 15F

| | start | end | origin |
|---|---|---|---|
| 117. | 28 | 53 | >gi|14250068|gb|BC008439.1| Homo sapiens ferritin; light polypeptide; mRNA (cDNA clone MGC:14642 IMAGE:4093482); |
| 118. | 32 | 57 | >gi|15530276|gb|BC013928.1| Homo sapiens ferritin; light polypeptide; mRNA (cDNA clone MGC:24228 IMAGE:3839120); |
| 119. | 34 | 61 | >gi|16359090|gb|BC016009.1| Homo sapiens ferritin; heavy polypeptide 1; mRNA (cDNA clone MGC:27328 IMAGE:4666545); |
| 120. | 1278 | 1305 | >gi|16549428|dbj|AK054816.1| Homo sapiens cDNA FLJ30254 fis; clone BRACE2002441; highly similar to Ferritin heavy chain (EC 1.16.3.1) |
| 121. | 32 | 57 | >gi|16740988|gb|BC016346.1| Homo sapiens ferritin; light polypeptide; mRNA (cDNA clone MGC:24392 IMAGE:4066010); |
| 122. | 32 | 57 | >gi|16741008|gb|BC016354.1| Homo sapiens ferritin; light polypeptide; mRNA (cDNA clone MGC:24480 IMAGE:4092360); |
| 123. | 32 | 57 | >gi|16876868|gb|BC016715.1| Homo sapiens ferritin; light polypeptide; mRNA (cDNA clone MGC:24401 IMAGE:4067055); |
| 124. | 31 | 56 | >gi|18203881|gb|BC021670.1| Homo sapiens ferritin; light polypeptide; mRNA (cDNA clone MGC:22710 IMAGE:4051089); |
| 125. | 12 | 39 | >gi|21104437|dbj|AB062402.1| Homo sapiens OK/SW-cl.84 mRNA for ferritin-heavy polypeptide 1; |
| 126. | 32 | 57 | >gi|28894134|gb|AY207005.1| Homo sapiens ferritin-like protein mRNA |
| 127. | 27 | 52 | >gi|33096740|emb|BX571748.1| Homo sapiens mRNA cDNA DKFZp686L19147 (from clone DKFZp686L19147); |
| 128. | 1 | 24 | >gi|33873848|gb|BC018990.2| Homo sapiens ferritin; light polypeptide; mRNA (cDNA clone MGC:20176 IMAGE:3503710); |
| 129. | 9 | 36 | >gi|34189606|gb|BC011359.2| Homo sapiens ferritin; heavy polypeptide 1; mRNA (cDNA clone MGC:18238 IMAGE:4157296); |
| 130. | 12 | 39 | >gi|34190319|gb|BC013724.2| Homo sapiens ferritin; heavy polypeptide 1; mRNA (cDNA clone MGC:17255 IMAGE:3857790); |
| 131. | 32 | 57 | >gi|37573984|gb|BC058820.1| Homo sapiens ferritin; light polypeptide; mRNA (cDNA clone MGC:61835 IMAGE:4049525); |
| 132. | 31 | 56 | >gi|38541892|gb|BC062708.1| Homo sapiens ferritin; light polypeptide; mRNA (cDNA clone MGC:71996 IMAGE:4774403); |
| 133. | 1 | 28 | >gi|39645111|gb|BC063514.1| Homo sapiens ferritin; heavy polypeptide 1; mRNA (cDNA clone MGC:70834 IMAGE:3882345); |
| 134. | 30 | 57 | >gi|42490865|gb|BC066341.1| Homo sapiens ferritin; heavy polypeptide 1; mRNA (cDNA clone MGC:87457 IMAGE:5288688); |
| 135. | 32 | 59 | >gi|44890439|gb|BC066961.1| Homo sapiens ferritin; heavy polypeptide 1; mRNA (cDNA clone MGC:87456 IMAGE:4796312); |
| 136. | 10 | 37 | >gi|47125325|gb|BC070494.1| Homo sapiens ferritin; heavy polypeptide 1; mRNA (cDNA clone IMAGE:6009374); partial cds |
| 137. | 16 | 43 | >gi|49256418|gb|BC073750.1| Homo sapiens ferritin; heavy polypeptide 1; mRNA (cDNA clone MGC:88754 IMAGE:6256153); |
| 138. | 59 | 86 | >gi|56682958|ref|NM_002032.2| Homo sapiens ferritin; heavy polypeptide 1 (FTH1); mRNA |

Figure 15G

| | start | end | origin |
|---|---|---|---|
| 139. | 28 | 53 | >gi|56682960|ref|NM_000146.3| Homo sapiens ferritin; light polypeptide (FTL); mRNA |
| 140. | 1458 | 1481 | >gi|62088291|dbj|AB209356.1| Homo sapiens mRNA for fatty acid desaturase 3 variant protein |
| 141. | 34 | 61 | >gi|74356467|gb|BC104643.1| Homo sapiens ferritin; heavy polypeptide 1; mRNA (cDNA clone MGC:104426 IMAGE:4043391); |
| 142. | 34 | 61 | >gi|76779198|gb|BC105802.1| Homo sapiens ferritin; heavy polypeptide 1; mRNA (cDNA clone IMAGE:4717046); partial cds |
| 143. | 6891 | 6914 | >gi|113204433|ref|NM_003607.3| Homo sapiens CDC42 binding protein kinase alpha (DMPK-like) (CDC42BPA); transcript variant B; mRNA |
| 144. | 6648 | 6671 | >gi|113204434|ref|NM_014826.4| Homo sapiens CDC42 binding protein kinase alpha (DMPK-like) (CDC42BPA); transcript variant A; mRNA |
| 145. | 28 | 53 | >gi|164697506|dbj|AK311773.1| Homo sapiens cDNA; FLJ92034; highly similar to Homo sapiens ferritin; light polypeptide (FTL); mRNA |
| 146. | 104 | 129 | >gi|169160875|ref|XM_001722297.1| PREDICTED: Homo sapiens similar to hCG1648021 (LOC642337); mRNA |
| 147. | 3 | 32 | >gi|15076950|gb|AF285177.1|AF285177 Canis familiaris ferritin mRNA |
| 148. | 3 | 32 | >gi|50978755|ref|NM_001003080.1| Canis lupus familiaris ferritin; heavy polypeptide 1 (FTH1); mRNA |
| 149. | 21 | 46 | >gi|73970829|ref|XM_845705.1| PREDICTED: Canis familiaris similar to ferritin light chain 1 (LOC608625); mRNA |
| 150. | 316 | 341 | >gi|73977528|ref|XM_847150.1| PREDICTED: Canis familiaris similar to Ferritin light chain 1 (Ferritin L subunit 1) (LOC609811); mRNA |
| 151. | 15 | 40 | >gi|73998112|ref|XM_534978.2| PREDICTED: Canis familiaris similar to ferritin light chain 1 (LOC477783); mRNA |
| 152. | 14 | 39 | >gi|21435815|gb|AY112742.1| Equus caballus ferritin heavy chain mRNA |
| 153. | 14 | 39 | >gi|154350229|ref|NM_001100413.1| Equus caballus ferritin heavy chain (FT); mRNA |
| 154. | 30 | 57 | >gi|194224682|ref|XM_001495020.2| PREDICTED: Equus caballus similar to ferritin heavy chain (LOC100062546); mRNA |
| 155. | 1 | 26 | >gi|194227936|ref|XM_001914641.1| PREDICTED: Equus caballus hypothetical protein LOC100146482 (LOC100146482); mRNA |
| 156. | 14 | 41 | >gi|286151|dbj|D15071.1|PIGFE Sus scrofa mRNA for ferritin heavy-chain; |
| 157. | 14 | 41 | >gi|47522775|ref|NM_213975.1| Sus scrofa ferritin; heavy polypeptide 1 (FTH1); mRNA |
| 158. | 16 | 43 | >gi|28189736|dbj|AB098993.1| Bos taurus mRNA for similar to ferritin H subunit; partial cds; clone: ORCS11746 |
| 159. | 29 | 54 | >gi|28189936|dbj|AB099093.1| Bos taurus mRNA for similar to ferritin L subunit; partial cds; clone: ORCS13934 |
| 160. | 20 | 45 | >gi|42564198|gb|AY528246.1| Bos taurus ferritin light polypeptide (FTL) mRNA |
| 161. | 20 | 45 | >gi|54262148|ref|NM_174792.3| Bos taurus ferritin; light polypeptide (FTL); mRNA |
| 162. | 33 | 56 | >gi|57864498|dbj|AB099065.2| Bos taurus mRNA for similar to ferritin H subunit; partial cds; clone: ORCS13217 |

Figure 15H

| | start | end | origin |
|---|---|---|---|
| 163. | 28 | 55 | >gi|58760373|gb|AY911329.1| Bos taurus clone IMAGE:7961468 ferritin heavy polypeptide 1 mRNA |
| 164. | 33 | 58 | >gi|73586641|gb|BC103021.1| Bos taurus ferritin; light polypeptide; mRNA (cDNA clone MGC:128093 IMAGE:7954568); |
| 165. | 29 | 56 | >gi|86827677|gb|BC105376.1| Bos taurus ferritin; heavy polypeptide 1; mRNA (cDNA clone MGC:128102 IMAGE:7942224); |
| 166. | 29 | 56 | >gi|88319924|ref|NM_174062.3| Bos taurus ferritin; heavy polypeptide 1 (FTH1); mRNA |
| 167. | 1051 | 1074 | >gi|126010816|gb|BC133520.1| Bos taurus fatty acid desaturase domain family; member 6; mRNA (cDNA clone MGC:151555 IMAGE:8281070); |
| 168. | 1051 | 1074 | >gi|126165302|ref|NM_001081722.1| Bos taurus fatty acid desaturase domain family; member 6 (FADS6); mRNA |
| 169. | 29 | 56 | >gi|154426177|gb|BC151549.1| Bos taurus ferritin; heavy polypeptide 1; mRNA (cDNA clone MGC:179308 IMAGE:7342905); |
| 170. | 46 | 71 | >gi|194663447|ref|XM_001251063.2| PREDICTED: Bos taurus similar to ferritin L subunit (LOC782921); mRNA |
| 171. | 39 | 66 | >gi|194667562|ref|XM_591595.4| PREDICTED: Bos taurus similar to Ferritin; heavy polypeptide 1; transcript variant 1 (LOC513842); mRNA |
| 172. | 36 | 61 | >gi|194668159|ref|XM_001251437.2| PREDICTED: Bos taurus similar to ferritin L subunit (LOC784025); mRNA |
| 173. | 36 | 63 | >gi|194673278|ref|XM_001250935.2| PREDICTED: Bos taurus similar to Ferritin; heavy polypeptide 1 (LOC782705); mRNA |
| 174. | 46 | 71 | >gi|194677015|ref|XM_001251302.2| PREDICTED: Bos taurus similar to ferritin L subunit (LOC783220); mRNA |
| 175. | 31 | 56 | >gi|194677850|ref|XM_001254819.2| PREDICTED: Bos taurus similar to ferritin L subunit (LOC788801); mRNA |
| 176. | 38 | 63 | >gi|194678436|ref|XM_001250276.2| PREDICTED: Bos taurus similar to ferritin L subunit (LOC785297); mRNA |
| 177. | 33 | 58 | >gi|1560|emb|X14578.1| Rabbit mRNA for ferritin light chain subunit 5'end |
| 178. | 8 | 35 | >gi|191071|gb|M99692.1|CRUFERR Hamster iron binding protein (ferretin) mRNA |
| 179. | 1 | 24 | >gi|193268|gb|J04716.1|MUSFERLA Mouse ferritin light chain; |
| 180. | 30 | 57 | >gi|6753911|ref|NM_010239.1| Mus musculus ferritin heavy chain 1 (Fth1); mRNA |
| 181. | 35 | 60 | >gi|12832084|dbj|AK002242.1| Mus musculus adult male kidney cDNA; RIKEN full-length enriched library; clone:0610006G13 product:ferritin light chain 1; full insert sequence |
| 182. | 33 | 58 | >gi|12832103|dbj|AK002253.1| Mus musculus adult male kidney cDNA; RIKEN full-length enriched library; clone:0610006K08 product:ferritin light chain 1; full insert sequence |
| 183. | 33 | 58 | >gi|12832607|dbj|AK002547.1| Mus musculus adult male kidney cDNA; RIKEN full-length enriched library; clone:0610011I07 product:ferritin light chain 1; full insert sequence |
| 184. | 34 | 59 | >gi|12846842|dbj|AK011009.1| Mus musculus 13 days embryo liver cDNA; RIKEN full-length enriched library; clone:2510027K02 product:ferritin light chain 1; full insert sequence |

Figure 15I

| | start | end | origin |
|---|---|---|---|
| 185. | 33 | 58 | >gi|12846879|dbj|AK011029.1| Mus musculus 13 days embryo liver cDNA; RIKEN full-length enriched library; clone:2510030C10 product:ferritin light chain 1; full insert sequence |
| 186. | 35 | 60 | >gi|12847239|dbj|AK011244.1| Mus musculus 10 days embryo whole body cDNA; RIKEN full-length enriched library; clone:2600017I12 product:ferritin light chain 1; full insert sequence |
| 187. | 8 | 35 | >gi|15126787|gb|BC012314.1| Mus musculus ferritin heavy chain 1; mRNA (cDNA clone MGC:19422 IMAGE:3488821); |
| 188. | 13 | 38 | >gi|18044715|gb|BC019840.1| Mus musculus ferritin light chain 1; mRNA (cDNA clone MGC:29974 IMAGE:5123770); |
| 189. | 39 | 64 | >gi|26353689|dbj|AK088647.1| Mus musculus 2 days neonate thymus thymic cells cDNA; RIKEN full-length enriched library; clone:E430022I20 product:ferritin light chain 1; full insert sequence |
| 190. | 30 | 57 | >gi|26389189|dbj|AK027998.1| Mus musculus 18-day embryo whole body cDNA; RIKEN full-length enriched library; clone:1110070P14 product:ferritin heavy chain; full insert sequence |
| 191. | 1 | 24 | >gi|51858896|gb|BC081462.1| Mus musculus ferritin light chain 1; mRNA (cDNA clone MGC:102130 IMAGE:6823712); |
| 192. | 11 | 36 | >gi|53734661|gb|BC083350.1| Mus musculus ferritin light chain 1; mRNA (cDNA clone MGC:102131 IMAGE:6824407); |
| 193. | 13 | 38 | >gi|55154578|gb|BC085309.1| Mus musculus ferritin light chain 1; mRNA (cDNA clone MGC:103171 IMAGE:6489467); |
| 194. | 2 | 27 | >gi|62185706|gb|BC092259.1| Mus musculus ferritin light chain 1; mRNA (cDNA clone MGC:103170 IMAGE:5125514); |
| 195. | 30 | 57 | >gi|74137852|dbj|AK139622.1| Mus musculus 2 cells egg cDNA; RIKEN full-length enriched library; clone:B020006O06 product:ferritin heavy chain; full insert sequence |
| 196. | 30 | 57 | >gi|74139311|dbj|AK169004.1| Mus musculus 17 days pregnant adult female amnion cDNA; RIKEN full-length enriched library; clone:I920073F02 product:ferritin heavy chain; full insert sequence |
| 197. | 34 | 59 | >gi|74139487|dbj|AK169100.1| Mus musculus 17 days pregnant adult female amnion cDNA; RIKEN full-length enriched library; clone:I920080A13 product:ferritin light chain 1; full insert sequence |
| 198. | 35 | 60 | >gi|74139601|dbj|AK169159.1| Mus musculus 17 days pregnant adult female amnion cDNA; RIKEN full-length enriched library; clone:I920086H18 product:ferritin light chain 1; full insert sequence |
| 199. | 33 | 60 | >gi|74139912|dbj|AK153195.1| Mus musculus bone marrow macrophage cDNA; RIKEN full-length enriched library; clone:I830127C18 product:ferritin heavy chain; full insert sequence |
| 200. | 33 | 60 | >gi|74139920|dbj|AK153199.1| Mus musculus bone marrow macrophage cDNA; RIKEN full-length enriched library; clone:I830127D09 product:ferritin heavy chain; full insert sequence |
| 201. | 33 | 60 | >gi|74151068|dbj|AK147082.1| Mus musculus 17 days embryo heart cDNA; RIKEN full-length enriched library; clone:I920099K06 product:ferritin heavy chain; full insert sequence |

Figure 15J

| | start | end | origin |
|---|---|---|---|
| 202. | 30 | 57 | >gi|74151861|dbj|AK150628.1| Mus musculus bone marrow macrophage cDNA; RIKEN full-length enriched library; clone:I830012O08 product:ferritin heavy chain; full insert sequence |
| 203. | 33 | 60 | >gi|74177921|dbj|AK150679.1| Mus musculus bone marrow macrophage cDNA; RIKEN full-length enriched library; clone:I830013J05 product:ferritin heavy chain; full insert sequence |
| 204. | 30 | 57 | >gi|74177953|dbj|AK150693.1| Mus musculus bone marrow macrophage cDNA; RIKEN full-length enriched library; clone:I830013M05 product:ferritin heavy chain; full insert sequence |
| 205. | 30 | 57 | >gi|74185436|dbj|AK151192.1| Mus musculus bone marrow macrophage cDNA; RIKEN full-length enriched library; clone:I830026K07 product:ferritin heavy chain; full insert sequence |
| 206. | 33 | 60 | >gi|74185529|dbj|AK151241.1| Mus musculus bone marrow macrophage cDNA; RIKEN full-length enriched library; clone:I830027C06 product:ferritin heavy chain; full insert sequence |
| 207. | 35 | 60 | >gi|74185554|dbj|AK151255.1| Mus musculus bone marrow macrophage cDNA; RIKEN full-length enriched library; clone:I830027E10 product:ferritin light chain 1; full insert sequence |
| 208. | 16 | 43 | >gi|74191587|dbj|AK151399.1| Mus musculus bone marrow macrophage cDNA; RIKEN full-length enriched library; clone:I830029C02 product:ferritin heavy chain; full insert sequence |
| 209. | 30 | 57 | >gi|74192829|dbj|AK159243.1| Mus musculus osteoclast-like cell cDNA; RIKEN full-length enriched library; clone:I420011I19 product:ferritin heavy chain; full insert sequence |
| 210. | 32 | 57 | >gi|74195356|dbj|AK167410.1| Mus musculus 14 days embryo liver cDNA; RIKEN full-length enriched library; clone:I530012G11 product:ferritin light chain 1; full insert sequence |
| 211. | 30 | 57 | >gi|74195980|dbj|AK151609.1| Mus musculus bone marrow macrophage cDNA; RIKEN full-length enriched library; clone:I830032D05 product:ferritin heavy chain; full insert sequence |
| 212. | 30 | 57 | >gi|74198737|dbj|AK151675.1| Mus musculus bone marrow macrophage cDNA; RIKEN full-length enriched library; clone:I830033H17 product:ferritin heavy chain; full insert sequence |
| 213. | 34 | 59 | >gi|74207417|dbj|AK152030.1| Mus musculus bone marrow macrophage cDNA; RIKEN full-length enriched library; clone:I830045K08 product:ferritin light chain 1; full insert sequence |
| 214. | 34 | 59 | >gi|74208246|dbj|AK145265.1| Mus musculus mammary gland RCB-0527 Jyg-MC(B) cDNA; RIKEN full-length enriched library; clone:G930030L06 product:ferritin light chain 1; full insert sequence |
| 215. | 34 | 59 | >gi|74212180|dbj|AK168310.1| Mus musculus CRL-1722 L5178Y-R cDNA; RIKEN full-length enriched library; clone:I730089E24 product:ferritin light chain 1; full insert sequence |

Figure 15K

| | start | end | origin |
|---|---|---|---|
| 216. | 30 | 57 | >gi\|74212345\|dbj\|AK152071.1\| Mus musculus bone marrow macrophage cDNA; RIKEN full-length enriched library; clone:I830047B18 product:ferritin heavy chain; full insert sequence |
| 217. | 30 | 57 | >gi\|74214002\|dbj\|AK150262.1\| Mus musculus bone marrow macrophage cDNA; RIKEN full-length enriched library; clone:G530150D16 product:ferritin heavy chain; full insert sequence |
| 218. | 30 | 55 | >gi\|74214666\|dbj\|AK152385.1\| Mus musculus bone marrow macrophage cDNA; RIKEN full-length enriched library; clone:I830067K24 product:ferritin light chain 1; full insert sequence |
| 219. | 32 | 57 | >gi\|74214682\|dbj\|AK152393.1\| Mus musculus bone marrow macrophage cDNA; RIKEN full-length enriched library; clone:I830067O04 product:ferritin light chain 1; full insert sequence |
| 220. | 34 | 59 | >gi\|74216902\|dbj\|AK145658.1\| Mus musculus blastocyst blastocyst cDNA; RIKEN full-length enriched library; clone:I1C0026K01 product:ferritin light chain 1; full insert sequence |
| 221. | 34 | 59 | >gi\|74219657\|dbj\|AK150480.1\| Mus musculus bone marrow macrophage cDNA; RIKEN full-length enriched library; clone:I830008E24 product:ferritin light chain 1; full insert sequence |
| 222. | 30 | 55 | >gi\|74219659\|dbj\|AK150481.1\| Mus musculus bone marrow macrophage cDNA; RIKEN full-length enriched library; clone:I830008F04 product:ferritin light chain 1; full insert sequence |
| 223. | 30 | 57 | >gi\|74219710\|dbj\|AK150508.1\| Mus musculus bone marrow macrophage cDNA; RIKEN full-length enriched library; clone:I830008M07 product:ferritin heavy chain; full insert sequence |
| 224. | 30 | 57 | >gi\|74219750\|dbj\|AK168601.1\| Mus musculus 17 days embryo kidney cDNA; RIKEN full-length enriched library; clone:I920037M17 product:ferritin heavy chain; full insert sequence |
| 225. | 34 | 59 | >gi\|74219992\|dbj\|AK168735.1\| Mus musculus 17 days pregnant adult female amnion cDNA; RIKEN full-length enriched library; clone:I920048K01 product:ferritin light chain 1; full insert sequence |
| 226. | 33 | 60 | >gi\|74220235\|dbj\|AK152542.1\| Mus musculus bone marrow macrophage cDNA; RIKEN full-length enriched library; clone:I830078K18 product:ferritin heavy chain; full insert sequence |
| 227. | 34 | 59 | >gi\|74220277\|dbj\|AK152564.1\| Mus musculus bone marrow macrophage cDNA; RIKEN full-length enriched library; clone:I830079H19 product:ferritin light chain 1; full insert sequence |
| 228. | 658 | 685 | >gi\|74220413\|dbj\|AK152702.1\| Mus musculus bone marrow macrophage cDNA; RIKEN full-length enriched library; clone:I830082N06 product:ferritin heavy chain; full insert sequence |
| 229. | 34 | 59 | >gi\|74220773\|dbj\|AK152612.1\| Mus musculus bone marrow macrophage cDNA; RIKEN full-length enriched library; clone:I830081C12 product:ferritin light chain 1; full insert sequence |

Figure 15L

| | start | end | origin |
|---|---|---|---|
| 230. | 35 | 60 | >gi|74223082|dbj|AK168862.1| Mus musculus 17 days pregnant adult female amnion cDNA; RIKEN full-length enriched library; clone:I920061K21 product:ferritin light chain 1; full insert sequence |
| 231. | 34 | 59 | >gi|74223090|dbj|AK168866.1| Mus musculus 17 days embryo kidney cDNA; RIKEN full-length enriched library; clone:I920061M18 product:ferritin light chain 1; full insert sequence |
| 232. | 30 | 57 | >gi|74225482|dbj|AK153017.1| Mus musculus bone marrow macrophage cDNA; RIKEN full-length enriched library; clone:I830119B06 product:ferritin heavy chain; full insert sequence |
| 233. | 1 | 24 | >gi|76779286|gb|BC106145.1| Mus musculus ferritin light chain 1; mRNA (cDNA clone MGC:118079 IMAGE:5068947); |
| 234. | 13 | 38 | >gi|76780238|gb|BC106146.1| Mus musculus ferritin light chain 1; mRNA (cDNA clone MGC:118080 IMAGE:6476394); |
| 235. | 29 | 54 | >gi|94401564|ref|XM_973894.1| PREDICTED: Mus musculus similar to ferritin light chain 1; transcript variant 2 (LOC634386); mRNA |
| 236. | 41 | 66 | >gi|94401566|ref|XM_909091.2| PREDICTED: Mus musculus similar to ferritin light chain 1; transcript variant 1 (LOC634386); mRNA |
| 237. | 3823 | 3846 | >gi|110815852|ref|NM_001042611.1| Mus musculus ceruloplasmin (Cp); transcript variant 1; mRNA |
| 238. | 81 | 106 | >gi|114326465|ref|NM_010240.2| Mus musculus ferritin light chain 1 (Ftl1); mRNA |
| 239. | 69 | 94 | >gi|130485276|ref|NM_008049.2| Mus musculus ferritin light chain 2 (Ftl2); mRNA |
| 240. | 93 | 118 | >gi|149264342|ref|XM_001478411.1| PREDICTED: Mus musculus similar to ferritin light chain 1 (LOC634386); mRNA |
| 241. | 68 | 93 | >gi|149264481|ref|XM_001471608.1| PREDICTED: Mus musculus predicted gene; EG665937 (EG665937); mRNA |
| 242. | 22 | 47 | >gi|204136|gb|M18812.1|RATFERUTR Rat ferritin light subunit 5' untranslated region (UTR) |
| 243. | 33 | 60 | >gi|38014710|gb|BC060581.1| Rattus norvegicus ferritin heavy chain 1; mRNA (cDNA clone IMAGE:6922002); partial cds |
| 244. | 37 | 62 | >gi|38181802|gb|BC061525.1| Rattus norvegicus ferritin light chain 1; mRNA (cDNA clone MGC:72644 IMAGE:6921603); |
| 245. | 6 | 33 | >gi|50927648|gb|BC078892.1| Rattus norvegicus ferritin heavy chain 1; mRNA (cDNA clone IMAGE:7189574); partial cds |
| 246. | 14 | 39 | >gi|55778686|gb|BC086583.1| Rattus norvegicus ferritin light chain 1; mRNA (cDNA clone MGC:105275 IMAGE:7307718); |
| 247. | 14 | 39 | >gi|56788989|gb|BC088756.1| Rattus norvegicus ferritin light chain 1; mRNA (cDNA clone MGC:105276 IMAGE:7307747); |
| 248. | 20 | 47 | >gi|58477731|gb|BC089817.1| Rattus norvegicus ferritin heavy chain 1; mRNA (cDNA clone IMAGE:7124353); partial cds |
| 249. | 20 | 47 | >gi|66911978|gb|BC097341.1| Rattus norvegicus ferritin heavy chain 1; mRNA (cDNA clone IMAGE:7446591); partial cds |
| 250. | 14 | 41 | >gi|83404986|gb|BC111078.1| Rattus norvegicus ferritin heavy chain 1; mRNA (cDNA clone IMAGE:7387633); partial cds |

Figure 15M

| | start | end | origin |
|---|---|---|---|
| 251. | 37 | 62 | >gi|84000578|ref|NM_022500.3| Rattus norvegicus ferritin; light polypeptide (Ftl); mRNA |
| 252. | 32 | 57 | >gi|109459039|ref|XM_001056161.1| PREDICTED: Rattus norvegicus similar to Ferritin light chain 2 (Ferritin L subunit 2) (Ferritin subunit LG) (LOC680217); mRNA |
| 253. | 38 | 63 | >gi|109459270|ref|XM_574537.2| PREDICTED: Rattus norvegicus similar to ferritin light chain (predicted) (RGD1566189_predicted); mRNA |
| 254. | 32 | 57 | >gi|109462410|ref|XM_001061623.1| PREDICTED: Rattus norvegicus similar to Ferritin light chain 2 (Ferritin L subunit 2) (Ferritin subunit LG) (LOC682465); mRNA |
| 255. | 38 | 63 | >gi|109462698|ref|XM_001077872.1| PREDICTED: Rattus norvegicus similar to ferritin light chain (predicted) (RGD1566189_predicted); mRNA |
| 256. | 35 | 60 | >gi|109480319|ref|XM_576192.2| PREDICTED: Rattus norvegicus similar to Ferritin light chain (Ferritin L subunit) (predicted) (RGD1560687_predicted); mRNA |
| 257. | 35 | 60 | >gi|109481675|ref|XM_001078366.1| PREDICTED: Rattus norvegicus similar to Ferritin light chain (Ferritin L subunit) (predicted) (RGD1560687_predicted); mRNA |
| 258. | 40 | 65 | >gi|109511223|ref|XM_577041.2| PREDICTED: Rattus norvegicus similar to Ferritin light chain 2 (Ferritin L subunit 2) (Ferritin subunit LG) (predicted) (RGD1561055_predicted); mRNA |
| 259. | 40 | 65 | >gi|109512652|ref|XM_001070733.1| PREDICTED: Rattus norvegicus similar to Ferritin light chain 2 (Ferritin L subunit 2) (Ferritin subunit LG) (predicted) (RGD1561055_predicted); mRNA |
| 260. | 1 | 24 | >gi|117558588|gb|BC127507.1| Rattus norvegicus ferritin heavy chain 1; mRNA (cDNA clone IMAGE:7445527); partial cds |
| 261. | 6 | 33 | >gi|16416388|dbj|AB073371.1| Cavia porcellus mRNA for ferritin heavy chain; |
| 262. | 39 | 70 | >gi|67043813|gb|AY998625.1| Pelodiscus sinensis ferritin heavy chain mRNA partial cds |
| 263. | 5 | 36 | >gi|32479248|gb|AY321299.1| Crassostrea gigas ferritin GF1 (GF1) mRNA |
| 264. | 1 | 28 | >gi|32479250|gb|AY321300.1| Crassostrea gigas ferritin GF2 (GF2) mRNA |
| 265. | 27 | 56 | >gi|89515093|gb|DQ437112.1| Bufo gargarizans ferritin H mRNA |
| 266. | 9 | 42 | >gi|152143914|gb|EU010238.1| Holothuria glaberrima ferritin mRNA |
| 267. | 1 | 26 | >gi|3192912|gb|AF068224.1| Ixodes ricinus ferritin (Fer) mRNA |
| 268. | 18 | 41 | >gi|150036369|emb|AM419433.1| Chionodraco rastrospinosus mRNA for ferritin heavy chain (ftH gene) |
| 269. | 7 | 38 | >gi|156380912|ref|XM_001631961.1| Nematostella vectensis predicted protein (NEMVEDRAFT_v1g235103) partial mRNA |
| 270. | 9 | 32 | >gi|33333948|gb|AF547223.1| Pinctada fucata ferritin-like protein mRNA |
| 271. | 48 | 73 | >gi|157284013|gb|EF628371.1| Pimephales promelas ferritin heavy chain mRNA |
| 272. | 29 | 62 | >gi|110734441|gb|DQ821494.1| Haliotis discus discus ferritin subunit 2 mRNA |
| 273. | 4 | 27 | >gi|197725772|gb|EU714166.1| Epinephelus coioides ferritin heavy subunit mRNA |
| 274. | 31 | 66 | >gi|67772035|gb|AY909464.1| Siniperca chuatsi clone C132 ferritin middle subunit mRNA partial cds |
| 275. | 35 | 58 | >gi|37779021|gb|AY190695.1| Pagrus major ferritin heavy chain mRNA partial cds |
| 276. | 36 | 59 | >gi|115344219|gb|DQ915952.1| Epinephelus awoara ferritin heavy subunit mRNA |

Figure 15N

| | start | end | origin |
|---|---|---|---|
| 277. | 2 | 25 | >gi|27728699|gb|AY175376.1| Branchiostoma belcheri tsingtaunese ferritin mRNA |
| 278. | 11 | 46 | >gi|33520123|gb|AY277909.1| Branchiostoma belcheri tsingtaunese ferritin mRNA |
| 279. | 36 | 59 | >gi|162949441|gb|EU302524.1| Oncorhynchus masou formosanus ferritin-H subunit (ftH) mRNA |
| 280. | 1 | 28 | >gi|37683082|gb|AY422797.1| Rhipicephalus haemaphysaloides haemaphysaloides ferritin mRNA |
| 281. | 3 | 30 | >gi|45479210|gb|AY550979.1| Hyalomma asiaticum asiaticum ferritin mRNA |
| 282. | 461 | 484 | >gi|50420262|ref|XM_458664.1| Debaryomyces hansenii CBS767 hypothetical protein (DEHA0D05269g) partial mRNA |
| 283. | 11 | 44 | >gi|71044432|gb|DQ069277.1| Meretrix meretrix ferritin subunit mRNA |
| 284. | 32 | 67 | >gi|68303300|gb|DQ058411.1| Apostichopus japonicus ferritin mRNA |
| 285. | 3145 | 3168 | >gi|118361198|ref|XM_001013830.1| Tetrahymena thermophila SB210 cation channel family protein (TTHERM_00427510) partial mRNA |
| 286. | 280 | 309 | >gi|145490324|ref|XM_001431126.1| Paramecium tetraurelia hypothetical protein (GSPATT00033618001) partial mRNA |
| 287. | 280 | 309 | >gi|145510776|ref|XM_001441281.1| Paramecium tetraurelia hypothetical protein (GSPATT00038939001) partial mRNA |
| 288. | 1086 | 1109 | >gi|212538210|ref|XM_002149225.1| Penicillium marneffei ATCC 18224 FAD binding domain protein; mRNA |

Figure 16

| | start | end | origin |
|---|---|---|---|
| 1. | 1859 | 1888 | >gi|221139765|ref|NM_000617.2| Homo sapiens solute carrier family 11 (proton-coupled divalent metal ion transporters), member 2 (SLC11A2), mRNA |
| 2. | 1784 | 1815 | >gi|2921273|gb|AF029758.1|AF029758 Mus musculus natural resistance associated macrophage protein-2 (Nramp2) mRNA, C-terminal exon alternative splice variant |
| 3. | 1825 | 1856 | >gi|6981287|ref|NM_013173.1| Rattus norvegicus solute carrier family 11 (proton-coupled divalent metal ion transporters), member 2 (Slc11a2), mRNA |

Figure 17
A.
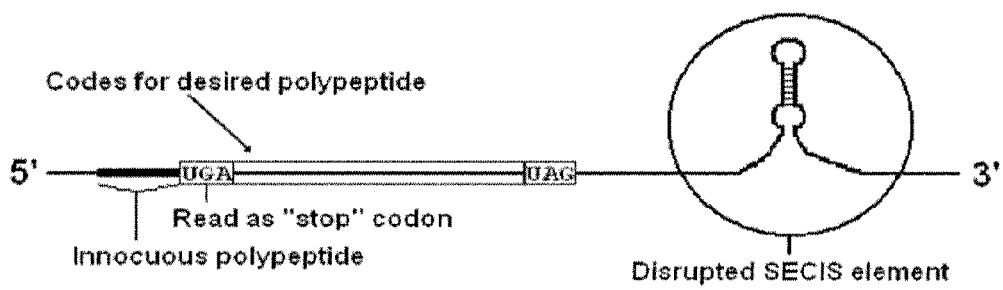
B.
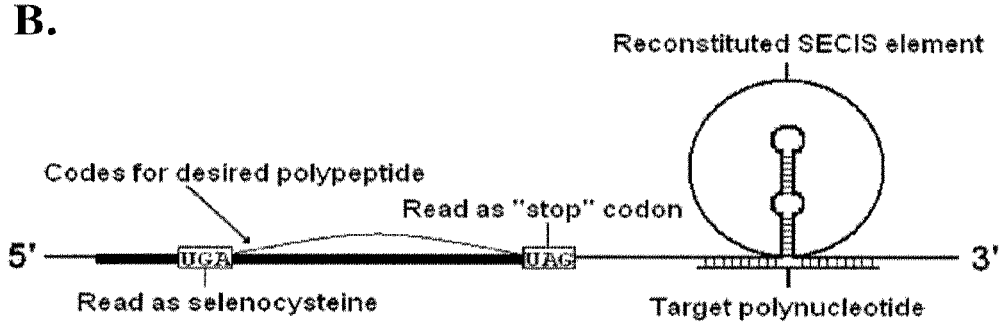

Figure 18A

| | start | end | origin |
|---|---|---|---|
| 1. | 600 | 663 | >gi|198427211|ref|XM_002128679.1| PREDICTED: Ciona intestinalis similar to selenoprotein K (LOC100184686); mRNA |
| 2. | 1576 | 1643 | >gi|12408008|gb|AF322071.1|AF322071 Danio rerio selenoprotein Pa mRNA |
| 3. | 2048 | 2124 | >gi|12408008|gb|AF322071.1|AF322071 Danio rerio selenoprotein Pa mRNA |
| 4. | 667 | 736 | >gi|29165357|gb|AY221264.1| Danio rerio selenoprotein T1a mRNA |
| 5. | 659 | 728 | >gi|32451894|gb|BC054578.1| Danio rerio selenoprotein T; 1a; mRNA (cDNA clone MGC:63945 IMAGE:6791276) |
| 6. | 1534 | 1613 | >gi|37596695|gb|BC059656.1| Danio rerio selenoprotein P; plasma; 1a; mRNA (cDNA clone MGC:73338 IMAGE:4790285) |
| 7. | 2002 | 2078 | >gi|37596695|gb|BC059656.1| Danio rerio selenoprotein P; plasma; 1a; mRNA (cDNA clone MGC:73338 IMAGE:4790285) |
| 8. | 1532 | 1599 | >gi|39645918|gb|BC063960.1| Danio rerio selenoprotein P; plasma; 1a; mRNA (cDNA clone MGC:77663 IMAGE:6997155) |
| 9. | 2003 | 2079 | >gi|39645918|gb|BC063960.1| Danio rerio selenoprotein P; plasma; 1a; mRNA (cDNA clone MGC:77663 IMAGE:6997155) |
| 10. | 751 | 818 | >gi|45501113|gb|BC067158.1| Danio rerio selenoprotein P; plasma; 1a; mRNA (cDNA clone IMAGE:6525439) |
| 11. | 1222 | 1298 | >gi|45501113|gb|BC067158.1| Danio rerio selenoprotein P; plasma; 1a; mRNA (cDNA clone IMAGE:6525439) |
| 12. | 685 | 747 | >gi|53734005|gb|BC083376.1| Danio rerio selenoprotein M; mRNA (cDNA clone MGC:103431 IMAGE:7233960) |
| 13. | 784 | 852 | >gi|63101287|gb|BC095658.1| Danio rerio selenoprotein T; 2; mRNA (cDNA clone IMAGE:7409402) |
| 14. | 713 | 775 | >gi|157388998|ref|NM_178286.3| Danio rerio selenoprotein M (sepm); mRNA |
| 15. | 1595 | 1662 | >gi|157389011|ref|NM_178297.3| Danio rerio selenoprotein P; plasma; 1a (sepp1a); mRNA |
| 16. | 2066 | 2142 | >gi|157389011|ref|NM_178297.3| Danio rerio selenoprotein P; plasma; 1a (sepp1a); mRNA |
| 17. | 1564 | 1631 | >gi|161612236|gb|BC155821.1| Danio rerio selenoprotein P; plasma; 1a; mRNA (cDNA clone MGC:175059 IMAGE:7071048) |
| 18. | 2034 | 2110 | >gi|161612236|gb|BC155821.1| Danio rerio selenoprotein P; plasma; 1a; mRNA (cDNA clone MGC:175059 IMAGE:7071048) |
| 19. | 1564 | 1631 | >gi|166796356|gb|BC159240.1| Danio rerio selenoprotein P; plasma; 1a; mRNA (cDNA clone MGC:175065 IMAGE:9001368) |
| 20. | 2034 | 2110 | >gi|166796356|gb|BC159240.1| Danio rerio selenoprotein P; plasma; 1a; mRNA (cDNA clone MGC:175065 IMAGE:9001368) |
| 21. | 685 | 754 | >gi|167900445|ref|NM_178290.5| Danio rerio selenoprotein T; 1a (selt1a); mRNA |
| 22. | 819 | 887 | >gi|168480082|ref|NM_001098487.2| Danio rerio selenoprotein T; 2 (selt2); mRNA |
| 23. | 835 | 899 | >gi|169403975|ref|NM_001007281.2| Danio rerio glutathione peroxidase 1a (gpx1a); mRNA |
| 24. | 830 | 891 | >gi|198285586|gb|BT044016.1| Salmo salar clone HM5_0578 selenoprotein T-like mRNA |

Figure 18B

| | start | end | origin |
|---|---|---|---|
| 25. | 830 | 891 | >gi|213512656|ref|NM_001139761.1| Salmo salar selenoprotein T-like (LOC100194716); mRNA |
| 26. | 1692 | 1765 | >gi|224587811|gb|BT072678.1| Salmo salar clone ssal-rgf-536-075 Selenoprotein Pa precursor putative mRNA; pseudogene cds |
| 27. | 1016 | 1071 | >gi|28144871|gb|AY184803.1| Fundulus heteroclitus deiodinase type I (D1) mRNA |
| 28. | 663 | 727 | >gi|27696399|gb|BC043894.1| Xenopus laevis similar to selenoprotein T; mRNA (cDNA clone MGC:53828 IMAGE:5542417) |
| 29. | 673 | 762 | >gi|27924200|gb|BC044996.1| Xenopus laevis similar to selenoprotein T; mRNA (cDNA clone MGC:53056 IMAGE:5541863) |
| 30. | 1148 | 1206 | >gi|147899785|ref|NM_001092248.1| Xenopus laevis selenoprotein M (selm); mRNA |
| 31. | 663 | 727 | >gi|147901026|ref|NM_001086037.1| Xenopus laevis similar to selenoprotein T (MGC53828); mRNA |
| 32. | 673 | 762 | >gi|147902017|ref|NM_001086118.1| Xenopus laevis similar to selenoprotein T (MGC53056); mRNA |
| 33. | 661 | 728 | >gi|37590945|gb|BC059764.1| Xenopus tropicalis selenoprotein T; mRNA (cDNA clone MGC:75917 IMAGE:5383677) |
| 34. | 432 | 499 | >gi|77623962|emb|CR855814.2| Xenopus tropicalis finished cDNA; clone TTpA003b03 |
| 35. | 673 | 740 | >gi|77626433|emb|CR760355.2| Xenopus tropicalis finished cDNA; clone TNeu015n05 |
| 36. | 673 | 740 | >gi|143771655|ref|NM_203537.2| Xenopus (Silurana) tropicalis selenoprotein T (selt); mRNA |
| 37. | 1550 | 1611 | >gi|53127427|emb|AJ719438.1| Gallus gallus mRNA for hypothetical protein; clone 2f9 |
| 38. | 1550 | 1611 | >gi|156671207|ref|NM_001031609.2| Gallus gallus selenoprotein P; plasma; 1 (SEPP1); mRNA |
| 39. | 431 | 488 | >gi|67970295|dbj|AB169408.1| Macaca fascicularis testis cDNA; clone: QtsA-19841; similar to human selenoprotein H (SELH); mRNA; RefSeq: NM_170746.2 |
| 40. | 1478 | 1539 | >gi|67971165|dbj|AB169844.1| Macaca fascicularis brain cDNA; clone: QtrA-12102; similar to human selenoprotein P; plasma; 1 (SEPP1); mRNA; RefSeq: NM_005410.1 |
| 41. | 2834 | 2900 | >gi|108999801|ref|XR_014267.1| PREDICTED: Macaca mulatta similar to selenoprotein N; 1 isoform 2 precursor (LOC719707); mRNA |
| 42. | 1333 | 1394 | >gi|109077123|ref|XM_001087397.1| PREDICTED: Macaca mulatta similar to selenoprotein P precursor (LOC698917); mRNA |
| 43. | 464 | 521 | >gi|109106230|ref|XR_012596.1| PREDICTED: Macaca mulatta similar to selenoprotein H (LOC704535); mRNA |
| 44. | 2614 | 2680 | >gi|114554845|ref|XR_022872.1| PREDICTED: Pan troglodytes similar to selenoprotein N; 1 (LOC456649); mRNA |
| 45. | 661 | 718 | >gi|114642405|ref|XR_020651.1| PREDICTED: Pan troglodytes selenoprotein H (LOC743806); mRNA |

Figure 18C

| | start | end | origin |
|---|---|---|---|
| 46. | 1508 | 1569 | >gi\|169403954\|ref\|NM_001115115.1\| Pan troglodytes selenoprotein P; plasma; 1 (SEPP1); mRNA |
| 47. | 1479 | 1540 | >gi\|55730133\|emb\|CR859629.1\| Pongo abelii mRNA; cDNA DKFZp459B039 (from clone DKFZp459B039) |
| 48. | 1479 | 1540 | >gi\|197101232\|ref\|NM_001133990.1\| Pongo abelii selenoprotein P; plasma; 1 (SEPP1); mRNA |
| 49. | 1730 | 1794 | >gi\|257451\|gb\|S48220.1\| Homo sapiens type I 5' iodothyronine deiodinase mRNA |
| 50. | 2510 | 2576 | >gi\|6649220\|gb\|AF166125.1\|AF166125 Homo sapiens selenoprotein N mRNA; partial cds |
| 51. | 2921 | 2987 | >gi\|16197697\|emb\|AJ306399.1\| Homo sapiens partial mRNA for selenoprotein N (SEPN1 gene) |
| 52. | 1482 | 1543 | >gi\|16198414\|gb\|BC015875.1\| Homo sapiens selenoprotein P; plasma; 1; mRNA (cDNA clone MGC:27488 IMAGE:4715833) |
| 53. | 3605 | 3666 | >gi\|20988609\|gb\|BC030009.1\| Homo sapiens selenoprotein P; plasma; 1; mRNA (cDNA clone IMAGE:4822966); with apparent retained intron |
| 54. | 1877 | 1938 | >gi\|21755536\|dbj\|AK096125.1\| Homo sapiens cDNA FLJ38806 fis; clone LIVER2005728; moderately similar to SELENOPROTEIN P PRECURSOR |
| 55. | 660 | 717 | >gi\|24431321\|gb\|AF536829.1\| Homo sapiens selenoprotein H mRNA |
| 56. | 1457 | 1518 | >gi\|25455660\|gb\|BC040075.1\| Homo sapiens selenoprotein P; plasma; 1; mRNA (cDNA clone MGC:47713 IMAGE:5770225) |
| 57. | 1460 | 1521 | >gi\|28374452\|gb\|BC046152.1\| Homo sapiens selenoprotein P; plasma; 1; mRNA (cDNA clone MGC:57675 IMAGE:6192976) |
| 58. | 2125 | 2191 | >gi\|33873017\|gb\|BC021028.2\| Homo sapiens selenoprotein N; 1; mRNA (cDNA clone IMAGE:3622007) |
| 59. | 1586 | 1652 | >gi\|34192906\|gb\|BC042154.2\| Homo sapiens selenoprotein N; 1; mRNA (cDNA clone IMAGE:4551053) |
| 60. | 1586 | 1652 | >gi\|34194045\|gb\|BC015638.2\| Homo sapiens selenoprotein N; 1; mRNA (cDNA clone IMAGE:4637019) |
| 61. | 1489 | 1550 | >gi\|37596693\|gb\|BC058919.1\| Homo sapiens selenoprotein P; plasma; 1; mRNA (cDNA clone MGC:65090 IMAGE:6195379) |
| 62. | 764 | 821 | >gi\|46370090\|ref\|NM_170746.2\| Homo sapiens chromosome 11 open reading frame 31 (C11orf31); mRNA |
| 63. | 2921 | 2987 | >gi\|47578098\|ref\|NM_020451.2\| Homo sapiens selenoprotein N; 1 (SEPN1); transcript variant 1; mRNA |
| 64. | 2819 | 2885 | >gi\|47578100\|ref\|NM_206926.1\| Homo sapiens selenoprotein N; 1 (SEPN1); transcript variant 2; mRNA |
| 65. | 1508 | 1569 | >gi\|62530390\|ref\|NM_005410.2\| Homo sapiens selenoprotein P; plasma; 1 (SEPP1); transcript variant 1; mRNA |
| 66. | 1747 | 1811 | >gi\|89357933\|ref\|NM_000792.5\| Homo sapiens deiodinase; iodothyronine; type I (DIO1); transcript variant 1; mRNA |
| 67. | 1603 | 1667 | >gi\|89357934\|ref\|NM_001039715.1\| Homo sapiens deiodinase; iodothyronine; type I (DIO1); transcript variant 3; mRNA |

Figure 18D

| # | start | end | origin |
|---|---|---|---|
| 68. | 1555 | 1619 | >gi|89357936|ref|NM_213593.3| Homo sapiens deiodinase; iodothyronine; type I (DIO1); transcript variant 2; mRNA |
| 69. | 1547 | 1611 | >gi|89357937|ref|NM_001039716.1| Homo sapiens deiodinase; iodothyronine; type I (DIO1); transcript variant 4; mRNA |
| 70. | 760 | 819 | >gi|90903236|ref|NM_002085.3| Homo sapiens glutathione peroxidase 4 (phospholipid hydroperoxidase) (GPX4); transcript variant 1; mRNA |
| 71. | 782 | 841 | >gi|90903237|ref|NM_001039847.1| Homo sapiens glutathione peroxidase 4 (phospholipid hydroperoxidase) (GPX4); transcript variant 2; mRNA |
| 72. | 849 | 908 | >gi|90903239|ref|NM_001039848.1| Homo sapiens glutathione peroxidase 4 (phospholipid hydroperoxidase) (GPX4); transcript variant 3; mRNA |
| 73. | 1507 | 1568 | >gi|110624237|dbj|AK225801.1| Homo sapiens mRNA for Selenoprotein P precursor variant; clone: FCC130F08 |
| 74. | 1537 | 1598 | >gi|148277017|ref|NM_001085486.1| Homo sapiens selenoprotein P; plasma; 1 (SEPP1); transcript variant 2; mRNA |
| 75. | 1596 | 1657 | >gi|148277021|ref|NM_001093726.1| Homo sapiens selenoprotein P; plasma; 1 (SEPP1); transcript variant 3; mRNA |
| 76. | 1497 | 1558 | >gi|169403967|ref|NM_001115118.1| Canis lupus familiaris selenoprotein P; plasma; 1 (SEPP1); mRNA |
| 77. | 956 | 1010 | >gi|197717770|gb|DQ898282.2| Sus scrofa glutathione peroxidase 2 (GPX2) mRNA |
| 78. | 1507 | 1568 | >gi|197717774|gb|EF113596.2| Sus scrofa selenoprotein P (Sepp1) mRNA |
| 79. | 1507 | 1568 | >gi|198282078|ref|NM_001134823.1| Sus scrofa selenoprotein P (SEPP1); mRNA |
| 80. | 1303 | 1366 | >gi|163705|gb|L10325.1|BOVSELGP Cow glutathione peroxidase (GPx) plasma isoform mRNA |
| 81. | 1403 | 1464 | >gi|6006350|dbj|AB032826.1| Bos taurus selp mRNA for selenoprotein P |
| 82. | 1549 | 1615 | >gi|94534945|gb|BC116119.1| Bos taurus selenoprotein N; 1; mRNA (cDNA clone IMAGE:8091454) |
| 83. | 1623 | 1684 | >gi|156631000|ref|NM_174459.3| Bos taurus selenoprotein P; plasma; 1 (SEPP1); mRNA |
| 84. | 2778 | 2844 | >gi|169234650|ref|NM_001114976.1| Bos taurus selenoprotein N; 1 (SEPN1); mRNA |
| 85. | 1209 | 1272 | >gi|536927|gb|U13705.1|MMU13705 Mus musculus domesticus C57BL/6J plasma glutathione peroxidase (MUSPGPX) mRNA |
| 86. | 1549 | 1616 | >gi|1495998|emb|X99807.1| M.musculus mRNA for selenoprotein P |
| 87. | 1489 | 1556 | >gi|12805068|gb|BC001991.1| Mus musculus selenoprotein P; plasma; 1; mRNA (cDNA clone MGC:5722 IMAGE:3486761) |
| 88. | 1488 | 1555 | >gi|12832443|dbj|AK002450.1| Mus musculus adult male kidney cDNA; RIKEN full-length enriched library; clone:0610010C08 product:selenoprotein P; plasma; 1; full insert sequence |
| 89. | 1191 | 1257 | >gi|12834716|dbj|AK003819.1| Mus musculus 18-day embryo whole body cDNA; RIKEN full-length enriched library; clone:1110019I12 product:selenoprotein N; 1; full insert sequence |

Figure 18E

| | start | end | origin |
|---|---|---|---|
| 90. | 474 | 531 | >gi\|12849465\|dbj\|AK012609.1\| Mus musculus 11 days embryo whole body cDNA; RIKEN full-length enriched library; clone:2700094K13 product:similar to Selenoprotein H [Homo sapiens]; full insert sequence |
| 91. | 413 | 479 | >gi\|18490560\|gb\|BC022585.1\| Mus musculus selenoprotein N; 1; mRNA (cDNA clone IMAGE:4036667); partial cds |
| 92. | 1488 | 1555 | >gi\|26097259\|dbj\|AK077265.1\| Mus musculus 11 days pregnant adult female ovary and uterus cDNA; RIKEN full-length enriched library; clone:5031434C21 product:selenoprotein P; plasma; 1; full insert sequence |
| 93. | 1314 | 1380 | >gi\|27693985\|gb\|BC043665.1\| Mus musculus selenoprotein N; 1; mRNA (cDNA clone IMAGE:5012596) |
| 94. | 1487 | 1554 | >gi\|74139323\|dbj\|AK169011.1\| Mus musculus 17 days pregnant adult female amnion cDNA; RIKEN full-length enriched library; clone:I920074D12 product:selenoprotein P; plasma; 1; full insert sequence |
| 95. | 1487 | 1554 | >gi\|74139599\|dbj\|AK169158.1\| Mus musculus 17 days pregnant adult female amnion cDNA; RIKEN full-length enriched library; clone:I920086D06 product:selenoprotein P; plasma; 1; full insert sequence |
| 96. | 1488 | 1555 | >gi\|74142101\|dbj\|AK169362.1\| Mus musculus 17 days pregnant adult female amnion cDNA; RIKEN full-length enriched library; clone:I920192G15 product:selenoprotein P; plasma; 1; full insert sequence |
| 97. | 1488 | 1555 | >gi\|74145110\|dbj\|AK146774.1\| Mus musculus 17 days pregnant adult female amnion cDNA; RIKEN full-length enriched library; clone:I920052L16 product:selenoprotein P; plasma; 1; full insert sequence |
| 98. | 512 | 569 | >gi\|74179101\|dbj\|AK171972.1\| Mus musculus activated spleen cDNA; RIKEN full-length enriched library; clone:F830023C16 product:similar to Selenoprotein H [Homo sapiens]; full insert sequence |
| 99. | 1488 | 1555 | >gi\|74192878\|dbj\|AK159269.1\| Mus musculus osteoclast-like cell cDNA; RIKEN full-length enriched library; clone:I420013J02 product:selenoprotein P; plasma; 1; full insert sequence |
| 100. | 1489 | 1556 | >gi\|74197218\|dbj\|AK159524.1\| Mus musculus osteoclast-like cell cDNA; RIKEN full-length enriched library; clone:I420022P13 product:selenoprotein P; plasma; 1; full insert sequence |
| 101. | 1488 | 1555 | >gi\|74198357\|dbj\|AK167611.1\| Mus musculus 15 days pregnant adult female placenta cDNA; RIKEN full-length enriched library; clone:I530025B11 product:selenoprotein P; plasma; 1; full insert sequence |
| 102. | 493 | 550 | >gi\|74198410\|dbj\|AK167638.1\| Mus musculus 14 days pregnant adult female placenta cDNA; RIKEN full-length enriched library; clone:I530025N05 product:similar to Selenoprotein H [Homo sapiens]; full insert sequence |
| 103. | 1485 | 1552 | >gi\|74204794\|dbj\|AK159894.1\| Mus musculus osteoclast-like cell cDNA; RIKEN full-length enriched library; clone:I420037A20 product:selenoprotein P; plasma; 1; full insert sequence |
| 104. | 1489 | 1556 | >gi\|74204825\|dbj\|AK159911.1\| Mus musculus osteoclast-like cell cDNA; RIKEN full-length enriched library; clone:I420037J18 product:selenoprotein P; plasma; 1; full insert sequence |

Figure 18F

| | start | end | origin |
|---|---|---|---|
| 105. | 1488 | 1555 | >gi|74213352|dbj|AK159935.1| Mus musculus osteoclast-like cell cDNA; RIKEN full-length enriched library; clone:I420038L13 product:selenoprotein P; plasma; 1; full insert sequence |
| 106. | 1485 | 1552 | >gi|74214220|dbj|AK168463.1| Mus musculus 17 days pregnant adult female amnion cDNA; RIKEN full-length enriched library; clone:I920024H22 product:selenoprotein P; plasma; 1; full insert sequence |
| 107. | 1485 | 1552 | >gi|74214433|dbj|AK168583.1| Mus musculus 17 days pregnant adult female amnion cDNA; RIKEN full-length enriched library; clone:I920036P08 product:selenoprotein P; plasma; 1; full insert sequence |
| 108. | 1488 | 1555 | >gi|74215929|dbj|AK148623.1| Mus musculus 2 days neonate sympathetic ganglion cDNA; RIKEN full-length enriched library; clone:7120425M02 product:selenoprotein P; plasma; 1; full insert sequence |
| 109. | 1488 | 1555 | >gi|74219803|dbj|AK168631.1| Mus musculus 17 days pregnant adult female amnion cDNA; RIKEN full-length enriched library; clone:I920040D13 product:selenoprotein P; plasma; 1; full insert sequence |
| 110. | 1488 | 1555 | >gi|74220015|dbj|AK168747.1| Mus musculus 17 days pregnant adult female amnion cDNA; RIKEN full-length enriched library; clone:I920049J07 product:selenoprotein P; plasma; 1; full insert sequence |
| 111. | 1488 | 1555 | >gi|74223204|dbj|AK168926.1| Mus musculus 17 days pregnant adult female amnion cDNA; RIKEN full-length enriched library; clone:I920065H09 product:selenoprotein P; plasma; 1; full insert sequence |
| 112. | 521 | 578 | >gi|82546880|ref|NM_001033166.2| Mus musculus RIKEN cDNA 2700094K13 gene (2700094K13Rik); transcript variant 1; mRNA |
| 113. | 496 | 553 | >gi|82546882|ref|NM_001037279.1| Mus musculus RIKEN cDNA 2700094K13 gene (2700094K13Rik); transcript variant 2; mRNA |
| 114. | 1971 | 2033 | >gi|110224441|ref|NM_001042513.1| Mus musculus thioredoxin reductase 1 (Txnrd1); transcript variant 2; mRNA |
| 115. | 1864 | 1926 | >gi|110224443|ref|NM_015762.2| Mus musculus thioredoxin reductase 1 (Txnrd1); transcript variant 3; mRNA |
| 116. | 2059 | 2121 | >gi|110224444|ref|NM_001042514.1| Mus musculus thioredoxin reductase 1 (Txnrd1); transcript variant 4; mRNA |
| 117. | 2188 | 2250 | >gi|110224446|ref|NM_001042523.1| Mus musculus thioredoxin reductase 1 (Txnrd1); transcript variant 1; mRNA |
| 118. | 1489 | 1556 | >gi|110735407|ref|NM_001042613.1| Mus musculus selenoprotein P; plasma; 1 (Sepp1); transcript variant 2; mRNA |
| 119. | 1506 | 1573 | >gi|110735409|ref|NM_009155.3| Mus musculus selenoprotein P; plasma; 1 (Sepp1); transcript variant 1; mRNA |
| 120. | 1572 | 1639 | >gi|110735410|ref|NM_001042614.1| Mus musculus selenoprotein P; plasma; 1 (Sepp1); transcript variant 3; mRNA |
| 121. | 2627 | 2693 | >gi|111118963|ref|NM_029100.2| Mus musculus selenoprotein N; 1 (Sepn1); mRNA |
| 122. | 1463 | 1530 | >gi|206893|gb|M63574.1|RATSELENOP Rat selenoprotein P mRNA |
| 123. | 1484 | 1551 | >gi|1020410|dbj|D25221.1| Rattus norvegicus mRNA for selenoprotein P |

Figure 18G

| | start | end | origin |
|---|---|---|---|
| 124. | 1492 | 1559 | >gi|47939024|gb|BC072539.1| Rattus norvegicus selenoprotein P; plasma; 1; mRNA (cDNA clone MGC:91714 IMAGE:7104195) |
| 125. | 361 | 418 | >gi|109485110|ref|XR_008210.1| PREDICTED: Rattus norvegicus similar to Selenoprotein H (predicted) (RGD1559935_predicted); mRNA |
| 126. | 1503 | 1570 | >gi|144953872|ref|NM_019192.2| Rattus norvegicus selenoprotein P; plasma; 1 (Sepp1); transcript variant 1; mRNA |
| 127. | 1575 | 1642 | >gi|144953873|ref|NM_001083911.1| Rattus norvegicus selenoprotein P; plasma; 1 (Sepp1); transcript variant 2; mRNA |
| 128. | 501 | 558 | >gi|169234952|ref|NM_001114939.1| Rattus norvegicus similar to Selenoprotein H (RGD1563348); mRNA |
| 129. | 449 | 517 | >gi|222789739|gb|EZ018171.1| TSA: Acropora millepora SeqIndex2569; mRNA sequence |
| 130. | 1040 | 1105 | >gi|76158277|gb|DQ214874.1| Taeniopygia guttata clone 0063P0014D11 putative selenoprotein mRNA |
| 131. | 1051 | 1116 | >gi|76158278|gb|DQ214875.1| Taeniopygia guttata clone 0061P0016C02 selenoprotein-like mRNA; complete sequence |
| 132. | 1048 | 1113 | >gi|76158279|gb|DQ214876.1| Taeniopygia guttata clone 0065P0025B05 putative selenoprotein mRNA |
| 133. | 1028 | 1093 | >gi|224057490|ref|XM_002195971.1| PREDICTED: Taeniopygia guttata selenoprotein-like (LOC100190318); mRNA |
| 134. | 1404 | 1465 | >gi|224090400|ref|XM_002193705.1| PREDICTED: Taeniopygia guttata selenoprotein P (LOC100231953); mRNA |
| 135. | 174 | 237 | >gi|21308129|gb|AY067496.1| Schmidtea mediterranea unknown mRNA sequence |

Figure 19A

|   | start | end | origin |
|---|---|---|---|
| 1. | 1733 | 1808 | >gi|222425027|dbj|AB379907.1| Emiliania huxleyi EhSEP1 mRNA for thioredoxin reductase |
| 2. | 570 | 642 | >gi|23452029|gb|AF494050.1| Chlamydomonas reinhardtii selenoprotein SelW1 mRNA |
| 3. | 734 | 807 | >gi|221131586|ref|XM_002164109.1| PREDICTED: Hydra magnipapillata similar to selenoprotein T; 1a (LOC100209879); mRNA |
| 4. | 491 | 555 | >gi|60698385|gb|AY915729.1| Schistosoma japonicum SJCHGC09268 protein mRNA |
| 5. | 756 | 820 | >gi|115291343|gb|DQ907947.1| Litopenaeus vannamei selenoprotein M mRNA |
| 6. | 692 | 753 | >gi|75706902|gb|DQ172828.1| Boophilus microplus phospholipid-hydroperoxide glutathione peroxidase (PHGPx) mRNA |
| 7. | 674 | 743 | >gi|115973385|ref|XR_026176.1| PREDICTED: Strongylocentrotus purpuratus similar to selenoprotein T2 (LOC589324); mRNA |
| 8. | 600 | 663 | >gi|198427211|ref|XM_002128679.1| PREDICTED: Ciona intestinalis similar to selenoprotein K (LOC100184686); mRNA |
| 9. | 805 | 872 | >gi|198428862|ref|XM_002131362.1| PREDICTED: Ciona intestinalis similar to selenoprotein S (LOC100186840); mRNA |
| 10. | 1576 | 1643 | >gi|12408008|gb|AF322071.1|AF322071 Danio rerio selenoprotein Pa mRNA |
| 11. | 2048 | 2124 | >gi|12408008|gb|AF322071.1|AF322071 Danio rerio selenoprotein Pa mRNA |
| 12. | 965 | 1037 | >gi|12408010|gb|AF322072.1|AF322072 Danio rerio selenoprotein Pb mRNA |
| 13. | 667 | 736 | >gi|29165357|gb|AY221264.1| Danio rerio selenoprotein T1a mRNA |
| 14. | 358 | 426 | >gi|29648541|gb|AY216582.1| Danio rerio selenoprotein W1 mRNA |
| 15. | 543 | 613 | >gi|29648600|gb|AY216590.1| Danio rerio phospholipid hydroperoxide glutathione peroxidase A mRNA; partial cds |
| 16. | 673 | 743 | >gi|31419427|gb|BC053147.1| Danio rerio selenoprotein T; 1b; mRNA (cDNA clone MGC:63919 IMAGE:6790686) |
| 17. | 659 | 728 | >gi|32451894|gb|BC054578.1| Danio rerio selenoprotein T; 1a; mRNA (cDNA clone MGC:63945 IMAGE:6791276) |
| 18. | 1534 | 1613 | >gi|37596695|gb|BC059656.1| Danio rerio selenoprotein P; plasma; 1a; mRNA (cDNA clone MGC:73338 IMAGE:4790285) |
| 19. | 2002 | 2078 | >gi|37596695|gb|BC059656.1| Danio rerio selenoprotein P; plasma; 1a; mRNA (cDNA clone MGC:73338 IMAGE:4790285) |
| 20. | 1532 | 1599 | >gi|39645918|gb|BC063960.1| Danio rerio selenoprotein P; plasma; 1a; mRNA (cDNA clone MGC:77663 IMAGE:6997155) |
| 21. | 2003 | 2079 | >gi|39645918|gb|BC063960.1| Danio rerio selenoprotein P; plasma; 1a; mRNA (cDNA clone MGC:77663 IMAGE:6997155) |
| 22. | 751 | 818 | >gi|45501113|gb|BC067158.1| Danio rerio selenoprotein P; plasma; 1a; mRNA (cDNA clone IMAGE:6525439) |
| 23. | 1222 | 1298 | >gi|45501113|gb|BC067158.1| Danio rerio selenoprotein P; plasma; 1a; mRNA (cDNA clone IMAGE:6525439) |
| 24. | 685 | 747 | >gi|53734005|gb|BC083376.1| Danio rerio selenoprotein M; mRNA (cDNA clone MGC:103431 IMAGE:7233960) |

Figure 19B

| | start | end | origin |
|---|---|---|---|
| 25. | 668 | 738 | >gi|55925455|ref|NM_001007282.1| Danio rerio glutathione peroxidase 4a (gpx4a); mRNA |
| 26. | 992 | 1064 | >gi|56269441|gb|BC086844.1| Danio rerio selenoprotein P; plasma; 1b; mRNA (cDNA clone MGC:103690 IMAGE:7263305) |
| 27. | 409 | 477 | >gi|62204254|gb|BC092686.1| Danio rerio selenoprotein W; 1; mRNA (cDNA clone MGC:109781 IMAGE:7294946) |
| 28. | 784 | 852 | >gi|63101287|gb|BC095658.1| Danio rerio selenoprotein T; 2; mRNA (cDNA clone IMAGE:7409402) |
| 29. | 383 | 451 | >gi|156229947|gb|BC152097.1| Danio rerio selenoprotein W; 1; mRNA (cDNA clone MGC:173541 IMAGE:7926352) |
| 30. | 433 | 501 | >gi|156671212|ref|NM_178287.4| Danio rerio selenoprotein W; 1 (scpw1); mRNA |
| 31. | 726 | 796 | >gi|157276589|ref|NM_178292.4| Danio rerio selenoprotein T; 1b (selt1b); mRNA |
| 32. | 3260 | 3326 | >gi|157276600|ref|NM_001004295.2| Danio rerio selenophosphate synthetase 2 (sps2); mRNA |
| 33. | 713 | 775 | >gi|157388998|ref|NM_178286.3| Danio rerio selenoprotein M (sepm); mRNA |
| 34. | 1595 | 1662 | >gi|157389011|ref|NM_178297.3| Danio rerio selenoprotein P; plasma; 1a (sepp1a); mRNA |
| 35. | 2066 | 2142 | >gi|157389011|ref|NM_178297.3| Danio rerio selenoprotein P; plasma; 1a (sepp1a); mRNA |
| 36. | 1564 | 1631 | >gi|161612236|gb|BC155821.1| Danio rerio selenoprotein P; plasma; 1a; mRNA (cDNA clone MGC:175059 IMAGE:7071048) |
| 37. | 2034 | 2110 | >gi|161612236|gb|BC155821.1| Danio rerio selenoprotein P; plasma; 1a; mRNA (cDNA clone MGC:175059 IMAGE:7071048) |
| 38. | 1564 | 1631 | >gi|166796356|gb|BC159240.1| Danio rerio selenoprotein P; plasma; 1a; mRNA (cDNA clone MGC:175065 IMAGE:9001368) |
| 39. | 2034 | 2110 | >gi|166796356|gb|BC159240.1| Danio rerio selenoprotein P; plasma; 1a; mRNA (cDNA clone MGC:175065 IMAGE:9001368) |
| 40. | 685 | 754 | >gi|167900445|ref|NM_178290.5| Danio rerio selenoprotein T; 1a (selt1a); mRNA |
| 41. | 819 | 887 | >gi|168480082|ref|NM_001098487.2| Danio rerio selenoprotein T; 2 (selt2); mRNA |
| 42. | 835 | 899 | >gi|169403975|ref|NM_001007281.2| Danio rerio glutathione peroxidase 1a (gpx1a); mRNA |
| 43. | 1944 | 2009 | >gi|169790921|ref|NM_212789.3| Danio rerio deiodinase; iodothyronine; type II (dio2); mRNA |
| 44. | 1028 | 1100 | >gi|189515895|ref|XM_001923882.1| PREDICTED: Danio rerio selenoprotein P; plasma; 1b (sepp1b); mRNA |
| 45. | 907 | 969 | >gi|33113419|gb|AY255833.1| Oncorhynchus mykiss 15 kDa selenoprotein precursor (sep15) mRNA |
| 46. | 907 | 969 | >gi|185134878|ref|NM_001124454.1| Oncorhynchus mykiss 15 kDa selenoprotein precursor (sep15); mRNA |
| 47. | 830 | 891 | >gi|198285586|gb|BT044016.1| Salmo salar clone HM5_0578 selenoprotein T-like mRNA |
| 48. | 830 | 891 | >gi|213512656|ref|NM_001139761.1| Salmo salar selenoprotein T-like (LOC100194716); mRNA |

Figure 19C

| | start | end | origin |
|---|---|---|---|
| 49. | 667 | 736 | >gi|224587210|gb|BT072071.1| Salmo salar clone ssal-rgf-510-105 Selenoprotein T1a precursor putative mRNA; pseudogene cds |
| 50. | 1649 | 1716 | >gi|224587362|gb|BT072221.1| Salmo salar clone ssal-rgf-517-169 Selenoprotein Pa precursor putative mRNA; pseudogene cds |
| 51. | 1692 | 1765 | >gi|224587811|gb|BT072678.1| Salmo salar clone ssal-rgf-536-075 Selenoprotein Pa precursor putative mRNA; pseudogene cds |
| 52. | 663 | 727 | >gi|27696399|gb|BC043894.1| Xenopus laevis similar to selenoprotein T; mRNA (cDNA clone MGC:53828 IMAGE:5542417) |
| 53. | 673 | 762 | >gi|27924200|gb|BC044996.1| Xenopus laevis similar to selenoprotein T; mRNA (cDNA clone MGC:53056 IMAGE:5541863) |
| 54. | 2383 | 2449 | >gi|49904042|gb|BC076643.1| Xenopus laevis selenoprotein I; mRNA (cDNA clone MGC:78842 IMAGE:3402807) |
| 55. | 852 | 920 | >gi|50604160|gb|BC078025.1| Xenopus laevis MGC82712 protein; mRNA (cDNA clone MGC:82712 IMAGE:5130117) |
| 56. | 827 | 895 | >gi|51261705|gb|BC080110.1| Xenopus laevis MGC84676 protein; mRNA (cDNA clone MGC:84676 IMAGE:6945612) |
| 57. | 2346 | 2412 | >gi|146261166|ref|NM_001085478.1| Xenopus laevis selenoprotein I (seli); mRNA |
| 58. | 663 | 727 | >gi|147901026|ref|NM_001086037.1| Xenopus laevis similar to selenoprotein T (MGC53828); mRNA |
| 59. | 827 | 895 | >gi|147901975|ref|NM_001094097.1| Xenopus laevis MGC84676 protein (MGC84676); mRNA |
| 60. | 673 | 762 | >gi|147902017|ref|NM_001086118.1| Xenopus laevis similar to selenoprotein T (MGC53056); mRNA |
| 61. | 852 | 920 | >gi|148227553|ref|NM_001093656.1| Xenopus laevis MGC82712 protein (MGC82712); mRNA |
| 62. | 661 | 728 | >gi|37590945|gb|BC059764.1| Xenopus tropicalis selenoprotein T; mRNA (cDNA clone MGC:75917 IMAGE:5383677) |
| 63. | 830 | 901 | >gi|56972260|gb|BC088768.1| Xenopus tropicalis selenoprotein S; mRNA (cDNA clone MGC:108065 IMAGE:7003729) |
| 64. | 830 | 901 | >gi|58332803|ref|NM_001011476.1| Xenopus (Silurana) tropicalis selenoprotein S (sels); mRNA |
| 65. | 432 | 499 | >gi|77623962|emb|CR855814.2| Xenopus tropicalis finished cDNA; clone TTpA003b03 |
| 66. | 832 | 903 | >gi|77625836|emb|CR760118.2| Xenopus tropicalis finished cDNA; clone TNeu072i15 |
| 67. | 673 | 740 | >gi|77626433|emb|CR760355.2| Xenopus tropicalis finished cDNA; clone TNeu015n05 |
| 68. | 673 | 740 | >gi|143771655|ref|NM_203537.2| Xenopus (Silurana) tropicalis selenoprotein T (selt); mRNA |
| 69. | 485 | 553 | >gi|98986454|ref|NM_001025441.2| Gallus gallus selenoprotein K (SELK); mRNA |
| 70. | 509 | 577 | >gi|149413874|ref|XM_001514240.1| PREDICTED: Ornithorhynchus anatinus similar to selenoprotein T (LOC100087774); mRNA |

Figure 19D

| | start | end | origin |
|---|---|---|---|
| 71. | 392 | 466 | >gi\|67970450\|dbj\|AB169486.1\| Macaca fascicularis brain cDNA; clone: QccE-10579; similar to human selenoprotein W; 1 (SEPW1); mRNA; RefSeq: NM_003009.2 |
| 72. | 1478 | 1539 | >gi\|67971165\|dbj\|AB169844.1\| Macaca fascicularis brain cDNA; clone: QtrA-12102; similar to human selenoprotein P; plasma; 1 (SEPP1); mRNA; RefSeq: NM_005410.1 |
| 73. | 1101 | 1180 | >gi\|67971333\|dbj\|AB178958.1\| Macaca fascicularis testis cDNA clone: QtsA-10076; similar to human 15 kDa selenoprotein (SEP15); transcript variant 1; mRNA; RefSeq: NM_004261.3 |
| 74. | 364 | 438 | >gi\|2326176\|gb\|U67450.1\|MMU67450 Macaca mulatta selenoprotein W mRNA |
| 75. | 2834 | 2900 | >gi\|108999801\|ref\|XR_014267.1\| PREDICTED: Macaca mulatta similar to selenoprotein N; 1 isoform 2 precursor (LOC719707); mRNA |
| 76. | 1324 | 1405 | >gi\|109009577\|ref\|XR_013747.1\| PREDICTED: Macaca mulatta similar to 15 kDa selenoprotein isoform 1 precursor (LOC712469); mRNA |
| 77. | 720 | 783 | >gi\|109048749\|ref\|XR_013517.1\| PREDICTED: Macaca mulatta similar to selenoprotein T (LOC710572); mRNA |
| 78. | 1333 | 1394 | >gi\|109077123\|ref\|XM_001087397.1\| PREDICTED: Macaca mulatta similar to selenoprotein P precursor (LOC698917); mRNA |
| 79. | 364 | 438 | >gi\|112293280\|ref\|NM_001042737.1\| Macaca mulatta selenoprotein W; 1 (SEPW1); mRNA |
| 80. | 989 | 1054 | >gi\|168693632\|ref\|NM_001114750.1\| Macaca mulatta selenoprotein X; 1 (SEPX1); mRNA |
| 81. | 2640 | 2710 | >gi\|207113143\|ref\|NM_001135563.1\| Macaca mulatta selenoprotein I (SELI); mRNA |
| 82. | 2614 | 2680 | >gi\|114554845\|ref\|XR_022872.1\| PREDICTED: Pan troglodytes similar to selenoprotein N; 1 (LOC456649); mRNA |
| 83. | 114 | 182 | >gi\|114557524\|ref\|XM_513536.2\| PREDICTED: Pan troglodytes 15 kDa selenoprotein (LOC456995); mRNA |
| 84. | 1359 | 1440 | >gi\|114557524\|ref\|XM_513536.2\| PREDICTED: Pan troglodytes 15 kDa selenoprotein (LOC456995); mRNA |
| 85. | 733 | 796 | >gi\|114589840\|ref\|XM_001143719.1\| PREDICTED: Pan troglodytes similar to RIKEN cDNA 2810407C02 gene (LOC738216); mRNA |
| 86. | 642 | 709 | >gi\|114623794\|ref\|XR_020240.1\| PREDICTED: Pan troglodytes similar to selenoprotein T (LOC739117); mRNA |
| 87. | 992 | 1057 | >gi\|168693638\|ref\|NM_001114751.1\| Pan troglodytes selenoprotein X; 1 (SEPX1); mRNA |
| 88. | 1508 | 1569 | >gi\|169403954\|ref\|NM_001115115.1\| Pan troglodytes selenoprotein P; plasma; 1 (SEPP1); mRNA |
| 89. | 1479 | 1540 | >gi\|55730133\|emb\|CR859629.1\| Pongo abelii mRNA; cDNA DKFZp459B039 (from clone DKFZp459B039) |
| 90. | 946 | 1011 | >gi\|55730510\|emb\|CR859820.1\| Pongo abelii mRNA; cDNA DKFZp469G2418 (from clone DKFZp469G2418) |

Figure 19E

| | start | end | origin |
|---|---|---|---|
| 91. | 946 | 1011 | >gi|55730639|emb|CR859885.1| Pongo abelii mRNA; cDNA DKFZp469N0616 (from clone DKFZp469N0616) |
| 92. | 389 | 463 | >gi|56541765|emb|CR926472.1| Pongo abelii mRNA; cDNA DKFZp468P0916 (from clone DKFZp468P0916) |
| 93. | 946 | 1011 | >gi|197099471|ref|NM_001132674.1| Pongo abelii selenoprotein X; 1 (SEPX1); mRNA |
| 94. | 389 | 463 | >gi|197100509|ref|NM_001133657.1| Pongo abelii selenoprotein W; 1 (SEPW1); mRNA |
| 95. | 1479 | 1540 | >gi|197101232|ref|NM_001133990.1| Pongo abelii selenoprotein P; plasma; 1 (SEPP1); mRNA |
| 96. | 2577 | 2647 | >gi|197103027|ref|NM_001133664.1| Pongo abelii selenoprotein I (SELI); mRNA |
| 97. | 1444 | 1506 | >gi|36425|emb|Z11793.1| H.sapiens mRNA for selenoprotein P |
| 98. | 1730 | 1794 | >gi|257451|gb|S48220.1| Homo sapiens type I 5' iodothyronine deiodinase mRNA |
| 99. | 370 | 444 | >gi|2326174|gb|U67171.1|HSU67171 Human selenoprotein W (selW) mRNA |
| 100. | 359 | 433 | >gi|2384720|gb|AF015283.1| Homo sapiens selenoprotein W (SEPW1) mRNA |
| 101. | 1083 | 1164 | >gi|3095110|gb|AF051894.1|AF051894 Homo sapiens 15 kDa selenoprotein mRNA |
| 102. | 688 | 751 | >gi|4406702|gb|AF131856.1|AF131856 Homo sapiens clone 24856 mRNA sequence |
| 103. | 691 | 754 | >gi|6470250|gb|AF195141.1|AF195141 Homo sapiens selenoprotein T mRNA |
| 104. | 927 | 992 | >gi|6649218|gb|AF166124.1|AF166124 Homo sapiens selenoprotein X mRNA |
| 105. | 2510 | 2576 | >gi|6649220|gb|AF166125.1|AF166125 Homo sapiens selenoprotein N mRNA; partial cds |
| 106. | 1894 | 1960 | >gi|6649222|gb|AF166126.1|AF166126 Homo sapiens selenoprotein Zf1 mRNA |
| 107. | 1914 | 1980 | >gi|6649224|gb|AF166127.1|AF166127 Homo sapiens selenoprotein Zf2 mRNA |
| 108. | 939 | 1004 | >gi|10438878|dbj|AK026128.1| Homo sapiens cDNA: FLJ22475 fis; clone HRC10666; highly similar to AF166124 Homo sapiens selenoprotein X mRNA |
| 109. | 2072 | 2146 | >gi|10439635|dbj|AK026717.1| Homo sapiens cDNA: FLJ23064 fis; clone LNG04783; highly similar to AF015283 Homo sapiens selenoprotein W (hSelW) mRNA |
| 110. | 902 | 967 | >gi|10441424|gb|AF187272.1|AF187272 Homo sapiens methionine sulfoxide reductase mRNA |
| 111. | 1083 | 1164 | >gi|11138954|gb|AF288991.1|AF288991 Homo sapiens 15 kDa selenoprotein (SEP15) mRNA; alternatively spliced |
| 112. | 864 | 929 | >gi|13111912|gb|BC003127.1| Homo sapiens selenoprotein X; 1; mRNA (cDNA clone MGC:3344 IMAGE:2905838) |
| 113. | 1109 | 1190 | >gi|13529007|gb|BC005294.1| Homo sapiens 15 kDa selenoprotein; mRNA (cDNA clone MGC:12358 IMAGE:4041321) |
| 114. | 724 | 787 | >gi|14710882|gb|BC006012.1| Homo sapiens selenoprotein T; mRNA (cDNA clone MGC:14845 IMAGE:4333083) |
| 115. | 691 | 754 | >gi|14713585|gb|BC008411.1| Homo sapiens selenoprotein T; mRNA (cDNA clone MGC:14546 IMAGE:4132578) |

Figure 19F

| | start | end | origin |
|---|---|---|---|
| 116. | 2921 | 2987 | >gi|16197697|emb|AJ306399.1| Homo sapiens partial mRNA for selenoprotein N (SEPN1 gene) |
| 117. | 1482 | 1543 | >gi|16198414|gb|BC015875.1| Homo sapiens selenoprotein P; plasma; 1; mRNA (cDNA clone MGC:27488 IMAGE:4715833) |
| 118. | 665 | 728 | >gi|16306968|gb|BC009556.1| Homo sapiens selenoprotein T; mRNA (cDNA clone MGC:10108 IMAGE:3899430) |
| 119. | 685 | 748 | >gi|16307068|gb|BC009611.1| Homo sapiens selenoprotein T; mRNA (cDNA clone MGC:14805 IMAGE:4093231) |
| 120. | 1096 | 1177 | >gi|16741016|gb|BC016359.1| Homo sapiens 15 kDa selenoprotein; mRNA (cDNA clone MGC:24512 IMAGE:4096759) |
| 121. | 1065 | 1146 | >gi|18203835|gb|BC021697.1| Homo sapiens 15 kDa selenoprotein; mRNA (cDNA clone MGC:24367 IMAGE:4051151) |
| 122. | 713 | 776 | >gi|20070974|gb|BC026350.1| Homo sapiens selenoprotein T; mRNA (cDNA clone MGC:26803 IMAGE:4796883) |
| 123. | 3605 | 3666 | >gi|20988609|gb|BC030009.1| Homo sapiens selenoprotein P; plasma; 1; mRNA (cDNA clone IMAGE:4822966); with apparent retained intron |
| 124. | 400 | 474 | >gi|21619749|gb|BC032546.1| Homo sapiens selenoprotein W; 1; mRNA (cDNA clone MGC:45316 IMAGE:5535970) |
| 125. | 1104 | 1185 | >gi|21734221|emb|AL833575.1| Homo sapiens mRNA; cDNA DKFZp686D2056 (from clone DKFZp686D2056) |
| 126. | 1877 | 1938 | >gi|21755536|dbj|AK096125.1| Homo sapiens cDNA FLJ38806 fis; clone LIVER2005728; moderately similar to SELENOPROTEIN P PRECURSOR |
| 127. | 706 | 769 | >gi|22760823|dbj|AK075006.1| Homo sapiens cDNA FLJ90525 fis; clone NT2RP4001001; highly similar to Selenoprotein T precursor |
| 128. | 684 | 747 | >gi|23272673|gb|BC036738.1| Homo sapiens selenoprotein T; mRNA (cDNA clone MGC:45090 IMAGE:5540243) |
| 129. | 378 | 452 | >gi|24659287|gb|BC039597.1| Homo sapiens selenoprotein W; 1; mRNA (cDNA clone MGC:48860 IMAGE:6015153) |
| 130. | 1457 | 1518 | >gi|25455660|gb|BC040075.1| Homo sapiens selenoprotein P; plasma; 1; mRNA (cDNA clone MGC:47713 IMAGE:5770225) |
| 131. | 1460 | 1521 | >gi|28374452|gb|BC046152.1| Homo sapiens selenoprotein P; plasma; 1; mRNA (cDNA clone MGC:57675 IMAGE:6192976) |
| 132. | 377 | 451 | >gi|28839049|gb|BC047893.1| Homo sapiens selenoprotein W; 1; mRNA (cDNA clone MGC:57701 IMAGE:6204763) |
| 133. | 1165 | 1229 | >gi|32492910|gb|AY324825.1| Homo sapiens selenoprotein V mRNA |
| 134. | 1165 | 1229 | >gi|33186894|ref|NM_182704.1| Homo sapiens selenoprotein V (SELV); mRNA |
| 135. | 2043 | 2103 | >gi|33519425|ref|NM_182729.1| Homo sapiens thioredoxin reductase 1 (TXNRD1); transcript variant 3; mRNA |
| 136. | 2170 | 2230 | >gi|33519427|ref|NM_182742.1| Homo sapiens thioredoxin reductase 1 (TXNRD1); transcript variant 2; mRNA |
| 137. | 1933 | 1993 | >gi|33519429|ref|NM_182743.1| Homo sapiens thioredoxin reductase 1 (TXNRD1); transcript variant 4; mRNA |

Figure 19G

|  | start | end | origin |
|---|---|---|---|
| 138. | 2280 | 2340 | >gi|33519431|ref|NM_003330.2| Homo sapiens thioredoxin reductase 1 (TXNRD1); transcript variant 1; mRNA |
| 139. | 2125 | 2191 | >gi|33873017|gb|BC021028.2| Homo sapiens selenoprotein N; 1; mRNA (cDNA clone IMAGE:3622007) |
| 140. | 2434 | 2504 | >gi|33879119|gb|BC021229.2| Homo sapiens selenoprotein I; mRNA (cDNA clone MGC:14164 IMAGE:4111329) |
| 141. | 1586 | 1652 | >gi|34192906|gb|BC042154.2| Homo sapiens selenoprotein N; 1; mRNA (cDNA clone IMAGE:4551053) |
| 142. | 1586 | 1652 | >gi|34194045|gb|BC015638.2| Homo sapiens selenoprotein N; 1; mRNA (cDNA clone IMAGE:4637019) |
| 143. | 375 | 449 | >gi|34783047|gb|BC000581.2| Homo sapiens selenoprotein W; 1; mRNA (cDNA clone MGC:1621 IMAGE:3162433) |
| 144. | 697 | 760 | >gi|37181295|gb|AY358095.1| Homo sapiens clone DNA16428 SELT (UNQ150) mRNA |
| 145. | 701 | 764 | >gi|37181297|gb|AY358096.1| Homo sapiens clone DNA16445 SELT (UNQ150) mRNA |
| 146. | 1489 | 1550 | >gi|37596693|gb|BC058919.1| Homo sapiens selenoprotein P; plasma; 1; mRNA (cDNA clone MGC:65090 IMAGE:6195379) |
| 147. | 510 | 584 | >gi|42544245|ref|NM_003009.2| Homo sapiens selenoprotein W; 1 (SEPW1); mRNA |
| 148. | 197 | 265 | >gi|42741647|ref|NM_004261.3| Homo sapiens 15 kDa selenoprotein (SEP15); transcript variant 1; mRNA |
| 149. | 1401 | 1482 | >gi|42741647|ref|NM_004261.3| Homo sapiens 15 kDa selenoprotein (SEP15); transcript variant 1; mRNA |
| 150. | 197 | 265 | >gi|42741649|ref|NM_203341.1| Homo sapiens 15 kDa selenoprotein (SEP15); transcript variant 2; mRNA |
| 151. | 1351 | 1432 | >gi|42741649|ref|NM_203341.1| Homo sapiens 15 kDa selenoprotein (SEP15); transcript variant 2; mRNA |
| 152. | 733 | 796 | >gi|42789379|ref|NM_016275.3| Homo sapiens selenoprotein T (SELT); mRNA |
| 153. | 968 | 1033 | >gi|45439350|ref|NM_016332.2| Homo sapiens selenoprotein X; 1 (SEPX1); mRNA |
| 154. | 2921 | 2987 | >gi|47578098|ref|NM_020451.2| Homo sapiens selenoprotein N; 1 (SEPN1); transcript variant 1; mRNA |
| 155. | 2819 | 2885 | >gi|47578100|ref|NM_206926.1| Homo sapiens selenoprotein N; 1 (SEPN1); transcript variant 2; mRNA |
| 156. | 676 | 739 | >gi|47940088|gb|BC071699.1| Homo sapiens selenoprotein T; mRNA (cDNA clone MGC:87960 IMAGE:5548565) |
| 157. | 2571 | 2641 | null |
| 158. | 1508 | 1569 | >gi|62530390|ref|NM_005410.2| Homo sapiens selenoprotein P; plasma; 1 (SEPP1); transcript variant 1; mRNA |
| 159. | 1854 | 1920 | >gi|87196331|ref|NM_006440.3| Homo sapiens thioredoxin reductase 2 (TXNRD2); nuclear gene encoding mitochondrial protein; mRNA |

Figure 19H

| | start | end | origin |
|---|---|---|---|
| 160. | 1747 | 1811 | >gi|89357933|ref|NM_000792.5| Homo sapiens deiodinase; iodothyronine; type I (DIO1); transcript variant 1; mRNA |
| 161. | 1603 | 1667 | >gi|89357934|ref|NM_001039715.1| Homo sapiens deiodinase; iodothyronine; type I (DIO1); transcript variant 3; mRNA |
| 162. | 1555 | 1619 | >gi|89357936|ref|NM_213593.3| Homo sapiens deiodinase; iodothyronine; type I (DIO1); transcript variant 2; mRNA |
| 163. | 1547 | 1611 | >gi|89357937|ref|NM_001039716.1| Homo sapiens deiodinase; iodothyronine; type I (DIO1); transcript variant 4; mRNA |
| 164. | 760 | 819 | >gi|90903236|ref|NM_002085.3| Homo sapiens glutathione peroxidase 4 (phospholipid hydroperoxidase) (GPX4); transcript variant 1; mRNA |
| 165. | 782 | 841 | >gi|90903237|ref|NM_001039847.1| Homo sapiens glutathione peroxidase 4 (phospholipid hydroperoxidase) (GPX4); transcript variant 2; mRNA |
| 166. | 849 | 908 | >gi|90903239|ref|NM_001039848.1| Homo sapiens glutathione peroxidase 4 (phospholipid hydroperoxidase) (GPX4); transcript variant 3; mRNA |
| 167. | 1130 | 1194 | >gi|109658779|gb|BC117331.1| Homo sapiens selenoprotein V; mRNA (cDNA clone MGC:150940 IMAGE:40125882) |
| 168. | 1092 | 1173 | >gi|110623628|dbj|AK225252.1| Homo sapiens mRNA for 15 kDa selenoprotein precursor variant; clone: DMC03465 |
| 169. | 1091 | 1172 | >gi|110624075|dbj|AK225640.1| Homo sapiens mRNA for 15 kDa selenoprotein precursor variant; clone: SPL08543 |
| 170. | 1507 | 1568 | >gi|110624237|dbj|AK225801.1| Homo sapiens mRNA for Selenoprotein P precursor variant; clone: FCC130F08 |
| 171. | 524 | 579 | >gi|111154061|ref|NM_017846.4| Homo sapiens tRNA selenocysteine 1 associated protein 1 (TRNAU1AP); transcript variant 1; mRNA |
| 172. | 2609 | 2679 | >gi|144094257|ref|NM_033505.2| Homo sapiens selenoprotein I (SELI); mRNA |
| 173. | 1537 | 1598 | >gi|148277017|ref|NM_001085486.1| Homo sapiens selenoprotein P; plasma; 1 (SEPP1); transcript variant 2; mRNA |
| 174. | 1596 | 1657 | >gi|148277021|ref|NM_001093726.1| Homo sapiens selenoprotein P; plasma; 1 (SEPP1); transcript variant 3; mRNA |
| 175. | 2208 | 2268 | >gi|148277070|ref|NM_001093771.1| Homo sapiens thioredoxin reductase 1 (TXNRD1); transcript variant 5; mRNA |
| 176. | 6070 | 6136 | >gi|148277090|ref|NM_000793.4| Homo sapiens deiodinase; iodothyronine; type II (DIO2); transcript variant 2; mRNA |
| 177. | 6378 | 6444 | >gi|148277091|ref|NM_013989.3| Homo sapiens deiodinase; iodothyronine; type II (DIO2); transcript variant 1; mRNA |
| 178. | 5804 | 5870 | >gi|148277092|ref|NM_001007023.2| Homo sapiens deiodinase; iodothyronine; type II (DIO2); transcript variant 3; mRNA |
| 179. | 1645 | 1712 | >gi|148277093|ref|NM_001362.3| Homo sapiens deiodinase; iodothyronine; type III (DIO3); mRNA |
| 180. | 185 | 256 | >gi|194377595|dbj|AK294539.1| Homo sapiens cDNA FLJ53979 complete cds; highly similar to DnaJ homolog subfamily C member 11 |
| 181. | 721 | 784 | >gi|194390615|dbj|AK300315.1| Homo sapiens cDNA FLJ60886 complete cds; highly similar to Selenoprotein T precursor |

Figure 19I

| | start | end | origin |
|---|---|---|---|
| 182. | 713 | 776 | >gi|73990710|ref|XM_534307.2| PREDICTED: Canis familiaris similar to Selenoprotein T precursor (LOC477113); mRNA |
| 183. | 735 | 798 | >gi|73990712|ref|XM_849419.1| PREDICTED: Canis familiaris similar to selenoprotein T (LOC612992); mRNA |
| 184. | 1333 | 1407 | >gi|168693432|ref|NM_001114760.1| Canis lupus familiaris 15 kDa selenoprotein (SEP15); mRNA |
| 185. | 343 | 410 | >gi|169234736|ref|NM_001115012.1| Canis lupus familiaris selenoprotein W; 1 (SEPW1); mRNA |
| 186. | 1497 | 1558 | >gi|169403967|ref|NM_001115118.1| Canis lupus familiaris selenoprotein P; plasma; 1 (SEPP1); mRNA |
| 187. | 314 | 379 | >gi|194215691|ref|XM_001917462.1| PREDICTED: Equus caballus similar to Selenoprotein W (LOC100050195); mRNA |
| 188. | 1516 | 1577 | >gi|208022672|ref|NM_001135605.1| Equus caballus selenoprotein P; plasma; 1 (SEPP1); mRNA |
| 189. | 361 | 435 | >gi|14194264|gb|AF380118.1|AF380118 Sus scrofa selenoprotein W (SEPW) mRNA |
| 190. | 361 | 435 | >gi|47522779|ref|NM_213977.1| Sus scrofa selenoprotein W; 1 (SEPW1); mRNA |
| 191. | 747 | 814 | >gi|52350713|gb|AY609428.1| Sus scrofa clone Clu_11288.scr.msk.p1.Contig1; mRNA sequence |
| 192. | 1058 | 1129 | >gi|121486234|gb|EF178474.1| Sus scrofa 15kDa selenoprotein (Sep15) mRNA |
| 193. | 1058 | 1129 | >gi|146198758|ref|NM_001085443.1| Sus scrofa 15kDa selenoprotein (SEP15); mRNA |
| 194. | 1507 | 1568 | >gi|197717774|gb|EF113596.2| Sus scrofa selenoprotein P (Sepp1) mRNA |
| 195. | 1507 | 1568 | >gi|198282078|ref|NM_001134823.1| Sus scrofa selenoprotein P (SEPP1); mRNA |
| 196. | 1303 | 1366 | >gi|163705|gb|L10325.1|BOVSELGP Cow glutathione peroxidase (GPx) plasma isoform mRNA |
| 197. | 1494 | 1555 | >gi|1020397|dbj|D25220.1| Bos taurus mRNA for selenoprotein P like protein |
| 198. | 1403 | 1464 | >gi|6006350|dbj|AB032826.1| Bos taurus selp mRNA for selenoprotein P |
| 199. | 380 | 454 | >gi|73587346|gb|BC103044.1| Bos taurus similar to selenoprotein W; 1; mRNA (cDNA clone IMAGE:7985952) |
| 200. | 1549 | 1615 | >gi|94534945|gb|BC116119.1| Bos taurus selenoprotein N; 1; mRNA (cDNA clone IMAGE:8091454) |
| 201. | 757 | 820 | >gi|151553884|gb|BC149082.1| Bos taurus selenoprotein T; mRNA (cDNA clone MGC:151598 IMAGE:8314281) |
| 202. | 1623 | 1684 | >gi|156631000|ref|NM_174459.3| Bos taurus selenoprotein P; plasma; 1 (SEPP1); mRNA |
| 203. | 763 | 826 | >gi|168480076|ref|NM_001103103.2| Bos taurus selenoprotein T (SELT); mRNA |
| 204. | 2778 | 2844 | >gi|169234650|ref|NM_001114976.1| Bos taurus selenoprotein N; 1 (SEPN1); mRNA |
| 205. | 873 | 955 | >gi|42493188|gb|AY508121.1| Mesocricetus auratus clone 1(10) adrenal gland 15 kDa selenoprotein-like mRNA sequence |
| 206. | 1209 | 1272 | >gi|536927|gb|U13705.1|MMU13705 Mus musculus domesticus C57BL/6J plasma glutathione peroxidase (MUSPGPX) mRNA |

Figure 19J

| | start | end | origin |
|---|---|---|---|
| 207. | 1549 | 1616 | >gi|1495998|emb|X99807.1| M.musculus mRNA for selenoprotein P |
| 208. | 353 | 425 | >gi|2326180|gb|U67890.1|MMU67890 Mus musculus selenoprotein W (SelW) mRNA |
| 209. | 356 | 428 | >gi|2384722|gb|AF015284.1|AF015284 Mus musculus selenoprotein W (mSelW) mRNA |
| 210. | 5502 | 5565 | >gi|4206102|gb|AF096875.1|AF096875 Mus musculus type 2 deiodinase mRNA |
| 211. | 461 | 524 | >gi|6470252|gb|AF195142.1|AF195142 Mus musculus selenoprotein R mRNA |
| 212. | 354 | 426 | >gi|8995996|gb|AF241527.2|AF241527 Mus musculus selenoprotein W mRNA |
| 213. | 1284 | 1364 | >gi|11139619|gb|AF288740.1|AF288740 Mus musculus 15 kDa selenoprotein (Sep15) mRNA |
| 214. | 1489 | 1556 | >gi|12805068|gb|BC001991.1| Mus musculus selenoprotein P; plasma; 1; mRNA (cDNA clone MGC:5722 IMAGE:3486761) |
| 215. | 446 | 509 | >gi|12832246|dbj|AK002339.1| Mus musculus adult male kidney cDNA; RIKEN full-length enriched library; clone:0610008J12 product:selenoprotein R; full insert sequence |
| 216. | 1488 | 1555 | >gi|12832443|dbj|AK002450.1| Mus musculus adult male kidney cDNA; RIKEN full-length enriched library; clone:0610010C08 product:selenoprotein P; plasma; 1; full insert sequence |
| 217. | 445 | 508 | >gi|12832793|dbj|AK002652.1| Mus musculus adult male kidney cDNA; RIKEN full-length enriched library; clone:0610020P24 product:selenoprotein R; full insert sequence |
| 218. | 377 | 449 | >gi|12833170|dbj|AK002870.1| Mus musculus adult male kidney cDNA; RIKEN full-length enriched library; clone:0610040L01 product:selenoprotein W; muscle 1; full insert sequence |
| 219. | 818 | 881 | >gi|12833567|dbj|AK003112.1| Mus musculus adult male heart cDNA; RIKEN full-length enriched library; clone:1010001D24 product:selenoprotein R; full insert sequence |
| 220. | 446 | 509 | >gi|12834402|dbj|AK003624.1| Mus musculus 18-day embryo whole body cDNA; RIKEN full-length enriched library; clone:1110012E09 product:selenoprotein R; full insert sequence |
| 221. | 1191 | 1257 | >gi|12834716|dbj|AK003819.1| Mus musculus 18-day embryo whole body cDNA; RIKEN full-length enriched library; clone:1110019I12 product:selenoprotein N; 1; full insert sequence |
| 222. | 691 | 753 | >gi|12850128|dbj|AK013022.1| Mus musculus 10; 11 days embryo whole body cDNA; RIKEN full-length enriched library; clone:2810407C02 product:Selenoprotein T homolog [Homo sapiens]; full insert sequence |
| 223. | 1051 | 1131 | >gi|12860998|dbj|AK020419.1| Mus musculus 12 days embryo embryonic body between diaphragm region and neck cDNA; RIKEN full-length enriched library; clone:9430015P09 product:selenoprotein; full insert sequence |
| 224. | 834 | 914 | >gi|14714679|gb|BC010481.1| Mus musculus selenoprotein; mRNA (cDNA clone IMAGE:3482046); partial cds |
| 225. | 835 | 896 | >gi|14971094|gb|AF274027.1|AF274027 Mus musculus phospholipid hydroperoxide glutathione peroxidase mRNA; alternatively spliced |

Figure 19K

| | start | end | origin |
|---|---|---|---|
| 226. | 1052 | 1132 | >gi|18044683|gb|BC019792.1| Mus musculus selenoprotein; mRNA (cDNA clone MGC:30351 IMAGE:5003585) |
| 227. | 675 | 737 | >gi|18044794|gb|BC019970.1| Mus musculus RIKEN cDNA 2810407C02 gene; mRNA (cDNA clone MGC:28960 IMAGE:4458171) |
| 228. | 413 | 479 | >gi|18490560|gb|BC022585.1| Mus musculus selenoprotein N; 1; mRNA (cDNA clone IMAGE:4036667); partial cds |
| 229. | 603 | 665 | >gi|24416470|gb|BC038867.1| Mus musculus RIKEN cDNA 2810407C02 gene; mRNA (cDNA clone MGC:47969 IMAGE:1547418) |
| 230. | 371 | 443 | >gi|26080737|dbj|AK028124.1| Mus musculus adult male stomach cDNA; RIKEN full-length enriched library; clone:2210014P11 product:selenoprotein W; muscle 1; full insert sequence |
| 231. | 704 | 766 | >gi|26083058|dbj|AK032838.1| Mus musculus 12 days embryo male wolffian duct includes surrounding region cDNA; RIKEN full-length enriched library; clone:6720460L05 product:Selenoprotein T homolog [Homo sapiens]; full insert sequence |
| 232. | 705 | 767 | >gi|26092548|dbj|AK047958.1| Mus musculus 16 days embryo head cDNA; RIKEN full-length enriched library; clone:C130023K05 product:Selenoprotein T homolog [Homo sapiens]; full insert sequence |
| 233. | 1488 | 1555 | >gi|26097259|dbj|AK077265.1| Mus musculus 11 days pregnant adult female ovary and uterus cDNA; RIKEN full-length enriched library; clone:5031434C21 product:selenoprotein P; plasma; 1; full insert sequence |
| 234. | 1314 | 1380 | >gi|27693985|gb|BC043665.1| Mus musculus selenoprotein N; 1; mRNA (cDNA clone IMAGE:5012596) |
| 235. | 363 | 435 | >gi|30931041|gb|BC052719.1| Mus musculus selenoprotein W; muscle 1; mRNA (cDNA clone MGC:63277 IMAGE:6814242) |
| 236. | 1487 | 1554 | >gi|74139323|dbj|AK169011.1| Mus musculus 17 days pregnant adult female amnion cDNA; RIKEN full-length enriched library; clone:I920074D12 product:selenoprotein P; plasma; 1; full insert sequence |
| 237. | 1487 | 1554 | >gi|74139599|dbj|AK169158.1| Mus musculus 17 days pregnant adult female amnion cDNA; RIKEN full-length enriched library; clone:I920086D06 product:selenoprotein P; plasma; 1; full insert sequence |
| 238. | 1488 | 1555 | >gi|74142101|dbj|AK169362.1| Mus musculus 17 days pregnant adult female amnion cDNA; RIKEN full-length enriched library; clone:I920192G15 product:selenoprotein P; plasma; 1; full insert sequence |
| 239. | 1488 | 1555 | >gi|74145110|dbj|AK146774.1| Mus musculus 17 days pregnant adult female amnion cDNA; RIKEN full-length enriched library; clone:I920052L16 product:selenoprotein P; plasma; 1; full insert sequence |
| 240. | 615 | 677 | >gi|74145117|dbj|AK146778.1| Mus musculus 17 days embryo kidney cDNA; RIKEN full-length enriched library; clone:I920054H06 product:Similar to selenoprotein T (2810407C02Rik protein) homolog [Mus musculus]; full insert sequence |

Figure 19L

| | start | end | origin |
|---|---|---|---|
| 241. | 1063 | 1143 | >gi|74186693|dbj|AK159085.1| Mus musculus osteoclast-like cell cDNA; RIKEN full-length enriched library; clone:I420001C10 product:selenoprotein; full insert sequence |
| 242. | 1488 | 1555 | >gi|74192878|dbj|AK159269.1| Mus musculus osteoclast-like cell cDNA; RIKEN full-length enriched library; clone:I420013J02 product:selenoprotein P; plasma; 1; full insert sequence |
| 243. | 1045 | 1125 | >gi|74196906|dbj|AK159353.1| Mus musculus osteoclast-like cell cDNA; RIKEN full-length enriched library; clone:I420017N22 product:selenoprotein; full insert sequence |
| 244. | 1489 | 1556 | >gi|74197218|dbj|AK159524.1| Mus musculus osteoclast-like cell cDNA; RIKEN full-length enriched library; clone:I420022P13 product:selenoprotein P; plasma; 1; full insert sequence |
| 245. | 1488 | 1555 | >gi|74198357|dbj|AK167611.1| Mus musculus 15 days pregnant adult female placenta cDNA; RIKEN full-length enriched library; clone:I530025B11 product:selenoprotein P; plasma; 1; full insert sequence |
| 246. | 1485 | 1552 | >gi|74204794|dbj|AK159894.1| Mus musculus osteoclast-like cell cDNA; RIKEN full-length enriched library; clone:I420037A20 product:selenoprotein P; plasma; 1; full insert sequence |
| 247. | 1489 | 1556 | >gi|74204825|dbj|AK159911.1| Mus musculus osteoclast-like cell cDNA; RIKEN full-length enriched library; clone:I420037J18 product:selenoprotein P; plasma; 1; full insert sequence |
| 248. | 1488 | 1555 | >gi|74213352|dbj|AK159935.1| Mus musculus osteoclast-like cell cDNA; RIKEN full-length enriched library; clone:I420038L13 product:selenoprotein P; plasma; 1; full insert sequence |
| 249. | 1157 | 1229 | >gi|74213714|dbj|AK077113.2| Mus musculus adult male testis cDNA; RIKEN full-length enriched library; clone:4933406N18 product:Adult male testis cDNA; RIKEN full-length enriched library; clone:4933406N18 product:weakly similar to selenoprotein W; full insert sequence |
| 250. | 1485 | 1552 | >gi|74214220|dbj|AK168463.1| Mus musculus 17 days pregnant adult female amnion cDNA; RIKEN full-length enriched library; clone:I920024H22 product:selenoprotein P; plasma; 1; full insert sequence |
| 251. | 1485 | 1552 | >gi|74214433|dbj|AK168583.1| Mus musculus 17 days pregnant adult female amnion cDNA; RIKEN full-length enriched library; clone:I920036P08 product:selenoprotein P; plasma; 1; full insert sequence |
| 252. | 1488 | 1555 | >gi|74215929|dbj|AK148623.1| Mus musculus 2 days neonate sympathetic ganglion cDNA; RIKEN full-length enriched library; clone:7120425M02 product:selenoprotein P; plasma; 1; full insert sequence |
| 253. | 1488 | 1555 | >gi|74219803|dbj|AK168631.1| Mus musculus 17 days pregnant adult female amnion cDNA; RIKEN full-length enriched library; clone:I920040D13 product:selenoprotein P; plasma; 1; full insert sequence |
| 254. | 1488 | 1555 | >gi|74220015|dbj|AK168747.1| Mus musculus 17 days pregnant adult female amnion cDNA; RIKEN full-length enriched library; clone:I920049J07 product:selenoprotein P; plasma; 1; full insert sequence |

Figure 19M

| | start | end | origin |
|---|---|---|---|
| 255. | 1488 | 1555 | >gi\|74223204\|dbj\|AK168926.1\| Mus musculus 17 days pregnant adult female amnion cDNA; RIKEN full-length enriched library; clone:I920065H09 product:selenoprotein P; plasma; 1; full insert sequence |
| 256. | 1971 | 2033 | >gi\|110224441\|ref\|NM_001042513.1\| Mus musculus thioredoxin reductase 1 (Txnrd1); transcript variant 2; mRNA |
| 257. | 1864 | 1926 | >gi\|110224443\|ref\|NM_015762.2\| Mus musculus thioredoxin reductase 1 (Txnrd1); transcript variant 3; mRNA |
| 258. | 2059 | 2121 | >gi\|110224444\|ref\|NM_001042514.1\| Mus musculus thioredoxin reductase 1 (Txnrd1); transcript variant 4; mRNA |
| 259. | 2188 | 2250 | >gi\|110224446\|ref\|NM_001042523.1\| Mus musculus thioredoxin reductase 1 (Txnrd1); transcript variant 1; mRNA |
| 260. | 1489 | 1556 | >gi\|110735407\|ref\|NM_001042613.1\| Mus musculus selenoprotein P; plasma; 1 (Sepp1); transcript variant 2; mRNA |
| 261. | 1506 | 1573 | >gi\|110735409\|ref\|NM_009155.3\| Mus musculus selenoprotein P; plasma; 1 (Sepp1); transcript variant 1; mRNA |
| 262. | 1572 | 1639 | >gi\|110735410\|ref\|NM_001042614.1\| Mus musculus selenoprotein P; plasma; 1 (Sepp1); transcript variant 3; mRNA |
| 263. | 401 | 473 | >gi\|110735412\|ref\|NM_009156.2\| Mus musculus selenoprotein W; muscle 1 (Sepw1); mRNA |
| 264. | 1336 | 1416 | >gi\|110825968\|ref\|NM_053102.2\| Mus musculus selenoprotein (Sep15); mRNA |
| 265. | 486 | 549 | >gi\|110832840\|ref\|NM_013759.2\| Mus musculus selenoprotein X 1 (Sepx1); mRNA |
| 266. | 2627 | 2693 | >gi\|111118963\|ref\|NM_029100.2\| Mus musculus selenoprotein N; 1 (Sepn1); mRNA |
| 267. | 2562 | 2631 | >gi\|111119004\|ref\|NM_027652.2\| Mus musculus DNA segment; Chr 5; Wayne State University 178; expressed (D5Wsu178e); mRNA |
| 268. | 1104 | 1176 | >gi\|111159468\|ref\|NM_175033.3\| Mus musculus cDNA sequence BC089491 (BC089491); mRNA |
| 269. | 693 | 755 | >gi\|124376071\|gb\|BC132453.1\| Mus musculus RIKEN cDNA 2810407C02 gene; mRNA (cDNA clone MGC:164084 IMAGE:40130730) |
| 270. | 5504 | 5567 | >gi\|132566530\|ref\|NM_010050.2\| Mus musculus deiodinase; iodothyronine; type II (Dio2); mRNA |
| 271. | 2007 | 2076 | >gi\|142976633\|ref\|NM_009266.3\| Mus musculus selenophosphate synthetase 2 (Sephs2); mRNA |
| 272. | 727 | 789 | >gi\|143770877\|ref\|NM_001040396.2\| Mus musculus RIKEN cDNA 2810407C02 gene (2810407C02Rik); mRNA |
| 273. | 486 | 549 | >gi\|146141252\|gb\|BC090646.1\| Mus musculus selenoprotein X 1; mRNA (cDNA clone MGC:116594 IMAGE:30946285) |
| 274. | 693 | 755 | >gi\|187951946\|gb\|BC138424.1\| Mus musculus RIKEN cDNA 2810407C02 gene; mRNA (cDNA clone MGC:170049 IMAGE:8861444) |
| 275. | 450 | 513 | >gi\|187954730\|gb\|BC141146.1\| Mus musculus selenoprotein X 1; mRNA (cDNA clone MGC:176107 IMAGE:9055758) |
| 276. | 1463 | 1530 | >gi\|206893\|gb\|M63574.1\|RATSELENOP Rat selenoprotein P mRNA |

Figure 19N

| | start | end | origin |
|---|---|---|---|
| 277. | 361 | 434 | >gi|984811|gb|U25264.1|RNU25264 Rattus norvegicus skeletal muscle selenoprotein W (SelW) mRNA |
| 278. | 1484 | 1551 | >gi|1020410|dbj|D25221.1| Rattus norvegicus mRNA for selenoprotein P |
| 279. | 1093 | 1173 | >gi|38014584|gb|BC060547.1| Rattus norvegicus selenoprotein; mRNA (cDNA clone MGC:72709 IMAGE:6921948) |
| 280. | 1492 | 1559 | >gi|47939024|gb|BC072539.1| Rattus norvegicus selenoprotein P; plasma; 1; mRNA (cDNA clone MGC:91714 IMAGE:7104195) |
| 281. | 597 | 659 | >gi|56269771|gb|BC086953.1| Rattus norvegicus selenoprotein T; mRNA (cDNA clone MGC:109481 IMAGE:7321890) |
| 282. | 370 | 444 | >gi|56388784|gb|BC087625.1| Rattus norvegicus selenoprotein W; muscle 1; mRNA (cDNA clone MGC:105482 IMAGE:7316562) |
| 283. | 441 | 503 | >gi|56971229|gb|BC088086.1| Rattus norvegicus selenoprotein K; mRNA (cDNA clone MGC:108512 IMAGE:7326199) |
| 284. | 457 | 521 | >gi|62871704|gb|BC094309.1| Rattus norvegicus selenoprotein X; 1; mRNA (cDNA clone MGC:105753 IMAGE:7316479) |
| 285. | 703 | 765 | >gi|66393088|gb|AY995234.1| Rattus norvegicus selenoprotein T (Selt) mRNA |
| 286. | 1966 | 2026 | >gi|78191794|ref|NM_031614.2| Rattus norvegicus thioredoxin reductase 1 (Txnrd1); mRNA |
| 287. | 825 | 886 | >gi|90903228|ref|NM_001039849.1| Rattus norvegicus glutathione peroxidase 4 (Gpx4); transcript variant 2; mRNA |
| 288. | 723 | 784 | >gi|90903248|ref|NM_017165.2| Rattus norvegicus glutathione peroxidase 4 (Gpx4); transcript variant 1; mRNA |
| 289. | 484 | 548 | >gi|109490337|ref|XM_001058492.1| PREDICTED: Rattus norvegicus similar to Methionine-R-sulfoxide reductase (Selenoprotein X 1) (Selenoprotein R) (LOC681802); mRNA |
| 290. | 497 | 559 | >gi|111119007|ref|NM_207589.3| Rattus norvegicus selenoprotein K (Selk); mRNA |
| 291. | 1344 | 1424 | >gi|111494224|ref|NM_133297.2| Rattus norvegicus selenoprotein (Sep15); mRNA |
| 292. | 703 | 765 | >gi|142976606|ref|NM_001014253.2| Rattus norvegicus selenoprotein T (Selt); mRNA |
| 293. | 1503 | 1570 | >gi|144953872|ref|NM_019192.2| Rattus norvegicus selenoprotein P; plasma; 1 (Sepp1); transcript variant 1; mRNA |
| 294. | 1575 | 1642 | >gi|144953873|ref|NM_001083911.1| Rattus norvegicus selenoprotein P; plasma; 1 (Sepp1); transcript variant 2; mRNA |
| 295. | 467 | 531 | >gi|146229349|ref|NM_001044285.2| Rattus norvegicus selenoprotein X; 1 (Sepx1); mRNA |
| 296. | 949 | 1015 | >gi|165971290|gb|BC158767.1| Rattus norvegicus similar to selenoprotein V; mRNA (cDNA clone IMAGE:7115221); partial cds |
| 297. | 2501 | 2570 | >gi|195540096|gb|BC168235.1| Rattus norvegicus selenoprotein I; mRNA (cDNA clone MGC:188326 IMAGE:7444430) |
| 298. | 2501 | 2570 | >gi|197927190|ref|NM_001134754.1| Rattus norvegicus selenoprotein I (Seli); mRNA |
| 299. | 394 | 468 | >gi|218563681|ref|NM_013027.3| Rattus norvegicus selenoprotein W; 1 (Sepw1); mRNA |

Figure 19O

| | start | end | origin |
|---|---|---|---|
| 300. | 642 | 706 | >gi|126338101|ref|XR_030184.1| PREDICTED: Monodelphis domestica similar to selenoprotein T (LOC100011851); mRNA |
| 301. | 506 | 571 | >gi|222784032|gb|EZ012690.1| TSA: Acropora millepora SeqIndex14935; mRNA sequence |
| 302. | 449 | 517 | >gi|222789739|gb|EZ018171.1| TSA: Acropora millepora SeqIndex2569; mRNA sequence |
| 303. | 654 | 716 | >gi|222814235|gb|EZ042623.1| TSA: Acropora millepora SeqIndex8495; mRNA sequence |
| 304. | 421 | 489 | >gi|76158229|gb|DQ214826.1| Taeniopygia guttata clone 0061P0012D01 putative selenoprotein K variant 2 mRNA |
| 305. | 425 | 493 | >gi|76158230|gb|DQ214827.1| Taeniopygia guttata clone 0064P0014E11 putative selenoprotein K variant 1 mRNA |
| 306. | 436 | 504 | >gi|76158231|gb|DQ214828.1| Taeniopygia guttata clone 0058P0060C02 putative selenoprotein K variant 1-like mRNA; complete sequence |
| 307. | 434 | 502 | >gi|76158232|gb|DQ214829.1| Taeniopygia guttata clone 0058P0030A04 putative selenoprotein K variant 1 mRNA |
| 308. | 411 | 479 | >gi|76158233|gb|DQ214830.1| Taeniopygia guttata clone 0058P0047D11 putative selenoprotein K variant 2 mRNA |
| 309. | 428 | 496 | >gi|76158235|gb|DQ214832.1| Taeniopygia guttata clone 0058P0049C10 putative selenoprotein K variant 1 mRNA |
| 310. | 702 | 770 | >gi|76159469|gb|DQ216051.1| Taeniopygia guttata clone 0063P0009H04 putative selenoprotein T variant 1 mRNA |
| 311. | 712 | 780 | >gi|76159471|gb|DQ216052.1| Taeniopygia guttata clone 0064P0014B06 putative selenoprotein T variant 1 mRNA |
| 312. | 555 | 623 | >gi|76159472|gb|DQ216053.1| Taeniopygia guttata clone 0058P0039H06 putative selenoprotein T variant 1 mRNA |
| 313. | 721 | 789 | >gi|76159473|gb|DQ216054.1| Taeniopygia guttata clone 0064P0018H06 putative selenoprotein T variant 1 mRNA |
| 314. | 434 | 502 | >gi|120431712|gb|EF191716.1| Taeniopygia guttata clone 0062P0004D05 putative selenoprotein K variant 2 mRNA |
| 315. | 699 | 767 | >gi|224061157|ref|XM_002189242.1| PREDICTED: Taeniopygia guttata selenoprotein T-like (LOC100190446); mRNA |
| 316. | 428 | 496 | >gi|224066043|ref|XM_002196855.1| PREDICTED: Taeniopygia guttata selenoprotein K-like (LOC100190312); mRNA |

Figure 22

>NC_004102(positions 44-354), Hepatitis C virus, full IRES element
**CCTGTGAGGAACTACTGTCTTCACGCAGAAAGCGTCTAGCCATGGCGTTAGTATGAGTGTCGTGCAGCCTCC
AGG**acccccccctcccgggagagccatagtggtctgcggaaccggtgagtacaccggaattgccaggacgaccgggtcctttcttggataaacccgctcaatgcctggagatttgggcgtg
cccccgcaagactgctagccgagtagtgttgggtcgcgaaaggccttgtggtactgcctgatagggtgcttgcgagtgccccgggaggtctcgtagaccgtgcaccatgagcacgaatc
(SEQ ID NO:20)

>NC_009823(positions 43-353), Hepatitis C virus genotype 2, full IRES element
**CCTGTGAGGAACTACTGTCTTCACGCAGAAAGCGTCTAGCCATGGCGTTAGTATGAGTGTCGTACAGCCTCC
AGG**cccccccctcccgggagagccatagtggtctgcggaaccggtgagtacaccggaattgccgggaagactgggtcctttcttggataaacccactctatgcccggccatttgggcgtg
cccccgcaagactgctagccgagtagcgttgggttgcgaaaggccttgtggtactgcctgatagggtgcttgcgagtgccccgggaggtctcgtagaccgtgcaccatgagcacaaatc
(SEQ ID NO:21)

>NC_009824(positions 42-352), Hepatitis C virus genotype 3, full IRES element
**CCTGTGAGGAACTTCTGTCTTCACGCGGAAAGCGCCTAGCCATGGCGTTAGTACGAGTGTCGTGCAGCCTCC
AGG**acccccccctcccgggagagccatagtggtctgcggaaccggtgagtacaccggaatcgctggggtgaccgggtcctttcttggagcaacccgctcaatacccagaaatttgggcgt
gcccccgcgagatcactagccgagtagtgttgggtcgcgaaaggccttgtggtactgcctgatagggtgcttgcgagtgccccgggaggtctcgtagaccgtgcaacatgagcacacttc
(SEQ ID NO:22)

>NC_002657(positions 69-386), Classical swine fever virus, full IRES element
TCCCTCCAGCGACGGCCGAACTGGGCTAGCCATGCCCACAGTAGGACTAGCAAACGGAGGGActagccgtagtggcga
gctccctgggtggtctaagtcctgagtacaggacagtcgtcagtagttcgacgtgagcagaagcccacctcgagatgctatgtggacgagggcatgcccaagacacaccttaaccctagcgg
gggtcgctagggtgaaatcacaccacgtgatgggagtacgacctgatagggcgctgcagaggcccactattaggctagtataaaaatctctgctgtacatggcacatggagttgaatc (SEQ
ID NO:23)

>NC_001461(positions 76-399), Bovine viral diarrhea virus 1, full IRES element
CCCTCTCAGCGAAGGCCGAAAAGAGGCTAGCCATGCCCTTAGTAGGACTAGCATAATGAGGGGGGtagcaacagtg
gtgagttcgttggatggcttaagccctgagtacagggtagtcgtcagtggttcgacgccttggaataaaggtctcgagatgccacgtggacgagggcatgcccaaagcacatcttaacctgag
cgggggtcgcccaggtaaaagcagttttaaccgactgttacgaatacagcctgatagggtgctgcagaggcccactgtattgctactaaaaatctctgctgtacatggcacatggagttgatca
(SEQ ID NO:24)

Figure 23

| | 5' stem | internal | 3' stem | start | end | origin |
|---|---|---|---|---|---|---|
| 1. | CCTGTGAGG | AACTACTGTCTTCACGCAG AAAGGCGTCTAGCCATGGC GTTAGTATGAGTGTCGTGC AG | CCTCCAGG | 44 | 118 | >NC_004102|Hepatitis C virus, complete genome |
| 2. | CCTGTGAGG | AACTACTGTCTTCACGCAG AAAGGCGTCTAGCCATGGC GTTAGTATGAGTGTCGTAC AG | CCTCCAGG | 43 | 117

Figure 25A

| | miRBase ID | miRBase Accession | Organism | Parent structure | Mature Micro RNA Sequence |
|---|---|---|---|---|---|
| 1 | hsv1-miR-LAT | MIMAT0004479 | Herpes Simplex Virus 1 | stem-loop | UGGCGGCCCGGCCCGGGCC |
| 2 | hsv1-miR-H1 | MIMAT0003744 | Herpes Simplex Virus 1 | stem-loop | UGGAAGGACGGGAAGUGGAAG |
| 3 | hiv1-miR-H1 | MIMAT0004480 | Human immunodeficiency virus 1 | stem-loop | CCAGGGAGGCGUGCCUGGGC |
| 4 | hiv1-miR-N367 | MIMAT0004478 | Human immunodeficiency virus 1 | stem-loop | ACUGACCUUUGGAUGGUGCUUCAA |
| 5 | ebv-miR-BHRF1-1 | MIMAT0000995 | Epstein Barr virus | stem-loop | UAACCUGAUCAGCCCGGAGUU |
| 6 | ebv-miR-BHRF1-2 | MIMAT0000997 | Epstein Barr virus | stem-loop | UAUCUUUUGCGGCAGAAAUUGA |
| 7 | ebv-miR-BHRF1-2* | MIMAT0000996 | Epstein Barr virus | stem-loop | AAAUUCUGUGCAGCAGAUAGC |
| 8 | ebv-miR-BHRF1-3 | MIMAT0000998 | Epstein Barr virus | stem-loop | UAACGGGAAGUGUGUAAGCACA |
| 9 | ebv-miR-BART1-5p | MIMAT0000999 | Epstein Barr virus | stem-loop | UCUUAGUGGAAGUGACGUGCUGUG |
| 10 | ebv-miR-BART1-3p | MIMAT0003390 | Epstein Barr virus | stem-loop | UAGCACCGCUAUCCACUAUGUC |
| 11 | ebv-miR-BART2-5p | MIMAT0001000 | Epstein Barr virus | stem-loop | UAUUUCUGCAUUCGCCCUUGC |
| 12 | ebv-miR-BART2-3p | MIMAT0004744 | Epstein Barr virus | stem-loop | AAGGAGCGAUUUGGAGAAAAUAAA |
| 13 | ebv-miR-BART3 | MIMAT0003411 | Epstein Barr virus | stem-loop | CGCACCACUAGUCACCAGGUGU |
| 14 | ebv-miR-BART3* | MIMAT0003410 | Epstein Barr virus | stem-loop | ACCUAGUGUUAGUGUUGUGCU |
| 15 | ebv-miR-BART4 | MIMAT0003412 | Epstein Barr virus | stem-loop | GACCUGAUGCUGCUGGUGUGCU |
| 16 | ebv-miR-BART5 | MIMAT0003413 | Epstein Barr virus | stem-loop | CAAGGUGAAUAUAGCUGCCCAUCG |
| 17 | ebv-miR-BART6-5p | MIMAT0003414 | Epstein Barr virus | stem-loop | UAAGGUUGGUCCAAUCCAUAGG |
| 18 | ebv-miR-BART6-3p | MIMAT0003415 | Epstein Barr virus | stem-loop | CGGGGAUCGGACUAGCCUUAGA |
| 19 | ebv-miR-BART7 | MIMAT0003416 | Epstein Barr virus | stem-loop | CAUCAUAGUCCAGUGUCCAGGG |
| 20 | ebv-miR-BART7* | MIMAT0004815 | Epstein Barr virus | stem-loop | CCUGGACCUUGACUAUGAAACA |
| 21 | ebv-miR-BART8 | MIMAT0003417 | Epstein Barr virus | stem-loop | UACGGUUUCCUAGAUUGUACAG |
| 22 | ebv-miR-BART8* | MIMAT0003418 | Epstein Barr virus | stem-loop | GUCACAAUCUAUGGGGUGUAGA |
| 23 | ebv-miR-BART9 | MIMAT0003419 | Epstein Barr virus | stem-loop | UAACACUUCAUGGGUCCCGUAGU |

Figure 25B

| | mirBase ID | mirBase Accession | Organism | Parent structure | Mature Micro RNA Sequence |
|---|---|---|---|---|---|
| 24 | ebv-miR-BART9* | MIMAT0004816 | Epstein Barr virus | stem-loop | UACUGGACCCUGAAUUGGAAAC |
| 25 | ebv-miR-BART10 | MIMAT0003420 | Epstein Barr virus | stem-loop | UACAUAACCAUGGAGUUGGCUG U |
| 26 | ebv-miR-BART10* | MIMAT0004817 | Epstein Barr virus | stem-loop | GCCACUCUUUGGUUCUGUACA |
| 27 | ebv-miR-BART11-5p | MIMAT0003421 | Epstein Barr virus | stem-loop | UCAGACAGUUUGGUGCGUAGU UG |
| 28 | ebv-miR-BART11-3p | MIMAT0003422 | Epstein Barr virus | stem-loop | ACGCACACCAGGCUGACUGCC |
| 29 | ebv-miR-BART12 | MIMAT0003423 | Epstein Barr virus | stem-loop | UCCUGUGGUGUUUGGUGUGGUU |
| 30 | ebv-miR-BART13 | MIMAT0003424 | Epstein Barr virus | stem-loop | UGUAACUUGCCAGGGACGGGUG A |
| 31 | ebv-miR-BART13* | MIMAT0004818 | Epstein Barr virus | stem-loop | AACCGGCUCGUGGCUCGUACAG |
| 32 | ebv-miR-BART14 | MIMAT0003426 | Epstein Barr virus | stem-loop | UAAAUGCUGCAGUAGUAGGGAU |
| 33 | ebv-miR-BART14* | MIMAT0003425 | Epstein Barr virus | stem-loop | UACCCUACGCUGCCGAUUUACA |
| 34 | ebv-miR-BART15 | MIMAT0003713 | Epstein Barr virus | stem-loop | GUCAGUGGUUUUGUUCCUUGA |
| 35 | ebv-miR-BART16 | MIMAT0003714 | Epstein Barr virus | stem-loop | UUAGAUAGAGUGGGUGUGUGCU CU |
| 36 | ebv-miR-BART17-5p | MIMAT0003715 | Epstein Barr virus | stem-loop | UAAGAGGACGCAGGCAUACAAG |
| 37 | ebv-miR-BART17-3p | MIMAT0003716 | Epstein Barr virus | stem-loop | UGUAUGCCUGGUGUCCCCUUAG U |
| 38 | ebv-miR-BART18-5p | MIMAT0003717 | Epstein Barr virus | stem-loop | UCAAGUUCGCACUUCCUAUACA |
| 39 | ebv-miR-BART18-3p | MIMAT0004835 | Epstein Barr virus | stem-loop | UAUCGGAAGUUUGGCUCGUC |
| 40 | ebv-miR-BART19-5p | MIMAT0004836 | Epstein Barr virus | stem-loop | ACAUUCCCGCAAACAUGACAU G |
| 41 | ebv-miR-BART19-3p | MIMAT0003718 | Epstein Barr virus | stem-loop | UUUUGUUUGCUUGGAAUGCU |
| 42 | ebv-miR-BART20-5p | MIMAT0003719 | Epstein Barr virus | stem-loop | UAGCAGGCAUGUCUUCAUUCC |
| 43 | ebv-miR-BART20-3p | MIMAT0003720 | Epstein Barr virus | stem-loop | CAUGAAGGCACAGCCUGUUACC |
| 44 | hcmv-miR-UL22A | MIMAT0001574 | Human cytomegalovirus | stem-loop | UAACUAGCCUUCCCGUGAGA |
| 45 | hcmv-miR-UL22A* | MIMAT0001575 | Human cytomegalovirus | stem-loop | UCACCAGAAUGCUAGUUUGUAG |
| 46 | hcmv-miR-US25-1 | MIMAT0001581 | Human cytomegalovirus | stem-loop | AACCGCUCAGUGGCUCGGACC |
| 47 | hcmv-miR-US25-1* | MIMAT0004755 | Human cytomegalovirus | stem-loop | UCCGAACGCUAGGUCGUUCUC |

Figure 25C

| | mirBase ID | mirBase Accession | Organism | Parent structure | Mature Micro RNA Sequence |
|---|---|---|---|---|---|
| 48 | kshv-miR-K12-10a | MIMAT0002179 | Kaposi sarcoma-associated herpesvirus | stem-loop | UAGUGUUGUCCCCCGAGUGGC |
| 49 | kshv-miR-K12-10b | MIMAT0002180 | Kaposi sarcoma-associated herpesvirus | stem-loop | UGGUGUUGUCCCCCGAGUGGC |
| 50 | kshv-miR-K12-1 | MIMAT0002182 | Kaposi sarcoma-associated herpesvirus | stem-loop | AUUACAGGAAACUGGGUGUAAGC |
| 51 | kshv-miR-K12-2 | MIMAT0002183 | Kaposi sarcoma-associated herpesvirus | stem-loop | AACUGUAGUCCGGGUCGAUCUG |
| 52 | kshv-miR-K12-9 | MIMAT0002185 | Kaposi sarcoma-associated herpesvirus | stem-loop | CUGGGUAUACGCAGCUGCGUAA |
| 53 | kshv-miR-K12-9* | MIMAT0002184 | Kaposi sarcoma-associated herpesvirus | stem-loop | ACCCAGCUGCGUAAACCCCGCU |
| 54 | kshv-miR-K12-8 | MIMAT0002186 | Kaposi sarcoma-associated herpesvirus | stem-loop | UAGGGCGCGACUGAGAGAGCACG |
| 55 | kshv-miR-K12-7 | MIMAT0002187 | Kaposi sarcoma-associated herpesvirus | stem-loop | UGAUCCCAUGUUGCUGGCGCU |
| 56 | kshv-miR-K12-6-5p | MIMAT0002188 | Kaposi sarcoma-associated herpesvirus | stem-loop | CCAGCAGCACCUAAUCCAUCGG |
| 57 | kshv-miR-K12-6-3p | MIMAT0002189 | Kaposi sarcoma-associated herpesvirus | stem-loop | UGAUGGUUUUCGGGCUGUUGAG |
| 58 | kshv-miR-K12-5 | MIMAT0002190 | Kaposi sarcoma-associated herpesvirus | stem-loop | UAGGAUGCCUGGAACUUGCCGG |
| 59 | kshv-miR-K12-4-5p | MIMAT0002191 | Kaposi sarcoma-associated herpesvirus | stem-loop | AGCUAAACCGCAGUACUCUAGG |
| 60 | kshv-miR-K12-4-3p | MIMAT0002192 | Kaposi sarcoma-associated herpesvirus | stem-loop | UAGAAUACUGAGGCCUAGCUGA |
| 61 | kshv-miR-K12-3 | MIMAT0002193 | Kaposi sarcoma-associated herpesvirus | stem-loop | UCACAUUCUGAGGACGGCAGCGA |
| 62 | kshv-miR-K12-3* | MIMAT0002194 | Kaposi sarcoma-associated herpesvirus | stem-loop | UCGCGGUCACAGAAUGUGACA |

Figure 26A

| Family | Description |
|---|---|
| Entero_CRE | Enterovirus cis-acting replication element |
| Telomerase-vert | Vertebrate telomerase RNA |
| Phage_pRNA | Bacteriophage pRNA |
| IRES_HCV | Hepatitis C virus internal ribosome entry site |
| IRES_Aptho | Aphthovirus internal ribosome entry site (IRES) |
| Retro_dr1 | Retrovirus direct repeat 1 (dr1) |
| Corona_pk3 | Coronavirus 3' UTR pseudoknot |
| Tombus_3_IV | Tombusvirus 3' UTR region IV |
| Corona_package | Coronavirus packaging signal |
| Flavi_CRE | Flavivirus 3' UTR cis-acting replication element (CRE) |
| BLV_package | Bovine leukaemia virus RNA packaging signal |
| CTV_rep_sig | Citrus tristeza virus replication signal |
| Rubella_3 | Rubella virus 3' cis-acting element |
| AMV_RNA1_SL | Alfalfa mosaic virus RNA 1 5' UTR stem-loop |
| Tombus_3_III | Tombus virus defective interfering (DI) RNA region 3 |
| Rhino_CRE | Human rhinovirus internal cis-acting regulatory element (CRE) |
| IRES_Picorna | Picornavirus internal ribosome entry site (IRES) |
| Tymo_tRNA-like | Tymovirus/Pomovirus tRNA-like 3' UTR element |
| TAR | Trans-activation response element (TAR) |
| Alfamo_CPB | Alfalfa mosaic virus coat protein binding (CPB) RNA |
| HepC_CRE | Hepatitis C virus (HCV) cis-acting replication element (CRE) |
| BaMV_CRE | Bamboo mosaic potexvirus (BaMV) cis-regulatory element |
| HDV_ribozyme | Hepatitis delta virus ribozyme |
| Hairpin | Hairpin ribozyme |
| IRES_KSHV | Kaposi's sarcoma-associated herpesvirus internal ribosome entry site (IRES) |
| mir-BART1 | mir-BART1 microRNA precursor family |

Figure 26B

| Family | Description |
|---|---|
| mir-BART2 | mir-BART2 microRNA precursor family |
| mir-BHRF1-1 | mir-BHRF1-1 microRNA precursor family |
| mir-BHRF1-2 | mir-BHRF1-2 microRNA precursor family |
| mir-BHRF1-3 | mir-BHRF1-3 microRNA precursor family |
| Tombus_5 | Tombusvirus 5' UTR |
| Gammaretro_CES | Gammaretrovirus core encapsidation signal |
| Pox_AX_element | Poxvirus AX element late mRNA cis-regulatory element |
| IBV_D-RNA | Infectious bronchitis virus D-RNA |
| Entero_5_CRE | Enterovirus 5' cloverleaf cis-acting replication element |
| satBaMV_CRE | Bamboo mosaic virus satellite RNA cis-regulatory element |
| UPSK | UPSK RNA |
| IRES_EBNA | Epstein-Barr virus nuclear antigen (EBNA) IRES |
| Cardiovirus_CRE | Cardiovirus cis-acting replication element (CRE) |
| MPMV_package | Mason-Pfizer monkey virus packaging signal |
| JEV_hairpin | Japanese encephalitis virus (JEV) hairpin structure |
| RSV_PBS | Rous sarcoma virus (RSV) primer binding site (PBS) |
| HCV_SLVII | Hepatitis C virus stem-loop VII |
| Toga_5_CRE | Togavirus 5' plus strand cis-regulatory element |
| HCV_X3 | Hepatitis C virus 3'X element |
| BTE | Luteovirus cap-independent translation element (BTE) |
| SVLPA | Simian virus 40 late polyadenylation signal (SVLPA) |
| Corona_SL-III | Coronavirus SL-III cis-acting replication element (CRE) |
| EAV_LTH | Equine arteritis virus leader TRS hairpin (LTH) |
| Parecho_CRE | Human parechovirus 1 (HPeV1) cis regulatory element (CRE) |
| TCV_H5 | Turnip crinkle virus (TCV) repressor of minus strand synthesis H5 |
| Rota_CRE | Rotavirus cis-acting replication element (CRE) |

Figure 26C

| Family | Description |
|---|---|
| TCV_Pr | Turnip crinkle virus (TCV) core promoter hairpin (Pr) |
| s2m | Coronavirus 3' stem-loop II-like motif (s2m) |
| Entero_OriR | Enteroviral 3' UTR element |
| IRES_Cripavirus | Cripavirus internal ribosome entry site (IRES) |
| Corona_FSE | Coronavirus frameshifting stimulation element |
| Tombus_IRE | Tombusvirus internal replication element (IRE) |
| VA | VA RNA |
| Flavivirus_DB | Flavivirus DB element |
| HepE_CRE | Hepatitis E virus cis-reactive element |
| PVX_3 | Potato virus X cis-acting regulatory element |
| IRES_Tobamo | Tobamovirus internal ribosome entry site (IRES) |
| IRES_HepA | Hepatitis A virus internal ribosome entry site (IRES) |
| IRES_Pesti | Pestivirus internal ribosome entry site (IRES) |
| cHP | flavivirus capsid hairpin cHP |
| HCV_ARF_SL | Hepatitis C alternative reading frame stem-loop |
| CPEB3_ribozyme | Mammalian CPEB3 ribozyme |

Figure 27A

| Protein | Source | Source type | Reference |
|---|---|---|---|
| PB1-F2 | Influenza A | virus | Chen et al. (2002) Nat. Med. 7:1306-1312. |
| p13II | human T-lymphotopic virus (HTLV) | virus | Ciminale V. et al. (1999) Oncogene 18(31):4505-4514. |
| Apoptin (VP3) | Chicken Anemia Virus | virus | Teodoro et al. (1997) J. Virol. 71(3):1739-1746. |
| Core protein | Hepatitis C | virus | Zhu, N. et al. (1998). J. Virol. 72:3691-3697. |
| Orf C protein | Walleye dermal sarcoma virus (WDSV) | virus | Nudson W. A. et al. (2003) J. Gen. Virol. 84(Pt 2):375-381. |
| Erns | Pestivirus | virus | Bruschke, C. J. et al. (1997). J. Virol. 71:6692-6696. |
| E1 | Sindbis virus | virus | Jan, J. T. et al. (2000). J. Virol. 74:6425-6432.; Joe, A. K. et al. (1998). J. Virol. 72:3935-3943. |
| E2 | Sindbis virus | virus | Jan, J. T. et al. (2000). J. Virol. 74:6425-6432.; Joe, A. K. et al. (1998). J. Virol. 72:3935-3943. |
| ADP (adenovirus death protein) | Human Adenovirus | virus | Tollefson A. E. et al. (1996) Virology 220(1):152-162. |
| E1A | Human Adenovirus | virus | Teodoro et al. (1997) J. Virol. 71(3):1739-1746. |
| E4 | Human Adenovirus | virus | Teodoro et al. (1997) J. Virol. 71(3):1739-1746. |
| E4orf4 | Human Adenovirus | virus | Livne A, et al. (2001) J. Virol. 75(2):789-798. |
| E3 | Human Adenovirus | virus | Teodoro et al. (1997) J. Virol. 71(3):1739-1746. |
| Large T | SV40 | virus | Teodoro et al. (1997) J. Virol. 71(3):1739-1746. |
| E2 | Human Pappilomavirus | virus | Webster, K. et al. (2000). J. Biol. Chem. 275:87-94. |
| E7 | Human Pappilomavirus | virus | Teodoro et al. (1997) J. Virol. 71(3):1739-1746. |
| Tax | Human T-cell leukemia virus type 1 | virus | Teodoro et al. (1997) J. Virol. 71(3):1739-1746. |
| Tat | Simian Immunodeficiency Virus | virus | Teodoro et al. (1997) J. Virol. 71(3):1739-1746. |
| NSP | Parvovirus | virus | Teodoro et al. (1997) J. Virol. 71(3):1739-1746. |

Figure 27B

| Protein | Source | Source type | Reference |
|---|---|---|---|
| ORF5 (p25) | Porcine Reproductive and Respiratory Syndrome virus | virus | Teod minimum free energy of
-4.60 kcal/mol

MFE = - 3.60 kcal/mol target (hcmv-mir-us25-2-3p )

Figure 50
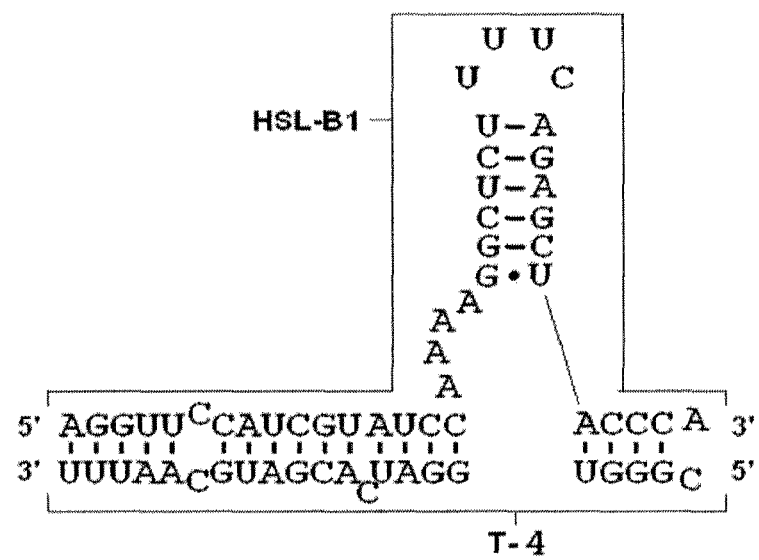
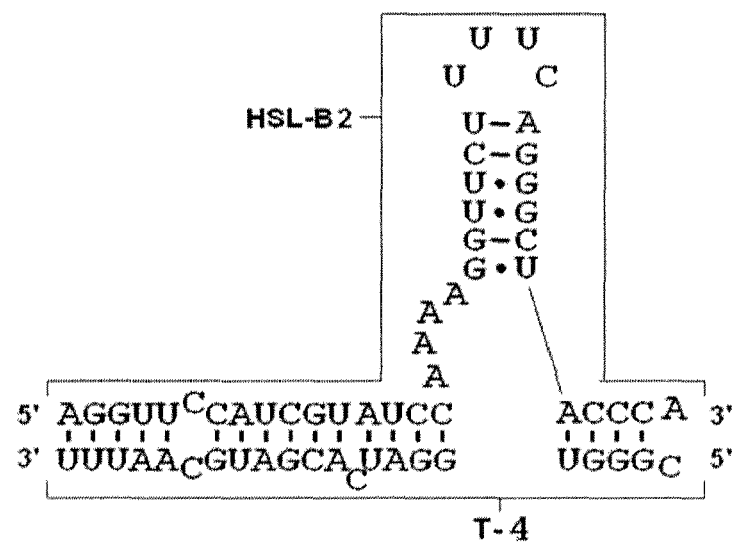

Figure 51
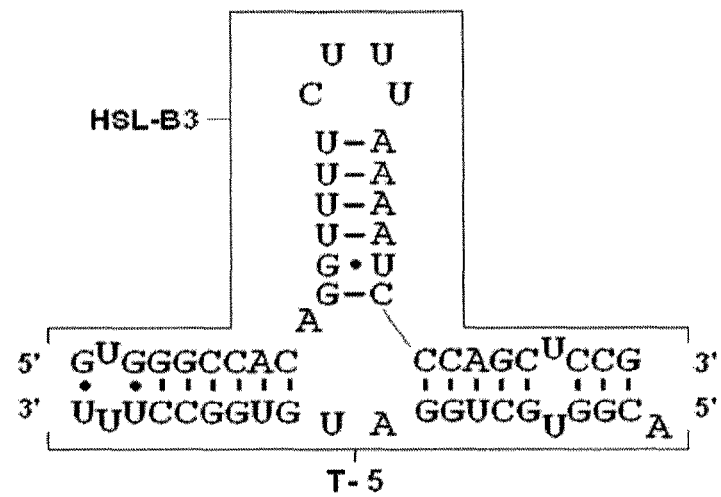
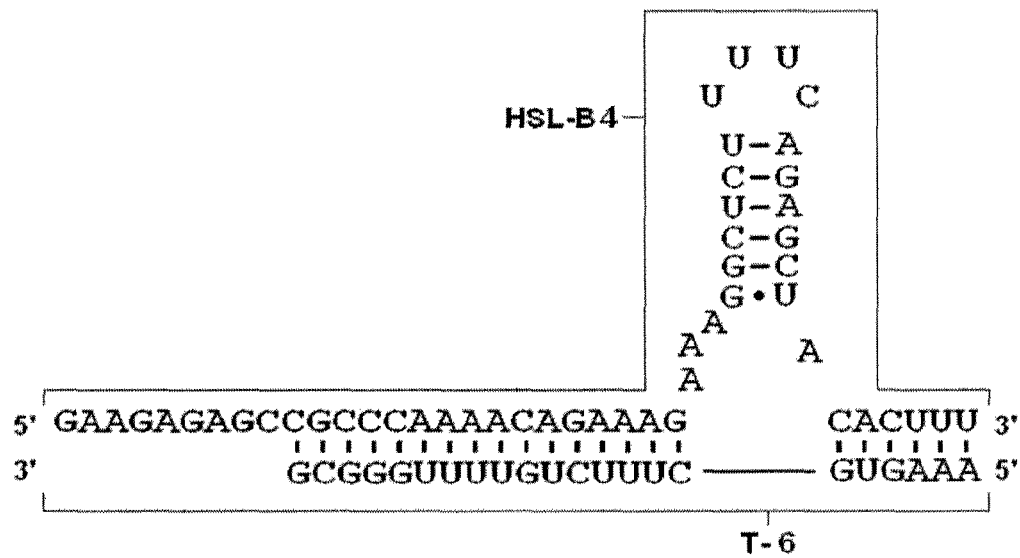

Figure 53

| | | | | Structure: H U<br>H H<br>U-A<br>Y-R<br>Y-R<br>Y-R<br>G-C<br>G-C<br>NNNNN NN |
|---|---|---|---|---|
| Name | UTRdb ID* | UTR Length | HSL Start | Sequence |
| STLAB_C01_1 | 3HSA054868 | 1955 | 23 | ccaaaggctctttcagagccac |
| STLAB_C01_2 | 3HSA041812 | 1251 | 39 | ccaaaggctcttttcagagcccc |
| STLAB_C01_3 | 3HSA027954 | 91 | 32 | ccaaaggctcttttaagagccac |
| STLAB_C01_4 | 3HSA076665 | 1104 | 25 | tcaaaggctcttttcagagccac |
| STLAB_C01_5 | 3HSA034695 | 87 | 23 | caaaaggctcttttcagagccac |
| STLAB_C01_6 | 3HSA079397 | 838 | 27 | ccaaaggctcttttcagagccac |
| STLAB_C01_7 | 3HSA082131 | 1146 | 45 | acaaaggcccttttaagggccac |
| STLAB_C01_8 | 3HSA047510 | 1225 | 35 | caaaaggctcttttcagagccac |
| STLAB_C01_9 | 3HSA083260 | 917 | 29 | aaaaaggcccttttagggcccc |
| STLAB_C01_10 | 3HSA083338 | 1844 | 46 | ccaacggctcttttcagggccac |
| STLAB_C01_11 | 3HSA083659 | 85 | 18 | taaaaggcccttttcagggccac |
| STLAB_C01_12 | 3HSA048427 | 1211 | 39 | ccaaaggctcttttcagagcccc |
| STLAB_C01_13 | 3HSA049188 | 136 | 63 | caaaaggctcttttcagagccac |
| STLAB_C01_14 | 3HSA094501 | 1592 | 29 | caaaaggcccttttcagggcccc |
| STLAB_C01_15 | 3HSA086570 | 106 | 31 | ccaaaggctcttttcagagccaa |
| STLAB_C01_16 | 3HSA086915 | 694 | 33 | caaaaggctcttttcagagccac |
| STLAB_C01_17 | 3HSA087013 | 941 | 31 | ccaaaggctcttttcagagccaa |
| STLAB_C01_18 | 3HSA089561 | 1896 | 26 | ccaaaggctcttctcagagccaa |
| STLAB_C01_19 | 3HSA091341 | 54 | 27 | gcaaaggctcttttcagagccac |
| STLAB_C01_20 | 3HSA058723 | 82 | 22 | ccaaaggctcttttcagagccac |
| STLAB_C01_21 | 3HSA058724 | 99 | 40 | ccaaaggctcttttcagagccac |
| STLAB_C01_22 | 3HSA014418 | 1827 | 46 | ccaacggctcttttcagggccac |
| STLAB_C01_23 | 3HSA004810 | 1080 | 45 | acaaaggcccttttaagggccac |
| STLAB_C01_24 | 3HSA010018 | 1176 | 39 | ccaaaggctcttttcagagcccc |
| STLAB_C01_25 | 5HSA066417 | 618 | 271 | acccaggctttatttagggccaa |

*UTRdb accessible at www.ba.itb.cnr.it/srs7bin/cgi-bin/wgetz?-page+top

Figure 54

| | mirBase ID | mirBase Accession | Organism | Parent structure | Mature Micro RNA Sequence |
|---|---|---|---|---|---|
| 1 | sv40-miR-S1-5p | MIMAT0003344 | Simian virus 40 | miR-S1 stem-loop | UGAGGGGCCUGAAAUGAGCCUU |
| 2 | ppt-miR319c | MIMAT0003135 | Physcomitrella patens | miR319c stem-loop | CUUGGACUGAAGGGAGCUCCC |
| 3 | ppt-miR319d | MIMAT0003136 | Physcomitrella patens | miR319d stem-loop | CUUGGACUGAAGGGAGCUCCC |
| 4 | ptc-miR319i | MIMAT0002010 | Populus trichocarpa | miR319i stem-loop | CUUGGGCUGAAGGGAGCUCCC |
| 5 | hsa-miR-518c* | MIMAT0002847 | Homo sapiens | miR-518c stem-loop | UCUCUGGAGGGAAGCACUUUCUG |
| 6 | ppt-miR319b | MIMAT0003134 | Physcomitrella patens | miR319b stem-loop | CUUGGACUGAAGGGAGCUCC |
| 7 | ppt-miR319a | MIMAT0003133 | Physcomitrella patens | miR319a stem-loop | CUUGGACUGAAGGGAGCUCC |
| 8 | ath-miR319c | MIMAT0001016 | Arabidopsis thaliana | miR319c stem-loop | UUUGGACUGAAGGGAGCUCCU |
| 9 | ath-miR319b | MIMAT0000512 | Arabidopsis thaliana | miR319b stem-loop | UUGGACUGAAGGGAGCUCCU |
| 10 | ptc-miR319f | MIMAT0002007 | Populus trichocarpa | miR319f stem-loop | UUUGGACUGAAGGGAGCUCCU |
| 11 | hcmv-mir-US33 | MI0001686 | Human cytomegalovirus | miR-US33 stem-loop | CACGGUUGAUUGUGCCGGACCGU GGGCGCGACGAAACCACGUCAC GGUCCGAGCACAUCCAAACGUG |
| 12 | ptc-miR319b | MIMAT0002003 | Populus trichocarpa | miR319b stem-loop | UUGGACUGAAGGGAGCUCCC |
| 13 | ame-miR-282 | MIMAT0001484 | Apis mellifera | miR-282 stem-loop | GAUUUAGCCUCUCCUAGGCUUUGU CUGU |
| 14 | ptc-miR319g | MIMAT0002008 | Populus trichocarpa | miR319g stem-loop | UUUGGACUGAAGGGAGCUCCU |
| 15 | gma-miR319a | MIMAT0001684 | Glycine max | miR319a stem-loop | UUUGGACUGAAGGGAGCUCCC |
| 16 | gma-miR319b | MIMAT0001685 | Glycine max | miR319b stem-loop | UUUGGACUGAAGGGAGCUCCC |
| 17 | cel-miR-56* | MIMAT0000027 | Caenorhabditis elegans | miR-56 stem-loop | UGGCGGAUCCAUUUUGGUUGUA |
| 18 | ptc-miR319c | MIMAT0002004 | Populus trichocarpa | miR319c stem-loop | UUUGGACUGAAGGGAGCUCCC |
| 19 | ath-miR319a | MIMAT0000511 | Arabidopsis thaliana | miR319a stem-loop | UUUGGACUGAAGGGAGCUCCU |
| 20 | ptc-miR319h | MIMAT0002009 | Populus trichocarpa | miR319h stem-loop | UUUGGACUGAAGGGAGCUCCU |
| 21 | ptc-miR319d | MIMAT0002005 | Populus trichocarpa | miR319d stem-loop | UUUGGACUGAAGGGAGCUCCU |
| 22 | ptc-miR319e | MIMAT0002006 | Populus trichocarpa | miR319e stem-loop | UUUGGACUGAAGGGAGCUCCU |
| 23 | mtr-miR319 | MIMAT0001653 | Medicago truncatula | miR319 stem-loop | UUUGGACUGAAGGGAGCUCCC |
| 24 | ptc-miR319a | MIMAT0002002 | Populus trichocarpa | miR319a stem-loop | UUUGGACUGAAGGGAGCUCCC |
| 25 | hcmv-miR-UL70-3p | MIMAT0003343 | Human cytomegalovirus | miR-UL70 stem-loop | GGGGAUGGGCUGGCGCGCGG |
| 26 | ath-miR447c | MIMAT0002115 | Arabidopsis thaliana | miR447c stem-loop | UUGGGGACGACAUCUUUUGUUG |
| 27 | dme-miR-306* | MIMAT0000394 | Drosophila melanogaster | miR-306 stem-loop | GGGGUCACUCUGUGCCUGUGC |
| 28 | ptc-miR474c | MIMAT0002066 | Populus trichocarpa | miR474c stem-loop | CAAAGCUGUUGGGUUGGCUGG G |

Figure 56A
tagttattaatgtacgtaaatccctcttaaatcttgtgacctgaaacaggaaatttagtcaccgtatgtaaactgaaaactgcactaaaaataac
aagatccaagttaagcaatttctgacccaaaagacaagttacttcacagacgcctccgatgctgatactttaataaatggactgcctaatgcttt
cctacattctgacaatatattaacactaattttatgtaactcccctacacttatactcctcattcaagggcacatgtaaacttgagtagaaatgattt
ctaatgtcaatgggagggaggtagaagagaaaaaacaaaaaaacaaaaaacccagaagcagcagagacccgtgggtggtttcatacag
gaaacagggtaaggctgcctggctctgcgggacgactcgccagtttgggcacaaagatggagcgtaggaaagaactcacagccgtgtcc
agtcacctacacctggtacaccatgccctgtggccaagtttacgcgtgctaccggctctatcctgttagcttcctcagcaggagaaacagcga
gcaggcccagccgcccggcgacccgcggagtgtcgcaacgacggccgcacgcaaatgaagccaccgagcacgcgcgtcgtgattcg
cgcgttccagggcggcgccggggcgagggagccggtctt atgtaaatgagaggcttctgtccgcgcgctcctattggccacggcgtcag
gacgcgtgtgagccaatgagagcgtcgggcggacaatcgggtctgcgtctatcaaaggg tgaggcgtcggcgccggagtaccgtttcct
ggttgtggccgttcgagatct<u>gatctcgagctcaagcttcgaattctgcagtcgacggtaccgcgggcccgggatccaccggtcgccacca</u>
<u>tggtgagcaagggcgaggagctgttcaccggggtggtgcccatcctggtcgagctggacggcgacgtaaacggccacaagttcagcgtg</u>
<u>tccggcgagggcgagggcgatgccacctacggcaagctgaccctgaagttcatctgcaccaccggcaagctgcccgtgccctggccca</u>
<u>ccctcgtgaccaccctgacctacggcgtgcagtgcttcagccgctaccccgaccacatgaagcagcacgacttcttcaagtccgccatgcc</u>
<u>cgaaggctacgtccaggagcgcaccatcttcttcaaggacgacggcaactacaagacccgcgccgaggtgaagttcgagggcgacacc</u>
<u>ctggtgaaccgcatcgagctgaagggcatcgacttcaaggaggacggcaacatcctggggcacaagctggagtacaactacaacagcca</u>
<u>caacgtctatatcatggccgacaagcagaagaacggcatcaaggtgaacttcaagatccgccacaacatcgaggacggcagcgtgcagc</u>
<u>tcgccgaccactaccagcagaacacccccatcggcgacggccccgtgctgctgcccgacaaccactacctgagcacccagtccgccctg</u>
<u>agcaaagaccccaacgagaagcgcgatcacatgtcctgctggagttcgtgaccgccgccgggatcactctcggcatggacgagctgta</u>
<u>caag</u>aagcttagccatggccttccgccggaggtggaggagcaggatgatggcgcgctgcccatgtcttgtgcccaggagagcgggatgg
accgtcaccctgcagcctgtgcttctgctaggatcaatgtgtagatgcgcggcc*cactgctcgcgtcggcccgcgtctctgtgatataacc
cccgcgagctcccaaaaaggctcttttcagagccacccactgaatcagataaagagttgtgtcacggtagccggtcttggtggcctttcc
tggccctgccccaaaagtaagagtgttcgtgttcctctgcttccttgcccatctgccgtggtttaccctggttagtttagtctgttgtcgcttcttt
ggtttcatgcccttgcctcgcgagcggataacgcggttctcgctgaccgtcccaagcatttagcccctatctgcccacaccttgtcctaca
caacactgtccctcactcagcgtccaccgcctgacccttcccaggactaagactcaactaggacgtctagg*cattctagttgtggtttgtc
caaactcatcaatgtatcttaaggcgtaaattgtaagcgttaatattttgttaaaattcgcgttaaattttttgttaaatcagctcatttttaaccaatag
gccgaaatcggcaaaatccctt ataaatcaaaagaatagaccgagatagggtt gagt gttgtt ccagtttggaacaagagt ccactattaaag
aacgtggactccaacgtcaaagggcgaaaaaccgtctatcagggcgatggcccactacgtgaaccatcaccctaatcaagttttttggggtc
gaggtgccgtaaagcactaaatcggaacc ctaaagggagcccccgatttagagcttgacggggaaagccggcgaacgtggcgagaaag
gaagggaagaaagcgaaaggagcgggcgctagggcgctggcaagtgtagcggtcacgctgcgcgtaaccaccacacccgccgcgctt
aatgcgccgctacagggcgcgtcaggtggcacttttcggggaaatgtgcgcggaacccctatttgtttatttttctaaatacattcaaatatgtat
ccgctcatgagacaataaccctgataaatgcttcaataatattgaaaaaggaagagtcctgaggcggaaagaaccagctgtggaatgtgtgt
cagttagggtgtggaaagtccccaggctccccagcaggcagaagtatgcaaagcatgcatctcaattagtcagcaaccaggtgtggaaag
tccccaggctccccagcaggcagaagtatgcaaagcatgcatctcaattagtcagcaaccatagtcccgcccctaactccgcccatcccgc
ccctaactccgcccagttccgcccattctccgccccatggctgactaattttttttatttatgcagaggccgaggccgcctcggcctctgagcta
ttccagaagtagtgaggaggcttttttggaggcctaggcttttgcaaagatcgatcaagagacaggatgaggatcgtttcgcatgattgaaca
agatggattgcacgcaggttctccggccgcttgggtggagaggctattcggctatgactgggcacaacagacaatcggctgctctgatgcc
gccgtgttccggctgtcagcgcaggggcgcccggttctttttgtcaagaccgacctgtccggtgccctgaatgaactgcaagacgaggcag
cgcggctatcgtggctggccacgacgggcgttccttgcgcagctgtgctcgacgttgtcactgaagcgggaagggactggctgctattgg
gcgaagtgccggggcaggatctcctgtcatctcaccttgctcctgccgagaaagtatccatcatggctgatgcaatgcggcggctgcatac
gcttgatccggctacctgcccattcgaccaccaagcgaaacatcgcatcgagcgagcacgtactcggatggaagccggtcttgtcgatcag
gatgatctggacgaagagcatcaggggctcgcgccagccgaactgttcgccaggctcaaggcgagcatgcccgacggcgaggatctcg
tcgtgacccatggcgatgcctgcttgccgaatatcatggtggaaaatggccgcttttctggattcatcgactgtggccggctgggtgtggcgg
accgctatcaggacatagcgttggctacccgtgatattgctgaagagcttggcggcgaatgggctgaccgcttcctcgtgctttacggtatcg
ccgctcccgattcgcagcgcatcgccttctatcgccttcttgacgagttcttctgagcgggactctggggttcgaaatgaccgaccaagcgac
gcccaacctgccatcacgagatttcgattccaccgccgccttctatgaaaggttgggcttcggaatcgttttccgggacgccggctggatgat

Figure 56B
cctccagcgcggggatctcatgctggagttcttcgcccaccctaggggggaggctaactgaaacacggaaggagacaataccggaaggaa
cccgcgctatgacggcaataaaaagacagaataaaacgcacggtgttgggtcgtttgttcataaacgcggggttcggtcccagggctggca
ctctgtcgatacccaccgagaccccattggggccaatacgcccgcgtttcttccttttccccaccccaccccccaagttcgggtgaaggcc
cagggctcgcagccaacgtcggggcggcaggccctgccatagcctcaggttactcatatatactttagattgatttaaaacttcatttttaattta
aaaggatctaggtgaagatccttttgataatctcatgaccaaaatcccttaacgtgagttttcgttccactgagcgtcagacccgtagaaaag
atcaaaggatcttcttgagatcctttttttctgcgcgtaatctgctgcttgcaaacaaaaaaaccaccgctaccagcggtggtttgtttgccggat
caagagctaccaactcttttccgaaggtaactggcttcagcagagcgcagataccaaatactgtccttctagtgtagccgtagttaggccac
cacttcaagaactctgtagcaccgcctacatacctcgctctgctaatcctgttaccagtggctgctgccagtggcgataagtcgtgtcttaccg
ggttggactcaagacgatagttaccggataaggcgcagcggtcgggctgaacggggggttcgtgcacacagcccagcttggagcgaac
gacctacaccgaactgagatacctacagcgtgagctatgagaaagcgccacgcttcccgaagggagaaaggcggacaggtatccggtaa
gcggcagggtcggaacaggagagcgcacgagggagcttccaggggggaaacgcctggtatctttatagtcctgtcgggtttcgccacctct
gacttgagcgtcgattttgtgatgctcgtcaggggggcggagcctatggaaaaacgccagcaacgcggcctttttacggttcctggccttt
gctggccttttgctcacatgttctttcctgcgttatcccctgattctgtggataaccgtattaccgccatgcat

Figure 57

| pSM2 structure: | miR30 5' | sense sequence | loop | antisense sequence | miR30 3' |
|---|---|---|---|---|---|
| 1 | SV40-S1-5p | TGCTGTTGACAGTGAGCG | CAGGCTCATTTCAGGCCCCTCA | TAGTGAAGCCACAGATGTA | TGAGGGGCCTGAAATGAGCCTT | TGCCTACTGCCTCGGA |
| 2 | Hsa miR-518c* | TGCTGTTGACAGTGAGCG | CGAAAGTGCTTCCCTCCAGAGA | TAGTGAAGCCACAGATGTA) | TCTCTGGAGGGAAGCACTTTCT | TGCCTACTGCCTCGGA |
| 3 | Mmu miR-134 | TGCTGTTGACAGTGAGCG | ACCCTCTGGTCAACCAGTCACA | TAGTGAAGCCACAGATGTA | TGTGACTGGTTGACCAGAGGG | TGCCTACTGCCTCGGA |

TRANS-ACTING RNA SWITCHES

CROSS-REFERENCE TO RELATED APPLICATIONS

This application is a national stage of International (PCT) Patent Application Serial No. PCT/US2010/035870, filed May 21, 2010, and published under PCT Article 21(2) in English, which claims priority to and the benefit of U.S. provisional patent application Ser. No. 61/180,670, filed May 22, 2009, the disclosure of each of which is incorporated herein by reference in its entirety.

FEDERAL FUNDING

This invention was made with government support under grant no. HG003679 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 12, 2012, is named SNY-003.txt and is 59,076 bytes in size.

FIELD OF THE INVENTION

The invention relates generally to recombinant or synthetic nucleic acid constructs that are capable of interacting with target polynucleotides such that the interaction modulates the structure of the nucleic acid construct, leading to a targeted biochemical change such as an altered expression of a polypeptide from an associated nucleic acid. More specifically, the invention relates to RNA constructs that either express or cease to express a polypeptide depending on the presence of a target polynucleotide.

BACKGROUND

In nature, RNA not only functions as a component of the information transfer processes, but also performs tasks that are typically accomplished by proteins, including molecular recognition and catalysis. For example, naturally-occurring RNA molecules can interact to induce conformational changes, which in turn initiate biochemical reactions and other cellular processes. A significant advantage could be gained if these interactions could be harnessed to induce specific cellular processes under particular conditions.

SUMMARY OF THE INVENTION

This invention relates, in part, to a class of new chemical structures that can modulate a biochemical activity within a selected environment. For example, these structures can modulate biochemical activity, through expression of polypeptides, in cells and tissue infected by a pathogen, neoplastic cells and tissues, cells and tissues deficient in one or more factors, and scientific and diagnostic assays. Selectivity is achieved by targeting a polynucleotide that is unique to, or in abundance in, the cells or tissue relative to other cells or tissue. Nucleic acid constructs within this class of chemical structures include RNA constructs which are an RNA that hybridizes with all or a portion of the target polynucleotide and which are selected such that the hybridization induces a new conformation of the RNA construct. The conformational change can take many forms, but typically acts as a trigger to activate, suppress, or modulate a cascade of biochemical events, leading to some prophylactic or therapeutic effect or providing a means of diagnosing the presence of a given target polynucleotide. For example, the new molecular conformation may allow for a polypeptide from an attached polypeptide coding region to be expressed in all cells containing the target polynucleotide. The polypeptide coding region may code for an apoptotic gene, for example. Thus, an RNA construct could target, for example, a viral RNA with the result that all virus-infected cells die and/or all viruses in virally-infected cells die and the infection is arrested. Alternatively, when placed in an expression environment containing a target polynucleotide, the RNA construct could allow for the expression of a encoded polypeptide which can be detected, thus providing a diagnostic tool.

Thus, one aspect of the invention involves an RNA construct that includes a non-naturally occurring, continuous sequence of ribonucleotide bases. These bases define a stem-loop. The RNA construct has simulated, three way junction joining regions 3' and 5' of the stem-loop structure. Each joining region can include no more than about 10 nucleotides. In addition, the RNA construct has a first region 5' of the 5' joining region, including bases complementary to a 3' region of the target polynucleotide, and a second region 3' of the 3' joining region, including bases complementary to a 5' region of the target polynucleotide. The base sequence of the first and second regions are selected to hybridize with complementary bases on the target polynucleotide and are spaced apart by an intermediate region on the target polynucleotide defining another three way junction joining region. In the presence of the target polynucleotide, the stem-loop conformation of the construct is stabilized compared to when the target polynucleotide is absent.

In one embodiment, at least one base in the stem of the structure is mismatched with its potential binding partner so as to reduce the stability of the stein-loop structure as compared with a wild-type form of the stem-loop structure. Alternatively, the stem-loop, in the context of the RNA construct, has increased minimum free energy (MFE) compared to the stem-loop in a wild-type context, such that the stem-loop of the RNA construct will be less stable than will the stem-loop in a wild-type context.

In another embodiment, the RNA construct also defines an RNA polypeptide coding region. In the absence of the target polynucleotide, the construct assumes a conformation that inhibiting association with an RNA binding protein and suppressing translation of the coding region. On the other hand, in the presence of the target polynucleotide, the construct assumes a stem-loop conformation promoting association with the RNA binding protein and promoting translation of the coding region.

In other embodiments, the construct is expressed is a cell and the polypeptide coding region encodes a polypeptide needed for survival of the cell, whereby only in the presence of a the target polynucleotide can the cell survive. In another embodiment, the construct is expressed in a cell and the polypeptide coding region encodes a polypeptide lethal to the cell. The cell can be an infected cell or a neoplastic cell, and the target polynucleotide can be expressed by the infecting organism or by the neoplastic cell. In another embodiment, the polypeptide coding region encodes a detectable marker polypeptide whose detection in the expression environment indicates the presence of an analyte comprising the target polynucleotide. In yet another embodiment, the construct has more than one stem-loop structure.

Another aspect of the invention involves an RNA construct for attachment to a polypeptide coding region of an RNA. The RNA construct modulates translation of a polypeptide from the coding region in response to the presence of a target single-stranded polynucleotide in an expression environment. The RNA construct comprises a non-naturally occurring, continuous sequence of ribonucleotide bases. These bases define a stem-loop structure which associates with an RNA binding protein present in the expression environment to suppress translation of the polypeptide coding region when the RNA construct is in a stem-loop conformation. The RNA construct has simulated, three way junction joining regions 3' and 5' of the stem-loop structure. Each joining region can include no more than about 10 nucleotides. In addition, the RNA construct has a first region 5' of the 5' joining region, including bases complementary to a 3' region of the target polynucleotide, and a second region 3' of the 3' joining region, including bases complementary to a 5' region of the target polynucleotide. The base sequence of the first and second regions are selected to hybridize with complementary bases on the target polynucleotide and are spaced apart by an intermediate region on the target polynucleotide defining another three way junction joining region. In the absence of the target polynucleotide, the construct assumes a conformation inhibiting association with the RNA binding protein and promoting translation of the polypeptide coding region. In the presence of the target polynucleotide, the construct assumes a stem-loop conformation promoting association with the RNA binding protein and inhibiting translation of the polypeptide coding region.

Any of the above aspects can include any of the following features. At least one base in the stem of the structure can be mismatched with its potential binding partner so as to reduce the stability of the stem-loop structure as compared with a wild-type form of the stem-loop structure. Alternatively, the stem-loop, in the context of the RNA construct, can have increased minimum free energy (MFE) compared to the stem-loop in a wild-type context, such that the stem-loop of the RNA construct will be less stable than will the stem-loop in a wild-type context. The continuous sequence of ribonucleotide bases can also include the polypeptide coding region of an RNA disposed 5' of the first region. Alternatively, the continuous sequence of ribonucleotide bases can include the polypeptide coding region of an RNA disposed 3' of the second region. The target polynucleotide can be characteristic of a pathogen, for example, a virus or a single-celled microorganism. The target polynucleotide can be expressed preferentially in a cell type of a multicellular organism, for example, a neoplastic cell. The target polynucleotide can include a synthetic target polynucleotide or single stranded DNA for transfection into a cell. The target polynucleotide can be double-stranded.

Another embodiment of any of the above aspects involves a DNA vector that includes a transcription unit encoding the RNA construct. Still another embodiment involves a cell comprising the RNA construct. The expression environment can be an infected cell or a neoplastic cell that expresses the target polynucleotide. The construct can have more than one stem-loop structure.

Another aspect of the invention involves a method for modulating translation of a polypeptide coding region, which involves providing a translatable RNA construct that includes a polypeptide coding region ligated to a non-naturally occurring RNA and introducing the translatable RNA construct into an expression system. The RNA includes a continuous sequence of ribonucleotide bases which define a stem-loop structure which associates with an RNA binding protein present in the expression environment to modulate translation of the polypeptide coding region when the RNA construct is in a stem-loop conformation. The RNA construct has simulated, three way junction joining regions 3' and 5' of the stem-loop structure. Each joining region can include no more than about 10 nucleotides. In addition, the RNA construct has a first region 5' of the 5' joining region, including bases complementary to a 3' region of the target polynucleotide, and a second region 3' of the 3' joining region, including bases complementary to a 5' region of the target polynucleotide. The base sequence of the first and second regions are selected to hybridize with complementary bases on the target polynucleotide and are spaced apart by an intermediate region on the target polynucleotide defining another three way junction joining region. The construct assumes a conformation inhibiting association with the RNA binding protein, and in the presence of the target polynucleotide, the construct assumes a stem-loop conformation promoting association with the RNA binding protein.

In one embodiment of this aspect of the invention, at least one base in the stem of the structure can be mismatched with its potential binding partner so as to reduce the stability of the stem duplex as compared with a wild-type form of the stem-loop structure. Alternatively, the stem-loop, in the context of the RNA construct, can have increased minimum free energy (MFE) compared to the stem-loop in a wild-type context, such that the stem-loop of the RNA construct will be less stable than will the stem-loop in a wild-type context. In another embodiment, the RNA construct is introduced into the expression environment by transfecting a DNA encoding the translatable RNA construct. The target polynucleotide can be characteristic of a pathogen, or can be expressed preferentially in a cell type of a multicellular organism. The cell type can be, for example, a neoplastic cell. The method can also include the additional step of introducing the target polynucleotide into the expression system. In another embodiment, the expression system is a cell and the polypeptide coding region encodes a polypeptide lethal to the cell. The cell can be an infected cell or a neoplastic cell, and the target polynucleotide, for example, an enzyme or pore-forming protein, can be expressed by the neoplastic cell or by the infecting organism. The construct can have more than one stem-loop structure.

In another embodiment of this aspect of the invention, the polypeptide coding region can encode a detectable marker, for example, a fluorescent marker. In yet another embodiment, translation of the coding region can be suppressed when the RNA binding protein binds to the stem-loop structure. Translation of the coding region can alternatively be promoted when the RNA binding protein binds to the stem-loop structure.

Another aspect of the invention can involve a method of killing preferentially, in a heterogeneous population of animal cells, target cells that harbor a single-stranded target polynucleotide having a known sequence. The method involves introducing into the heterogeneous cell population an RNA construct attached to a polypeptide coding region which encodes a polypeptide lethal to the target cells. The RNA construct is capable of modulating translation of the polypeptide coding region in response to the presence of the target single-stranded polynucleotide in the target cells. The RNA construct includes a non-naturally occurring, continuous sequence of ribonucleotide bases which define a stem-loop structure which associates with an RNA binding protein present in the target cells to promote translation of the polypeptide coding region when the construct is in a stem-loop conformation. The RNA construct has simulated, three way junction joining regions 3' and 5' of the stem-loop structure. Each joining region can include no more than about 10 nucleotides. In addition, the RNA construct has a first region 5' of the 5' joining region, including bases complementary to a 3' region of the target polynucleotide, and a second region 3' of the 3' joining region, including bases complementary to a 5' region of the target polynucleotide. The base sequence of the first and second regions are selected to hybridize with complementary bases on the target polynucleotide and are spaced apart by an intermediate region on the target polynucleotide defining another three way junction joining region. In cells where the target polynucleotide is absent, the construct assumes a conformation inhibiting association with the RNA binding protein and suppressing translation of the coding region. In cells where the target polynucleotide is present, the construct assumes a stem-loop conformation promoting association with the RNA binding protein and promoting translation of the coding region thereby to kill the cells.

In certain embodiments of this aspect of the invention, at least one base in the stem of the structure can be mismatched with its potential binding partner so as to reduce the stability of the stem duplex as compared with a wild-type form of the stem-loop structure. Alternatively, the stem-loop, in the context of the RNA construct, can have increased minimum free energy (MFE) compared to the stem-loop in a wild-type context, such that the stem-loop of the RNA construct will be less stable than will the stem-loop in a wild-type context. In other embodiments, the target polynucleotide is characteristic of a pathogen, such as a virus or a single-celled microorganism. In other embodiments, the target polynucleotide is expressed preferentially in a target cell type, such as a neoplastic cell, of a multicellular organism. The target cell can be an infected cell or a neoplastic cell, and the target polynucleotide can be expressed by the infecting organism or by the neoplastic cell. The polypeptide coding region can include a sequence encoding an enzyme or pore-forming protein. The construct can have more than one stem-loop structure.

Another aspect of the invention involves an RNA construct for attachment to a polypeptide coding region of an RNA and for modulating translation of a polypeptide from the coding region in response to the presence of a target single-stranded polynucleotide in an expression environment. The RNA construct includes a non-naturally occurring, continuous sequence of ribonucleotide bases defining a stem-loop structure, which promotes translation of the polypeptide coding region when the construct is in a stem-loop conformation; simulated, three way junction joining regions 3' and 5' of the stem-loop structure; a first region 5' of the 5' joining region including bases complementary to a 3' region of the target polynucleotide; and a second region 3' of the 3' joining region including bases complementary to a 5' region of the target polynucleotide. The base sequence of the first and second regions are selected to hybridize with complementary bases on the target polynucleotide spaced apart by an intermediate region on the target polynucleotide defining another three way junction joining region. In the absence of the target polynucleotide, the construct assumes a conformation suppressing translation of the polypeptide coding region, and in the presence of the target polynucleotide, the construct assumes a conformation promoting translation of the polypeptide coding region. This aspect of the invention can have any of the features described herein (above or below).

BRIEF DESCRIPTION OF THE FIGURES

The foregoing and other objects, features, and advantages of the present invention, as well as the invention itself, may be more fully understood from the following description of preferred embodiments, when read together with the accompanying drawings.

FIG. 2A shows a target polynucleotide stabilizing a stem-loop motif by binding at least a portion of the 5' and 3' flank regions. This represents a stabilizing interaction. FIG. 2B depicts a target polynucleotide binding an RNA construct and preventing the formation of the native secondary structure motif. This represents a destabilizing interaction. FIG. 2C is an example of a target polynucleotide binding to an RNA construct to form a double-stranded site that could be bound by an RBP. FIG. 2D shows a target polynucleotide ablating one RBP binding-site motif to allow formation of a second motif in a manner suggestive of a bacterial operon attenuation mechanism.

FIG. 6A shows a consensus structure (5' NNNGGGGANNCNUCCCCNN-3' (SEQ ID NO:1)) of an RBP binding site, and the gray area denotes a region where point mutations may be made to weaken stem-loop structure (asterisks show bases that are required for protein binding). The shaded boxes of FIG. 6B show point mutations made to the primary structure (sequence) at spots calculated to increase Minimum Free Energy (MFE) and reduce spontaneous formation of required secondary structure for RBP binding. The sequence of this RNA construct is (5' NNNUGGGANNCNUCUUUNN-3' (SEQ ID NO:2)). FIGS. 6C and D show an simulated three way junction (depicted generally in FIG. 6C), that will form when a target polynucleotide hybridizes to the RNA construct (SEQ ID NO:2) to stabilize the formation of the RBP binding site.

FIG. 7C shows the RNA construct with flank sequences (5'-AUCCCCUGCNNNUGGGANNCNUCUUUN-NGUCCGUGUCG-3') (SEQ ID NO:4), hybridized to the target polynucleotide to form a three-way junction.

FIG. 8A shows a J3 region of 0 nucleotides produced by the interaction of the target polynucleotide with the 5' flank region ACACCCCAAAA (SEQ ID NO:6) and the 3' flank region UCGAAGCACUUC (SEQ ID NO:7); FIG. 8B shows a J3 region of 1 nucleotide produced by the interaction of the target polynucleotide with the 5' flank region ACACCCCAAAA (SEQ ID NO:6) and the 3' flank region CGAAGCACUUC (SEQ ID NO:8); and FIG. 8C shows a J3 region of 2 nucleotides produced by the interaction of the target polynucleotide with the 5' flank region ACAC-CCCAAA (SEQ ID NO:9) and the 3' flank region CGAAG-CACUUC (SEQ ID NO:8).

FIGS. 11A-NN provide GenBank accession numbers for exemplary HSL sequences. "Start" and "end" refer to nucleotide positions at which the HSL starts and ends in the larger corresponding GenBank sequence indicated in the last column.

FIGS. 14A-S provide GenBank accession numbers for exemplary IRE1 sequences. "Start" and "end" refer to the positions in the larger corresponding GenBank sequences at which the IRE1 sequence can be found.

FIGS. 15A-N provide GenBank accession numbers for exemplary IRE2 sequences. "Start" and "end" refer to the positions in the larger corresponding GenBank sequences at which the IRE2 sequence can be found.

FIG. 16 provides GenBank accession numbers for exemplary IRE3 sequences. "Start" and "end" refer to the positions in the larger corresponding GenBank sequences at which the IRE3 sequence can be found.

FIGS. 18A-G provide GenBank accession numbers for exemplary SECIS1 sequences. "Start" and "end" refer to the positions in the larger corresponding GenBank sequences at which the SECIS1 sequence can be found.

FIGS. 19A-O provide GenBank accession numbers for exemplary SECIS2 sequences. "Start" and "end" refer to the positions in the larger corresponding GenBank sequences at which the SECIS2 sequence can be found.

FIG. 20A shows the general structure of an IRES element with domains II-IV depicted. FIG. 20B shows an IRES element from the Hepatitis C virus (SEQ ID NO:17). The internal start codon (AUG), located in domain IV, is shaded.

FIG. 21A shows the sequence of domain II (SEQ ID NO:18) from the IRES of Hepatitis C virus. FIG. 21B shows the base stem region ("N" nucleotides enclosed in a box) of domain II of the Hepatitis C virus that can be weakened by introduction of non-canonical base pairings (SEQ ID NO:19).

FIG. 22 shows sequences encoding naturally-occurring IRESes, with domain II sequences in bold uppercase. The first sequence (From Hepatitis C virus) corresponds to the sequence shown within the dotted line of FIG. 20B, with the bolded uppercase portion corresponding to the sequence shown in FIG. 21A.

FIG. 23 shows domain II sequences from the naturally-occurring IRESes of FIG. 22, with 5' stem, internal, and 3' stem regions indicated. Rows 1 to 5 correspond to SEQ ID NOS: 25 to 29.

FIG. 24A shows an RNA construct incorporating a weakened IRES motif that does not effectively form in the absence of a target polynucleotide. FIG. 24B shows the reconstituted IRES motif hybridized to a target polynucleotide.

FIGS. 25A-C show the results of a mirBase search for viral microRNAs (miRNAs). These miRNAs can be used as target polynucleotides. "Parent structure" refers to the RNA construct to which the miRNA binds. Rows 1-62 correspond to SEQ ID NOS: 30 to 91.

FIGS. 26A-C show the results from Rfam search on "virus" (www.sanger.ac.uk/cgi-bin/Rfam/queryrfam.p1?db=rfam& db=prosite&db=swiss&size=100&terms=virus).

FIGS. 27A-B show examples of polypeptides capable of causing cell death that can be encoded by a polypeptide coding region.

FIG. 28 discloses nucleotides 561-585, 621-646 and 727-748 of SEQ ID NO: 192.

FIG. 36A depicts a stem-loop structure (SEQ ID NO:99) to which the MS2 capsid protein binds. FIG. 36B depicts an MS2 binding site consensus sequence (SEQ ID NO:100).

FIG. 49 shows an HSL consensus sequence (SEQ ID NO:109) acquired from the: UTRSITE Signal Manager (www2.ba.itb.cnr.it/UTRSite/index.php/UTRSite%20signal/Signal/frmID/U0035), which was used as the starting point to design HSL-based RNA constructs.

FIG. 50 depicts the sequence and structure of the HSL-B1 (SEQ ID NO:110) and HSL-B2 (SEQ ID NO:111) RNA constructs bound to target polynucleotide T4 (SEQ ID NO:112).

FIG. 51 depicts the sequence and structure of HSL-B3 (nucleotides 23-57 of SEQ ID NO:113) and HSL-B4 (SEQ ID NO:114) RNA constructs bound to target polynucleotides T-5 (SEQ ID NO:115) and T-6 (SEQ ID NO:116), respectively.

FIG. 52 shows quantitation of band intensities, which was performed using Quantity One® software (BioRad, Hercules, Calif.).

FIG. 53 shows Histone Stem-Loop (HSL) sequence information, with STLAB_C01__01 to STLAB_C01__25 corresponding to SEQ ID NOS: 117 to 141. FIG. 53 discloses "NMMMMMGGYYYUHHUHARRRCCMM" as SEQ ID NO: 194.

FIG. 54 shows miRNAs that are aligned with the HSLs of FIG. 36 in a manner shown for FIG. 38. "Parent structure" refers to the structure to which the miRNA primarily binds. Rows 1-28 correspond to SEQ ID NOS: 142 to 169.

FIGS. 56A-B show a sequence for an RNA construct attached to a green fluorescent protein (GFP), a reporter construct (Pd4EGFP-N1 with stem-loop sequence) (SEQ ID NO:172). Double underlining shows the GFP sequence. Dashed underlining shows mouse ornithine decarboxylase (3' end of CDS) sequence. The histone sequence is shown in italics. Bold underlining shows the stem-loop sequence.

FIG. 57 shows sequences used for the design of shRNAs. shRNAs were expressed using standard retroviral delivery methods. The shRNA is initially expressed as a double-stranded hairpin precursor molecule that is processed by cellular machinery into the eventual expressed single-stranded miRNA, which will function as the target polynucleotide. The sequence for the eventual processed target polynucleotide is depicted in the "antisense sequence" column, but listed in the DNA form in which "T's" are listed in place of "U's." Rows 1-4 correspond to SEQ ID NOS: 173 to 175.

In FIG. 58A, RT-PCR was used to detect the presence or absence of GFP coding sequence (cds) RNA associated with the stem-loop binding protein (SLBP). This was determined with and without the co-expression of the SV40 target polynucleotide. A significant decrease can be observed in the presence of co-expressed SV40 microRNA as compared to the amount in the total RNA. FIG. 58B, GFP fluorescence was used determine the expression of the GFP fused HSL-RNA construct in the presence or absence of SV40 or mir518 competing miRNAs (target polynucleotide). An approximately 20% decrease in GFP expression is observable when SV40 miRNA is co-expressed with the GFP-HSL-RNA construct.

DETAILED DESCRIPTION

I. Introduction

A. Concept

Figure 1:
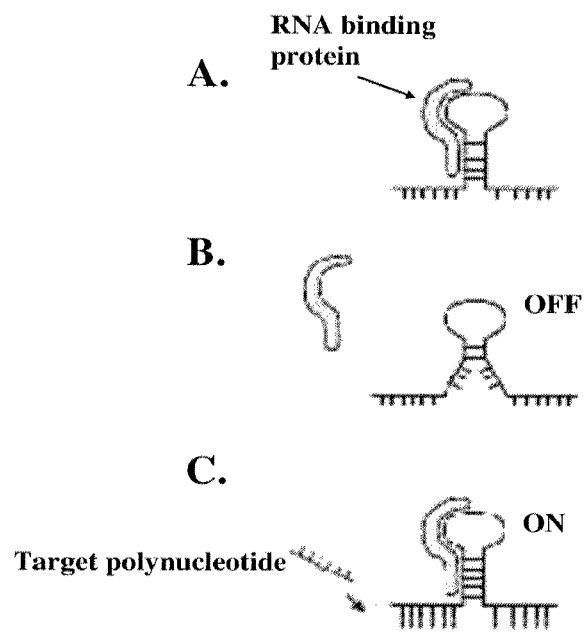
FIG. 1A shows an RNA stem-loop motif interacting with an RNA binding protein (RBP).
FIG. 1B shows an RNA construct of the present invention with a weakened stem that prevents formation of the stem-loop structure, therefore preventing RBP binding.
FIG. 1C shows an RNA construct, stabilized by a target polynucleotide and which forms a stem-loop structure capable of being bound by an RBP.

The present invention relates to the use of interactions between nucleic acid construct, such as an RNA construct, and a target polynucleotide, such as an RNA, as a functional switch. As disclosed herein, a very large number of RNA constructs of the type illustrated in FIG. 1 can be designed, each of which are stabilized in the presence of a target polynucleotide. In this scenario, an RNA construct is able to form a structure in the presence of a target polynucleotide, which results in some type of activity. For example, the formation of a stem-loop structure allows an RNA binding protein (RBP) to associate with the construct, thus promoting or inhibiting translation of a polypeptide coding region attached to the RNA construct. FIG. 1A illustrates an example of a stem-loop structure, which can act as an association-site for a specific protein involved in gene expression. In the presence of this structure, the protein associates with the RNA construct and promotes expression of the attached polypeptide coding region, often increasing protein production by many orders of magnitude.

In the design of RNA constructs according to the invention, the stem-loop structure of 1A is weakened so that the weakened structure will no longer efficiently associate with the protein (FIG. 1B). In the absence of a target polynucleotide, the RNA construct is less capable or incapable of forming a structure with which the RBP will associate. Thus, in the absence of a target polynucleotide, the attached polypeptide coding region will not be effectively expressed.

In order to be able to "turn on" this weakened RNA construct, a portion of the RNA construct is designed to base-pair with a target polynucleotide, often an RNA, such as an RNA from a pathogen or one present in a neoplastic cell. The target polynucleotide acts as a "splint" to reform the original stem-loop structure. FIG. 1C shows an example of an RNA construct-target polynucleotide complex with re-formed binding site potential for the RBP. This re-formed structure has the capacity to interact with the RBP in order to stimulate protein production of whatever polypeptide coding region is attached to the RNA construct. This approach may be used to express a polypeptide that restores function to an impaired cell, stimulates the immune system or kills a diseased or infected cell (or a pathogen within an infected cell).

Figure 2:
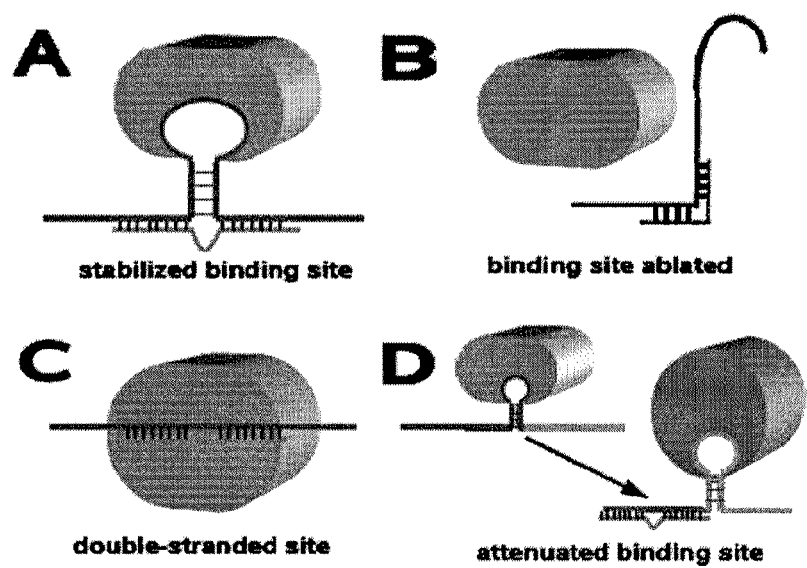
FIGS. 2A-D show examples of RNA construct-target polynucleotide interactions. It should be understood that these examples are illustrative of the general concept of a nucleic acid target binding to and changing the conformation of an RNA construct.
Figure 3:
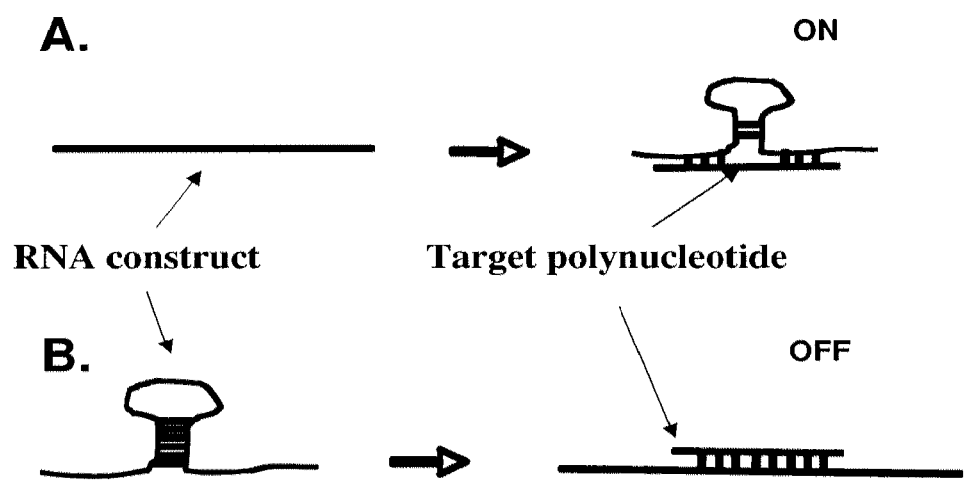
FIG. 3A shows an example of a strategy that uses an RNA construct-target polynucleotide interaction to affect the structure of an RNA construct, which modulates the activity of a secondary item such as an attached polypeptide coding region.
FIG. 3B shows an example of a target polynucleotide binding to an stem-loop motif, thereby disrupting the stem-loop structure such that an RBP can no longer bind.

More generally, at least four categories of RNA construct interactions with target polynucleotides can be used to influence RNA construct structure and, therefore, RBP binding site availability (FIGS. 2A-D). It should be understood that FIGS. 2A-D are intended to illustrate the principles of the invention and that although RNA is shown as the RNA construct in FIGS. 2A-D, the RNA construct may be any nucleic acid, such as RNA or DNA, which occurs naturally or is rationally designed. FIGS. 2A and 3A illustrate a first type of interaction, described above with reference to FIGS. 1A-C, relating to stabilizing a protein binding site. FIGS. 2B and 3B illustrate a second type of interaction in which RNA construct-target polynucleotide interactions are designed so that the target polynucleotide ablates the RNA construct structure and/or an RNA-binding protein binding site. These RNA construct-target polynucleotide interactions can facilitate or disrupt the association of an RNA-binding protein with its targeted regulatory element (FIGS. 2A and 2B, respectively). This type of interaction can exist in either a positive or negative fashion (i.e. "on" or "off") with respect to the stabilization of the RNA construct and can function upstream or downstream of the structure. Example 1 is representative of the interaction shown in FIG. 2A which may be used to turn on the expression of a polypeptide coding region. Examples 2 and 3 are representative of the interaction shown in FIG. 2B which be used to turn off the expression of a polypeptide coding region.

Another category of interaction is one in which the target polynucleotide-RNA construct interaction is itself the target of an RNA-binding protein (FIG. 2C) and therefore forms the switch. A double-stranded RNA-binding protein, or possibly a moonlighting DNA-binding protein, can target this type of structure. The final category of interaction combines one or more of the already described interactions into a complex switch (FIG. 2D). In this group, multiple RNA regulatory elements are simultaneously influenced by one or more target polynucleotide-RNA construct interactions. Specifically, the binding of one or more target polynucleotides to the RNA construct results in conformational changes in the structure of the message, such that a second regulatory element is revealed or masked. This class of target polynucleotide-RNA construct interaction utilizes a series of secondary structures, such as stem-loops, that are simultaneously influenced in a mutually exclusive switch-like manner dictating which of several possible regulatory elements will be accessible for use.

B. Uses

1. Expression of a Polypeptide to Kill a Cell or Pathogen

Polypeptide coding regions can be attached to RNA constructs that bind to any target polynucleotide that is a marker for infection or disease. This strategy can be used to target any pathogen, including viruses, bacteria, fungi or protozoa. Thus, the strategy can kill the cell harboring a pathogen and/or the pathogen itself. Beyond pathogens, this strategy can be used to eliminate diseased cells, such as neoplastic cells (e.g., cancer cells). In certain embodiments, an RNA construct connected to polypeptide coding region encoding a polypeptide able to kill a cell (e.g., a neoplastic cell or pathogenically infected cell) or pathogen is designed to bind to a target polynucleotide specifically expressed by, for example, a neoplastic cell or a pathogen. Polypeptide coding regions encoding death polypeptides include, for example, genes that induce apoptosis (e.g., caspases), pore-forming genes, or any other gene that would be toxic to a cell or pathogen. Multiple stem loop structures may be designed as part of the same RNA molecule to increase specificity. For example, two stem loop structures within the construct may be designed to bind different target polynucleotides, such that both target polynucleotides must be present to stabilize the RNA construct and promote translation. In another embodiment, two different types of stem-loop motifs (e.g., HSL and IRE) may be used as part of the same RNA molecule, so that the expression of the attached polypeptide coding region is more robust in a particular cell type (e.g., a cancer cell), in which SLBP and IRE RBPs are likely to be active. While selectivity is particularly important when expressing genes that are toxic to the cell, a construct with two or more stem-loop structures may be used in any of the embodiments of the invention described herein.

2. Diagnostic Testing and Imaging

In another embodiment, an RNA construct can be used to diagnose the presence of a particular target polynucleotide in a cell. In this strategy, a marker gene encoding any protein that can be visualized or otherwise detected (e.g., a fluorescent or luminescent protein) is attached to an RNA construct. This strategy can be used, for example, for diagnostic testing or to highlight specific cells or tissues during imaging. In one example, an RNA construct is designed to bind a viral target polynucleotide and is attached to Green Fluorescent Protein (GFP). When the construct is delivered to cells, only cells infected with the virus will fluoresce.

3. Directing Protein Expression in Certain Cells

Rather than simply killing a diseased cell, an RNA construct can be used to direct expression of an attached polypeptide coding region in a specific cell or tissue having a protein deficiency. For example, an RNA construct can be designed to bind to a target polynucleotide indicative of the protein deficiency. When the construct is delivered to cells, it will only direct expression of the protein in cells lacking the protein because the cells contain the target polynucleotide. In one alternative, if all cells of an organism (or cell culture) were lacking a given protein, an RNA construct could be designed to bind to a ubiquitously-expressed target polynucleotide, such that the attached gene would be expressed in all cells. In another alternative, an RNA construct could be designed to bind to a ubiquitously-expressed target polynucleotide, but the RNA construct could be delivered only to the cells or tissues lacking a given polypeptide. Using this strategy, the construct will only direct expression of the protein in cells lacking the protein because it will be delivered to only these cells. Combining administration of an RNA construct attached to a polypeptide coding region and RNAi is also contemplated. For example, for cells that not only lack a certain protein, but also make a defective version of that protein which contributes to the disease, an RNA construct can be administered together with RNAi which specifically targets the defective version of the protein. This strategy will not only eliminate the defective protein, but will also supply the wild-type protein. For example, RNAi targeting a defective Cystic Fibrosis Transmembrane Conductance Regulator (CFTR) and an RNA construct comprising a polypeptide coding region encoding wild-type R can be coadministered to a cell containing a defective CFTR. Table 1 provides examples of diseases that could be ameliorated by expression of the corresponding polypeptide using this type of a system.

TABLE 1

| Disease or Condition | Polypeptide(s) to be Expressed by Construct |
| --- | --- |
| Cystic Fibrosis | Cystic Fibrosis Transmembrane Conductance Regulator (CFTR) |
| Lysosomal storage disorders | Sulfatases, N-acetylglucosamine-1-phosphate transferase, Cathepsin A, GM2-AP, sphingolipid activator proteins, NPC1 and NPC2, or sialin |
| Mucopolysaccharidosis (subset type of lysosomal storage disease) | a-L-iduronidase, iduronate sulfatase, heparan sulfamidase, N-acetylglucosaminidase, N-acetylglucosamine 6-sulfatase, galactose 6-sulfatase, N-acetylgalactosamine 4-sulfatase, $\beta$-glucuronidase, or hyaluronidase |
| Fabry's disease | Enzyme alpha galactosidase A |
| Addiction Disorders | Dopamine receptor |
| Depression | Serotonin receptor, norepinephrine receptor, or dopamine receptor |
| Gaucher Disease | Acid $\beta$-glucosidase |
| Diabetes | Insulin |

Additionally, other polypeptides that may be useful include interleukins, reproductive hormones, plasminogen activators, human growth hormones, colony-stimulating factors, blood-clotting factors, erythropoietins, and interferons.

4. Selecting Cells Containing a Target Polynucleotide

In another embodiment of the invention, a DNA construct encoding the RNA construct of the invention can be transformed into a cell. The polypeptide coding region attached to the RNA construct encodes a polypeptide necessary for the continued survival of the cell. In the presence of a target polynucleotide, an RBP binds to the stabilized RNA construct and promotes translation of the polypeptide. In this scenario, only cells that contain the target polynucleotide will survive. In a variation of this embodiment, a population of cells is transformed with a DNA construct encoding the RNA construct in which the polypeptide coding region attached to the RNA construct encodes a polypeptide, for example a drug- or antibiotic-resistance gene (e.g., dihydrofolate reductase (DHFR), thymidine kinase, gene conferring resistance to neomycin, a neomycin analog such as G418, hydromycin, or puromycin) necessary for survival of the cell in a given environment. When transformed cells are placed into this environment (e.g., an environment containing a drug or antibiotic), only cells that (1) have been successfully transformed and (2) contain the target polynucleotide will survive.

5. Suppressing Translation of an Encoded Polypeptide in the Presence of a Target Polynucleotide In another embodiment, an RNA construct that binds to an RBP that suppresses, rather than enhances, expression may be used to express an attached polypeptide coding region in a cell that lacks a target polynucleotide. Then, if the target polynucleotide enters or becomes expressed in the cell, binding of the target polynucleotide to the RNA construct stabilizes the secondary structure, allowing the RBP to bind, which suppresses translation of the encoded polypeptide. This strategy can be used as a type of feedback loop, wherein, for example, a therapeutic protein is expressed until the cell achieves a certain level of health, at which time the target polypeptide is expressed, and the production of the therapeutic protein ceases. Should the cell return to an unhealthy state wherein the target polypeptide is no longer present, production of the therapeutic protein resumes.

6. Other Applications of an RNA Construct

Many other applications of this invention are contemplated. Essentially, the expression of any polypeptide coding region encoding a polypeptide can be activated using this approach as long as the environment in which the RNA construct is to be delivered contains the activating target polynucleotide. RNA-constructs can also be designed to activate proteins that would enhance processes already occurring within a cell. Genes that could be targeted include any cellular gene, such as those involved in immune cell activation (IL-2), cell growth (cyclin B2, hTert), or vascular development (VEGF), as well as any gene product from any pathogen such as viruses, bacteria, fungi or protozoa.

II. RNA Construct

A. General

Returning to FIG. 2A, the stabilizing interaction depicted is comprised of two nucleic acid components, the RNA construct that is engineered and ectopically supplied and a target polynucleotide, such as an RNA produced by a pathogen. The RNA construct is delivered as a weakened form of a stem-loop with an attached polypeptide coding region. The RNA construct comprises additional structural elements that aid in the binding of the target polynucleotide to the RNA construct and in the assumption of the proper three-dimensional structure. Specifically, the RNA construct typically contains nucleotides that will lack binding partners at joining regions formed when bound to a target polynucleotide, providing flexibility which enhances the RNA construct's ability to assume the conformation necessary for the RBP to associate and activate translation of an attached polypeptide coding region.

B. Construct Design

The following section describes how to design an RNA construct of the type illustrated in FIGS. 1A-C. Typically, the RNA construct will include a stem-loop structure that is designed to be unstable in the absence of a target polynucleotide, although other motifs are contemplated. In the presence of the target polynucleotide, the structure of the RNA construct is stabilized, allowing an RBP to associate with the construct and promote translation of the attached polypeptide coding region of interest. While some details of design will depend upon the stem-loop structure, and its corresponding mode of action, typically design of RNA constructs will involve the following steps (which need not be performed in the order listed).

1. Design of Three-Way Junctions

Figure 4:
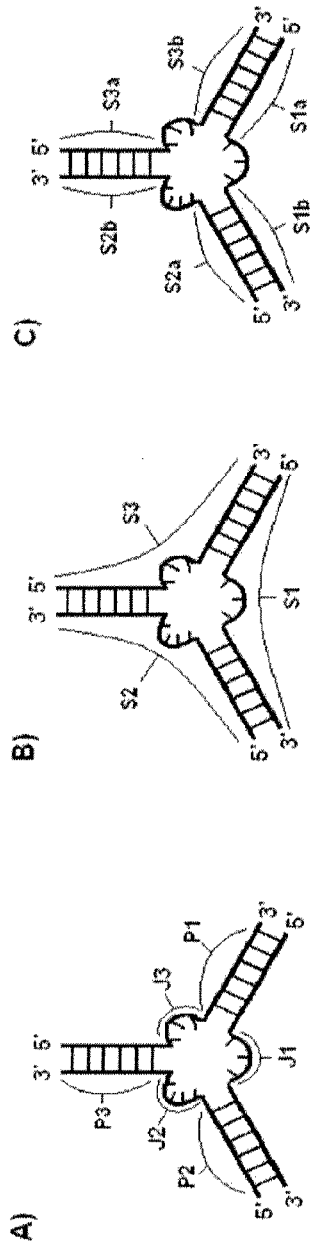
FIGS. 4A-C show the components and nomenclature of a three-way junction.
FIG. 4D shows the range of relative sizes of joining regions that give rise to the different three-way junction family members shown in FIG. 5. J1 corresponds to the junction region that connects the two helices most closely approaching a coaxial conformation. (See, e.g., Lescoute et al. (2006) RNA 12:83-93.)

Three-way junctions are found in nature. (See, e.g., Lescoute et al. (2006) RNA 12:83-93.) The present invention simulates these natural structures and utilizes these simulated three-way junctions as a pattern upon which to build an RNA construct. FIGS. 4A-C provide the nomenclature of the RNA constructs patterned on three-way junctions. This nomenclature will be used throughout the present patent application. FIG. 4A shows a three-way junction having three base-paired stems (P1, P2, and P3) of variable length and three corresponding joining regions (J1, J2, and J3). The joining regions each independently can be from 0 to about 10 unbound nucleotides, for example from about 2 to about 6 nucleotides. FIG. 4B shows the three-way junction of FIG. 4A, indicating the positions of the three RNA molecules of the junction. S1 through S3. S1 is the strand that connects P1 to P2 through J1, S2 is the strand that connects P2 to P3 through J2, and S3 is the strand that connects P3 to P1 through J3. FIG. 4C further divides the strands S1-S3 into 5' to 3' segments labeled "a" and "b." For example, S1 is divided into two segments, S1a being the segment of P1 leading into the J1 joining region and S1b being the segment of P2 leading out of the J1 joining region. S2 and S3 are each similarly divided into "a" and "b" segments.

When developing an RNA construct, the joining regions of the construct as well as the target polynucleotide are chosen according to FIG. 4D. Depending upon how the joining regions are chosen, one can design a construct from one of three families, Families A, B, or C (FIG. 4D). If an RNA construct patterned on Family A is desired, J3 is selected to include any number of nucleotides from 0 to about 10 and J2 is selected to include any number of nucleotides, from 0 to about 10, such that the number of nucleotides selected for J3 is less that the number selected for J2. J1 includes any number of nucleotides from 0 to about 10. In certain embodiments, the number of nucleotides selected for J3 is between 1 and 3, the number of unpaired nucleotides in region J2 is between 3 and 9, and the number of unpaired nucleotides in region J1 is between 0 and 4. If an RNA construct patterned on the Family B conformation is desired, J3 is selected to include any number of nucleotides from 0 to about 10 and should be approximately equal (e.g., equal to 0 to about 10) to the number selected for J2. J1 includes any number of nucleotides from 0 to about 10. In certain embodiments, the number of unpaired nucleotides in each region (J1, J2 and J3) is between 2 and 6. If an RNA construct patterned on Family C is desired, J3 is selected to include any number of nucleotides from 0 to about 10 and J2 is selected to include any number of nucleotides, from 0 to about 10, such that the number of nucleotides in J3 is greater than the number selected for J2. J1 includes any number of nucleotides from 0 to about 10. In certain embodiments, the number of nucleotides selected for J3 is between 3 and 9, the number of unpaired nucleotides in region J2 is between 1 and 5, and the number of unpaired nucleotides in region J1 is between 0 and 5.

Figure 5:
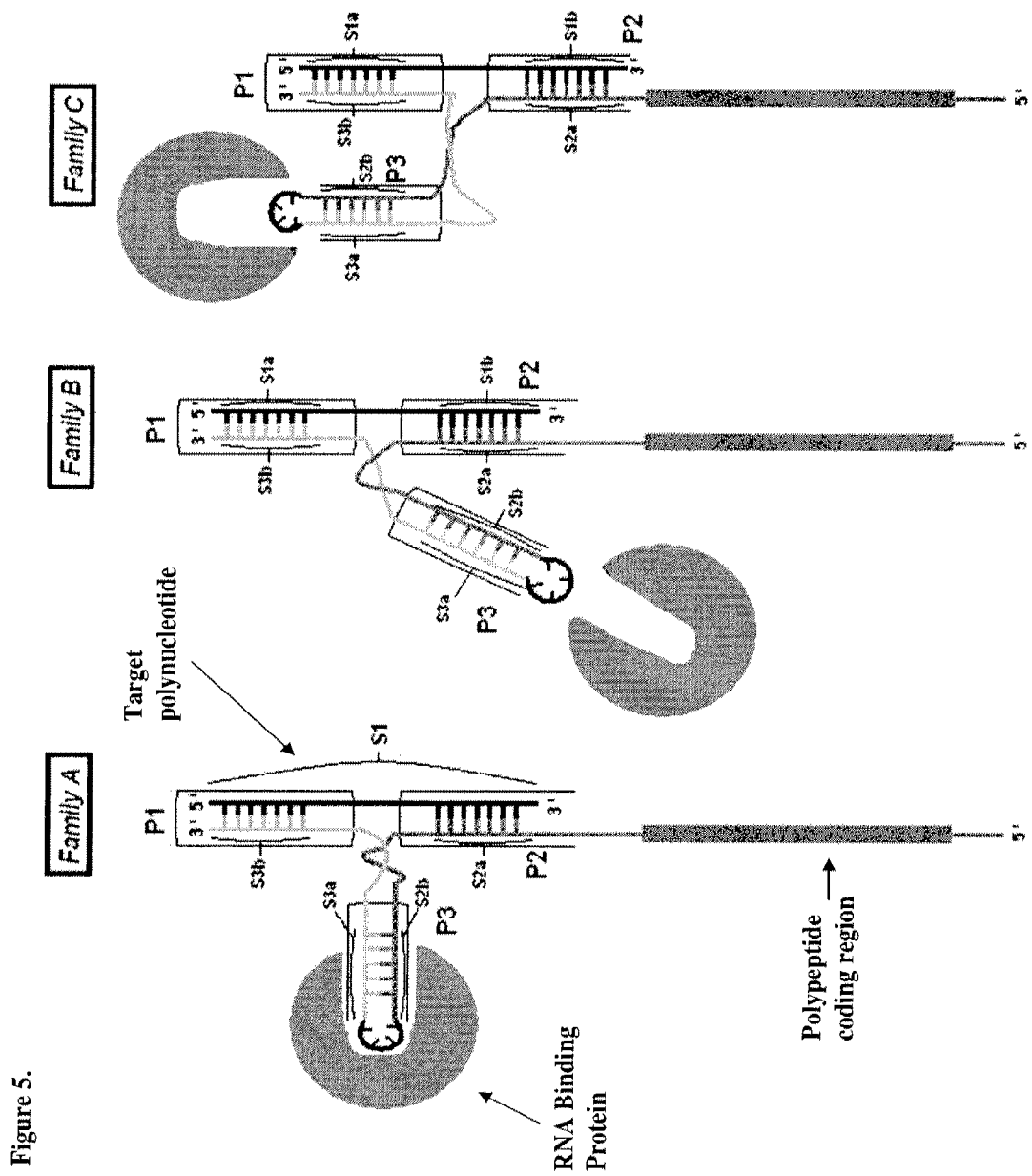
FIG. 5 shows examples of three-way junction family types. An RNA construct can form three basic conformations when hound to a target polynucleotide, corresponding to the three family types (A, B and C) of three-way junctions. Three-way junction conformation can affect the ability of RBPs to bind to a stem-loop.

The choice of three-way junction family will be governed by which of these conformations will not obstruct the activity (e.g., RBP binding) of the reinforced stem-loop. FIG. 5 depicts a generalized example of the family selection process, using a construct in which stem P3 forms the stem-loop, a polypeptide coding region is attached to strand S2a, and strand S1 is the target polynucleotide. In this example, the Family A structure was chosen because it allows the RBP of interest to associate with the stem-loop. Families B and C are not used in this example because P2 and P1, respectively, obstruct the RBP from binding to the stem-loop. In other examples, Family B or Family C might provide a better platform, depending upon the steric interactions of the RBP with the stem-loop. In the exemplary RNA construct and attached polynucleotide coding region, strand S2a is attached to the polynucleotide region which optionally can be flanked by 3' and 5' untranslated regions (UTRs). Also, although this exemplary RNA construct has the stem-loop structure 3' to the polynucleotide coding region, in some instances it might be located 5' to the polynucleotide coding region.

Tertiary interactions of bases in the joining regions with bases in the stem regions, as identified by crystallography in natural forms of three way junctions, may be engineered. On this basis, one can change the conformation to improve a given activity or increase stability, so long as the changes do not interfere with the RBP associating with the stem-loop.

2. Design of Weakened Stem-Loop

To design a weakened stem-loop, point mutations are engineered in the wild-type (including a consensus motif sequence) by introducing non-canonical base pairs (i.e., mismatches) so that structure formation, without a trans-acting support, is no longer energetically favorable. The resulting weakened structure typically should not form bonds strong enough to spontaneously establish an active form of the structure, and when structure is re-formed via trans-acting stabilization, the bond distances typically should not interfere with function. The positions and identity of nucleotides important for activity typically are identified so that these bases are not changed. While vital nucleotides typically are not altered, the nucleotide with which a given vital nucleotide pairs may be able to be altered to weaken the stem without sacrificing binding to the reconstituted structure. Stem nucleotides that only provide structural integrity can be altered to reduce thermodynamic favorability of stem formation. In this case, both bases of a pair can be altered if desired. Canonical base pairs are defined as A-U, U-A, G-C, C-G. There are a number of alternative pairings such as G-U and U-U with varying energy levels and bond distance. The choice as to which bases should be substituted is made with the awareness that if relative bond distance and/or conformation of certain bases in the stem is important to activity, appropriate non-canonical pairings should be chosen (See, for example, Leontis, et al. (2002) NUCLEIC ACIDS RESEARCH 30(16):3497-3531.) For example, to weaken a canonical cis Watson-Crick/Watson-Crick G-C base pair while preserving C1'-C1' bond length distance (10.3 angstroms), a G-U base pair (10.2 angstroms) should be substituted rather than, for example, a U-U base pair (8.1 angstroms). Table 2 provides bond lengths of canonical and non-canonical cis Watson-Crick/Watson-Crick base pairings and allows for selection of appropriate pairings.

TABLE 2

| Pairing | C1' - C1' distance |
| --- | --- |
| U - U | 8.1 Å |
| C - C | 8.5 Å |
| U - G | 10.2 Å |
| G - U | 10.2 Å |
| C - G | 10.3 Å |
| A - U | 10.3 Å |
| U - A | 10.3 Å |
| G - C | 10.3 Å |
| C - A | 10.4 Å |
| A - C | 10.4 Å |
| U - C | 11.8 Å |
| C - U | 11.8 Å |
| A - A | 12.3 Å |
| G - A | 12.5 Å |
| A - G | 12.5 Å |

In addition to bond distance, bond angles and their effects on helix twist and stem "kink" may be considered.

In the case of an RBP binding site, a consensus structure, which can be generated by binding assays, typically is the starting point, but any wild-type sequence (including any consensus sequence) can be used. Although the discussion of RNA construct design principles herein typically refers to an RNA sequence as the starting point, it should be understood that not only RNA sequences but also equivalent DNA sequences can be used. As the skilled artisan understands, an RNA sequence is equivalent to the sequence of a coding strand of genomic DNA or cDNA, because RNA that is transcribed from genomic DNA or cDNA has an identical sequence to the coding strand sequence of the genomic DNA or cDNA (with "T" nucleotides in the DNA sequence and "U" nucleotides in the RNA sequence). Thus, the design principles described herein are applicable when using RNA as a starting point or DNA as a starting point.

Figure 6:
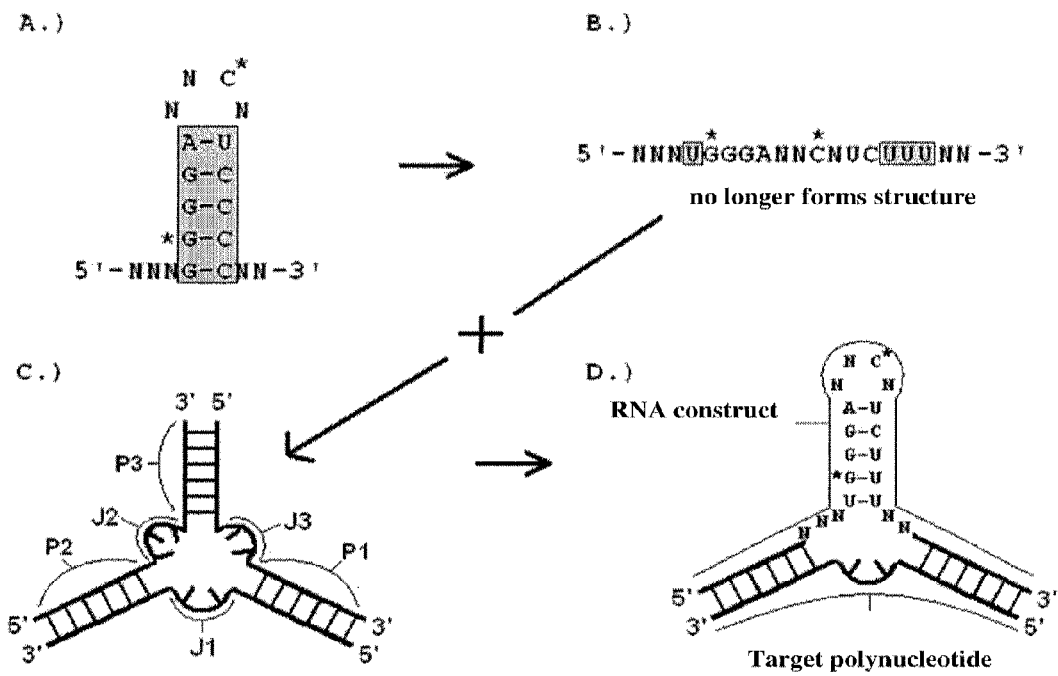
FIGS. 6A-D show a mock example of an RNA construct using a stem-loop element.

In order to demonstrate the concepts of the present invention, a generalized, mock stem-loop consensus sequence is depicted in FIG. 6A, with "N" denoting any nucleotide. Nucleotides in the paired stem portion of the structure, indicated by a shaded box, are mutated so that the structure can no longer spontaneously form. Nucleotides indicated by an asterisk are vital to RBP binding and therefore are not altered. FIG. 6B shows that a G to U mutation was made at the fourth nucleotide from the 5' end, and C to U mutations were made for the three nucleotides at positions 3, 4 and 5, counting from the 3' end. Each mutation depicted in FIG. 6B is indicated by a shaded box. Point mutations were made at spots calculated to increase minimum free energy (MFE) and reduce spontaneous formation of required secondary structure for RBP binding. FIG. 6D shows the structure formed by the binding of the weakened stem-loop structure to its target polynucleotide which follows the pattern of the three-way junction structure depicted in FIG. 6C. In this instance, J3 is 2, J2 is 3, and J1 is 2. Once the weakened stem-loop has been reinforced by the binding of the target polynucleotide, the relevant RBP can associate with the RNA construct and alter transcription of an attached polynucleotide coding region (not shown).

3. Design of Flank Regions

Figure 7:
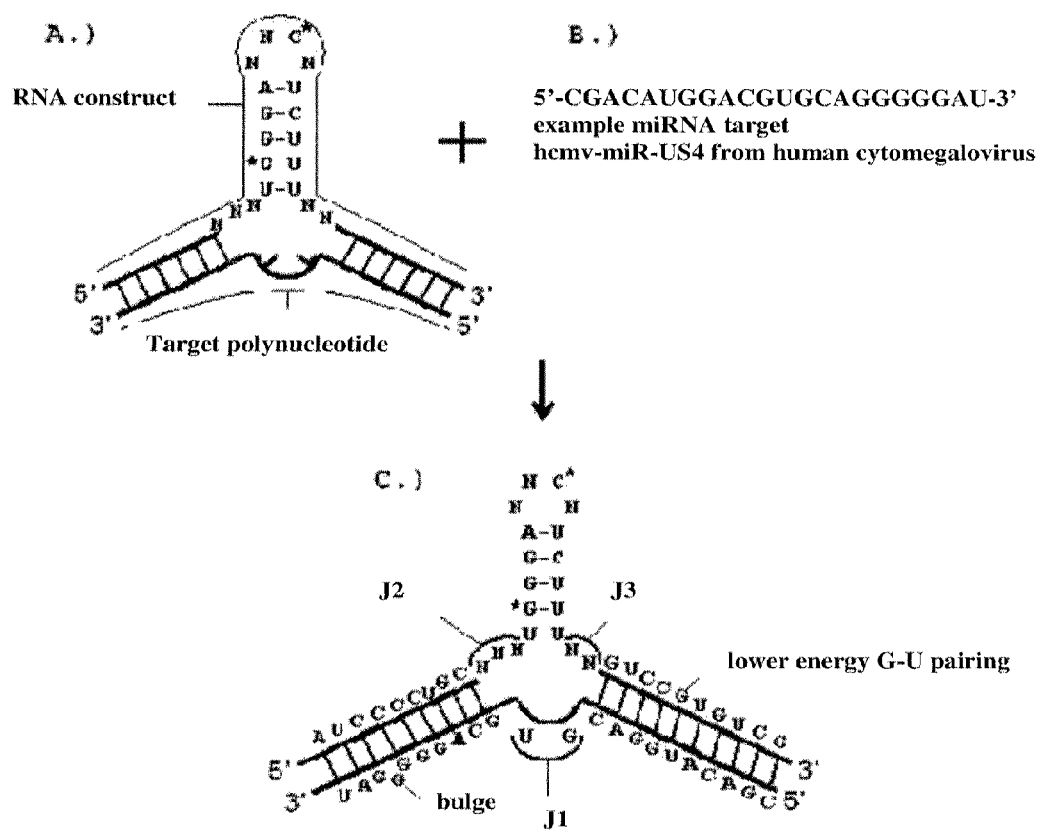
FIGS. 7A-C show an example of the RNA construct (SEQ ID NO: 2) of FIGS. 6A-D (FIG. 7A) designed to hybridize to a HCMV miRNA-US4 target polynucleotide (5'-CGACAUGGACGUGCAGGGGGAU-3' (SEQ ID NO:3) (FIG. 7B).

Flank regions are the regions of nucleotides adjacent to the stem on the 5' and 3' sides of the stem-loop structure that form two of the three joining regions and that bind to the target polynucleotide. FIGS. 7A-C illustrate the design of the 3' and 5' regions that flank the stem-loop of the mock RNA construct of FIGS. 6A-D. FIG. 7A depicts the hypothetical stem-loop previously shown in FIG. 6D. FIG. 7B shows an example target polynucleotide, a naturally-occurring microRNA from human cytomegalovirus, hcmv-miR-US4. In this example, the "N" nucleotides directly adjacent to the stem portion of the RNA construct form the unpaired nucleotides of the joining region. The three unpaired Ns correspond to the J2 region and the two unpaired Ns correspond to the J3 region of the three-way junction. Because the J2 region contains more unpaired nucleotides than does the J3 region, a Family A structure will form. These unpaired nucleotides can be any nucleotide, provided that they do not hybridize to the unpaired U and G nucleotides that make up the J1 joining region formed by the target polynucleotide or otherwise disrupt the structure of the junction. The nucleotides that make up the flank regions of the RNA construct distal to the joining regions are selected to hybridize to the chosen target polynucleotide, as shown in FIG. 7C. Flank sequences should either have no specific nucleotide requirements, so that perfect pairing can be achieved, or those bases that must retain specific identity should fall in an simulated joining region, be a canonical match for the appropriate bases in the target polynucleotide or provide a beneficial mismatch to avoid a non-reversible hybridization with the target polynucleotide. Regardless of whether specific requirements for flank nucleotides exist, the strength of binding of the RNA construct to the target polynucleotide can be affected by introducing non-canonical base pairings (i.e., mismatches) (e.g., "lower energy G-U pairing," FIG. 7C) or by leaving out a base in the flank such that a nucleotide in the target polynucleotide is left unpaired, forming a bulge ("bulge," FIG. 7C).

Figure 8:
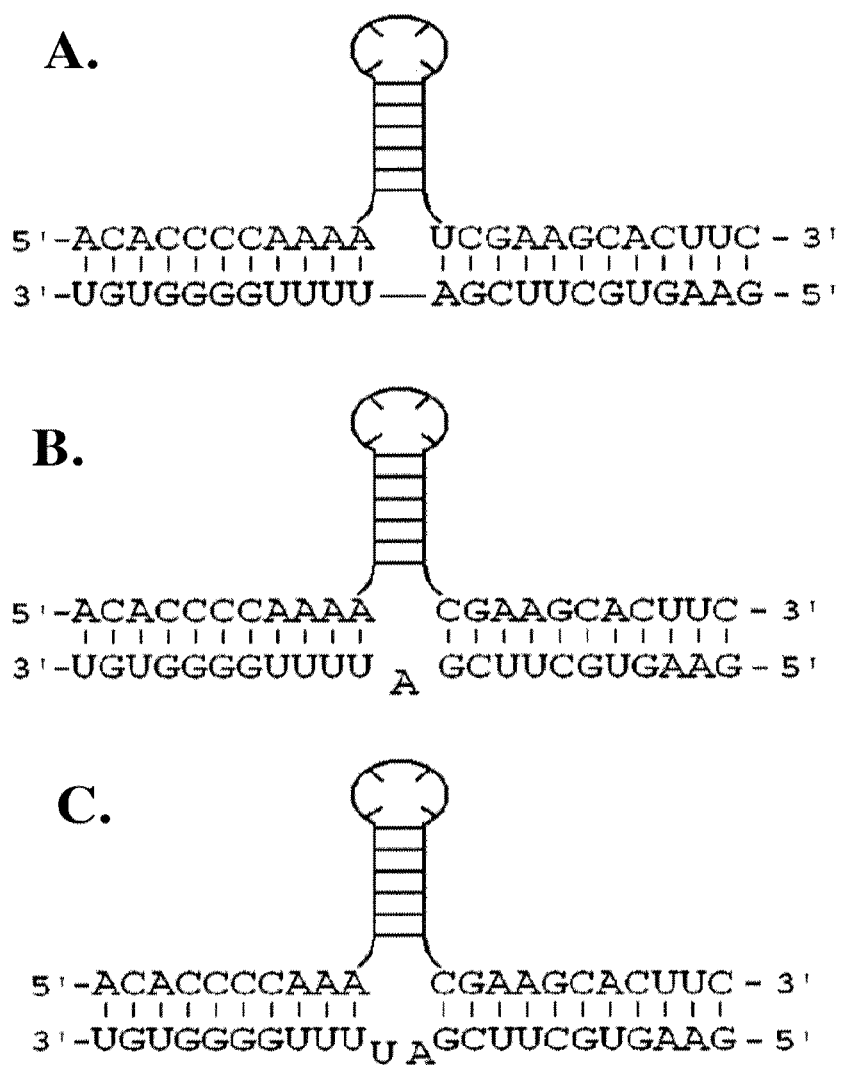
FIGS. 8A-C show that the interaction between flank regions of an RNA construct and target polynucleotide (hsa-miR-373, mirBase No. MIMAT0000726; 5'-GAAGUGCU-UCGAUUUUGGGGUGU-3' (SEQ ID NO:5)) can produce J3 regions of varying sizes.

As shown in FIGS. 8A-C, the nucleotides chosen for the flank regions will dictate the size of the joining region defined by the target polynucleotide sequence. Again, these figures are intended to illustrate the principles of the invention. In FIG. 8A, the flank sequences are designed to pair with each nucleotide of the target polynucleotide sequence, forming a junction size of zero. In FIG. 8B, the flank sequences are designed such that one nucleotide of the target polynucleotide sequence is left without a binding partner, forming a junction size of one. FIG. 8C shows an example of flank sequences designed to leave two nucleotides of the target polynucleotide sequence without binding partners, forming a junction size of two.

Design of an RNA construct can be aided by use of any number of existing informatic RNA folding programs such as mfold, Sfold and the Vienna software. In addition, RNAFold can be used to examine optimal folds of a single RNA molecule; RNACofold can be used to examine optimal folds of two interacting RNA molecules; MiRanda or RNAHybrid can be used as part of high throughput screens to find naturally occurring instances of RNA-target polynucleotide interactions; and JMol can be used for visualizing existing crystal structures. These tools predict the probable structure of RNA and can be used in the design of complementary RNA constructs with predictable structural influences upon contact with the target polynucleotide. Depending on the target polynucleotide sequence, structural aspects may be exploited in the design of the RNA construct, especially with respect to areas of uniqueness in the target polynucleotide. Examples of this strategy include hairpin, stem-loops, cloverleafs, kissing complexes and other conformational structures known to result from traditional RNA-RNA interactions.

4. SELEX Approach

Generally, SELEX (Systematic Evolution of Ligands by Exponential Enrichment) is a method for generating a ligand of interest by taking a population of randomly-generated ligands (e.g., small molecules, polynucleotides or polypeptides) and systematically selecting and amplifying ligands that meet chosen criteria. To select for a ligand of interest, a very large polynucleotide library of random sequences is synthesized. Next, the sequences are exposed to a target binding partner (e.g., a protein or small molecule). Unbound sequences are removed, and the bound sequences are eluted and amplified. The amplified population is again exposed to the target binding partner, and the process is repeated. The stringency of binding and elution conditions can be increased to preferentially enrich only the tightest binding sequences. After a number of cycles, the remaining sequences are identified.

An RNA construct can be produced using a combination of the design approach outlined above and a SELEX-like approach. Use of a SELEX-like approach allows efficient screening of a large range of all possible RNA construct sequences for the best functional candidates. Designing an RNA construct with a SELEX-like approach has several steps in common with the above-described design approach, including choosing a functional motif for the RNA construct (e.g., histone stem-loop); identifying nucleotides important for desired activity (e.g., binding to an RBP); choosing a target polynucleotide sequence, such as an miRNA (e.g., HCMV-miR-US4 or miR-373), which is specific to a desired environment (e.g., HCMV-infected cells or breast cancer cells); and designing the flank sequences of the RNA construct by choosing the region of the target polynucleotide sequence to which the RNA construct will bind.

Figure 9:
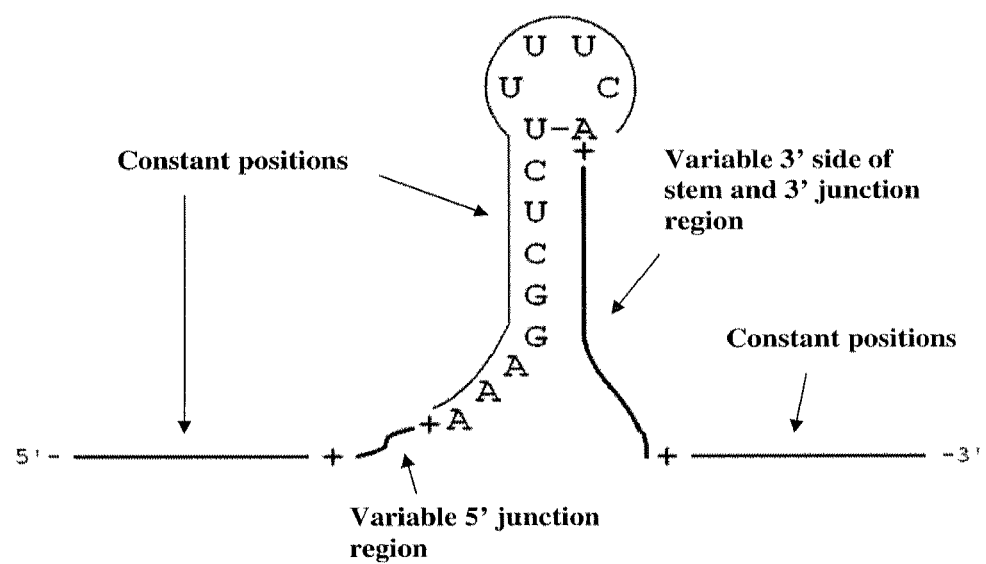
FIG. 9 shows an example of a SELEX approach to designing an RNA construct. A library of sequences is constructed in which regions containing nucleotides critical for RBP binding (5'-AAAGGCUCUUUUCA-3' (SEQ ID NO:10), in this example) and regions designed to hybridize to a target polynucleotide are held constant, while remaining regions are varied at random.

A SELEX-like approach may be taken by keeping the flank sequences and nucleotides critical to the functioning of the motif constant and randomly generating sequences for the remaining positions. Specifically, a library of nucleic acids is generated having sequences in which the constant positions are the same in each sequence, and random nucleotides are placed into the variable positions. FIG. 9 depicts an example of this approach using the histone stem-loop motif. In FIG. 9, three regions of nucleotides are kept constant during the SELEX procedure: a region that includes nucleotides required for the stem-loop binding protein (SLBP) to bind, as well as the two flank regions that correspond to the target polynucleotide sequence that has been chosen. FIG. 9 also depicts the two regions that are varied with randomly generated sequences: the 5'-most joining region (bold line flanked by "+" signs) and the right side of the stem to the 3'-most joining region (bold line flanked by "+" signs). The 5' most joining region can be 0-7 nucleotides long, which will produce a joining region of 3-10 bases including the three adenines directly 3' to the stem. The 3' side of the stem and 3'-most joining region can be 5-15 nucleotides long. This region should include at least 5 nucleotides, so that each base of the 3' side of the stem will be paired, and can include up to 10 nucleotides to make up the 3' most joining region.

A starting library of potential RNA constructs having sequences in which constant positions are kept constant, and variable regions containing random sequences, is initially screened. In the initial screen, nucleic acids having sequences that bind to a protein of interest (e.g., an RBP) in the absence of the target polynucleotide are removed. Then, remaining nucleic acids are exposed to the protein of interest in the presence of the target polynucleotide, and unbound nucleic acids are removed. Bound nucleic acids are eluted, amplified, and the process is repeated under desired stringency conditions. Nucleic acids that remain after multiple rounds of selection are identified and further tested for desired activity. For example, identified nucleic acids may be attached to a polypeptide coding region that includes one or more reporter genes, placed in an expression environment in the presence or absence of the target polynucleotide and assayed to determine whether the reporter gene is expressed. Desired RNA constructs will be those that express the reporter gene only in the presence of the target polynucleotide.

C. Histone Stem-Loop (HSL)

1. HSL Biology and Sequences

The principles of RNA construct design can be applied to a histone stem-loop starting point. For example, a wild-type histone stem-loop (HSL) motif (including a consensus sequence of a HSL motif) can be used as the starting point for further design of an RNA construct in accordance with the principles described above.

Figure 10:
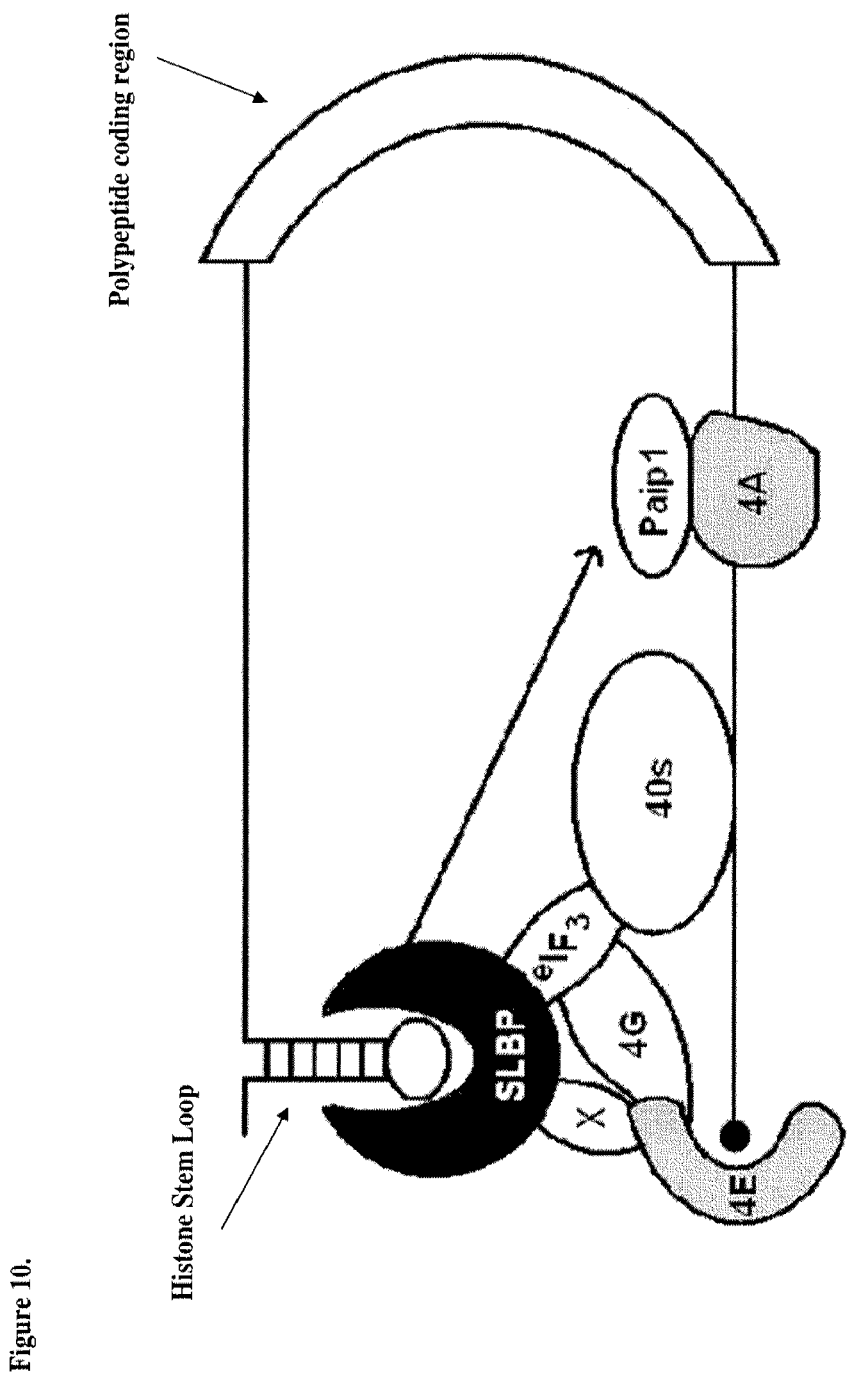
FIG. 10 shows a model of the proposed biological mechanism of action of the HSL motif (and an RNA construct based on a HSL motif). The stem-loop binding protein (SLBP) bound to an RNA construct may act through one or more complexes to promote translation of an attached polypeptide coding region.

Metazoan cell cycle-regulated histone mRNAs are the only known cellular mRNAs that do not terminate in a poly(A) tail. Instead, these messages terminate in a conserved HSL motif, which functions to increase translation. The HSL motif is recognized and bound by "Stem-loop Binding Protein" (SLBP), an RBP, which is believed to upregulate the translation of one or more adjacent polypeptide coding regions through the action of a protein complex, shown in FIG. 10 (see, Gorgonio et al. (2005) RNA 11:1030-1042). As illustrated in FIG. 10, the SLBP binds the HSL in the 3' UTR of the encoded polypeptide. Without wishing to be bound by the theory, the SLBP may interact with eukaryotic initiation factor 3 (eIF3) and other factors, represented by protein "X," that interact with eIF4E ("4E" in FIG. 10) and eIF4G ("4G" in FIG. 10), which in turn binds to the 5' cap (black circle). The formation of this complex may aid in the recruitment of the small ribosomal subunit (40s). In addition, the SLBP may directly bind Paip1, a protein thought to act in a manner similar to eIF4E, which binds eIF4A ("4A" in FIG. 10) to mediate translation. Alternatively, Paip1 simply may act to stabilize the complex.

According to the methods of the present invention, an RNA construct can be designed with a HSL weakened sufficiently to prevent formation of the stem-loop, thereby preventing upregulation of an adjacent polypeptide coding region. The HSL of the RNA construct can be reactivated by binding to a target polynucleotide that stabilizes the stem-loop structure, thereby enabling activation of translation. The advantages of using the HSL motif are that it is well-studied and described, minimal translation occurs when it is inactive, and it achieves orders of magnitude of increased translation when active.

The HSL motif has a conserved size and structure. The visual depiction of this is shown in the following HSL consensus sequence.

```
H U

H   H

U-A

Y-D

Y-D

Y-D

G-Y

5'-MMMG-YMM-3'          (SEQ ID NO: 177)
Consensus Sequence I
```

| FASTA code | Nucleotide |
|---|---|
| A | Adenosine |
| C | Cytidine |
| G | Guanine |
| T | Thymidine |
| U | Uridine |
| R | G A (purine) |
| Y | T U C (pyrimidine) |
| K | G T U (keto) |
| M | A C (amino) |
| S | G C (strong) |
| W | A T U (weak) |
| B | G T U C |
| D | G A T U |
| H | A C T U |
| V | G C A |
| N | A G C T U (any) |
| — | Gap of indeterminate length |

In the HSL, one or more of the guanines at the base of the 5' side stem, the adenine on the 3' side stem, and the first and third uridines in the loop are typically needed for binding to a SLBP. The remaining nucleotides are more variable. However, in some instances the bases that are typically needed for binding to a SLBP may be altered even if some amount of activity is lost. Examples of naturally occurring HSL sequences are identified in FIG. 11 by GenBank number, and can be accessed at www.ncbi.nlm.nih.gov/. "Start" and "end" indicate the location of the HSL sequence within the entire nucleotide sequence. Accordingly, any HSL consensus sequence or sequence from FIG. 11 can by used as the starting point to construct an RNA construct according to the invention.

While the HSL consensus sequence can be described visually, it can also be described using the logic search pattern ("PatSearch description") described in Grillo, et al. (2003) NUCLEIC ACIDS RESEARCH 31(13)3608-3612.

The PatSearch description for the HSL described visually above is:

```
r1 = {AU, UA, GC, CG, GU, UG}

MMM p1 = GGYYY U HHUH A r1~p1 MM
```

"r1" indicates the rules for pairing to be applied to the consensus sequence. For example, the HSL stem can include "AU" base pairings, "UA" base pairings, "GC" base pairings, "CG" base pairings, "GU" base pairings, and "UG" base pairings. The next line shows the consensus sequence, beginning at the 5' end with three "M" nucleotides. Next, "p1" indicates the first pattern of the consensus sequence, "GGYYY," which represents the 5' side of the stem. The next nucleotides in the sequence are UHHUHA, which represent the loop. Next, "r1~p1" indicates that the pairing rules "r1" must be applied to the "p1" sequence to furnish the 3' side of the stem. Finally, the 3' end of the consensus sequence has two amino nucleotides, "MM."

Other examples of HSL consensus sequences are shown below.

```
Consensus Sequence II
                        (SEQ ID NO: 178)
        Y U
       U   N
        U-A
        Y-R
        Y-R
        Y-R
        G-C
5'-MMMMG-CMM-3'

Consensus Sequence III
                        (SEQ ID NO: 179)
         H U
        H   H
         U-A
         Y-R
         Y-R
         Y-R
         G-C
5'-NMMMMG-CMM-3'
```

It should be understood that any wild-type HSL sequence (including a consensus sequence) can be used as the starting point to make any number of RNA constructs. From this wild-type HSL, at least one stem-weakening mutation is incorporated into the construct to decrease the formation of the stem-loop structure in the absence of a target polynucleotide. Consensus sequences that include non-canonical base pairings (i.e., mismatches) are considered to be weakened when such a pairing (e.g., a GU or a UG pairing) is chosen, even if the consensus sequence is broad enough to include non-canonical pairings at those same positions (e.g., because some wild-type sequences falling within the consensus sequence have canonical base pairing, rather than non-canonical base pairing, at the location). Alternatively, an RNA construct can contain a wild-type stem-loop if the stem-loop, in the context of the RNA construct, has an increased Minimum Free Energy (MFE) compared to the stem-loop in a wild-type context, such that the stem-loop of the RNA construct will be less stable than will the stem-loop in a wild-type context.

2. Design of an Example RNA Construct when Starting from an HSL Motif

Figure 12:
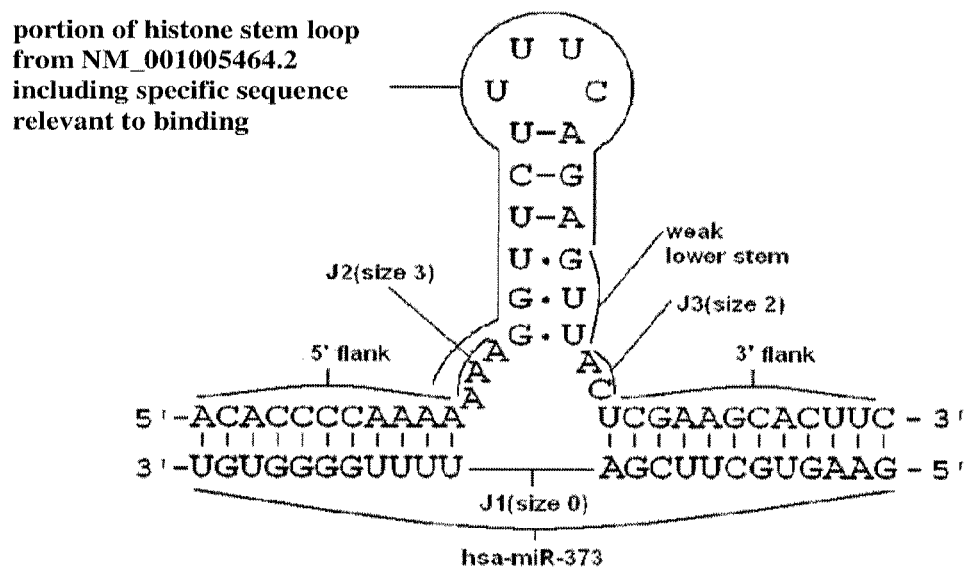
FIG. 12 shows an example of an RNA construct based on histone stem-loop Consensus Sequence I. Two GU pairings and one UG pairing are designed at the lower portion of the stem to weaken it, such that formation of the stem-loop structure is dependent on the association with a target polynucleotide (hsa-miR-373 (SEQ ID NO:11) in this example). This RNA construct has the nucleotide sequence 5'-ACAC-CCCAAAAAAGGUUCUUUUCAGAG-UUACUCGAAGCACUUC-3' (SEQ ID NO:12)).

This section illustrates the design of an RNA construct, shown in FIG. 12, starting from Consensus Sequence 1.

a. Joining Regions

When designing an RNA construct based on an HSL motif, the size of the J2 joining region can be chosen so that the RNA construct-target polynucleotide structure forms a Family A, Family B or Family C structure. In the example depicted in FIG. 12, Family A is chosen. Family A likely allows the most favorable nucleic acid structure for binding to the SLBP. This is typically true of RNA constructs based upon the HSL structure.

HSL Consensus Sequence I begins with three "M" nucleotides. In FIG. 12, all three "M" nucleotides are chosen to be unpaired "A" nucleotides, thereby forming a J2 region of 3 nucleotides. However, the size of the joining region can be decreased by choosing all or some of the "M" nucleotides to be nucleotides that pair with the target polynucleotide. The size of the J2 region also can be increased by adding nucleotides 5' to the "MMM" region that do not pair with the target polynucleotide.

The HSL consensus sequence ends with two "M" nucleotides. In FIG. 12, the two "M" nucleotides are chosen to be unpaired "AC," thereby forming the J3 joining region. As with the J2 joining region, the size of the J3 joining region can be decreased by choosing all or some of the "M" nucleotides to be nucleotides that pair with the target polynucleotide, or it can be increased by adding nucleotides 5' to the "MM" region that do not pair with the target polynucleotide. The J1 joining region in this example contains no nucleotides. Thus, this example has a Family A structure due to the choice of joining regions.

b. Weakening the Stem

The HSL consensus sequence has the sequence "GGYYY" on the 5' side of the stem, corresponding to "GGUUC" in FIG. 12. Although the "r1" pairing rules are broad enough to include the non-canonical base pairings GU and UG in the stem, use of non-canonical base pairings (i.e., mismatches) at these positions, rather than canonical base pairs, can produce a weakened stem suitable for use with the present invention. Therefore, the choice of three CU base pairings in the stem, depicted in FIG. 12, weakens the stem to prevent formation of the stem-loop in the absence of the target polynucleotide.

c. Flank Regions

Flank regions can be designed according to the principles discussed above. The flank regions of the RNA construct include two of the three joining regions as well as sequence that is complementary to the target polynucleotide. In the example shown in FIG. 12, the flank regions include the three-way joining regions J2 ("AAA") and J3 ("AC"), corresponding to "MMM and "MM," respectively, in the consensus sequence. The nucleotides distal to the joining regions contain nucleotides that hybridize to the target sequence, which in this example is the human microRNA hsa-miR-373.

As described above, the selected HSL sequence is then further modified to attach the polypeptide coding region using standard molecular biological protocols.

D. Iron Response Element (IRE)

Alternatively, a wild type Iron Response Element (IRE), including a consensus sequence of an IRE motif, can be used as the starting point for functional design of an RNA construct in accordance with the principles described above. The IRE is an stem-loop motif with a binding site for RBPs such as iron-responsive binding proteins, for example, aconitase 1 (ACO1, also known as iron-responsive element binding protein 1 or IRP1) and iron-responsive element binding protein 2 (IREB-2, also know as IRP2). IREs occur naturally in the 3' and 5' UTRs of mRNAs that encode iron metabolism proteins. Translation may be up or down regulated depending upon whether the IRE is located in the 3' or 5' UTR and on the concentration of iron. Typically, IREs located in the 5' UTR of an mRNA inhibit translation, while IREs located in the 3' UTR stabilize mRNA, leading to increased translation. Additionally, iron-responsive binding proteins actively bind IREs when cellular iron concentration is low. For example, the transferrin receptor mRNA contains an IRE in its 3' UTR, and therefore more transferrin is produced and more iron will be transported into the cell. Conversely, the ferritin H and L subunit mRNAs contain IREs in their 5' UTRs and are suppressed when iron concentration is low (i.e., do not make proteins that incorporate iron if it is not available). As cellular iron concentration increases, IRP1 degrades and IRP2 deactivates, thus decreasing production of transferrin and increasing production of H and L ferritin subunits. (See also Matthias W. Hentze and Lukas C. Kuhn (1996) Proc. Natl. Acad. Sci. USA, Vol. 93, pp. 8175-8182).

Figure 13:
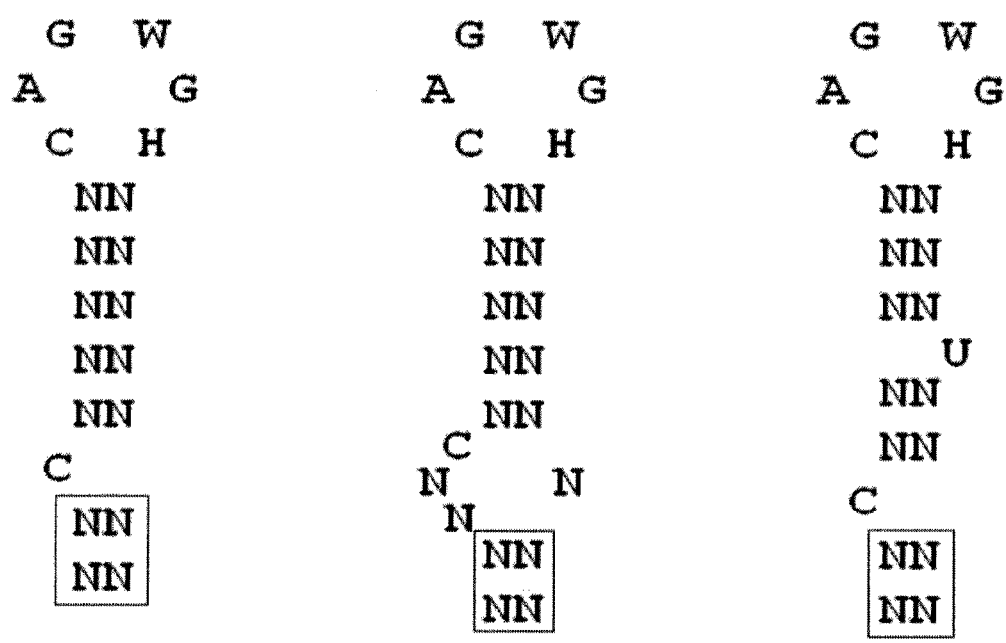
FIG. 13A shows an RNA construct incorporating a weakened Iron Response Element (IRE) motif that does not effectively form in the absence of a target polynucleotide.
FIG. 13B shows the reconstituted IRE motif hybridized to a target polynucleotide.
FIG. 13C shows examples of IRE1 (5'-NNCNNNNNCAGWGHNNNNNNN-3' (SEQ ID NO:13)), IRE2 (5'-NNNNCNNNNNCAGWGHNNNNNNNN-3' (SEQ ID NO:14)), and IRE3 (5'-NNCNNNNNCAG-WGHNNNUNNNN-3' (SEQ ID NO:15)) consensus sequences (left to right, respectively).

In one strategy, depicted in FIG. 13A, an RNA construct is engineered from the wild-type sequence of an IRE (including a consensus sequence). The RNA construct includes one or more weakened IREs and is located in the 3' UTR adjacent to the polypeptide coding region. As shown in FIG. 13B, the presence of a target polynucleotide stabilizes the IRE. The stabilized IRE associates with an RBP, which prevents degradation of the RNA construct, leading to increased translation. This strategy can be modified to have an RNA construct including at least two weakened IREs located in the 3' UTR adjacent to the polypeptide coding region. These two IREs can be designed to bind to two different target polynucleotides, such that the presence of both target polynucleotides allows for the desired increase in translation.

In another strategy, an RNA construct is engineered from the wild-type sequence of an IRE (including a consensus sequence). The RNA construct includes one or more weakened IREs and is located in the 5' UTR adjacent to the polypeptide coding region. The presence of a target polynucleotide stabilizes the IRE. The stabilized IRE associates with an RBP, leading to translation inhibition.

In another strategy, RNA constructs are weakened IREs and are located both in the 5' and 3' UTRs adjacent to the polypeptide coding region. In this strategy, the flank regions of the weakened IREs in the 5' and 3' UTRs are designed to bind to different target polynucleotides. For example, the flank regions of the 3' UTR RNA construct are designed to bind a target polynucleotide ("target 1") found in target cells, and the flank regions of the 5' UTR RNA construct are designed to bind a target polynucleotide ("target 2") not found in the target cells. When the two RNA constructs adjacent the polypeptide coding region are introduced into target cells, The 3' RNA construct is stabilized by the binding of target 1, and translation of the encoded polypeptide will increase. At a desired time point, target 2 can be introduced in the target cells to inhibit translation.

The structure of the IRE motif is conserved but the exact composition of nucleotides can be variable, providing a useful platform for design of an RNA construct. Three subtypes of IRE consensus sequences can be used as a starting point from which to design an RNA construct. FIG. 13C shows an example of each type of IRE consensus sequence. No specific requirements exist for the nucleotide composition of the paired bases of the stem (except that they must follow the "r1" pairing rules described below) or for the composition of the flank sequences. The lack of specific base requirements gives a large degree of flexibility for designing an RNA construct based on the consensus IRE sequences or specific naturally-occurring IRE sequences in accordance with the strategies outlined above. The boxed portions of the consensus sequences indicate the regions where the stem may be weakened by introducing non-canonical base pairings (i.e., mismatches). This lower stem region can be 2 to 6 nucleotides long in certain embodiments of the invention.

The PatSearch pattern for IRE subtype 1 is as follows:

```
1.) IRE1
r1 = {AU, UA, GC, CG, GU, UG} p1 = 2 . . . 8 C p2 = 5 . . . 5 CAGWGH r1~p2 r1~p1
```

"r1" indicates the rules for pairing to be applied to the consensus sequence. For example, the IRE1 consensus sequence can include "AU" base pairings, "UA" base pairings, "GC" base pairings, "CG" base pairings, "GU" base pairings, and "UG" base pairings. The IRE1 consensus sequence begins at the 5' end with the first pattern, "p1," which forms the first part of the 5' side of the stem. "p1" defines a string of 2 to 8 nucleotides of any composition (A, G, C, or U). The next part of the 5' side of the stem is an unpaired "C" nucleotide, followed by the second pattern "p2," the last part of the 5' stem. "p2" defines a string of exactly 5 nucleotides of any composition (A, G, C, or U). Following "p2" is the loop, which consists of the sequence "CAGWGH." Following the loop is the first part of the 3' side of the stem, which can be any string of nucleotides that pairs to the "p2" pattern, provided that the nucleotides follow the "r1" rules for pairing (as indicated by the PatSearch description "r1~p2"). The final part of the 3' stem can be any string of nucleotides that pairs to the "p1" pattern, provided that the nucleotides follow the "r1" rules for pairing (as indicated by the PatSearch description "r1~p1"). Examples of specific naturally-occurring IRE1 sequences are identified in FIG. 14 by GenBank number, and can be accessed at www.ncbi.nlm.nih.gov/. "Start" and "end" indicate the location of the IRE1 sequence within the entire nucleotide sequence.

The PatSearch pattern for IRE subtype 2 is as follows:

```
2.) IRE2
r1 = {AU, UA, GC, CG, GU, UG} p3 = 2 . . . 8 NNC p4 = 5 . . . 5 CAGWGH r1~p4 N r1~p3
```

"r1" indicates the rules for pairing to be applied to the consensus sequence. For example, the IRE2 consensus sequence can include "AU" base pairings, "UA" base pairings, "GC" base pairings, "CG" base pairings, "GU" base pairings, and "UG" base pairings. The IRE2 consensus sequence begins at the 5' end with the first pattern, "p3," which forms the first part of the 5' side of the stem. "p3" defines a string of 2 to 8 nucleotides of any composition (A, G, C, or U). The next part of the 5' side of the stem is the sequence "NNC," which will be unpaired. Next, the second pattern, "p4," forms the last part of the 5' stem. "p4" defines a string of exactly 5 nucleotides of any composition (A, G, C, or U). Following "p4" is the loop, which consists of the sequence "CAGWGH." Following the loop is the first part of the 3' side of the stem, which can be any string of nucleotides that pairs to the "p4" pattern, provided that the nucleotides follow the "r1" rules for pairing (as indicated by the PatSearch description "r1~p4"). The second part of the 3' stem can be any single unpaired nucleotide "N." The final part of the 3' stem can be any string of nucleotides that pairs to the "p3" pattern, provided that the nucleotides follow the "r1" rules for pairing (as indicated by the PatSearch description "r1~p3"). Examples of specific naturally-occurring IRE2 sequences are identified in FIG. 15 by GenBank number, and can be accessed at www.ncbi.nlm.nih.gov/. "Start" and "end" indicate the location of the IRE2 sequence within the entire nucleotide sequence.

The PatSearch pattern for IRE subtype 3 is as follows:

```
3.) IRE3
r1 = {AU, UA, GC, CG, GU, UG} p5 = 6 . . . 8 C p6 = 2 . . . 2 p7 = 3 . . . 3 CAGWGH r1~p7 U r1~p6 r1~p5
```

"r1" indicates the rules for pairing to be applied to the consensus sequence. For example, the IRE3 consensus sequence can include "AU" base pairings, "UA" base pairings, "GC" base pairings, "CG" base pairings, "GU" base pairings, and "UG" base pairings. The IRE3 consensus sequence begins at the 5' end with the first pattern, "p5," which forms the first part of the 5' side of the stem. "p5" defines a string of 6 to 8 nucleotides of any composition (A, G, C, or U). The next part of the 5' side of the stem is an unpaired "C" nucleotide, followed by the second pattern "p6," which makes up the third part of the 5' stem. "p6" defines a string of exactly 2 nucleotides of any composition (A, G, C, or U). The final part of the 5' stem is the pattern "p7," which consists of exactly 3 nucleotides. Following "p7" is the loop, which consists of the sequence "CAGWGH." Following the loop is the first part of the 3' side of the stem, which can be any string of nucleotides that pairs to the "p7" pattern, provided that the nucleotides follow the "r1" rules for pairing (as indicated by the PatSearch description "r1~p7"). The second part of the 3' stem is the unpaired nucleotide "U." The next part of the 3' stem can be any string of nucleotides that pairs to the "p6" pattern, provided that the nucleotides follow the "r1" rules for pairing (as indicated by the PatSearch description "r1~p6"). The final part of the 3' stem can be any string of nucleotides that pairs to the "p5" pattern, provided that the nucleotides follow the "r1" rules for pairing (as indicated by the PatSearch description "r1~p5"). Examples of specific naturally-occurring IRE3 sequences are identified in FIG. 16 by GenBank number, and can be accessed at www.ncbi.nlm.nih.gov/. "Start" and "end" indicate the location of the IRE3 sequence within the entire nucleotide sequence.

E. SECIS

Alternatively, a wild type Selenocysteine Insertion Element (SECIS), including a consensus sequence of a SECIS motif, can be used as the starting point for functional design of an RNA construct in accordance with the principles described above. Two varieties of SECIS elements exist, type 1 and type 2 (SECIS1, SECIS2). An active SECIS element present in the 3'UTR of an mRNA causes the translation machinery to reinterpret a UGA stop codon as a selenocysteine residue. Selenocysteine incorporation at UGA codons also uses specialized trans-acting factors. They include a selenocysteine-specific tRNA, an elongation factor specific for this tRNA and a SECIS-binding protein, (e.g., SBP2, which is an RBP), which recruits the elongation factor to the selenoprotein mRNA. Ribosomal Protein L30 also binds the SECIS element. It is believed that a complex of SELB (the specialized elongation factor), Sec-tRNA$^{Sec}$ (selenocysteine tRNA), GTP (guanosine triphosphate), SBP2 and SECIS form and then associate with the ribosome via L30. At this point, a conformational change in the SECIS element triggers the release of Sec-tRNA$^{Sec}$ and GTP hydrolysis, which allows incorporation of the selenocysteine residue into the polypeptide. (See, e.g., Chavatte et al. (2005) NATURE STRUCTURAL AND MOLECULAR BIOLOGY 12:408-418.)

Figure 17:
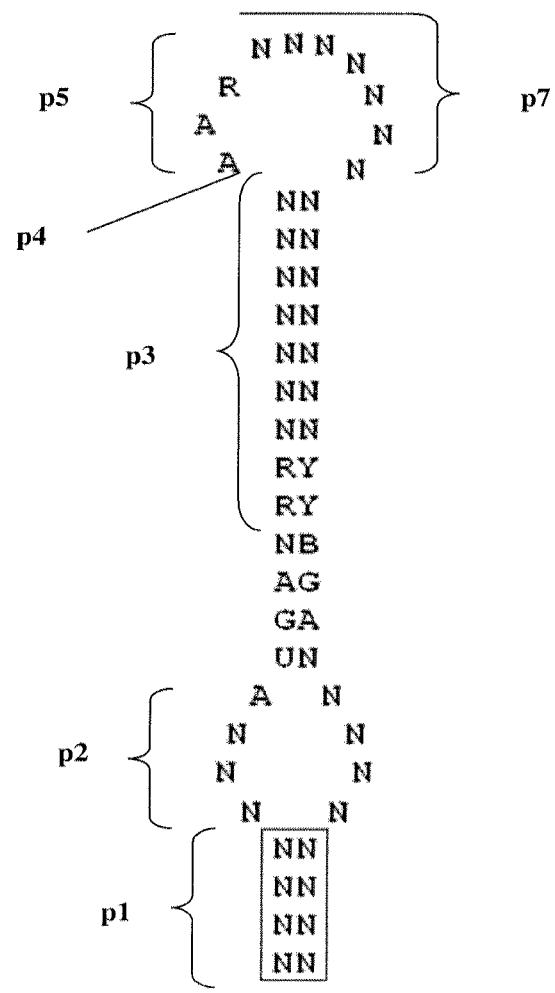
FIG. 17A shows an RNA construct incorporating a weakened Selenocysteine insertion sequence (SECIS) Element that does not effectively form in the absence of a target polynucleotide.
FIG. 17B shows the reconstituted SECIS motif hybridized to a target polynucleotide.
FIG. 17C shows an example of a SECIS consensus sequence (5'-NNNNNNAUGANR-RNNNNNNNAARNNNNNNNNNNNNN NYYBGANNNNNNNN-3') (SEQ ID NO:16).

As shown in FIG. 17A, an RNA construct is designed and placed adjacent to a region encoding an innocuous, small polypeptide ending in a UGA stop codon, which is followed by the desired polypeptide coding region. The RNA construct is a weakened SECIS element located in the 3' UTR adjacent the polypeptide coding region. In the absence of a stabilizing target polynucleotide, only the small, innocuous peptide is translated. As shown in FIG. 17B, the presence of a stabilizing target polynucleotide causes the SECIS element (the RNA construct) to become active, which in turn causes the translation machinery to read the UGA stop codon as a selenocysteine, thereby producing a polypeptide that includes the innocuous peptide, the selenocysteine residue, and the desired polypeptide from the polypeptide coding region. In addition, when the SECIS element of the RNA construct is inactive (for example, when no target polynucleotide is present) the polypeptide encoded by the polypeptide coding region will not be produced. FIG. 17C shows an example of a SECIS consensus sequence for SECIS1.

The PatSearch description for the SECIS type 1 consensus sequence is as follows:

```
A.) SECIS1
r1 = {AU, UA, GC, CG, GU, UG} p1 = 4 . . . 19 p2 = 2 . . . 9 R

UGAN p3 = 8 . . . 12 p4 = 0 . . . 3 p5 = aav p7 = 7 . . . 10 r1~p3[1, 0, 0]

p3:(((^RR |^MC) |^SU) 6 . . . 10)

NGAN p8 = 2 . . . 9 r1~p1
```

"r1" indicates the rules for pairing to be applied to the consensus sequence. For example, the SECIS1 consensus sequence can include "AU" base pairings, "UA" base pairings, "GC" base pairings, "CG" base pairings, "GU" base pairings, and "UG" base pairings. The SECIS1 consensus sequence begins at the 5' end with the first pattern, "p1," which forms the first part of the 5' side of the stem. "p1" defines a string of 4 to 19 nucleotides of any composition (A, G, C, or U). The next part of the 5' side of the stem is the second pattern "p2," which defines a string of 2 to 9 unpaired nucleotides of any composition (A, C, C, or U), followed by an "R." The next part of the 5' side of the stem is the string of nucleotides "UGAN." The next part of the 5' side of the stem is defined by the pattern "p3," which consists of 8-12 nucleotides. "p3" is further defined by the PatSearch description, "p3:(((^RR|^MC)|^SU)6 . . . 10)," which indicates that "p3" must start with either "RR," "MC," or "SU" followed by 6-10 nucleotides of any composition (making up 8-12 nucleotides total). Pattern "p4" defines the 5' end of the loop, which can be 0 to 3 nucleotides of any composition (A, G, C, or U). The loop continues with pattern "p5," defined by the string of nucleotides "AAV." The loop continues with pattern "p7," which consists of 7 to 10 nucleotides of any composition (A, G, C, or U). Following the loop is the first part of the 3' side of the stem, which can be any string of nucleotides that pairs to the "p3" pattern, provided that the nucleotides follow the "r1" rules for pairing. The PatSearch description, "r1~p3[1,0,0]" indicates that the nucleotides in this section can, but are not required to, incorporate 1 mismatch, 0 insertions, and 0 deletions. The second part of the 3' stem is the string of nucleotides "NGAN." The next part of the 3' stem consists of 2 to 9 unpaired nucleotides of any composition (A, G, C, or U). The final part of the 3' stem can be any string of nucleotides that pairs to the "p1" pattern, provided that the nucleotides follow the "r1" rules for pairing. Examples of specific naturally-occurring SECIS type 1 sequences are identified in FIG. 18 by GenBank number, and can be accessed at www.ncbi.nlm.nih.gov/. "Start" and "end" indicate the location of the SECIS1 sequence within the entire nucleotide sequence.

The PatSearch description for the SECIS type 2 consensus sequence is as follows:

```
B.) SECIS2
r1 = {AU, UA, GC, CG, GU, UG} p1 = 4 . . . 19 p2 = 2 . . . 9 A

UGAN p3 = 8 . . . 12 p3:(((^RR |^MC) |^SU) 6 . . . 10)

p4 = 0 . . . 3 p5 = AAV p6 = 11 . . . 14 p6:(0 . . . 1 p7 = 2 . . . 7 3 . . . 6 r1~p7 0 . . . 3$)

(((r1~p3[1, 0, 0] |r1~p3[1, 1, 0])

|r1~p3[1, 0, 1]) |r1~p3[0, 1, 1])

NGAN p10 = 2 . . . 9 r1~p1
```

"r1" indicates the rules for pairing to be applied to the consensus sequence. For example, the SECIS2 consensus sequence can include "AU" base pairings, "UA" base pairings, "GC" base pairings, "CG" base pairings, "GU" base pairings, and "UG" base pairings. The SECIS2 consensus sequence begins at the 5' end with the first pattern, "p1," which forms the first part of the 5' side of the stem. "p1" defines a string of 4 to 19 nucleotides of any composition (A, G, C, or U). The next part of the 5' side of the stem is the second pattern "p2," which defines a string of 2 to 9 unpaired nucleotides of any composition (A, G, C, or U), followed by an "A." The next part of the 5' side of the stem is the string of nucleotides "UGAN." The next part of the 5' side of the stem is defined by the pattern "p3," which consists of 8-12 nucleotides. "p3" is further defined by the PatSearch description, "p3:(((^rr|^mc)|^su)6 ... 10)," which indicates that "p3 must start with either "RR," "MC," or "SU" followed by 6-10 nucleotides of any composition (making up 8-12 nucleotides total). Pattern "p4" defines the 5' end of the loop, and can be 0 to 3 nucleotides of any composition (A, G, C, or U). The loop continues with pattern "p5," defined by the string of nucleotides "AAV." The loop continues with pattern "p6," which consists of 11 to 14 nucleotides which begins with 0 to 1 nucleotide of any compositions (A, G, C, or U), followed by the pattern p7, which can be 2 to 7 nucleotides of any composition (A, G, C, or U) followed by 3 to 6 nucleotides, provided that the last 3 nucleotides, which will form the first part of the 3' side of the stem, follow the "r1" rules for pairing. The next part of the 3' side of the stem can be any string of nucleotides that pairs to the "p3" pattern, provided that the nucleotides follow the "r1" rules for pairing. The PatSearch description, "(((r1~p3[1,0,0]|r1~p3[1,0,1])|r1~p3[1,0,1]) |r1~p3[0,1,1])" indicates that the nucleotides in this section can (but are not required to) incorporate 1 mismatch, 0 insertions, and 0 deletions; 1 mismatch, 1 insertion, and 0 deletions; 1 mismatch, 0 insertions, and 1 deletion; or 0 mismatches, 1 insertion, and 1 deletion. The second part of the 3' stem is the string of nucleotides "NGAN." Pattern 10 defines the next part of the 3' stem, which consists of 2 to 9 unpaired nucleotides of any composition (A, G, C, or U). The final part of 3' stem can be any string of nucleotides that pairs to the "p1" pattern, provided that the nucleotides follow the "r1" rules for pairing. Examples of specific naturally-occurring SECIS type 2 sequences are identified in FIG. 19 by GenBank number, and can be accessed at www.ncbi.nlm.nih.gov/. "Start" and "end" indicate the location of the SECIS2 sequence within the entire nucleotide sequence.

F. Internal Ribosome Entry Site (IRES)

Alternatively, a wild type Internal Ribosomal Entry Site (IRES), including a consensus sequence of a IRES motif, can be used as the starting point for functional design of an RNA construct in accordance with the principles described above. The IRES is located in the 5' UTR of mRNA and allows for 5' cap-independent initiation of translation. Multiple forms have been identified and some interact with different factors to begin translation. For example, some IRESes bind eIF4G to initiate translation, while some act by directly binding to the 40S subunit. However, IRESes are not known to bind to an RBP. Instead, proper formation of the IRES facilitates binding of proteins that make up the translation machinery itself (e.g., eIF4G or the 40S subunit).

Figure 20:
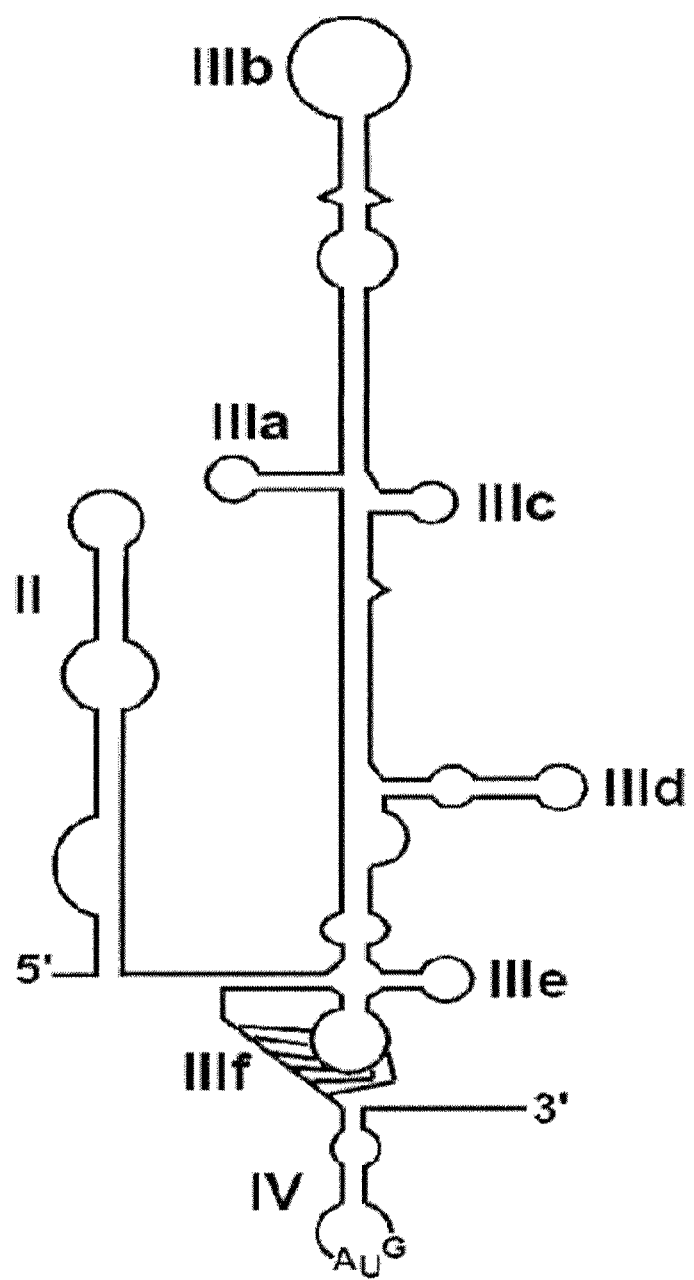
FIGS. 20A-B show a motif from the internal ribosome entry site (IRES) element which can be used as the RBP target in an RNA construct.
Figure 20:
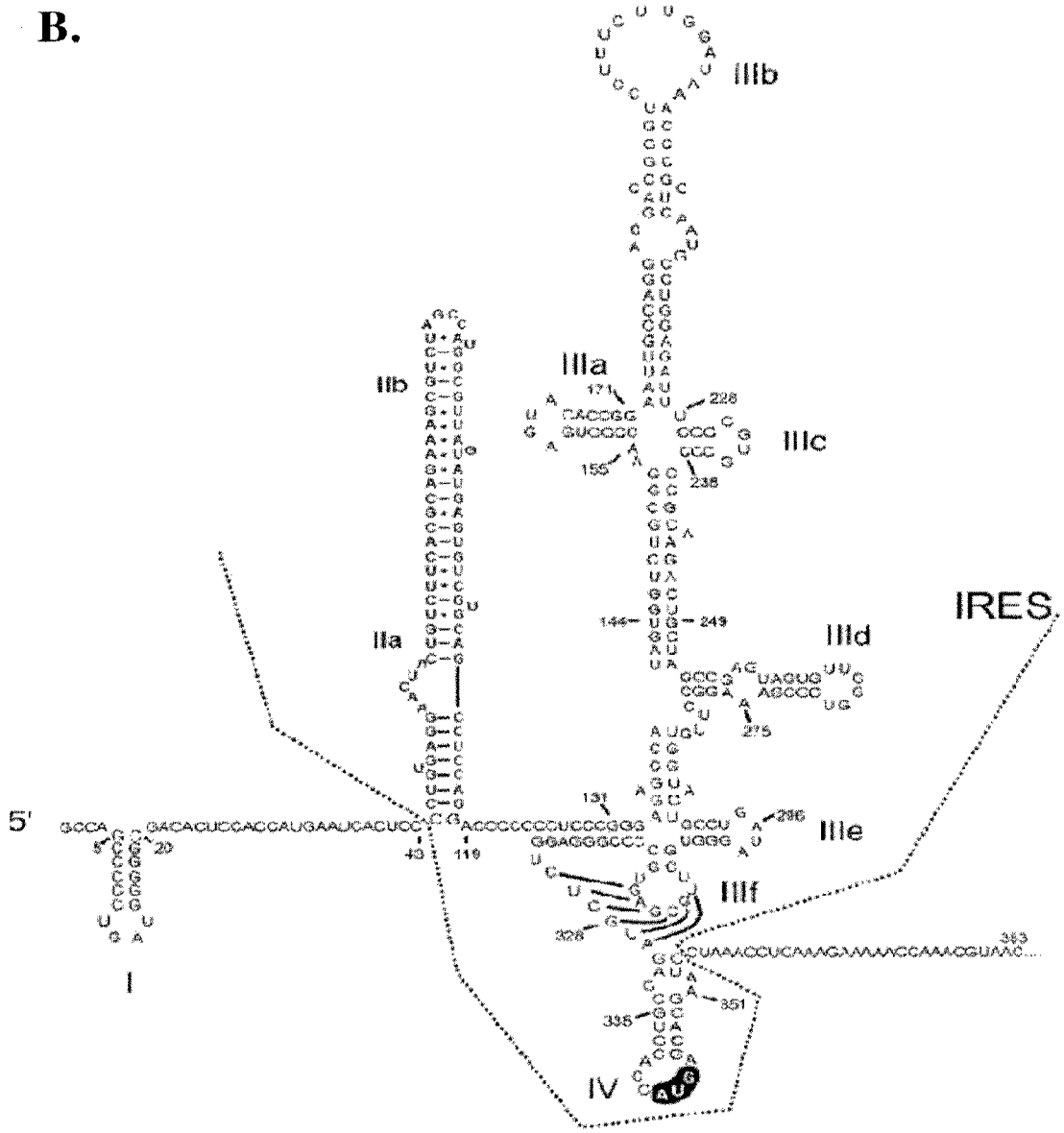
Figure 21:
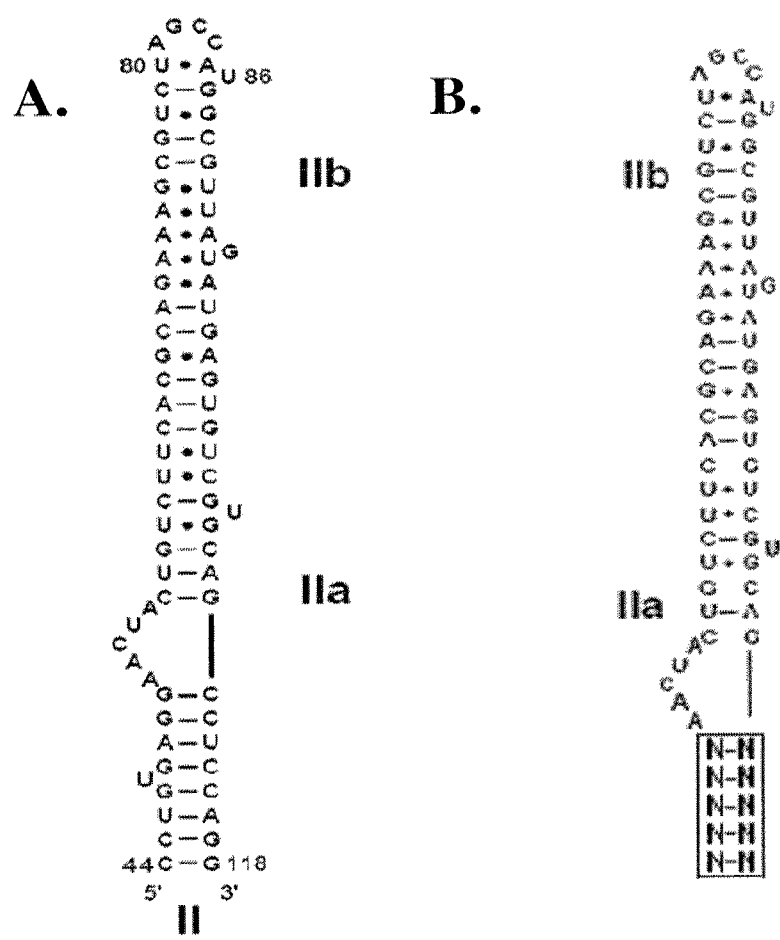
FIGS. 21A-B show an exemplary portion of an IRES element that can be used as the basis of an RNA construct. This portion is the region of the internal ribosome entry site (IRES) element that corresponds to domain II in the Hepatitis C virus.
Figure 24:
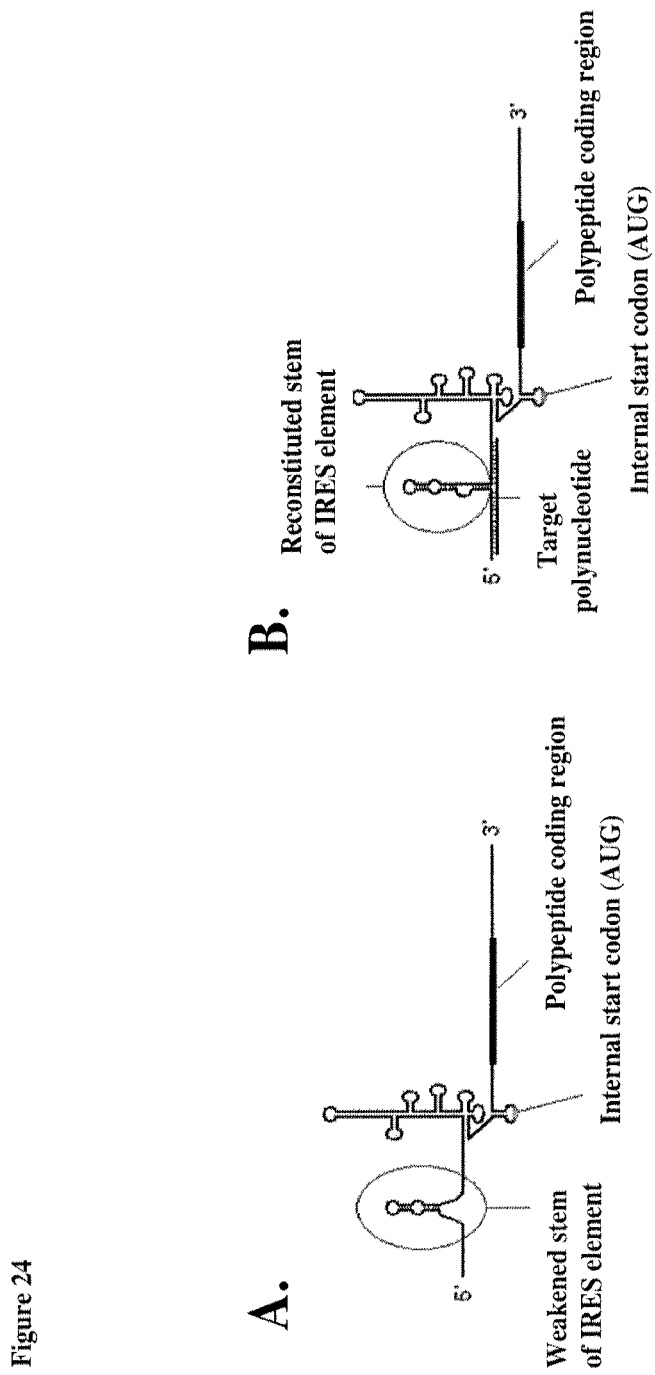
FIGS. 24A-B show target polynucleotide stabilization of an RNA construct incorporating an IRES motif.

IRESes typically are large and more complex than a simple stem-loop. A few flaviviruses have an IRES with similar structure, shown generally in FIG. 20A. One example of an IRES of this type is the Hepatitis C virus IRES shown in FIG. 20B. One part of that structure, referred to as "domain II" in the Hepatitis C virus, can be used as a starting point for making an RNA construct (see FIG. 21A). FIG. 21A shows domain II (labeled IIa and IIb) from the Hepatitis C virus, and FIG. 21B depicts the region of nucleotides, labeled "N," that can be modified to design an RNA construct. For example, nucleotides can be modified to weaken the stem, and flank nucleotides can be designed to match a target polynucleotide sequence. Examples of flavivirus IRESes with similar structure, including a domain II region in bold, are shown in FIG. 22. The sequences for other specific naturally-occurring IRES motifs from which an RNA construct can be designed are identified in FIG. 23 by GenBank number, and can be accessed at www.ncbi.nlm.nih.gov/. "Start" and "end" indicate the location of the IRES sequence within the entire nucleotide sequence. Any of the sequences can by modified to produce an RNA construct.

As shown in FIG. 24A, an RNA construct can be designed to encode a weakened domain II-like structure, which is followed by the remaining IRES structure, including a start codon in the stem-loop corresponding to domain IV of the Hepatitis C IRES, which is in turn followed by the desired polypeptide coding region. The 5' cap can be modified with an alternate base such that the cap is able to prevent exonuclease degradation of the RNA construct, but translation cannot be initiated from the cap. More particularly, the syntheses of mRNA cap analogs modified with boranophosphate moiety at either the alpha or beta-position of the 5',5'-triphosphate bridge (m(7)Gppp(BH3)G, m(7)Gpp(BH3)pG and m(7)Gpp(BH3)pm(7)G) have been described. The preliminary biological characterization of these compounds revealed that they have high affinity for translational factor eIF4E and high potency to inhibit cap-dependent translation in a cell free system. The analogs modified at the beta-position were also found to be resistant to DcpS decapping pyrophosphatase. Thus, in the absence of a stabilizing target polynucleotide, translation cannot be initiated from the cap or from the IRES, so nothing is translated. As shown in FIG. 24B, the presence of a stabilizing target polynucleotide causes the weakened IRES element of the RNA construct to become active, which in turn causes the translation machinery to initiate translation at the internal start codon, thereby translating the polypeptide coding region. Unlike RNA constructs based on HSL, IRE, or SECIS motifs, RNA constructs based on IRES motifs do not bind to an RBP. Rather, proper formation of the IRES element is required for binding of one or more proteins that make up the translation machinery itself. Thus, although the invention typically is described herein with regard to a change in structure of the RNA construct that leads to a change in the ability of an RBP to bind to the RNA construct and, thus modulates expression of a polypeptide coding region, it should be understood that the description of how to make and use RNA constructs applies equally to embodiments, such as RNA constructs based on the IRES, where a change in RNA structure leads to modulation of polypeptide coding region expression without involvement of an RBP. Use of the IRES motif is advantageous because it is independent of the cell cycle, and multiple variations of the IRES exist that can be used to produce a variety of RNA constructs suitable for use in many different expression environments.

III. Target Polynucleotides

Target polynucleotides can be any endogenous polynucleotide (e.g., a DNA or an RNA, such as a coding RNA, non-coding RNA, regulatory RNA, or microRNA) that is present in, or characterizes, a particular cell type or tissue in which a polypeptide coding region attached to an RNA construct of the present invention is to be expressed. Alternatively, a target polynucleotide can be one that has been exogenously supplied to an expression environment. An expression environment is any environment in which a polypeptide coding region can be expressed (e.g., a naturally-occurring cell, such as a neoplastic cell or infected cell; a non-naturally occurring cell; or a cell-free expression system (e.g., available from Life Technologies, Foster City, Calif.), such as rabbit reticulocyte lysate, wheat germ extract or *E. coli* cell-free system). Target polynucleotides bind to the flank regions of an RNA construct, typically stabilizing the secondary structure of the RNA construct, for example, the stem-loop. (It should be understood that, while the text focuses on a target polynucleotide that stabilizes an RNA construct, it can have other effects, such as those described for FIGS. 2A-D.) Stabilization of the secondary structure allows for the modulation of translation of a polypeptide coding region, allowing for specific expression of, or the inhibition of expression of, a desired polypeptide in an expression environment containing a target polynucleotide. A target polynucleotide can be, but is not limited to, a viral polynucleotide, a bacterial polynucleotide, an polynucleotide expressed in a neoplastic cell, or a polynucleotide characteristic of a protein deficiency. Target polynucleotides can be found in, for example, but not limited to, a virally- or bacterially-infected cell, a neoplastic cell, a diseased cell, a tissue, a cell culture, or a sample containing polynucleotides (e.g., a blood sample).

Target polynucleotides can be any non-coding or coding polynucleotide. Typically, though, they are non-coding RNAs, such as microRNAs. Factors for choosing a target polynucleotide having appropriate activity at the RNA construct are that the target polynucleotide be found in the expression environment into which the RNA construct is placed and, preferably, in an abundant manner. In general, the target polynucleotide can function regardless of specific size, sequence, or structure, and a complementary flanking region of an RNA construct can be designed to be specific for any target polynucleotide once it has been identified and sequenced. The RNA construct so designed should change its structure in the presence of the target polynucleotide, thus creating a "switch" with one structural state forming in the absence of the target polynucleotide and another structural state being created in the presence of a target polynucleotide. The specific structure and/or sequence of the target polynucleotide is chosen for its ability to confer a change in the RNA construct structure and thus its activity state.

Selection of a target polynucleotide is based on multiple criteria including, but not limited to, uniqueness, prevalence, and energetics. For example, a target polynucleotide sequence should be unique enough so that the structure of the RNA construct is reinforced and becomes active only in the targeted environment. For instance, a viral microRNA (miRNA) that occurs in infected cells can be used as a target polynucleotide if it is sufficiently different from host sequences in non-infected cells to prevent activation of the RNA construct and translation of the polypeptide coding region where not intended. In addition, the target polynucleotide should be present in sufficient quantity to increase the likelihood that it will interact with the RNA construct. The sequence of the target polynucleotide also should allow for the RNA construct to base pair with a favorable energy minimization to promote structure formation. For example, the calculated MFE (minimum free energy) structure should be such that the target polynucleotide is predicted to hybridize the RNA construct's flank regions as desired (rather than the RNA construct folding with itself and the target polynucleotide folding with itself or the RNA construct and the target polynucleotide hybridizing in a manner other than what is desired).

1. Uniqueness

One factor in selecting a target polynucleotide, such as a viral RNA, is the degree to which the target polynucleotide can selectively (and specifically) activate the RNA construct. Ideally, this occurs uniquely in the desired environment such as the targeted cell or tissue. The desired selectivity may result from several factors including the target polynucleotide sequence and/or quantity.

The most direct manner to achieve specificity of the target polynucleotide will result as a consequence of the uniqueness of its primary sequence. For example, there are many examples of viral specific expressed RNAs that are different from any known human sequence. Example 2 details just one of these situations, where SV40 microRNA differs from its cellular microRNA counterpart by several nucleotides. These sequence differences can be used to design the RNA construct such that they are optimized. Logically, it is expected that the longer the sequence is, the more likely it will have sufficient uniqueness to serve as the basis for designing a complementary specific RNA construct.

2. Prevalence

An additional approach to the specificity issue is to take advantage of target polynucleotides that are uniquely expressed in a desired tissue or cell-type. For instance, one could still use a viral target polynucleotide that had an exact cellular counterpart, if the cellular RNA was only expressed at an irrelevant time point (such as during embryogenesis) or in an unrelated cell type that would not be exposed to the RNA construct. Despite the lack of sequence or structural uniqueness, distinctively expressed (or distributed) target polynucleotides could still be used to activate the RNA construct.

Likewise, if there is a substantial difference in the quantity of the target polynucleotide being expressed in a desired environment relative to an environment in which expression of the RNA construct is not desired, then selective activation of the RNA construct can still be achieved. For example, in the case of a viral target polynucleotide that has an exact cellular (host) counterpart, the cellular version could be expressed at very low background levels but during the course of viral infection, a 10,000-fold increase could be produced in infected cells. This quantitative difference could serve to produce the desired selectivity.

3. Identifying Target Polynucleotides

Target polynucleotides according to the present invention can be identified from a number of sources. For example, to target virally-infected cells, the flanking regions of an RNA construct can be designed to be complementary to microRNAs expressed by viruses. First, using the mirBase web resource (www.microrna.sanger.ac.uk/sequences/) for microRNAs, a search using the keywords "virus" and "viral" was performed. microRNA sequences from viruses known to infect humans were compiled (FIG. 25). These sequences can be used as target polynucleotides, and particularly as target polynucleotides for anti-viral compounds effective against the organisms listed in FIG. 25 as well as related organisms. Second, the rFam web resource (www.sanger.ac.uk/Software/Rfam/) provides a collection of known and putative non-coding RNA "families." A keyword search of this set using "virus" returned a list of 69 "families" shown in FIG. 26. Many sequences belonging to viruses that infect humans are contained in this set. Again, these sequences can be used as targets. Third and more broadly, using the NCBI (National Center for Biotechnology Information) viral genome resource (www.ncbi.nlm.nih.gov/genomes/VIRUSES/viruses.html), a list of viruses known to infect human hosts also was developed. Complete genome sequences with annotation are downloaded for these viruses and are parsed to extract sequence portions not designated as protein coding regions. This will include well-defined 3' and 5' UTR segments from known messages. However, it also will consist of sequence regions whose purpose has not been identified, but that may be expressed as part of the post transcriptional regulatory process. Again, these sequences can be used as targets. All of these resources can be checked periodically for new data.

The same approach can be taken for any pathogen. For example, the rFam database, which includes many non coding RNA families, can be used and the mirBase databases, which includes many microRNAs coded by viruses and animals, can be used. Additionally, NCBI genome entries can be reviewed individually for particular organisms of interest. Moreover, the same approach can be taken for any diseased cell, such as a neoplastic cell. For example, miRNAs from the mirBase database (microna.sanger.ac.uk/sequences/) can be examined. Additionally, other disease-specific target polynucleotides, such as RNAs, known in the art can be used. Examples of cancer-specific RNAs include, but are not limited to, the human breast cancer-specific microRNA hsa-miR-373 and the testicular cancer-specific microRNA hsa-miR-520c. miR-373 and miR-520c have been shown to be involved in metastatic breast cancer and testicular cancer, respectively, and not present in normal adult tissue. They may play a role in other cancer types as well. The other isoforms of hsa-miR-520 (see Table 4) are also contemplated to be useful.

TABLE 4

| mirBase ID | mirBase Accession | Mature miRNA Sequence |
|---|---|---|
| hsa-miR-520a-5p | MIMAT0002833 | CUCCAGAGGGAAGUACUUUCU (SEQ ID NO: 180) |
| hsa-miR-520a-3p | MIMAT0002834 | AAAGUGCUUCCCUUUGGACUGU (SEQ ID NO: 181) |
| hsa-miR-520b | MIMAT0002843 | AAAGUGCUUCCUUUUAGAGGG (SEQ ID NO: 182) |
| hsa-miR-520c-5p | MIMAT0005455 | CUCUAGAGGGAAGCACUUUCUG (SEQ ID NO: 183) |
| hsa-miR-520c-3p | MIMAT0002846 | AAAGUGCUUCCUUUUAGAGGGU (SEQ ID NO: 184) |
| hsa-miR-520d-5p | MIMAT0002855 | CUACAAAGGGAAGCCCUUUC (SEQ ID NO: 185) |
| hsa-miR-520d-3p | MIMAT0002856 | AAAGUGCUUCUCUUUGGUGGGU (SEQ ID NO: 186) |
| hsa-miR-520e | MIMAT0002825 | AAAGUGCUUCCUUUUUGAGGG (SEQ ID NO: 187) |
| hsa-miR-520f | MIMAT0002830 | AAGUGCUUCCUUUUAGAGGGUU (SEQ ID NO: 188) |
| hsa-miR-520g | MIMAT0002858 | ACAAAGUGCUUCCCUUUAGAGUGU (SEQ ID NO: 189) |
| hsa-miR-520h | MIMAT0002867 | ACAAAGUGCUUCCCUUUAGAGU (SEQ ID NO: 190) |

4. Experimental Validation of Target Polynucleotide Expression

One direct way to empirically identify viral target polynucleotides is to infect cell cultures with virus and sequence the expressed polynucleotides using a viral specific custom tiling-array strategy or second generation sequencing technologies. The resulting polynucleotide that is identified is compared to polynucleotides from non-infected control cell cultures. Unique viral polynucleotides found to be expressed in abundance are good candidates for use as a viral specific target polynucleotides. These could include microRNAs, non-coding RNAs, regulatory RNAs and even genic/coding RNAs.

A similar procedure can be used to identify target polynucleotides for other pathogens. Moreover, target polynucleotides can be identified for diseased cells, such as neoplastic cells, by comparing the RNA being expressed between a diseased cell and a normal cell. Unique polynucleotides expressed in abundance in a diseased cell are good candidates for use as a diseased-cell specific target polynucleotide.

IV. Polypeptide Coding Region

A polypeptide coding region may be attached 5' or 3' of an RNA construct of the present invention. In the presence of a target polynucleotide, the RNA construct will undergo a conformational change which can either promote or inhibit association with an RBP. The RBP will, in turn, promote or inhibit translation of the polypeptide coding region. In one embodiment of the invention, the presence of a target polynucleotide will promote translation of an attached polypeptide coding region, allowing for the directed expression of a desired polypeptide in a target expression environment, for example, a cell. For example, a death gene may be chosen to kill an undesirable cell (or pathogen in a cell), or a reporter gene may be chosen to detect a target polynucleotide. Generally, it is contemplated that the polypeptide coding region will be chosen to suit any of the uses described herein.

A polypeptide coding region can be attached to an RNA construct in any number of ways known in molecular biology. If an RNA construct and polypeptide coding region are to be produced from a DNA vector, a DNA vector incorporating both the RNA construct and polypeptide coding region can be produced. DNA fragments encoding all or a portion of the polypeptide coding region can be obtained from any source, for example, from a cDNA library or amplified from genomic DNA using polymerase chain reaction (PCR). DNA encoding the polypeptide coding region, or portions thereof, together with the remaining portions of the RNA construct can be inserted into an appropriate expression or amplification vector using standard ligation techniques. Alternatively, an RNA construct can be synthesized using any of a number of methods known in the art, and chemically linked to a polypeptide coding region. Vectors suitable for use with the present invention and methods of construction are discussed in more detail below.

1. Death Genes

Figure 27B:
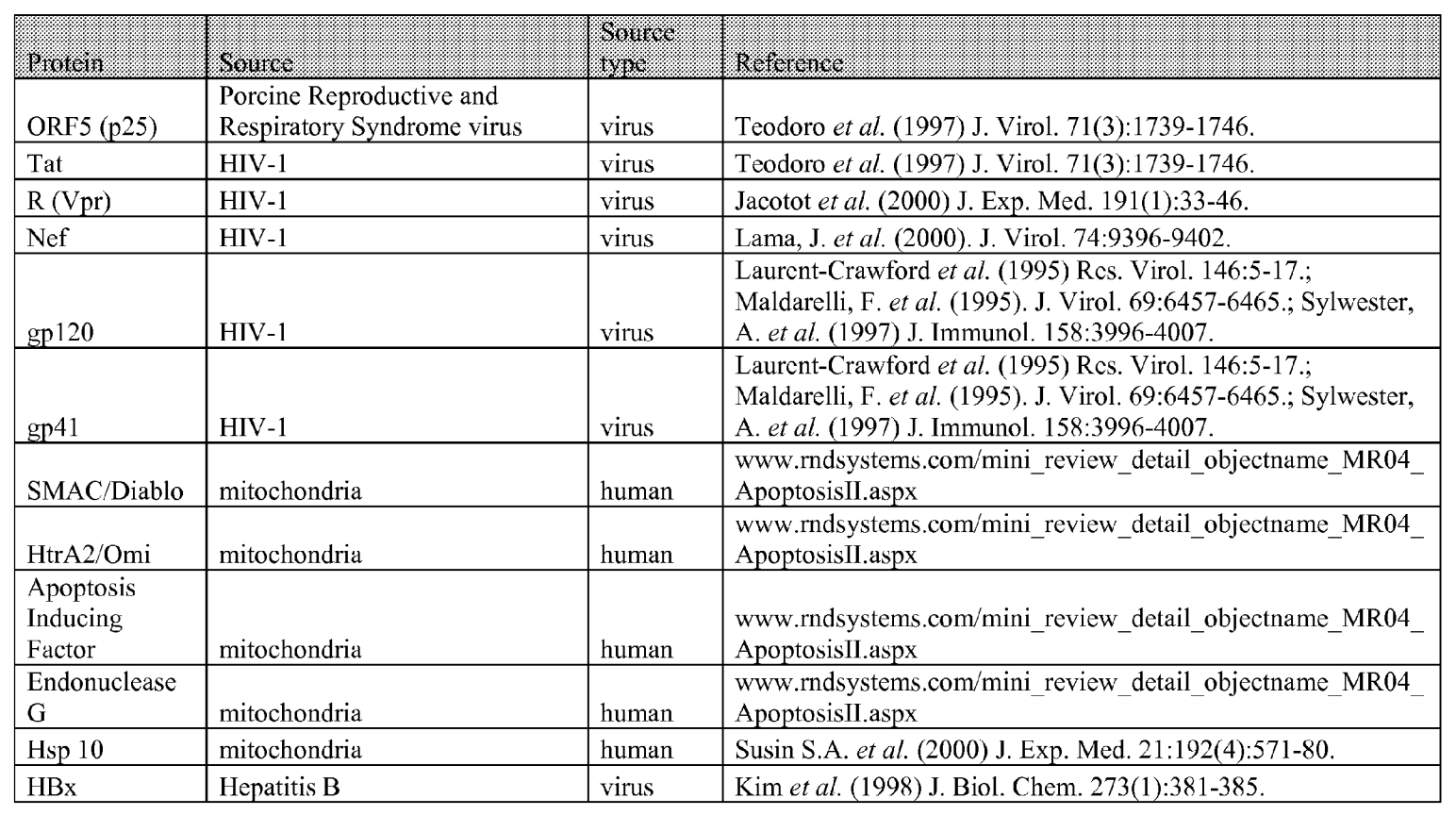

It is contemplated that the stabilization of the RNA construct in the presence of a target polynucleotide can either turn on or off expression of a death gene (a polypeptide coding region), as described previously. Examples of turning on a death gene would be for the RNA construct, when activated, to allow the expression of killer genes, such as one of the caspases. Alternatively, when the RNA construct is activated, the expression of a gene is turned off which in turn turns "ON" the production of a death gene. Examples of death genes include, but are not limited to, caspase family genes such as CASP1, CASP2, CASP3, CASP4, CASP5, CASP6, CASP7, CASP8, CASP9, CASP10, CASP14 and death domain family genes such as CRADD, DAPK1, DAPK2, FADD, RIPK1, TNFRSF10A, TNFRSF10B, TNFRSF11B, TNFRSF1A, TNFRSF21, TNFRSF25, TNFRSF6, TRADD. Other death genes that may be used are Bcl-2, Bax, Bcl-x, p53, ICE, and Cytochrome C. Additional death polypeptides encoded by "death genes" are listed in FIG. 27 (Parts 1 and 2).

2. Reporter Genes

It is further contemplated that the stabilization of the RNA construct in the presence of a target polynucleotide can either turn on or off expression of a reporter gene (a polypeptide coding region), as described previously. A reporter gene is a gene that encodes a detectable marker. For example, the RNA construct, when activated by the presence of a target polynucleotide, can allow for the expression of any number of reporter genes suitable for use with the present invention. Examples of target polynucleotides that can activate an RNA construct include but are not limited to a viral target polynucleotide, a bacterial target polynucleotide, a target polynucleotide characteristic of a neoplastic cell, or a target polynucleotide characteristic of any disease or condition listed in Table 1. Examples of reporter genes suitable for use with the present invention include LacZ, luciferase (e.g., firefly luciferase (FL) from *Photinus pyralis* and *Renilla* luciferase (RL) from *Renilla reniformis*), green fluorescent protein (GFP) and its derivatives (e.g., eGFP, eCFP, eYFP), ferritin, tyrosine hydroxylase, myoglobin, hemoglobin, protein amide H, transferrin receptor, truncated progesterone receptor, β-galactosidase, and non human receptor proteins whose ligands can incorporate detectable tags (e.g., radiolabels, gadolinium). Any protein that can be detected (i.e. a detectable marker) can function as a reporter gene for use with the present invention. Methods of detection are described in detail below.

V. Production, Administration and Testing of an RNA Construct

1. Production of an RNA Construct DNA encoding the RNA construct (and, optionally, a polypeptide coding region) of the present invention can be prepared in any number of ways known in the art. DNA fragments encoding portions of the RNA construct can be obtained from any source, for example, from a cDNA library or amplified from genomic DNA using polymerase chain reaction (PCR). Methods for isolating nucleic acids, synthesizing nucleic acids, hybridizing nucleic acids, making and screening cDNA libraries, and performing PCR are well known in the art (see, e.g., Gubler et al, (1983), GENE 25:263-269; Sambrook et al. (2nd ed. 1989) MOLECULAR CLONING, A LABORATORY MANUAL; Ausubel et al., eds. (1994) CURRENT PROTOCOLS IN MOLECULAR BIOLOGY), as are PCR methods (see U.S. Pat. Nos. 4,683,195 and 4,683,202; Innis et al., eds (1990) PCR PROTOCOLS: A GUIDE TO METHODS AND APPLICATIONS). Expression libraries are also well known to those of skill in the art. Additional basic texts disclosing the general methods of use in this invention include Kriegler (1990) GENE TRANSFER AND EXPRESSION: A LABORATORY MANUAL.

In an exemplary embodiment, at least a portion of a contemplated RNA constructs are chemically synthesized. The single stranded molecules that comprise RNA constructs may be synthesized using any of a variety of techniques known in the art, such as those described in Usman et al. (1987) J. AM. CHEM. SOC. 109:7845; Scaringe et al. (1990) NUCLEIC ACIDS RES. 18:5433; Wincott et al. (1995) NUCLEIC ACIDS RES. 23:2677-2684; and Wincott et al. (1997) METHODS MOL. BIO. 74:59. The synthesis of oligonucleotides makes use of common nucleic acid protecting and coupling groups, such as dimethoxytrityl at the 5'-end and phosphoramidites at the 3'-end. As a non-limiting example, small scale syntheses may be conducted on an Applied Biosystems synthesizer using a 0.2 mmol scale protocol with a 2.5 min. coupling step for 2'-O-methylated nucleotides. Alternatively, syntheses at the 0.2 mmol scale may be performed on a 96-well plate synthesizer from Protogene (Palo Alto, Calif.). However, a larger or smaller scale of synthesis is also within the scope of the present invention. Suitable reagents for oligonucleotide synthesis, methods for RNA deprotection, and methods for RNA purification are known to those of skill in the art.

Alternative methods of chemical synthesis well known to the skilled artisan (see, for example, Engels et al. (1989) ANGEW. CHEM. INTL. ED. 28:716-734) include, for example, phosphotriester, phosphoramidite, and H-phosphonate methods for nucleic acid synthesis. Another method for such chemical synthesis is polymer-supported synthesis using standard phosphoramidite chemistry. Nucleic acids larger than about 100 nucleotides can be synthesized as several fragments using these methods. The fragments then can be ligated together to form the full length encoded RNA construct.

DNA encoding the RNA construct, or portions thereof, (and, optionally, a polypeptide coding region) can be inserted into an appropriate expression or amplification vector using standard ligation techniques. The vector is typically selected to be functional in the particular expression environment employed (i.e., the vector is compatible with the host cell machinery such that amplification of the RNA construct and/or expression of the RNA construct can occur). DNA encoding the RNA construct may be amplified/expressed in prokaryotic, yeast, insect (baculovirus systems) and/or eukaryotic host cells. These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al. (1995) PROC. NATL. ACAD. SCI. USA 92:1292).

RNA constructs and, optionally, polypeptide coding regions can be expressed and purified using common molecular biology and biochemistry techniques. For example, recombinant expression vectors can be used which can be engineered to carry an encoded RNA construct and, optionally, polypeptide coding region into a host cell to provide for expression of the RNA construct and attached polypeptide coding region. Such vectors, for example, can be introduced into a host cell by transfection means including, but not limited to, heat shock, calcium phosphate, DEAE-dextran, electroporation or liposome-mediated transfer. Recombinant expression vectors include, but are not limited to, *Escherichia coli* based expression vectors such as BL21 (DE3) pLysS, COS cell-based expression vectors such as CDM8 or pDC201, or CHO cell-based expression vectors such as pED vectors. An RNA construct and, optionally, polypeptide coding region can be linked to one of any number of promoters in an expression vector that can be activated in the chosen cell line. In an embodiment, a cassette (RNA construct and promoter) is carried by a vector that contains a selectable marker such that cells receiving the vector can be identified.

For example, promoters to express the RNA construct within a cell line can be drawn from those that are functionally active within the host cell. Such promoters can include, but are not limited to, a T7 promoter, a CMV promoter, a SV40 early promoter, a herpes TK promoter, and others known in recombinant DNA technology. Inducible promoters can be used, and include promoters such as metallothionine promoter (MT), mouse mammary tumor virus promoter (MMTV), and others known to those skilled in the art. Exemplary selectable markers and their attendant selection agents can be drawn, for example, from the group including, but not limited to, ampicillin, kanamycin, aminoglycoside phosphotransferase/G418, hygromycin-B phosphotransferase/hygromycin-B, and amplifiable selection markers such as dihydrofolate reductase/methotrexate and others known to skilled practitioners.

Additional elements for directing the replication and transcription of an RNA construct and, optionally, polypeptide coding region) can be included in a vector to express RNA constructs in a variety of cell types, including but not limited to, eukaryotic, prokaryotic, insect, plant and yeast. For example, microorganisms such as bacteria can be transformed with recombinant bacteriophage DNA, plasmid DNA or cosmid DNA expression vectors containing the RNA construct coding sequences; yeast can be transformed with recombinant yeast expression vectors containing the RNA construct coding sequences; insect cell systems can be infected with recombinant virus expression vectors (e.g., baculovirus) containing the RNA construct coding sequences; plant cell systems can be infected with recombinant virus expression vectors (e.g., cauliflower mosaic virus CaMV; tobacco mosaic virus, TMV) or transformed with recombinant plasmid expression vectors (e.g., Ti plasmid) containing the RNA construct coding sequences.

Typically, the vectors used in any of the host cells will contain at least a 5' flanking sequence (also referred to as a promoter) and, optionally, other regulatory elements, such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the DNA encoding the polypeptide coding region, and a selectable marker element. Suitable modifications may be made to the 5' cap in order to direct translation of the encoded polypeptide using cap-independent mechanisms. Such modifications are well-known in the art (Kowalska, J. et al. (2008) NUCLEIC ACIDS SYMP. SER. 52:289-90).

The recombinant RNA construct expression vectors can be DNA plasmids or viral vectors. RNA construct-expressing viral vectors can be constructed based on, but not limited to, adeno-associated virus (for a review, see Muzyczka et al. (1992) CURR. TOPICS IN MICRO. AND IMMUNOL. 158:97-129), adenovirus (sec, for example, Berkner et al. (1988) BIOTECH-NIQUES 6:616; Rosenfeld et al. (1991) SCIENCE 252:431-434; and Rosenfeld et al. (1992) CELL 68:143-155), or alphavirus as well as others known in the art. Retroviruses have been used to introduce a variety of genes into many different cell types, including epithelial cells, in vitro and/or in vivo (see for example Eglitis, et al. (1985) SCIENCE 230:1395-1398; Danos and Mulligan (1988) PROC. NATL. ACAD. SCI. USA 85:6460-6464; Wilson et al. (1988) PROC. NATL. ACAD. SCI. USA 85:3014-3018; Armentano et al., (1990) PROC. NATL. ACAD. SCI. USA 87:61416145; Huber et al. (1991) PROC. NATL. ACAD. SCI. USA 88:8039-8043; Ferry et al. (1991), PROC. NATL. ACAD. SCI. USA 88:8377-8381; Chowdhury et al. (1991), SCIENCE 254:1802-1805; van Beusechem. et al. (1992) PROC. NATL. ACAD. SCI. USA 89:7640-19; Kay et al. (1992) Human Gene Therapy 3:641-647; Dai et al. (1992) PROC. NATL. ACAD. SCI. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transcribing the RNA constructs of the present invention can be produced by transfecting the recombinant retroviral genome into suitable packaging cell lines such as PA317 and Psi-CRIP (Cornette et al. (1991) HUMAN GENE THERAPY 2:5-10; Cone et al., 1984, PROC. NATL. ACAD. SCI. USA 81:6349). Recombinant adenoviral vectors can be used to infect a wide variety of cells and tissues in susceptible hosts (e.g., rat, hamster, dog, and chimpanzee) (Hsu et al. (1992) J. INFECTIOUS DISEASE, 166:769), and also have the advantage of not requiring mitotically active cells for infection.

2. Testing an RNA Construct

A DNA vector encoding an RNA construct, and optionally a polypeptide coding region can be transfected into desired cell culture lines or cell-free expression systems, with or without target polynucleotide, and tested to determine whether stem formation, recruitment of an RBP, and/or translation of an encoded polypeptide can occur in the presence of a target polynucleotide.

The ability of an RNA construct to form a stem-loop and bind an RBP in the presence of a target sequence can be tested by incorporating a label, for example, a radiolabel, fluorescent label, or luminescent label, into the RNA construct. The RNA construct, target polynucleotide and any additional desired reagents, such as buffers, may be added to the appropriate RBP. If a target polynucleotide is present, the RNA construct assumes a structure to which the RBP can bind. The RBP is then isolated and the presence of label is assayed. Detection of the label indicates that the RNA construct has attained the structure required for binding to the RBP, which further indicates that the target nucleotide is present. Alternatively, assays useful for detecting the binding of an RNA construct to an RBP, but that do not require labeled RNA construct, include, but are not limited to, absorbance assays, immunoassays, assays for enzymatic activity of the RBP and Western blots.

Examples of suitable fluorescent labels include fluorescein isothiocyanate (FITC), 5,6-carboxymethyl fluorescein, Texas red, nitrobenz-2-oxa-1,3-diazol-4-yl(NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye®, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine. Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uraninc B, Uvitex SFC, Xylene Orange, and XRITC.

Other useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4-tetrachlorofluorescein (TET), 2',4',5',7',1, 4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

It is further contemplated that labels that detect a structural change in a polynucleotide can be incorporated into an RNA construct or directly into a nucleotide of the RNA construct to detect the conformational change that results upon binding to a target polynucleotide. Many such labels are known to those of skill in the art. Examples of labels suitable for use in the disclosed method are radioactive isotopes, fluorescent molecules, phosphorescent molecules, enzymes, antibodies, and ligands. More specifically, molecular beacons, Amplifluors®, FRET probes, cleavable FRET probes, TaqMan® probes, scorpion primers, fluorescent triplex oligonucleotides including but not limited to triplex molecular beacons or triplex FRET probes, fluorescent water-soluble conjugated polymers, PNA probes or QPNA probes, for example, can be used to activate or quench a given label based on stem formation.

Stem activated labels are labels or pairs of labels where fluorescence is increased or altered by formation of a stem structure. Stem activated labels can include an acceptor fluorescent label and a donor moiety such that, when the acceptor and donor are in proximity (when the nucleic acid strands containing the labels form a stem structure), fluorescence resonance energy transfer from the donor to the acceptor causes the acceptor to fluoresce. Stem activated labels are typically pairs of labels positioned on nucleic acid molecules, such as the sides of the stem-loop, such that the acceptor and donor are brought into proximity when a stem structure is formed in the nucleic acid molecule. If the donor moiety of a stem activated label is itself a fluorescent label, it can release energy as fluorescence (typically at a different wavelength than the fluorescence of the acceptor) when not in proximity to an acceptor (that is, when a stem structure is not formed). When the stem structure forms, the overall effect would then be a reduction of donor fluorescence and an increase in acceptor fluorescence. FRET probes are an example of the use of stem activated labels, the operational principles of which can be adapted for use with RNA constructs.

Stem quenched labels are fluorescent labels positioned on a nucleic acid such that when a stem structure forms a quenching moiety is brought into proximity such that fluorescence from the label is quenched. When the stem is disrupted, the quenching moiety is no longer in proximity to the fluorescent label and fluorescence increases. Examples of this effect can be found in molecular beacons, fluorescent triplex oligonucleotides, triplex molecular beacons, triplex FRET probes, and QPNA probes, the operational principles of which can be adapted for use with RNA constructs.

Examples of labels that can be incorporated into nucleic acids include nucleotide analogs such as BrdUrd (5-bromodeoxyuridine, Hoy et al., (1993) MUTATION RESEARCH 290: 217-230), aminoallyldeoxyuridine (Henegariu et al., (2000) NATURE BIOTECHNOLOGY 18:345-348), 5-methylcytosine (Sano et al., (1988) BIOCHIM. BIOPHYS. ACTA 951:157-165), bromouridine (Wansick et al. (1993) J. CELL BIOLOGY 122:283-293) and nucleotides modified with biotin (Langer et al., (1981) PROC. NATL. ACAD. SCI. USA 78:6633) or with suitable haptens such as digoxygenin (Kerkhof (1992) ANAL. BIOCHEM. 205: 359-364). Suitable fluorescence-labeled nucleotides are Fluorescein-isothiocyanate-dUTP, Cyanine-3-dUTP and Cyanine-5-dUTP (Yu et al. (1994) NUCLEIC ACIDS RES. 22:3226-3232). An exemplary nucleotide analog label for DNA is BrdUrd (bromodeoxyuridine, BrdUrd, BrdU, BUdR, Sigma-Aldrich Co.). Other useful nucleotide analogs for incorporation of label into DNA are AA-dUTP (aminoallyl-deoxyuridine triphosphate, Sigma-Aldrich Co.), and 5-methyl-dCTP (Roche Molecular Biochemicals). A useful nucleotide analog for incorporation of label into RNA is biotin-16-UTP (biotin-16-uridine-5'-triphosphate, Roche Molecular Biochemicals). Fluorescein, Cy3, and Cy5 can be linked to dUTP for direct labelling. Cy3.5 and Cy7 are available as avidin or anti-digoxygenin conjugates for secondary detection of biotin- or digoxygenin-labelled probes.

Labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2-dioxetane-3-2'-(5'-chloro)tricyclo[3.3.1.1$^3$,7]decane]-4-yl)phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Methods for detecting and measuring signals generated by labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary label coupled to the antibody.

3. Administration of an RNA Construct

Any of the delivery methods known in the art suitable for use with RNA-based drugs are contemplated to work for RNA constructs according to the invention. For example, recombinant vectors capable of expressing RNA constructs are delivered as described above, and persist in target cells. Alternatively, viral vectors can be used that provide for transient expression of RNA constructs. Such vectors can be repeatedly administered as necessary. Once expressed, the RNA constructs bind to target polynucleotides and undergo a conformational change, for example, strengthening of a stem-loop structure. Delivery of RNA construct-expressing vectors can be systemic, such as by intravenous or intramuscular administration, by administration to target cells ex-planted from a multicellular organism followed by reintroduction into the multicellular organism, or by any other means that allows for introduction into a desired target cell.

DNA plasmids carrying RNA constructs can be transfected into target cells as a complex with cationic lipid carriers (e.g. Oligofectamine) or non-cationic lipid-based carriers (e.g. Transit-TKO™). Multiple lipid transfections for RNA constructs targeting different regions of a single target polynucleotide or multiple target polynucleotides over a period of a week or more are also contemplated by the present invention. Successful introduction of the vectors of the invention into host cells can be monitored using various known methods. For example, transient transfection can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

Alternatively, RNA constructs can be produced in cell culture and isolated, or can be chemically synthesized, and administered. Absorption or uptake of an RNA construct can occur through unaided diffusive or active cellular processes, or by auxiliary agents or devices. An RNA construct may be introduced into a cell, either in vitro or where the cell is part of a living organism. If the cell is part of an organism, introduction into the cell will include delivery to the organism. For example, for in vivo delivery, an RNA construct can be injected into a tissue site or administered systemically. In vitro introduction into a cell includes methods known in the art such as electroporation and lipofection.

An RNA construct can be chemically modified to enhance stability. The nucleic acids of the invention may be synthesized and/or modified by methods well established in the art, such as those described in CURRENT PROTOCOLS IN NUCLEIC ACID CHEMISTRY, Beaucage, S. L. et al. (Edrs.), John Wiley & Sons, Inc., New York, N.Y., USA, which is hereby incorporated herein by reference. Chemical modifications may include, but are not limited to 2' modifications, introduction of non-natural bases, covalent attachment to a ligand, and replacement of phosphate linkages with thiophosphate linkages.

In yet another embodiment, nucleotides may be modified to prevent or inhibit the activation of cellular enzymes, such as, for example, without limitation, certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner (1995) NAT. MED. 1:1116-8). Thus, at least one 2'-hydroxyl group of the nucleotides on an RNA construct is replaced by a chemical group, for example, by a 2'-amino or a 2'-methyl group.

Conjugating a ligand to an RNA construct can enhance its cellular absorption. In certain instances, a hydrophobic ligand is conjugated to the RNA construct to facilitate direct permeation of the cellular membrane. Alternatively, the ligand conjugated to the RNA construct is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs. See Manoharan et al., (2002) ANTISENSE & NUCLEIC ACID DRUG DEVELOPMENT 12(2): 103-28. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. RNA constructs bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, et al. (1998) PHARM. RES. 15:1540-5. Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides results in improved resistance to nucleases. Representative examples of cationic ligands are propylammonium and dimethylpropylammonium.

A composition that includes an RNA construct (it should be understood that the RNA construct compositions and administration methods referenced below include both RNA constructs and DNA vectors encoding an RNA construct) can be delivered to a subject by a variety of routes. Exemplary routes include intrathecal, parenchymal, intravenous, nasal, oral, parenteral and ocular delivery. An RNA construct can be incorporated into pharmaceutical compositions suitable for administration. For example, compositions can include one or more species of an RNA construct and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, site-specific injection (e.g. delivery directly to a tumor or other site of disease), or intrathecal or intraventricular administration.

In general, an RNA construct can be administered by any suitable method. As used herein, topical delivery can refer to the direct application of an RNA construct to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA construct to the epidermis or dermis of a subject, or to specific strata thereof, or to an underlying tissue.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA construct can be administered to a subject by pulmonary delivery. Pulmonary delivery compositions can be delivered by inhalation by the patient of a dispersion so that the RNA construct within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, metered-dose devices, and dry powder dispersion devices. One of the benefits of using an atomizer or inhaler is that the potential for contamination is minimized because the devices are self contained. Dry powder dispersion devices, for example, deliver drugs that may be readily formulated as dry powders. An RNA construct may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

An RNA construct can be modified such that it is capable of traversing the blood brain barrier. For example, the RNA construct can be conjugated to a molecule that enables the agent to traverse the barrier. Such modified RNA construct can be administered by any desired method, such as by intraventricular or intramuscular injection, or by pulmonary delivery, for example.

An RNA construct can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA construct can also be applied via an ocular patch.

An RNA construct can be administered by an oral or nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

VI. Detection Assays

In one aspect of the invention, the RNA construct is used to detect the presence of a target polynucleotide. The target polynucleotide may exist in any expression environment, including, but not limited to, a cell, such as an infected or neoplastic cell; a sample comprising components of a cell; a mixture of polynucleotides; or a cell culture. The RNA construct is designed such that, in the presence of a target polynucleotide, a conformational change occurs, which leads to detection of the RNA construct.

The RNA construct of the invention, when operably linked with a reporter gene, allows one to determine whether a target polynucleotide is present or absent in a variety of expression environments and for a variety of purposes. For example, methods utilizing the RNA construct can either be scientific or commercial diagnostic assays. The target polynucleotide is either itself the molecule of interest to be detected or is a marker whose detection allows identification of another molecule, an organism of interest, or a health state of a patient. For example, the target polynucleotide could be unique to a particular pathogen, and the presence of the target polynucleotide would indicate presence of the pathogen. Alternatively, the target polynucleotide could be a marker for whether a patient has, or is likely to develop, a disease and/or whether a patient is likely to respond to, or is responding to, a particular therapeutic intervention. Samples to be assayed can be a cell culture, a disrupted cell culture, media from a cell culture, or a patient sample. Patient samples can include, but are not limited to, a tissue or body fluid sample. The tissue sample can be any tissue of the body, such as breast tissue, colon tissue, prostate tissue, pancreas tissue, liver tissue, bone tissue, cardiac tissue, lung tissue, skin, endothelium, and hair. The body fluid sample can be selected from any body fluid, such as blood, serum, plasma, stool, urine, sputum, nipple aspirate, pus, semen, saliva, and cerebrospinal fluid.

In practice, a sample to be assayed is obtained. To the extent the sample contains the cellular components needed to express the reporter gene when the RNA construct associates with the target polynucleotide (if present), the RNA construct linked with the reported gene can be directly added to the sample and incubated to allow expression of the reporter gene. The expressed reporter gene is then detected. If the sample does not have the cellular components needed to express the reporter gene, these can be added along with the RNA construct linked to the reporter gene. The reporter gene can be a detectable marker. For example, a color-forming, luminescent or fluorescent molecule such as LacZ, luciferase (e.g., firefly luciferase (FL) from *Photinus pyrulis* and *Renilla* luciferase (RL) from *Renilla reniformis*), green fluorescent protein (GFP) and its derivatives (e.g., eGFP, eCFP, eYFP), can be used. In the presence of a target polynucleotide, the RNA construct assumes a conformation to which an RBP can bind, promoting translation of the encoded detectable molecule. Detection of the expressed reporter gene (directly or indirectly) indicates the presence of the target polynucleotide.

Alternatively, any polypeptide that can be detected by any number of methods known in the art, such as a Western blot, can be encoded by the polynucleotide coding region and used in accordance with the methods of the present invention to detect the presence of a target polynucleotide. Polypeptides that can be detected in living organisms using magnetic resonance or a PET scan, for example, can also be used. For example, the polypeptide coding region can encode ferritin, tyrosine hydroxylase, myoglobin, hemoglobin, protein amide H, transferrin receptor, truncated progesterone receptor, β-galactosidase, or non human receptor proteins whose ligands can incorporate detectable tags (e.g., radiolabels, gadolinium).

EXAMPLES

Example 1

Figure 28:
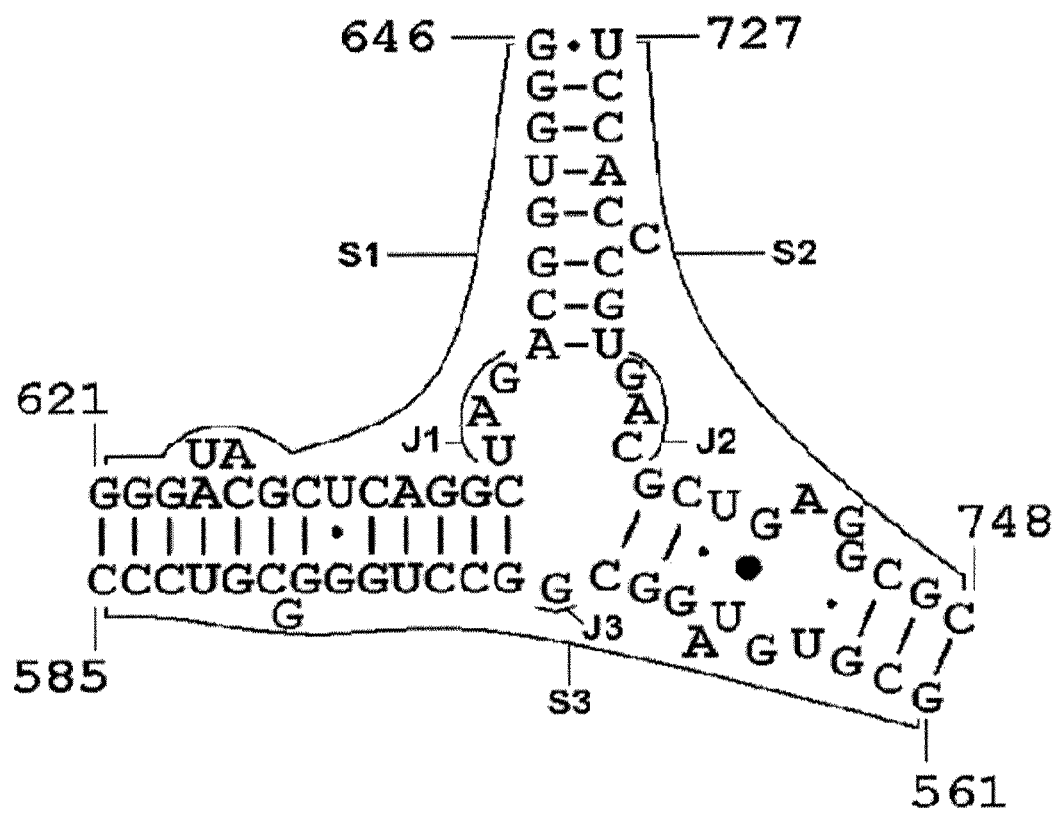
FIG. 28 shows a naturally-occurring three-way junction region from the 16S ribosomal subunit of *Thermus thermophilus*, (Protein Data Bank entry 1J5E, Chain A). Nucleotides labeled with numbers (561, 585, 621, 646, 727, and 748) indicate the corresponding nucleotide positions in the sequence of the 16S ribosomal subunit. (SEQ ID NO:192).

Design of a Stem-Loop RNA Construct Starting From a Naturally-Occurring *Thermus thermophilus* Three-Way Junction To validate the design principles of the present invention, an RNA construct based on a naturally occurring, Family A three-way junction in the 16S ribosomal subunit of *Thermus thermophilus* (Protein Data Bank entry 1J5E, Chain A), shown in FIG. 28, is examined. The structure of the ribosomal subunit has been determined by X-ray crystallography. While this example does not begin with a wild type sequence and build the RNA construct as described above, it does validate the principles of construction of an RNA construct insofar as this structure follows the rules and principles of the invention. The sequence of the 16S ribosomal subunit is as follows:

Part I: Design of an RNA Construct and Target Sequence

Figure 29:
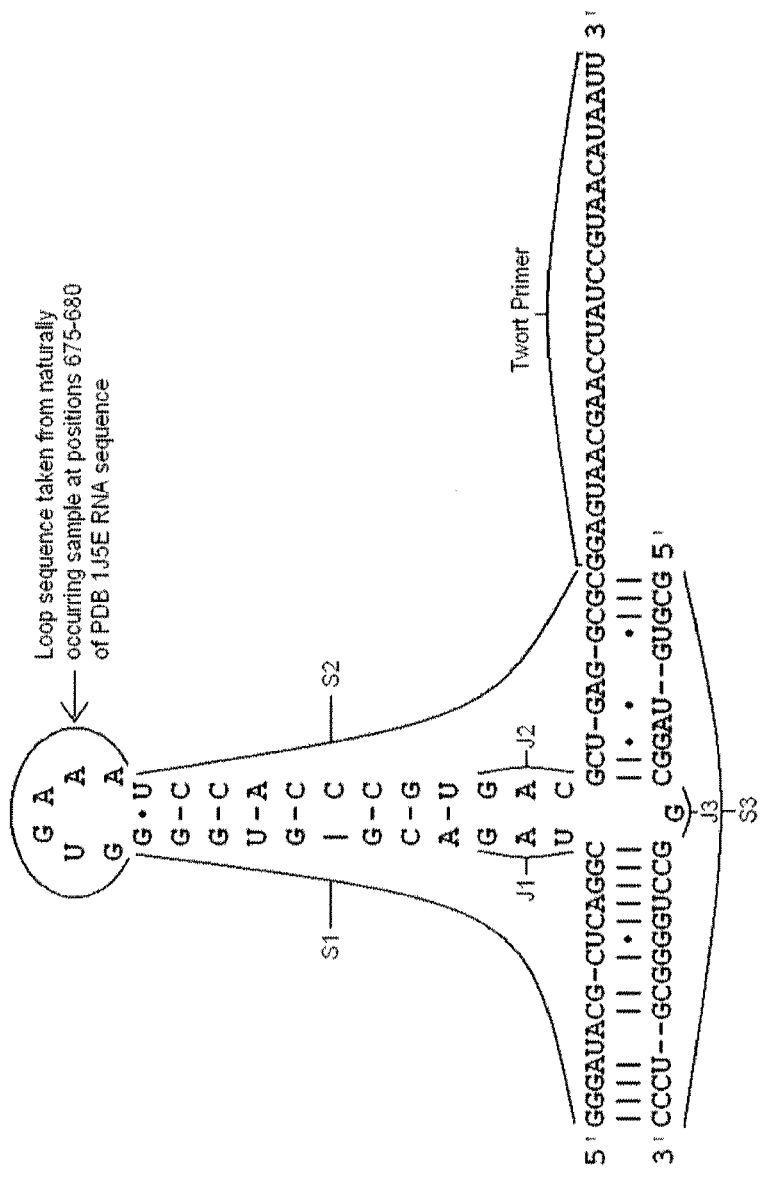
FIG. 29 shows an RNA construct (5'-GGGAUACGCU-CAGGCUAGACGGUGGGGUGAAAUCCAC-CCGUGACGCUGAGGCGCGG AGUAACGAAC-CUAUCCGUAACAUAAUU-3') (SEQ ID NO:93)) and target polynucleotide (5'-GCGUGUAGGCGGC-CUGGGGCGUCCC-3') (SEQ ID NO:94)) designed from the naturally-occurring three-way junction from the 16S ribosomal subunit of *Thermus thermophilus*, shown in FIG. 28. The loop sequence was taken from a naturally-occurring stem-loop (positions 675-680) in the same naturally-occurring 16S ribosomal subunit RNA (SEQ ID NO: 95).
Figure 30:
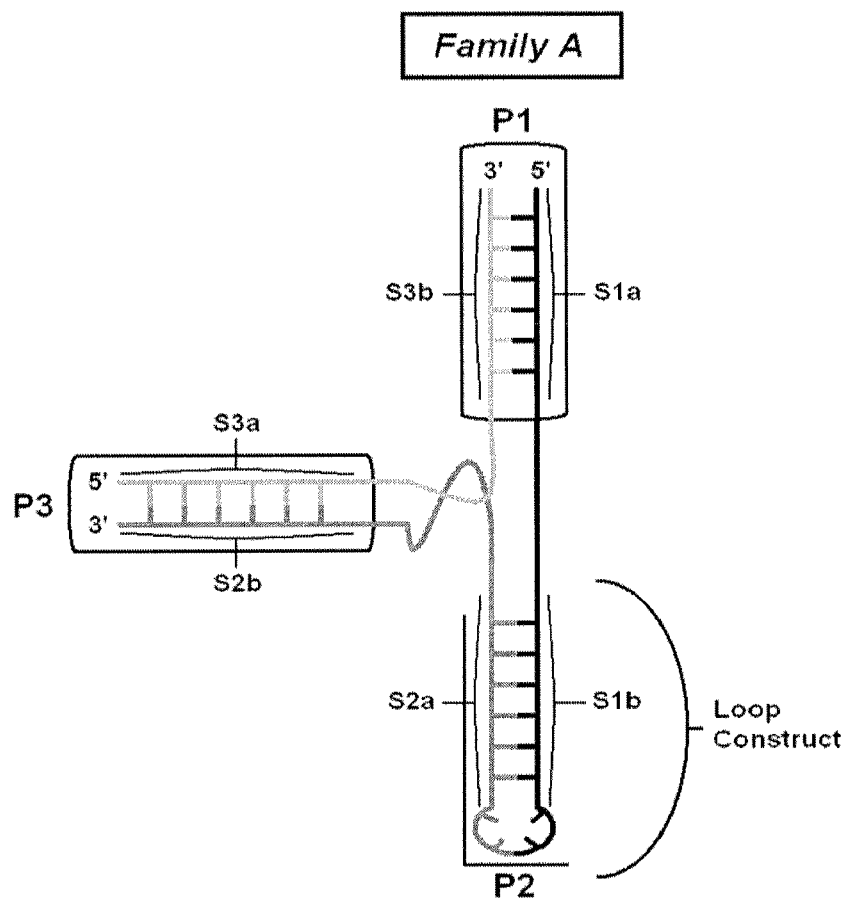
FIG. 30 shows that, due to the size of the junction joining regions in the RNA construct of FIG. 29, the RNA construct is expected to produce a Family A type junction, in which P3 is located about midway between P1 and P2. This configuration will allow an RBP to access the stem-loop of the RNA construct.

The sequences of the three-way junction of *Thermus thermophilus* are separated into their constituent segments and two of these segments are joined using the naturally-occurring loop found within the same *Thermus thermophilus* 16S ribosomal subunit sequence (positions 675-680 of Protein Data Bank entry 1J5E). The predicted three way junction structure of this RNA construct (in this instance, two sides of the three-way junction of *Thermus thermophilus* along with the naturally-occurring loop found within the same *Thermus thermophilus* 16S ribosomal subunit sequence), when bound to a target polynucleotide (in this instance, one side of the three-way junction of *Thermus thermophilus*), is shown in FIG. 29. The underlined portions of SEQ ID NO: 192 correspond to the sequences used in the RNA construct (the second underlined portion corresponds to the 5' side of RNA construct, the third underlined portion corresponds to the loop, and the fourth underlined portion corresponds to the 3' side of the RNA construct) and target polynucleotide (the first underlined portion). The region notated as "Twort Primer" in FIG. 29 is used for experimental validation of secondary structure formation as explained below. Additionally, as shown in FIG. 29, J1 is three bases, J2 is three bases and J3 is one base. According to FIG. 4D, this combination of joining regions forms a Family A structure. FIG. 30 shows the Family A structure that this RNA construct is predicted to form, and the loop of the RNA construct is highlighted. Thus, as shown in FIGS. 29 and 30, the experimental construct follows the joining region guidelines of the invention for a stem-loop RNA construct.

Prior to performing an in vivo experiment, the potential secondary structures formed by the RNA construct and target polynucleotide separately and together were analyzed with secondary structure predicting tools (RNAFold for each individual sequence and RNACofold for two sequences acting on (SEQ ID NO: 192)

```
UUUGUUGGAGAGUUUGAUCCUGGCUCAGGGUGAACGCUGGCGGCGUGCCUAAGACAUGCAAGUCGUGCGGGCCGCGGGGUUUUAC

UCCGUGGUCAGCGGCGGACGGGUGAGUAACGCGUGGGUGACCUACCCGGAAGAGGGGGACAACCCGGGGAAACUCGGGCUAAUCC

CCCAUGUGGACCCGCCCCUUGGGGUGUGUCCAAAGGCCUUUGCCCGCUUCCGGAUGGGCCCGCGUCCCAUCAGCUAGUUGGUGGG

GUAAUGGCCCACCAAGGCGACGACGGGUAGCCGGUCUGAGAGGAUGGCCGGCCACAGGGGCACUGAGACACGGGCCCACUCCUA

CGGGAGGCAGCAGUUAGGAAUCUUCCGCAAUGGGCGCAAGCCUGACGGAGCGACGCCGCUUGGAGGAAGAAGCCCUUCGGGUGU

AAACUCCUGAACCCGGGACGAAACCCCCGACGAGGGGACUGACGGUACCGGGGUAAUAGCGCCGGCCAACUCCGUGCCAGCAGCC

GCGGUAAUACGGAGGGCGCGAGCGUUACCCGGAUUCACUGGGCGUAAAGGGCGUGUAGGCGGCCUGGGGCCUCCCAUGUGAAAGA

CCACGGCUCAACCGUGGGGAGCGUGGGAUACGCUCAGGCUAGACGGUGGGAGAGGGUGGUGGAAUUCCCGGAGUAGCGGUGAAA

UGCGCAGAUACCGGGAGGAACGCCGAUGGCGAAGGCAGCCACCUGGUCCACCCGUGACGCUGAGGCGCGAAAGCGUGGGGAGCAA

ACCGGAUUAGAUACCCGGGUAGUCCACGCCCUAAACGAUGCGCGCUAGGUCUCUGGGUCUCCUGGGGGCCGAAGCUAACGCGUUA

AGCGCGCCGCCUGGGGAGUACGGCCGCAAGGCUGAAACUCAAAGGAAUUGACGGGGCCCGCACAAGCGGUGGAGCAUGUGGUUU

AAUUCGAAGCAACGCGAAGAACCUUACCAGGCCUUGACAUGCUAGGGAACCCGGGUGAAAGCCUGGGGUGCCCCGCGAGGGGAGC

CCUAGCACAGGUGCUGCAUGGCCGUCGUCAGCUCGUGCCGUGAGGUGUUGGGUUAAGUCCCGCAACGAGCGCAACCCCCGCCGUU

AGUUGCCAGCGGUUCGGCCGGGCACUCUAACGGGACUGCCCGCGAAAGCGGGAGGAAGGAGGGGACGACGUCUGGUCAGCAUGGC

CCUUACGGCCUGGGCGACACACGUGCUACAAUGCCCACUACAAAGCGAUGCCACCCGGCAACGGGAGCUAAUCGCAAAAAGGUG

GGCCCAGUUCGGAUUGGGGUCUGCAACCCGACCCCAUGAAGCCGGAAUCGCUAGUAAUCGCGGAUCAGCCAUGCCGCGGUGAAUA

CGUUCCCGGGCCUUGUACACACCGCCCGUCACGCCAUGGGAGCGGGCUCUACCCGAAGUCGCCGGGAGCCUACGGGCAGGCGCCG

Figure 31:
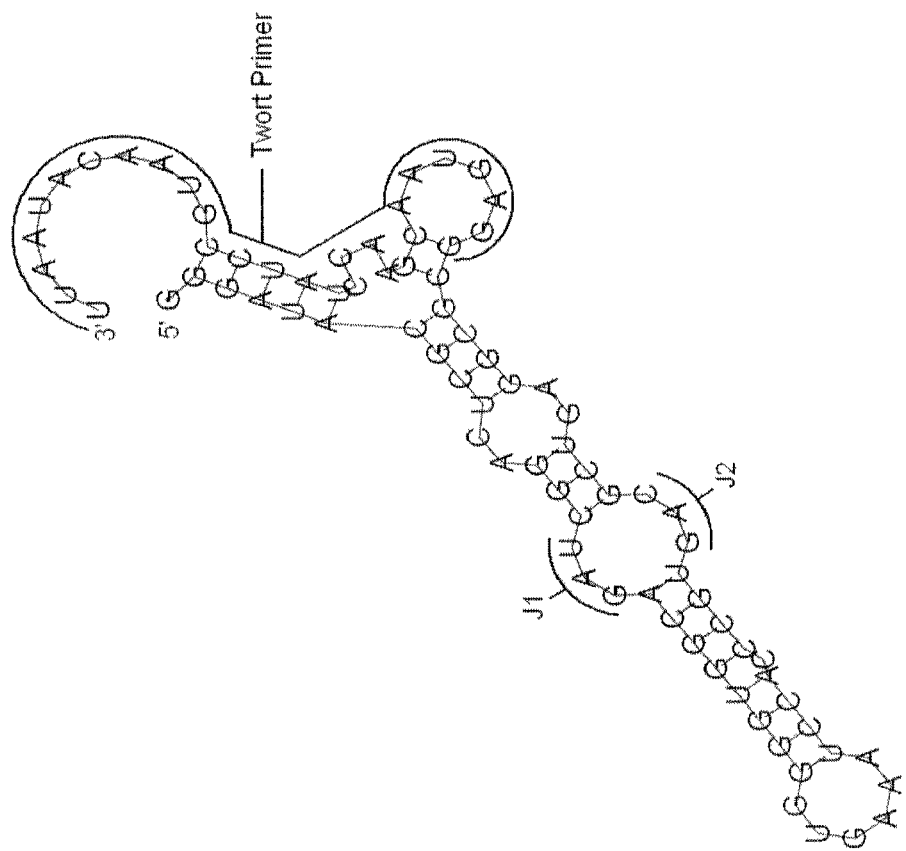
FIG. 31 shows the fold prediction for the Minimum Free Energy (MFE) structure of the RNA construct (SEQ ID NO:96) of FIG. 29. The reduction in free energy predicted to occur as a result of the folding of the RNA construct alone is −25.00 kcal/mol.
Figure 32:
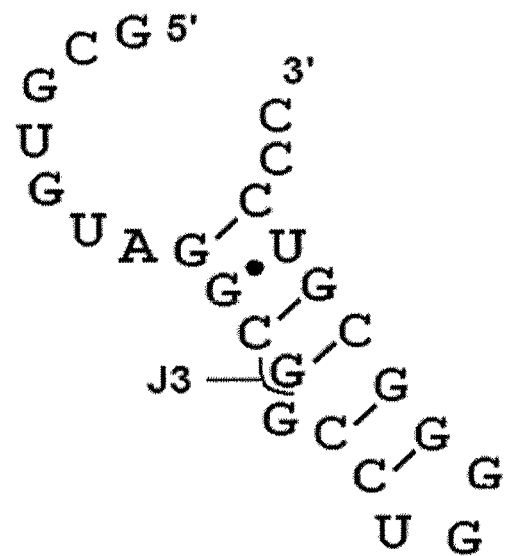
FIG. 32 shows the fold prediction for the Minimum Free Energy (MFE) structure of the target polynucleotide (SEQ ID NO:97) of FIG. 29. The reduction in free energy predicted to occur as a result of the folding of the target polynucleotide alone is −4.60 kcal/mol.
Figure 33:
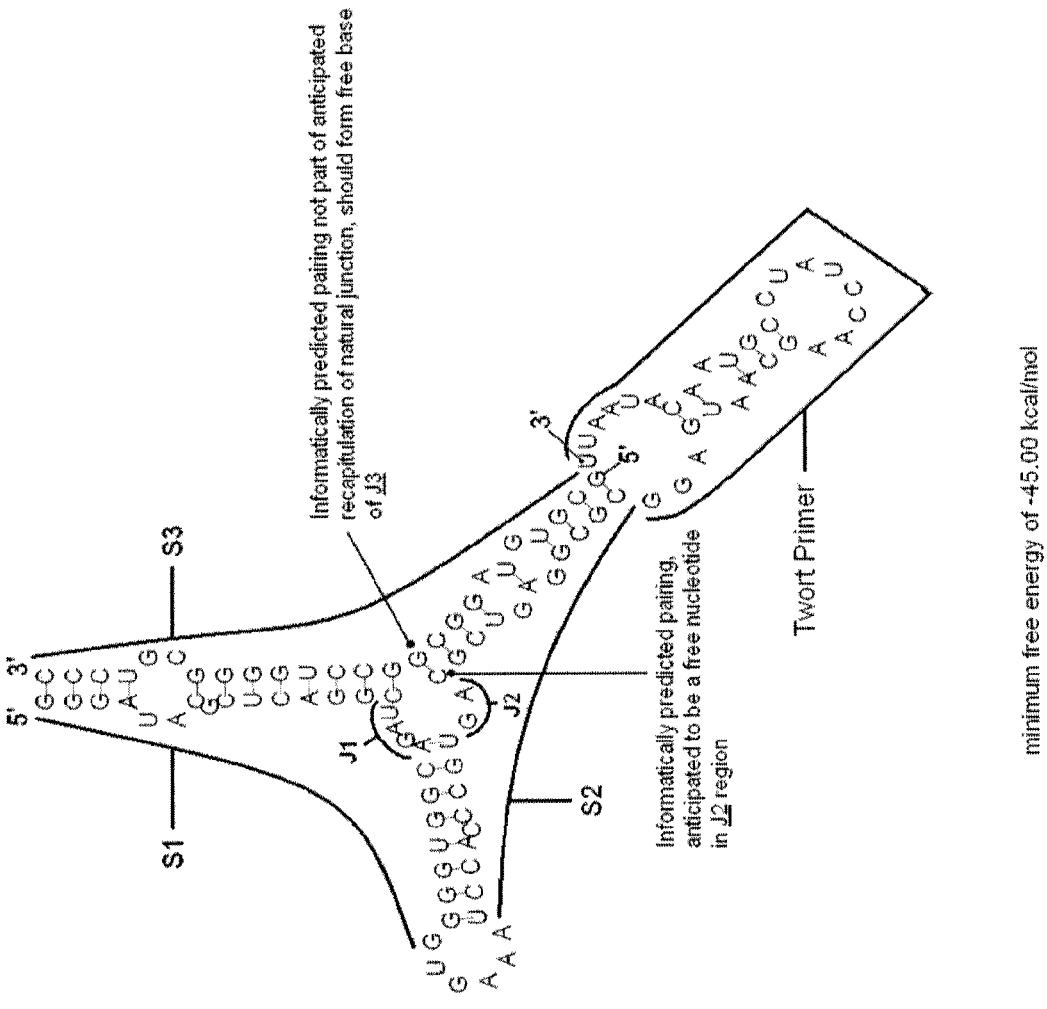
FIG. 33 shows the fold prediction for the Minimum Free Energy (MFE) structure of the RNA construct (SEQ ID NO:96) bound to the target polynucleotide (SEQ ID NO:97) as shown in FIG. 29. The reduction in free energy predicted to occur as a result of the folding of the RNA construct alone is −45.00 kcal/mol, greater than the sum of the reduction in free energy (−29.60 kcal/mol) for the RNA construct alone and the target polynucleotide alone, indicating that the combined structure is more stable and therefore more likely to form.

AGGGUAGGGCCCGUGACUGGGGCGAAGUCGUAACAAGGUAGCUGUACCGGAAGGUGCGGCUGGAUCACCUCCUUUCU
``` each other). The intent of this analysis was to predict the structure and the associated reduction in free energy for the sequences folded alone versus together. If the overall reduction in free energy is greater for the sequences folded together (into the desired secondary structure) versus the sum of their individual folds (i.e., the secondary structure assumed), they are more likely to interact as desired. FIG. 31 shows the fold prediction for the Minimum Free Energy (MFE) structure of the RNA construct. FIGS. 32 and 33 show the same for the target polynucleotide and the combined RNA construct-target polynucleotide, respectively.

The reduction in free energy predicted to occur as a result of the folding of the RNA construct alone is −25.00 kcal/mol. The reduction in free energy predicted to occur as a result of the folding of the target polynucleotide alone is −4.60 kcal/mol. Thus, the sum reduction in free energy for the individual sequence predictions is −29.60 kcal/mol (−25.00 kcal/mol+−4.60 kcal/mol). The MFE value of the two sequences folding together into the desired structure is −45.00 kcal/mol. This interaction shows a net free energy reduction of more than 15 kcal/mol beyond the two sequences folding independently, indicating that it is energetically favorable for the RNA construct and target polynucleotide to fold together rather than separately. Therefore, the RNA construct and target polynucleotide are more likely to interact to form the predicted structure than not.

Part II: Expressing and Testing the RNA Construct In Vitro

The next steps of the experiment are performed as follows.

DNA oligonucleotide templates are designed using the T7 promoter to express both the RNA construct and the target polynucleotide. This RNA construct and target polynucleotide is transcribed and used for in vitro experiments.

To test whether the RNA construct and target polynucleotide form the desired structure in vivo, the RNA construct and target polynucleotide are exposed to chemical probes. The more reactive bases (e.g., unpaired adenines and cytosines for DMS probing) are altered in such a way that they stop transcription during a primer extension. By comparing relative counts of varying length transcripts, the reactivity (hence the likelihood of being base paired) of each base in the sequence is determined. That information is used in conjunction with a partition function based algorithm (i.e., RNAFold) to make a determination as to what structure is present. The Twort primer that is incorporated into the RNA construct is present specifically to allow this analysis, as explained below.

In order to experimentally validate a change in conformation of RNA structure, the high-throughput chemical mapping approach "CAFA" (Capillary Automated Footprinting Analysis, Mitra et al. (2008) NUCLEIC ACIDS RES. 36, e63) is used. Chemical mapping (specifically dimethyl sulfoxide (DMS) and hydroxyl radical (.OH) footprinting) in conjunction with the CAFA high-throughput approach is used to experimentally validate the predicted conformational rearrangements in the three-way junction (Mitra et al. (2008) NUCLEIC ACIDS RES. 36, e63).

Chemical mapping techniques leverage the unique chemical reactivity of probes (either chemical or enzymatic) to detect aspects of nucleic acid structure (Donis-Keller et al. (1977) NUCLEIC ACIDS RES. 4, 2527-2538; Goldrick and Kessler (2003) CURRENT PROTOCOLS IN NEUROSCIENCE/EDITORIAL BOARD, Jacqueline N Crawley et al., Chapter 5, Unit 5 1; Vicens et al. (2007) RNA 13, 536-548). Certain chemicals react differently depending on the conformation of the nucleic acid. One such probe is dimethyl sulfoxide (DMS), which reacts selectively with unpaired adenines and cytosines (Tijerina et al. (2007) NATURE PROTOCOLS 2, 2608-2623). DMS is often used to determine the secondary structure of an RNA molecule (Lempereur et al. (1985) NUCLEIC ACIDS RES. 13, 8339-8357). Another probe is the hydroxyl radical (.OH), which selectively cleaves surface exposed nucleotides defining the inside and outside of an RNA molecule (Latham and Cech (1989) SCIENCE 245, 276-282). Common to all forms of chemical mapping is a selective modification or cleavage of the nucleic acid. Determining the degree of cleavage at each nucleotide provides structural information on the RNA. In the case of DMS mapping, adenines and cytosines that exhibit a high degree of modification after DMS treatment are unpaired, while low degree of modification indicates base-paired nucleotides (Lempercur et al. (1985) NUCLEIC ACIDS RES. 13, 8339-8357; Tijerina et al. (2007) NATURE PROTOCOLS 2, 2608-2623).

Detecting chemical modification or cleavage in a nucleic acid is straight forward thanks to reverse transcription coupled with primer extension (Tijerina et al. (2007) NATURE PROTOCOLS 2, 2608-2623). Chemical modifications (e.g. methylation) stop the reverse transcription reaction selectively, allowing for the degree of modification to be probed at each site (Lempercur et al., 1985, supra). The higher the extent of methylation at a particular site, the more cDNA of that length will be produced. Determining the relative populations of different cDNA products (of different length) therefore yields the degree of chemical modification at the corresponding site on the RNA.

Recent advances in capillary electrophoresis sequencing technology (Araya et al. (2007) METHODS 42, 141-149; Quigley and Dovichi (2004) ANALYTICAL CHEMISTRY 76, 4645-4658) now allow for such analyses to be carried out in highly optimized, multiplex systems like the Beckman CEQ 8000 instrument. CAFA allows chemical mapping reactions to be performed and analyzed in 96-well plates, completely eliminating the need for gel electrophoresis. CAFA is also a software package with custom algorithms that allow accurate determination of the peak intensities, even in overlapping regions of the spectrum.

DMS Chemical Probing:

DMS chemical probing measures the degree of base-pairing by selectively methylating unpaired nucleotides. The degree of methylation at each nucleotide is evaluated by reverse-transcription, as the reverse-transcriptase will stop if it encounters a methylated nucleotide. The results of a partition function calculation can be directly compared to this type of probing. The DMS results are used to confirm the computational predictions and assess the predictive ability of the partition function calculation.

.OH Radical Chemical Probing (Footprinting):

.OH footprinting measures the solvent-accessibility of nucleotides by selectively cleaving the backbone of exposed nucleotides (Latham and Cech (1989) SCIENCE 245, 276-282). The .OH data complements DMS data as it reports on any global rearrangements in the RNA. Collecting this data allows examination of actual differences in nucleotide accessibility to solvent (and thus exogenous molecule binding) that result from the RNA structure reconstitution. Together, these two data sets will provide both the 2D and 3D consequences of structure/conformation changes of the 3-way junctions of the experimental RNA construct.

Structural characterizations will be performed under three experimental conditions; CE buffer, 100 mM KCl and 10 mM MgCl$_2$. Salt conditions are well known to affect RNA folding (Laederach et al. (2007) PROC. NATL. ACAD. SCI. USA 104, 7045-7050), and characterizing the effect of mutations on RNA in different electrostatic environments will provide further insight into the degree of structural rearrangements that are caused by the mutation. The experimental data collected will provide comprehensive insight into the structure/conformation changes of the 3-way junctions in the RNA construct.

Alternatively, in vitro RNA binding assays will be done to demonstrate that the target polynucleotide and RNA construct associate, reinforcing the stem structure. Association also can be determined experimentally by separation on a native polyacrylamide electrophoretic gel.

Part III: Use of a Reporter Gene to Test the RNA Construct In Vivo

Once it has been confirmed that the simulated three way junction can form as a result of the RNA construct and target polynucleotide interacting, additional experiments described below can be performed to confirm that the structure of the RNA construct, when bound to the target polynucleotide, will allow it to interact with an RBP and promote translation of an attached polypeptide coding region. Instead of a Twort primer, a polypeptide coding region that encodes a fluorescent reporter will be included in the RNA construct. Following transfection of the RNA construct into an in vivo system, translation of the reporter gene in the presence or absence of target polynucleotide can be measured. It is anticipated that some translation of the reporter gene will take place even in the absence of the target polynucleotide, because the stem will not have been weakened. However, removing the three-way junction from the surrounding context of the entire 16S ribosomal subunit may weaken stem formation, in which case it is anticipated that translation of the reporter gene will only occur in the presence of the target polynucleotide.

Mutations that will modify the strength of the stem, or the binding of the flanking regions to the target polynucleotide, can be introduced as desired to prevent stem formation in the absence of the target polynucleotide. The RNA construct then can be introduced into cells and fluorescence can be measured in the absence of, and in the presence of, a target polynucleotide. If fluorescence occurs in the absence of the target polynucleotide, additional stem-weakening mutations can be introduced. If no fluorescence occurs in the presence of the target polynucleotide, nucleotides can be altered to increase either the likelihood of association of the RNA construct with the target polynucleotide, or to increase the strength of the stem.

Part IV: Variations

Figure 34:
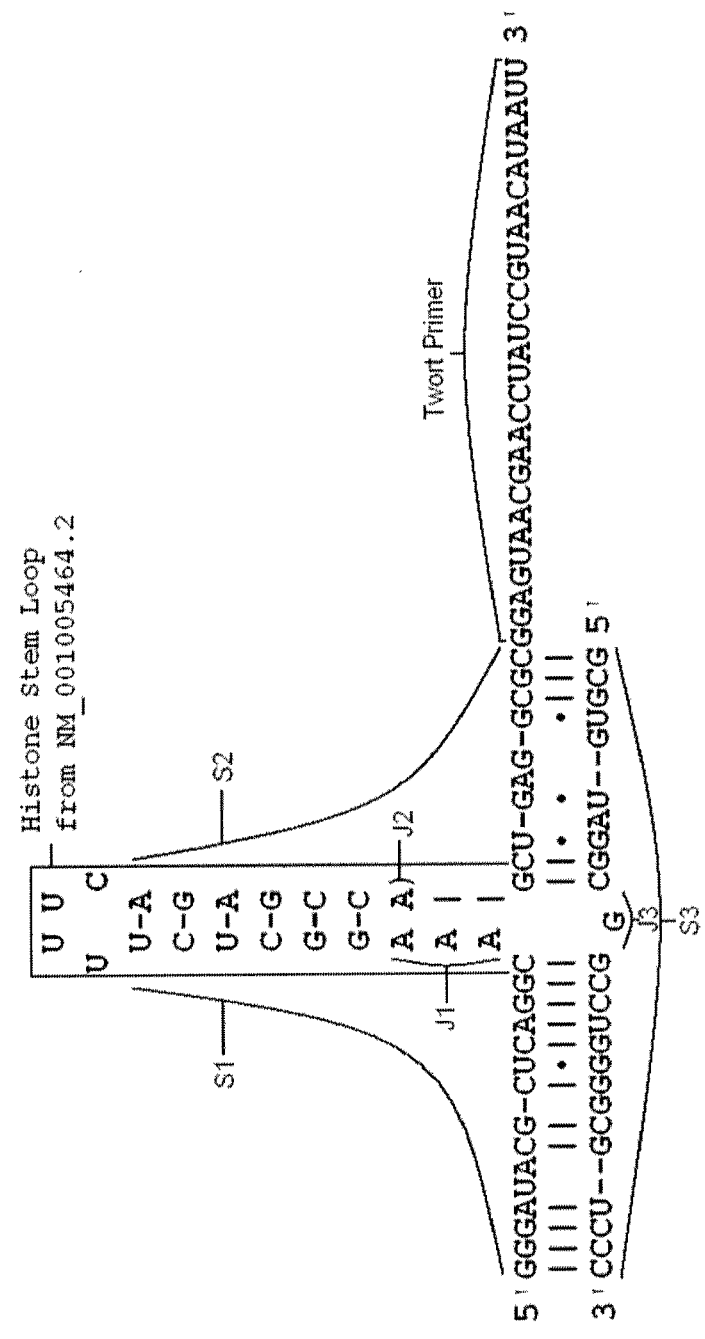
FIG. 34 shows an RNA construct (5'-GGGAUACGCU-CAGGCAAAGGCUCUUUUCAGAGC-CAGCUGAGGCGCGGAGUAACGAAC-CUAUCCGUAACAUAAUU-3') (SEQ ID NO:98)), which can be designed using a histone stem-loop consensus sequence rather than the stem-loop designed based on a *Thermus thermophilus* three-way junction shown in FIG. 29. The target polynucleotide (SEQ ID NO:97) in this example is the same as that shown in FIG. 29.
Figure 35:
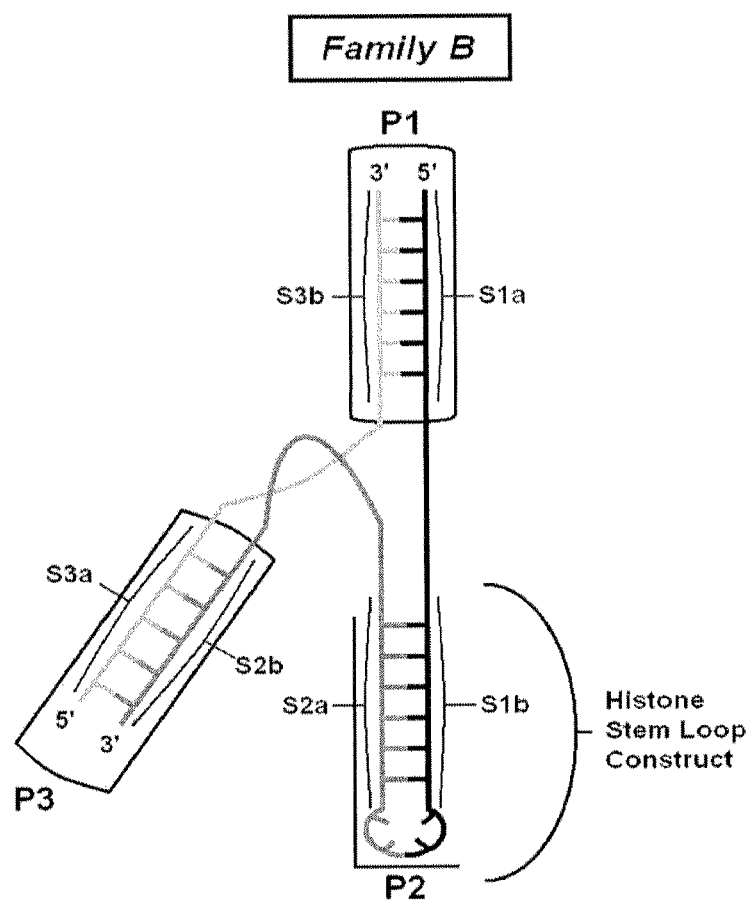
FIG. 35 shows that the RNA construct of FIG. 34 is predicted to form a Family B type three-way junction when bound to a target polynucleotide.

To demonstrate that RNA constructs can be made from different stem-loop motifs, a variation of the RNA construct that incorporates a Histone Stem-loop (HSL) motif can be designed (FIG. 34). Based on the free nucleotide proportions in the joining region, this RNA construct is likely to adopt a Family B conformation, such that the motif-bearing helix P2 will be in closer proximity to helix P3 (see FIG. 35). Insofar as J1 is three bases, J2 is one base and J3 is one base, this conformation is also predicted by FIG. 4D. Steps similar to those illustrated above can be used to test the ability of the RNA construct to promote translation of a polypeptide coding region, and to modify the construct if necessary.

It is anticipated that the RNA construct described in FIG. 29 will interact with the target polynucleotide as shown and that the interaction will adhere to the principles outlined above. Moreover, it is anticipated that the HSL variation, shown in FIG. 34, will interact with the target polynucleotide as shown and will promote translation of the polypeptide coding region.

Example 2

MS2 Protein-Binding RNA Constructs

The following demonstrates design of an RNA construct capable of binding an RBP only in the presence of a target.

Part I: Background

Figure 36:
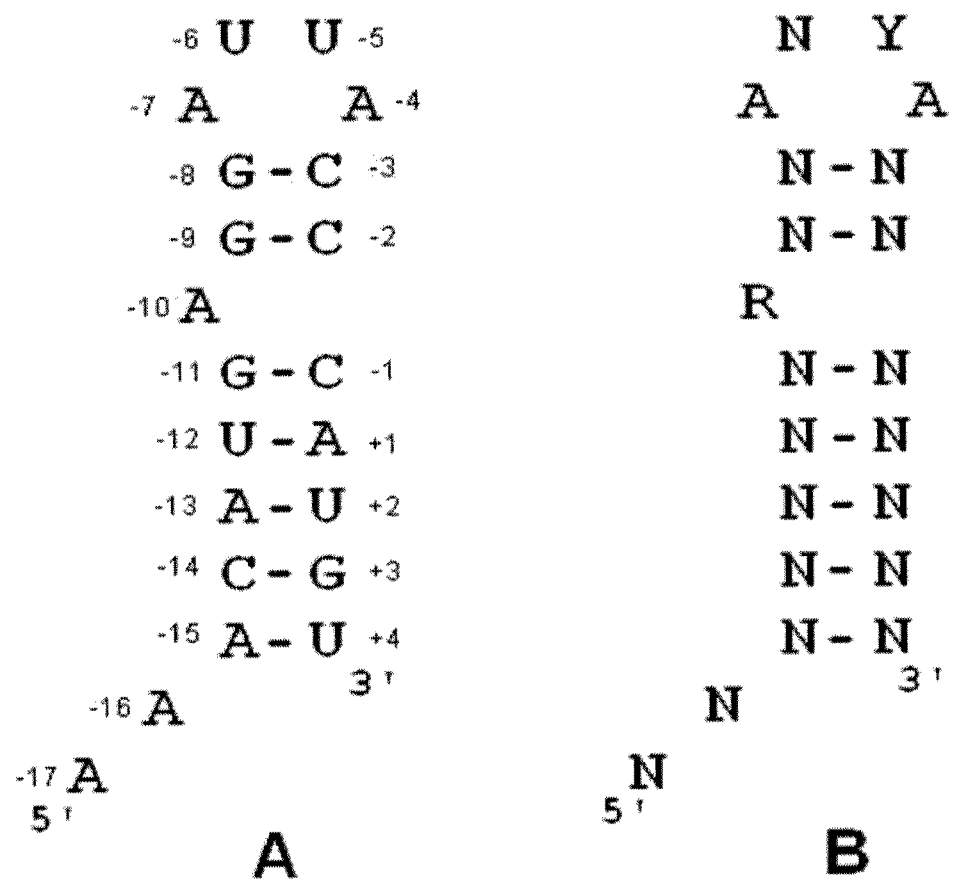

The bacteriophage MS2 capsid protein acts as a translational repressor by binding to a specific RNA stem-loop structure that contains the viral replicase translation initiation region (Peabody (1990) J. BIOL. CHEM. 265(10): 5684-5689). The structure of this stem-loop (FIG. 36) has been well studied, and the effects of various base mutations in the wild type have been characterized (Table 5, Schneider, et al. (1992) J. MOL. BIOL. 228(3):862-869). Additionally, high affinity variations have been found using the SELEX technique (Schneider, et al., supra).

TABLE 5

| Wild-type Position(s) | Nucleotide Variation | Relative Dissociation Constant |
|---|---|---|
| $A_{-17}$ | deletion | >3000 |
|  | G | 1.0 |
| $A_{-16}$ | G | 1.0 |
| $U_{-12}$-$A_{+1}$ | A-U | 1.1 |
| $G_{-11}$-$C_{-1}$ | C-G | 4.2 |
|  | U-A | 3.9 |
|  | G-G or C-C | >3000 |
| $A_{-10}$ | deletion | >3000 |
|  | C | >3000 |
|  | U | >3000 |
|  | G | 1.7 |
| $G_{-9}$-$C_{-2}$ | C-G | 3.4 |
|  | U-A | 9.5 |
| $G_{-8}$-$C_{-3}$ | C-G | 1.0 |
| $A_{-7}$ | C | 10 |
|  | U | >3000 |
| $U_{-6}$ | A | 3.0 |
|  | C | 1.0 |
|  | G | 3.0 |

TABLE 5-continued

| Wild-type Position(s) | Nucleotide Variation | Relative Dissociation Constant |
|---|---|---|
| $U_{-5}$ | A | 10 |
|  | C | 0.02-0.2 |
|  | G | 15 |
| $A_{-4}$ | C | >3000 |
|  | U | >3000 |
|  | G | >3000 |
| $A_{+1}$ to $U_{+4}$ | deletion | 330 |
| $U_{+2}$ to $U_{+4}$ | deletion | 1.7 |
| $G_{+3}$ to $U_{+4}$ | deletion | 1.0 |
| $U_{+4}$ | deletion | 1.0 |

Although MS2, in its natural context, functions as a translational repressor, the opposite effect can be attained by incorporating it as part of a Xenopus Poly-A Binding Protein (PABP) fusion protein (e.g., Coller et al., (1998) GENES AND DEVELOPMENT 12:3226-3235). Additionally, a mutant variation (LeCuyer, et al., (1995) BIOCHEM. 34(33): 10600-10606) of MS2 has been described that retains RNA binding capability but significantly reduces its tendency to form capsid particles. Previously, that mutant was incorporated as part of the fusion protein and used to show translational enhancement in messages where an MS2 recognition motif replaced the usual mRNA poly-A tail (Coller, supra). Here, a variant was designed using human PABP (MS2-PABP[human], Table 6) fused to the C-terminal end of MS2 protein and a hexa-his-containing peptide ("hexa-his" disclosed as SEQ ID NO: 92) preceding the N terminal region of the MS2.

TABLE 6

(Proteins)

| Label | Full Name | Sequence |
|---|---|---|
| MS2-PABP | MS2-PABP[human] fusion protein | MGSSHHHHHHSSGLVPRGSHMGPRASNFTQFVLVDNGGTGDVTVAPSN FANGVAEWISSNSRSQAYKVTCSVRQSSAQNRKYTIKVEVPKVATQTV GGEELPVAGWRSYLNMELTIPIFATNSDCELIVKAMQGLLKDGNPIPS AIAANSGIYASPSAPSYPMASLYVGDLHPFVTEAMLYEKFSPAGPILS IRVCRDMITRRSLGYAYVNFQQPADAERALDTMNFDVIKGKPVRIMWS QRDPSLRKSGVGNIFIKNLDKSIDNKALYDTFSAFGNILSCKVVCDEN GSKGYGFVHFETQEAAERAIEKMNGMLLNDRKVFVGRFKSRKEREAEL GARAKEFTNVYIKNFGEDMDDERLKDLFGKFGPALSVKVMTDESGKSK GFGFVSFERHEDAQKAVDEMNGKELNGKQIYVGRAQKKVERQTELKRK FEQMKQDRITRYQGVNLYVKNLDDGIDDERLRKEFSPFGTITSAKVMM EGGRSKGFGFVCFSSPEEATKAVTEMNGRIVATKPLYVALAQRKEERQ AHLTNQYMQRMASVRAVPNPVINPYQPAPPSGYFMAAIPQTQNRAAYY PPSQIAQLRPSPRWTAQGARPHPFQNMPGAIRPAAPRPPFSTMRPASS QVPRVMSTQRVANTSTQTMGPRPAAAAAAATPAVRTVPQYKYAAGVRN PQQHLNAQPQVTMQQPAVHVQGQEPLTASMLASAPPQEQKQMLGERLF PLIQAMHPTLAGKITGMLLEIDNSELLHMLESPESLRSKVDEAVAVLQ AHQAKEAAQKAVNSATGVPTV (SEQ ID NO: 95) |
| SLBP | Stem-loop Binding Protein [human recombinant] | MACRPRSPPRHQSRCDGDASPPSPARWSLGRKRRADGRRWRPEDAEEA EHRGAERRPESFTTPEGPKPRSRCSDWASAVEEDEMRTRVNKEMARYK RKLLINDFGRERKSSSGSSDSKESMSTVPADFETDESVLMRRQKQINY GKNTIAYDRYIKEVPRHLRQPGIHPKTPNKFKKYSRRSWDQQIKLWKV ALHFWDPPAEEGCDLQRTHPVDLESAESSSEPQTSSQDDFDVYSGTPT KVRHMDSQVEDEFDLEACLTEPLRDFSAMS (SEQ ID NO: 176) |

Figure 37:
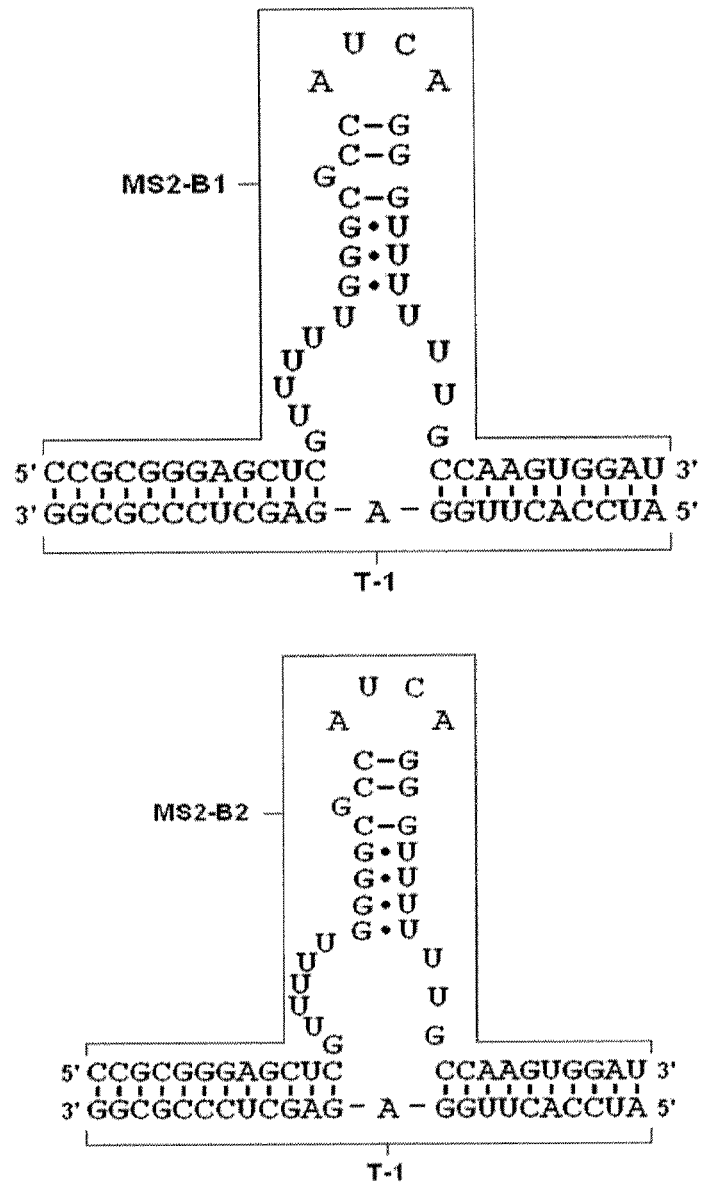
FIG. 37 shows RNA constructs MS2-B1 (SEQ ID NO:101) and MS2-B2 (SEQ ID NO:102) complexed with target polynucleotide hcmv-mir-us25-2-3p (T-1 (SEQ ID NO:103)).
Figure 38:
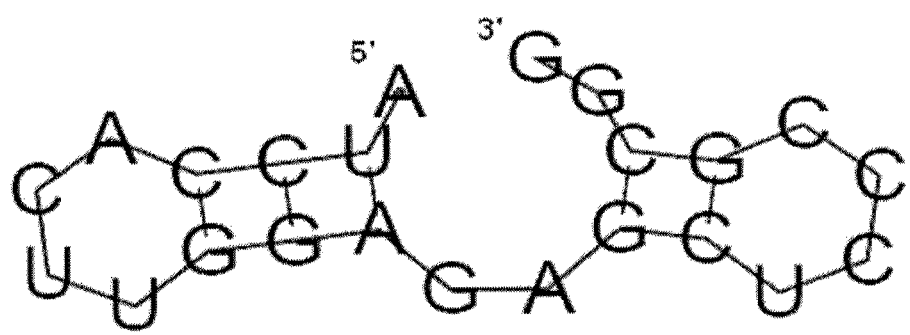
FIG. 38 shows the predicted folding pattern and minimum free energy (MFE) of the target hcmv-mir-us25-2-3p (T-1 (SEQ ID NO:103)) alone.
Figure 39:
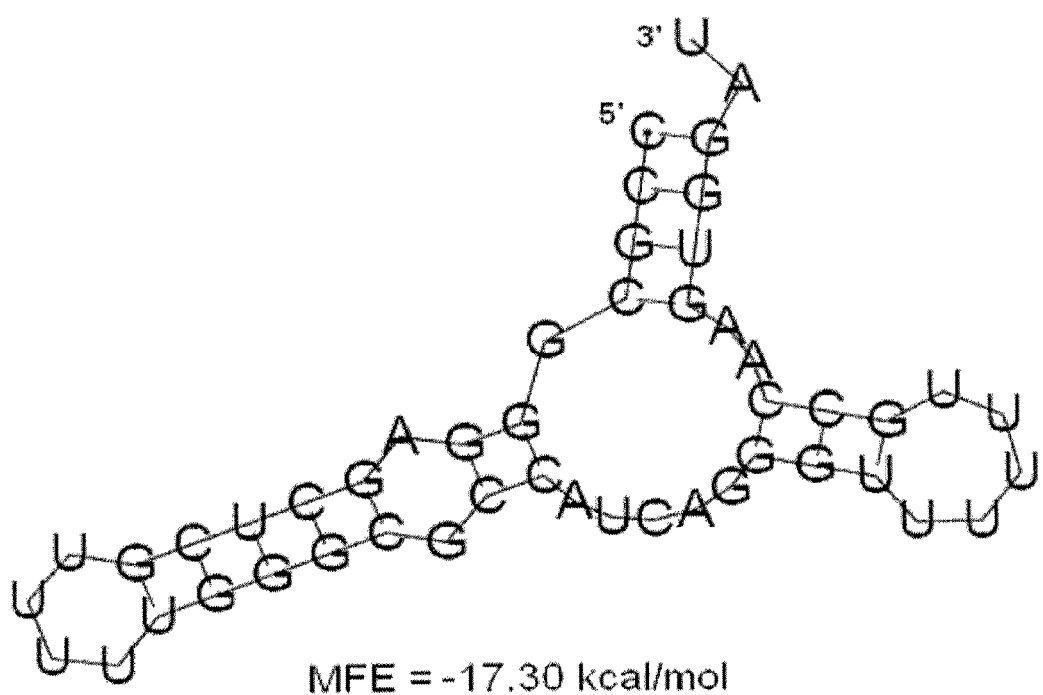
FIG. 39 shows the predicted folding pattern and minimum free energy (MFE) of the RNA construct MS2-B1 (SEQ ID NO:101) alone.
Figure 40:
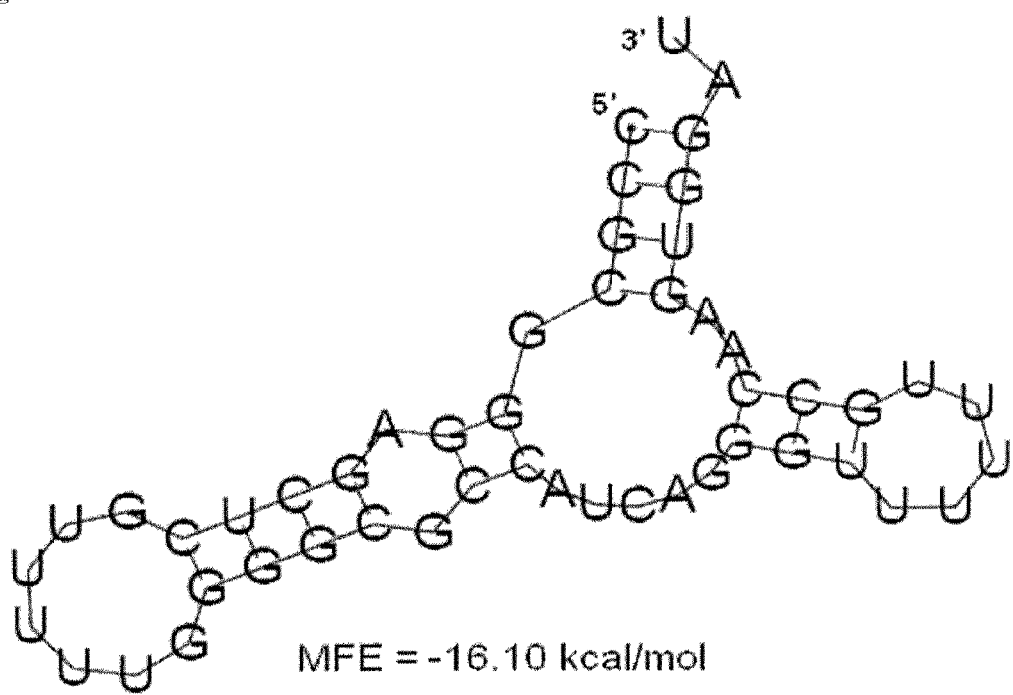
FIG. 40 shows the predicted folding pattern and minimum free energy (MFE) of the RNA construct MS2-B2 (SEQ ID NO:102) alone.
Figure 41:
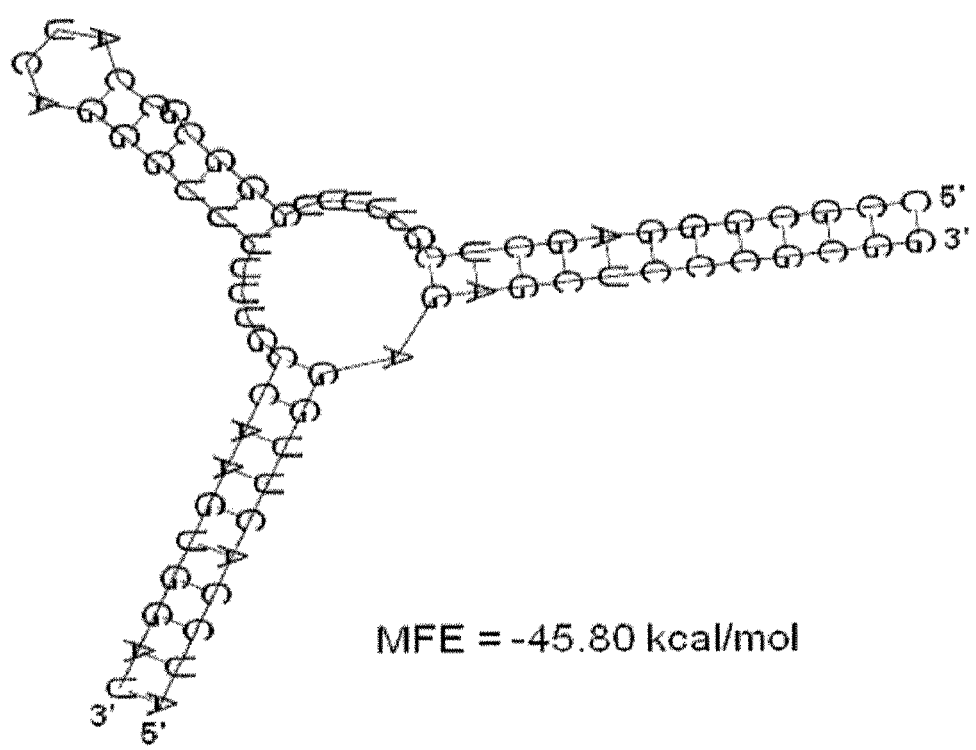
FIG. 41 shows the predicted folding pattern and minimum free energy (MFE) of the RNA construct MS2-B1 (SEQ ID NO:101) bound to its target polynucleotide, hcmv-mir-us25-2-3p (SEQ ID NO: 103).
Figure 42:
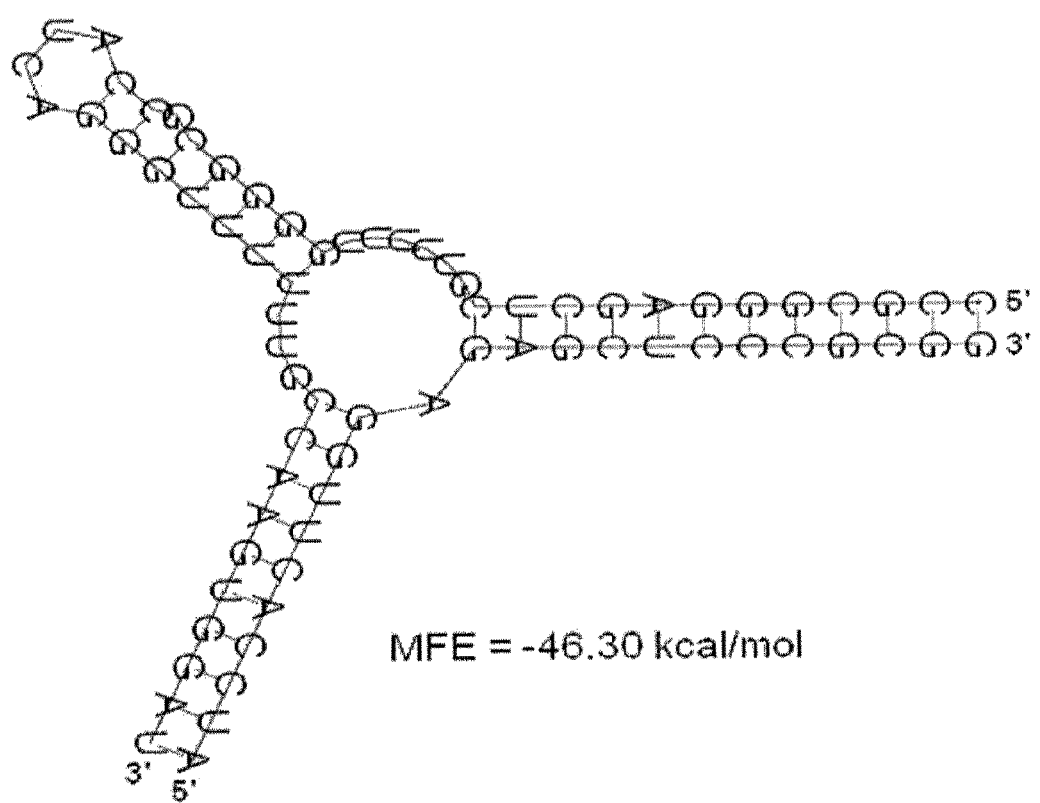
FIG. 42 shows the predicted folding pattern and minimum free energy (MFE) of the RNA construct MS2-B2 (SEQ ID NO:102) bound to its target polynucleotide, hcmv-mir-us25-2-3p (SEQ ID NO:103).

As shown in FIG. 37, two versions of an RNA construct, designated MS2-B1 and MS2-B2 (Table 7), were designed to bind to the target hcmv-mir-us25-2-3p (from human cytomegalovirus, Table 8). This target is an example of a naturally occurring non-coding RNA in a human pathogen. The RNA constructs were designated. Minor variations in stein strength and junctions region size exist between the two constructs.

TABLE 7

(RNA Constructs)

| Label | Description | Sequence |
|---|---|---|
| MS2-WT | Wild Type MS2 Motif | AAACAUGAGGAUUACCCAUGU (SEQ ID NO: 99) |
| MS2-P1 | Positive Control | AGAGAAACAUGAGGAUCACCCAUGUGAGACAGAGAGAG AG (SEQ ID NO: 191) |
| MS2-B1 | MS2_engineered_sxRNA2.0 | CCGCGGGAGCUCGUUUUUGGGCGCCAUCAGGGUUUUUU GCCAAGUGGAU (SEQ ID NO: 101) |
| MS2-B2 | MS2_engineered_sxRNA2.1 | CCGCGGGAGCUCGUUUUUGGGCGCCAUCACGGUUUUU UGCCAAGUGGAU (SEQ ID NO: 102) |
| MS2-B3 | MS2_engineered_sx.RNA3.1 | AACUAUACAACCGUUUUUGGGGCGCCAUUAGGGUCUUU UGCCUACCUCA (SEQ ID NO: 104) |
| MS2-B5 | MS2_engineered_sxRNA4.0 | AAAGUGUCAGAGUUUUUGGGGCGCCAUUAGGGUUUUUU GACGGUGUGG (SEQ ID NO: 107) |
| HSL-C1 | Histone Stem-loop Consensus | MMMMGGYYYUHHUHARRRCCMM (SEQ ID NO: 107) |
| HSL-P1 | NM_001005464.2(HIST2H3A): position 467-507 positive control histone stem-loop | AGGUUCCAUCGUAUCCAAAAGGCUCUUUUCAGAGCCAC CCA (SEQ ID NO: 193) |
| HSL-B1 | NM_001005464.2_minor_mutant(HIST2H3A): 467-507(U sub at 502) | AGGUUCCAUCGUAUCCAAAAGGCUCUUUUCAGAGCUAC CCA (SEQ ID NO: 110) |
| HSL-B2 | NM_001005464.2_major_mutant(HIST2H3A): 467-507(U sub at 489, G sub at 499,U sub at 502) | AGGUUCCAUCGUAUCCAAAAGGUUCUUUUCAGGGCUAC CCA (SEQ ID NO: 111) |
| HSL-B3 | NG_011683.1(SEPTEMBER 9): 215412-215468 | CCCGCCGUGGGGGUAACACCCUGUGGGCCACAGGUUUU CUUUAAAAUCCCAGCUCCG (SEQ ID NO: 113) |
| HSL-B4 | HSL_engineered_sxRNA1.0 | GAAGAGAGCCGCCCAAAACAGAAAGAAAGGCUCUUUUC AGAGCUACACUUU (SEQ ID NO: 114) |

TABLE 8

(Targets)

| Label | Description | Sequence |
|---|---|---|
| T-1 | hcmv-miR-us25-2-3p | AUCCACUUGGAGAGCUCCCGCGG (SEQ ID NO: 103) |
| T-2 | hsa-let-7e | UGAGGUAGGAGGUUGUAUAGUU (SEQ ID NO: 105) |
| T-3 | hsa-miR-220a | CCACACCGUAUCUGACACUUU (SEQ ID NO: 108) |
| T-4 | hsa-miR-363* | CGGGUGGAUCACGAUGCAAUUU (SEQ ID NO: 112) |
| T-5 | hsa-miR-1250 | ACGGUGCUGGAUGUGGCCUUU (SEQ ID NO: 115) |
| T-6 | xla-miR-427 | AAAGUGCUUUCUGUUUUGGGCG (SEQ ID NO: 116) |

Part II: Design Considerations

1) To generally weaken the wild type structure in the MS2-B1 construct, the stem's first base pairing was changed to U-U, and pairs 2-4 were changed to G-U. In MS2-B2, the first four pairs were changed to G-U which makes the pairing slightly stronger.
2) The A bulge at position −10 was changed to a G to prevent base pairing with the U's introduced to the lower stem.
3) The top 3 base pairings in the stem were changed from G-C to C-G to
   a.) prevent the upper C's from pairing with the G's introduced in the lower opposite side of the stem,
   b.) prevent the upper G's pairing with the U's introduced into the lower opposite side of the stem
   c.) promote the G bulge.
4) The U at position −5 was changed to a C to increase affinity for the protein when stem-loop structure forms and partially compensate for some of the other base changes made to weaken the structure.
5) The desired three-way junction conformation was "family A" as defined in FIG. 4 (and as described by Lescoute et al, supra) with the stem bearing helix at P3.
6) Unpaired nucleotides in the 5' portion of the stem-loop were therefore designated as part of the intended junction J2.
7) To avoid pairing interactions with the engineered stem's bases or with J3 bases, both J2 and J3 were composed primarily of U's, the exception being a single G at the 5' terminus of J2 and at the 3' terminus of J3 (explained below). While there is some propensity for U-U pairings, the torsion forces induced at the junction regions should prevent this, particularly in the lower part of the stem.
8) To obtain a family A-type three-way junction, the length of J2 was designed to be larger than J3. Because there may be some propensity for U-U pairings, particularly further away from the junction and which may be reinforced by the canonical and G-U-based helix, U's were included at position −15 and +4 as part of the stem and not the junction. If pairing does not occur, these bases contribute one nucleotide to both J2 and J3, maintaining the J2>J3 relationship. Therefore, the number of nucleotides comprising the J2 and J3 junction regions for MS2-B1 and MS2-B2 are 5 and 3 and 6 and 3, respectively.

9) A common characteristic of "family A" constructs is the presence of an A-G trans Hoogsteen-Sugar-Edge pairing at the interface side of P2. In order to promote this pairing, the flank region of the RNA construct was designed to leave an 'A' base near the center of the target sequence unpaired, and a 'G' base was placed at the 5' terminus of the J2 segment. To prevent an undesired interaction with the 3' terminus of the J3 region, a 'G' base was placed there, because a 'U' might have formed a canonical pairing with the target 'A', and a 'C' may have interacted with the 'G' introduced to J2 or with the 'G' upstream of the target 'A'. The potential for the trans Hoogsteen-Sugar-Edge interaction exists at the 'G' in the J2 interface due to the particular strand conformation and presentation of that base in relation to the 'A' in the target. Therefore, the 'G' in the J3 segment is less likely to interact with the 'A' in the target.

10) Finally, the flanking 5' and 3' sequences were designed to be perfectly complementary to the target, leaving a J1 of size 0 if the predicted trans Hoogsteen-Sugar-Edge pair forms, or size 1 if it docs not form. In either case, J1 conforms to the "family A" junction region size requirement.

Secondary structure and minimum free energy predictions for the target alone, the RNA construct alone and the RNA construct and target together were determined using RNAFold and RNACoFold and are shown in FIGS. 38-42. The MS2-B1 RNA construct and target showed a −24.9 kcal/mol net change versus the RNA construct and target individually, and the MS2-B2 RNA construct and target showed a −26.6 kcal/mol net change. These predictions indicated that the RNA construct and target would likely hybridize as intended.

Figure 43:
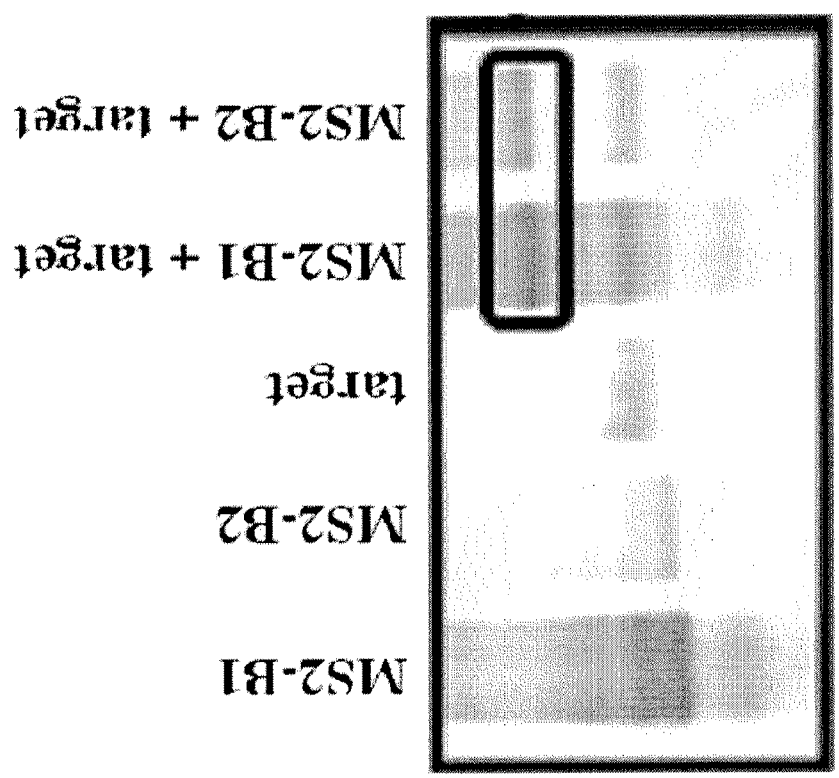
FIG. 43 shows a native PAGE in which a structure with a higher molecular weight than either RNA construct or target alone forms (see box), indicating that RNA constructs MS2-B1 and MS2-B2 are capable of stably binding target polynucleotide.

Part III: The RNA Construct Selectively Binds the MS2 Fusion Protein in the Presence of the Target Polynucleotide a. Native Gel Binding Experiment To determine whether the RNA construct bound the target, a binding experiment under native conditions was performed. All RNA used for the experiment was dissolved in a buffer containing 10 mM Tris-HCl (pH 8.0) and 100 mM NaCl. The MS2-B1 or MS2-B2 RNA construct and target were mixed in a 1:2 ratio and annealed at 85° C. for 3 minutes and gradually cooled to room temperature for about an hour. The resulting mixture was run on a native PAGE (15% TBE-PAGE) gel. FIG. 43, shows an upper band (identified by a box) with a lower electrophoretic mobility than either the RNA construct or target alone. This higher molecular weight species was most likely the RNA construct complexed with the target, indicating that the RNA construct was capable of binding the target.

b. RNA-Protein Interaction Studies Using Immunoprecipitation (IP)

Figure 44:
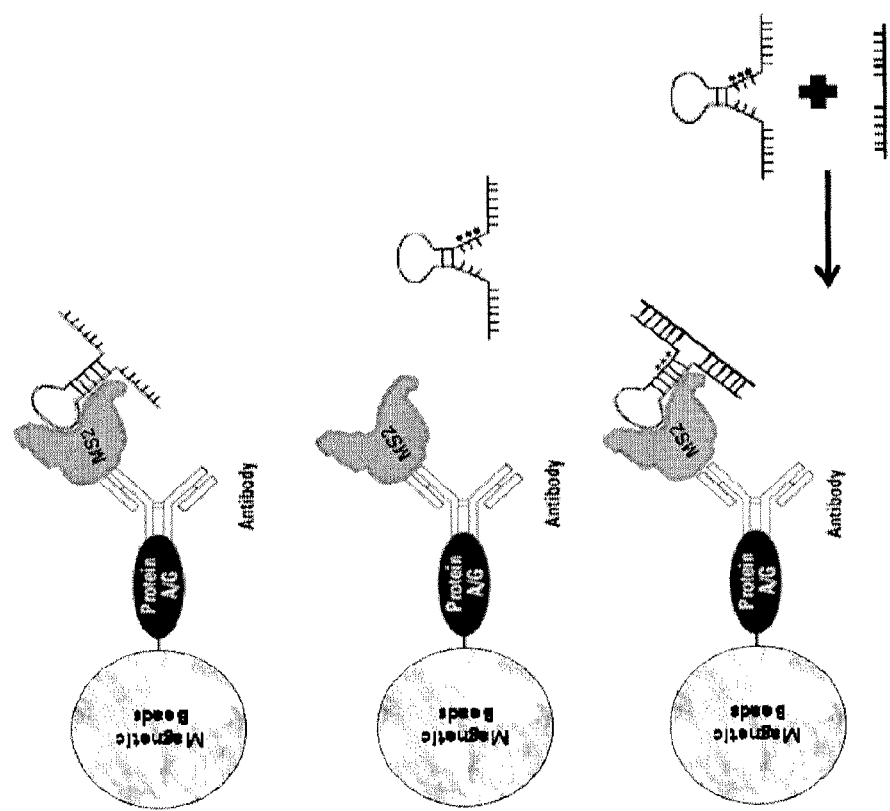
FIG. 44 shows a schematic representation of the immunoprecipitation of MS2 protein bound to an RNA construct-target complex.

Immunoprecipitation commonly used to precipitate a target protein from a solution using an antibody specific to the target protein. If the protein is also bound to other proteins or to RNA, forming a complex, the complex can be pulled down as an intact unit by co-precipitation. FIG. 44 is a schematic representation of a co-immunoprecipitation experiment for precipitating MS2 with an RNA construct and target bound thereto.

A slurry of magnetic beads (Dynabeads®, Invitrogen, Carlsbad, Calif.) coated in Protein A and G were mixed by vortexing, and 75 µl were transferred to a new tube and washed twice with 0.5 ml of NT-2. The beads were resuspended in 100 µl of NT-2 (50 mM Tris-HCl, pH 7.4, 150 mM NaCl, 1 mM $MgCl_2$, 0.05% NP-40), and 5 µg of anti-His tag antibody were added. Anti-his antibody was chosen because the MS2-PABP fusion protein has a His tag at the N-terminal end. The tube was mixed at room temperature overnight at 4° C., and then washed five times with 1 ml of NT-2. In parallel, RNA construct, target or RNA construct and target were added to respective tubes, heated to 85° C. for 5 minutes and gradually cooled down to room temperature to allow binding of RNA construct to target to occur. MS2-PABP was added to the tubes containing RNA construct, target or RNA construct and target and incubated at 37° C. for 1 hour.

The beads were resuspended in 900 µl of NET-2 (NT2, with 20 mM EDTA (pH 8.0), 10 µL 1 mM DTT, 200 Units Rnase OUT™ (Invitrogen, Carlsbad, Calif.)). RNA-protein complexes were added to the tubes containing the beads to which the anti-His antibody was bound and were mixed overnight at 4° C. The beads were washed six times with 1.0 ml of ice cold NT-2. Before the beads were spun down for the sixth wash, 100 µl of the bead slurry (out of 1 ml total volume) were removed for confirming protein pull down by Western. To remove protein, the beads were resuspended in 150 µl Proteinase K buffer and mixed at 55° C. for 30 min using a thermomixer. To precipitate RNA, 150 µl phenol-chloroform were added, mixed by vortexing, and centrifuged at 12,000 rpm for 5 min. The upper aqueous layer was removed and 150 µl chloroform added. The tubes were then mixed by vortexing and centrifuged. 50 µl 5M ammonium acetate, 5 µl of glycogen and 1.0 ml of cold 100% ethanol were added to the supernatant. The tubes were placed at −80° C. for half an hour. The tubes were then centrifuged at 14,000 rpm for 30 min, washed with 80% ethanol, and centrifuged again for 30 min. The resulting pellets were dried in a Speed-vac and resuspended in 10 µl of buffer (10 mm Tris (pH8.0), 100 mM NaCl).

Magnetic beads (Dynabeads™, Invitrogen, Carlsbad, Calif.) coated with protein A/G were used for the IPs. Since the MS2 fusion protein has a His tag at the N-terminal end, anti-His was chosen as the antibody. Anti-His was incubated with the beads overnight at 4° C. MS2 protein was incubated with the RNA construct and target, the RNA construct alone, or the target alone at 37° C. for 1 hour. The whole mixture was added to the anti-His bound beads and incubated overnight at 4° C. To verify RNA pull down, the beads were treated with proteinase k for protein digestion followed by phenol-chloroform extraction and ethanol precipitation.

Figure 45:
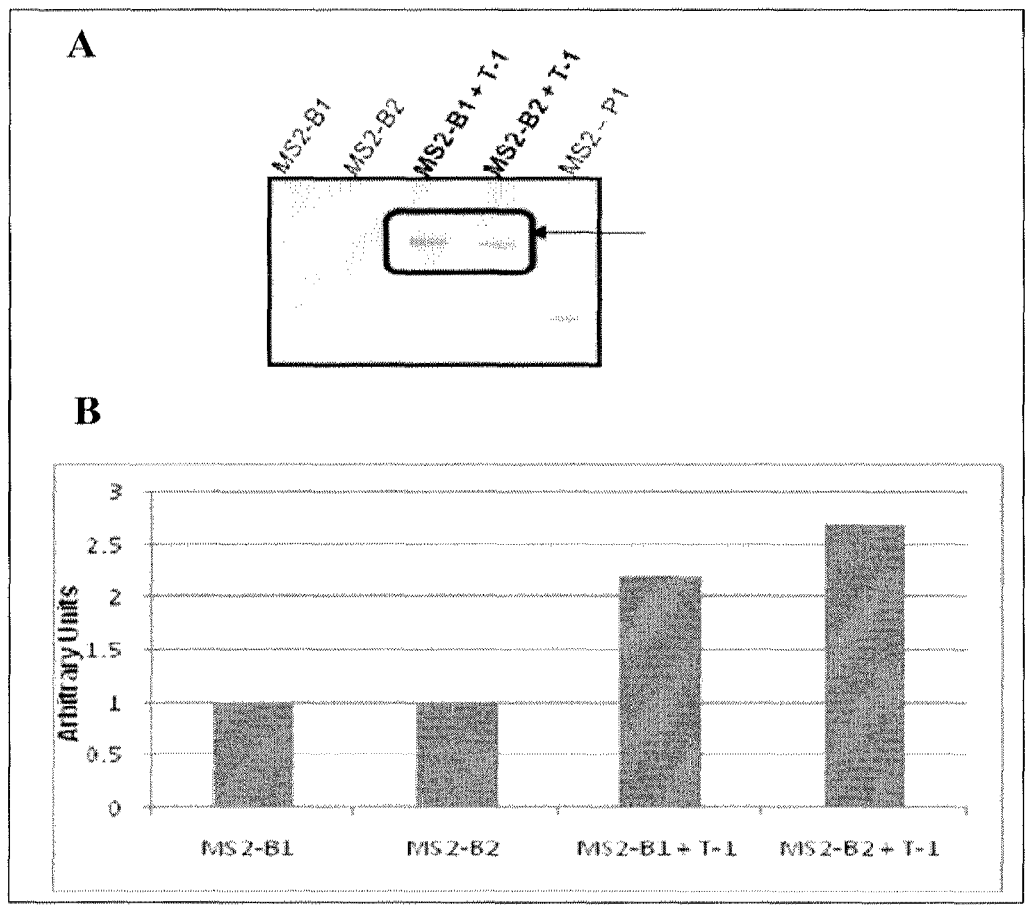
FIG. 45A provides a TBE-urea denatured gel showing that RNA construct-target complex (MS2-B1+T-1, lane 3 and MS2-B2+T-1, lane 4) is more efficiently co-immunoprecipitated with MS2 protein than is RNA construct alone (MS2-B1, lane 1 and MS2-B2, lane 2), indicating that the target polynucleotide stabilizes the structure of each RNA construct in a manner that is conducive to MS2 protein binding.
FIG. 45B shows quantitation of band intensities for the lanes indicated, which was performed using Quantity One® software (BioRad, Hercules, Calif.).

The precipitated samples were tested on a denaturing PAGE (10% TBE-Urea) gel. The bands of interest are marked on the gel (FIG. 45A). These bands represent the RNA construct-target complex which was pulled down along with the MS2 as a result of the protein-RNA interaction. An increase in binding of the RNA construct (MS2-B1 or MS2-B2) occurred in the presence of target, which was not seen in the absence of the target. A positive control was used which naturally forms a stem-loop which preferentially hinds to MS2. A band that may represent target-target binding was also seen. Self-hybridization of the target might have occurred, which according to RNA cofold prediction software, forms a stem-loop similar to the MS2 RNA. Band intensities were quantified using Quantity One software (FIG. 45B, BioRad, Hercules, Calif.).

Figure 46:
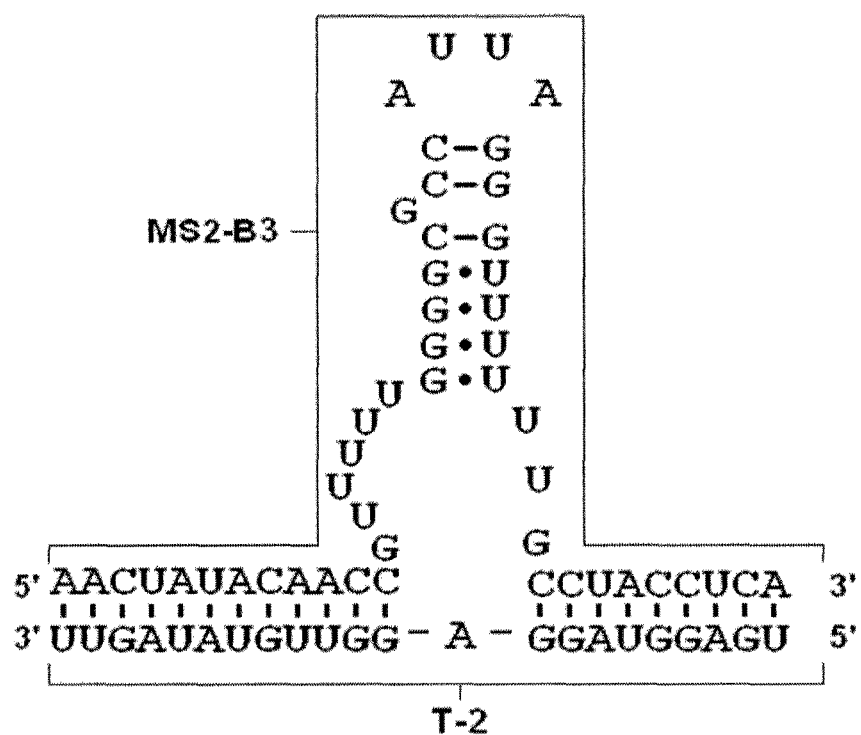
FIG. 46 depicts the sequence and structure of the MS2-B3 RNA construct (SEQ ID NO:104) bound to target polynucleotide T-2 (SEQ ID NO: 105).
Figure 47:
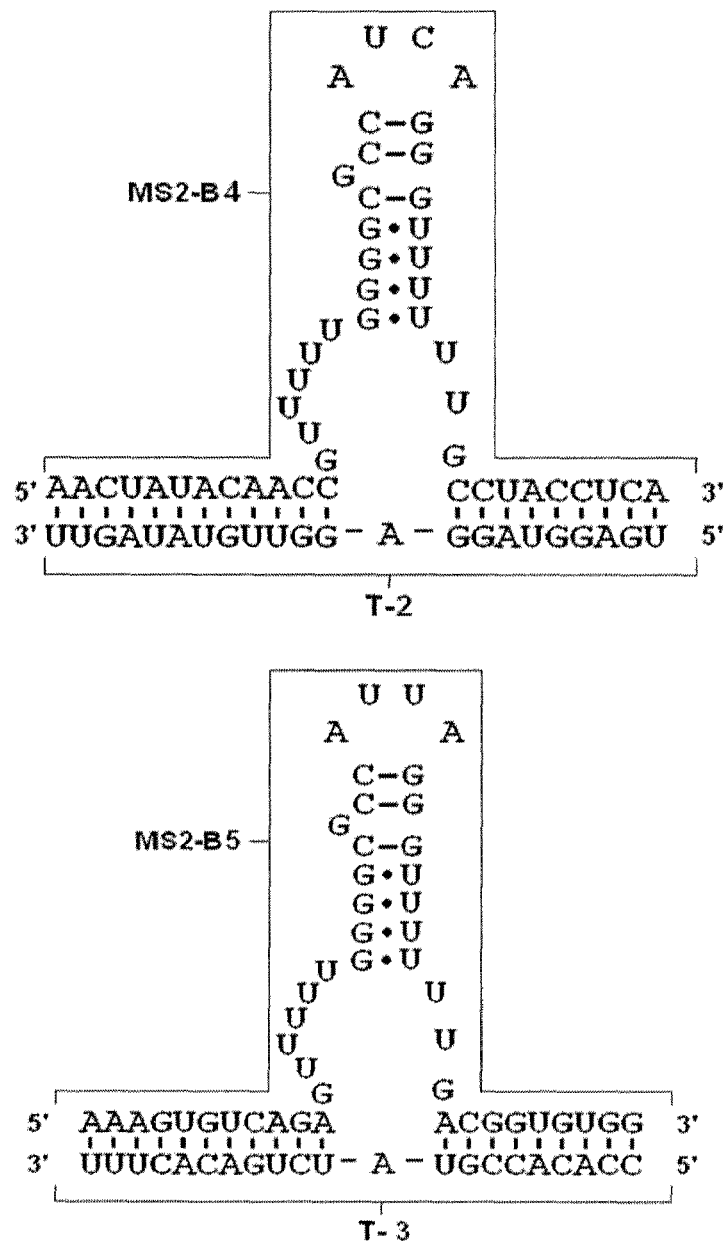
FIG. 47 depicts the sequence and structure of the MS2-B4 (SEQ ID NO:106) and MS2-B5 (SEQ ID NO:107) RNA constructs bound to target polynucleotides T-2 (SEQ ID NO: 105) and T-3 (SEQ ID NO: 108), respectively.
Figure 48:
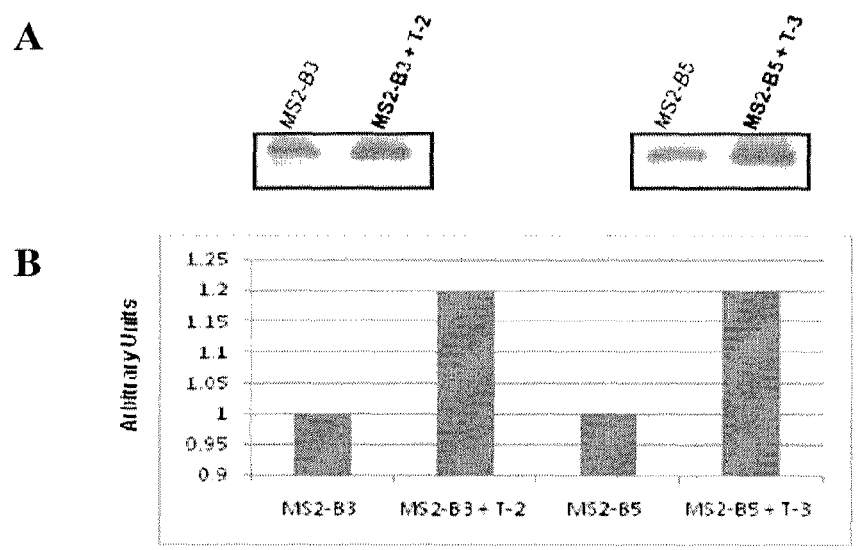
FIG. 48A provides a TBE-urea denatured gel showing that RNA construct-target complex (MS2-B3+T-2 or MS2-B5+T-3) is more efficiently co-immunoprecipitated with MS2 protein than is RNA construct alone (MS2-B3 and MS2-B5), indicating that the target polynucleotide stabilizes the structure of each RNA construct in a manner that is conducive to MS2 protein binding.
FIG. 48B shows quantitation of band intensities for the lanes indicated, which was performed using Quantity One® software (BioRad, Hercules, Calif.).

Additional MS2-RNA constructs were designed and designated MS2-B3-MS2-B5 (FIGS. 46-47, Table 7). Target polynucleotide sequences are shown in Table 8. Co-immunoprecipitation experiments were performed in the same manner for MS2-B3 and MS2-B5. Results are shown in FIG. 48.

Part IV: RNA Constructs Based on a Histone Stem-Loop (HSL) Motif

Figure 49:
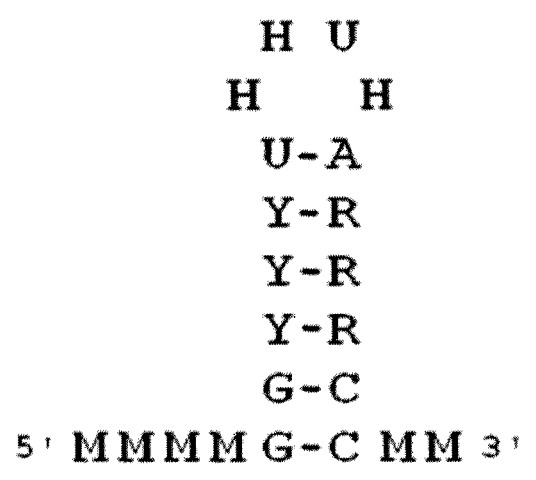
Figure 52:
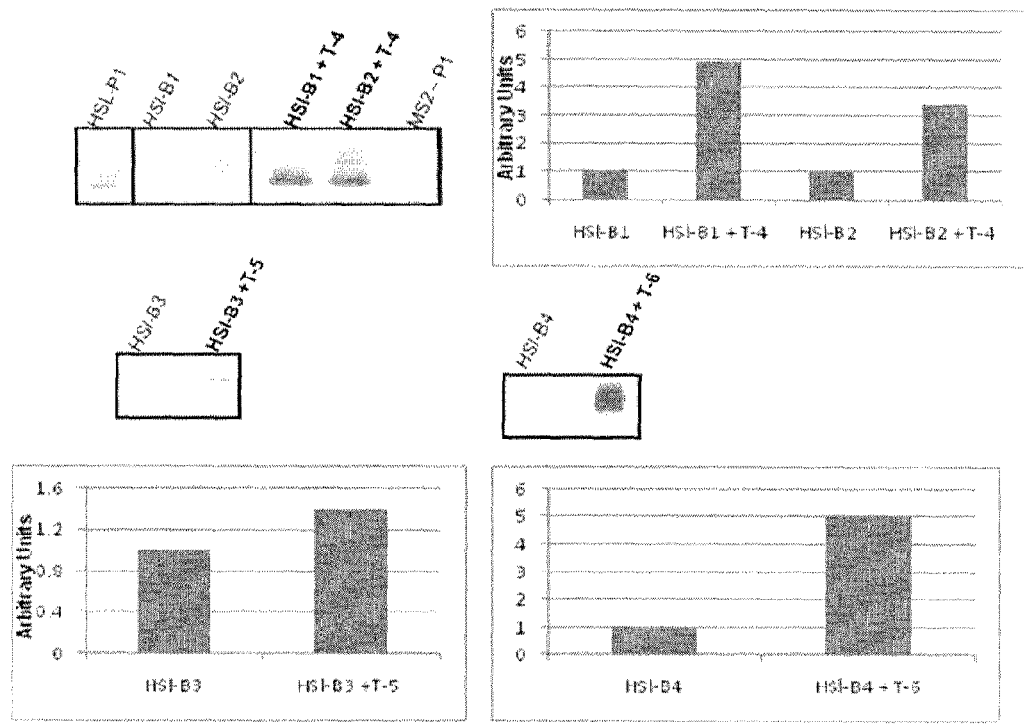
FIG. 52 provides a TBE-urea denatured gel showing that RNA construct-target complex (HSL-B1+T-4, HSL-B2+T-4, HSL-B3+T-5, and HSL-B4+T6) is more efficiently co-immunoprecipitated with Stem-loop Binding Protein (SLBP) than is RNA construct alone (HSL-B1, HSL-B2, HSL-B3, and HSL-B4), indicating that the target polynucleotide stabilizes the structure of each RNA construct in a manner that is conducive to SLBP binding.

A HSL consensus sequence shown in FIG. 49 (acquired from the: UTRSITE Signal Manager (www2.ba.itb.cnr.it/UTRSite/index.php/UTRSite%20signal/Signal/frmID/U0035) was used as the starting point to design HSL-based RNA constructs (HSL-B1-4, see Table 8, and FIGS. 50-51), which were tested as described above for their ability to bind SLBP in the presence of a target sequence (Table 7). Recombinant human SLBP was obtained by expression in an insect/baculovirus system by Genscript (Piscataway, N.J.). Results are shown in FIG. 52.

Example 3

Increasing Expression of a Polypeptide Coding Region 5' of an RNA Construct

To demonstrate that an RNA construct placed downstream of a polypeptide coding region is capable of increasing expression of the polypeptide coding region in the presence of a target polynucleotide, MS2-based RNA constructs are engineered and inserted downstream of a luciferase reporter gene. In the presence of a target sequence capable of binding to the RNA construct, the RNA construct is stabilized, allowing it to bind an MS2-polyA binding protein (PABP) fusion protein, which increases translation of the luciferase reported gene.

The luciferase gene from the Luciferase T7 control DNA vector (#L4821, Promega, Madison, Wis.) vector is used to construct a DNA vector for transcribing the RNA construct and subsequently translating luciferase. Restriction sites downstream of the T7-expressed luciferase gene are used to clone in DNA sequences encoding MS2-engineered RNA construct sequences, which allow for binding by either wild-type or MS2-PABP fusion protein. Control MS2-engineered RNA constructs, termed Positive control MS2 and Wild-Type MS2 motif, are constructed by annealing designed oligonucleotides to each other in overlapping region, filling in bases with DNA Polymerase I, Large (Klenow) fragment (#M0210, New England BioLabs, Ipswitch, Mass.), amplifying by PCR, and digesting the resulting DNA with SacI and BtgI (#R0156 and #R0608, respectively, New England BioLabs, Ipswitch, Mass.). Once the vector and MS2-RNA construct sequence insert are digested with their respective enzymes, T4 DNA ligase is used (#M0202, New England BioLabs, Ipswitch, Mass.) to attach the two sequences together and the resulting clones are transformed into *Escherichia coli* DH5α bacterial cells. Once the series of MS2-engineered RNA constructs are cloned downstream of the luciferase gene, purified DNA is linearized for in vitro transcription followed by in vitro translation in with and without the addition of the MS2-PABP fusion protein.

Part I: In Vitro Transcription of the Templates

After linearization of the plasmid with SacI, the DNA is purified with DNA Clean and Concentrator™ (#D4003, Zymo Research, Orange, Calif.). The DNA is then transcribed into uncapped RNA using Ambion® MEGAscript® T7 Kit (#AM1333, Applied Biosystems, Carlsbad, Calif.). 1 µg of linear template DNA is added to a 20 µL transcription reaction containing 8 µL ribonucleotides solution, 2 µL of 10× reaction buffer, 2 µL enzyme mix, and nuclease-free water. Also, capped RNA is manufactured using Ambion® mMESSAGE mMACHINE® T7 Kit (#AM1344, Applied Biosystems, Carlsbad, Calif.), with 1 µg of linear template DNA added to a 20 µL transcription reaction containing 10 µL 2×NTP/CAP solution, 2 µL of 10× reaction buffer, 2 µL enzyme mix, and nuclease-free water. The transcription reactions are incubated in an undisturbed environment at 37° C. overnight. After incubation, 1 µL of Ambion® TURBO® DNase (2 U/µL, Applied Biosystems, Carlsbad, Calif.) is added and incubated at 37° C. for another 15 minutes to remove the template DNA. The RNA is recovered by lithium chloride precipitation as the transcription reactions are mixed thoroughly with 30 µL of nuclease-free water and 30 µL of 7.5 M LiCl. The mixture is chilled at −20° C. for 30 minutes, and centrifuged at 4° C. for 15 minutes at 14,000 rpm to pellet the RNA. The supernatants are carefully removed and the pellets are washed with 1 mL of 70% ethanol to maximize removal of unincorporated nucleotides. The 70% ethanol is carefully removed after centrifuging again at 4° C. for 15 minutes at 14,000 rpm. The pellets are placed in a Speed vac for 5 minutes for drying, and the RNA is resuspended in nuclease-free water. The concentration of the RNA is determined by Nanodrop analysis (Nanodrop® 2000, Thermo Scientific, Waltham, Mass.), and the transcription products are analyzed by 1% agarose gel electrophoresis.

Part II: In Vitro Translation and Western Blot Analysis

To demonstrate that an RNA construct attached to a polypeptide coding region is capable of increasing expression of the polypeptide coding region in the presence of a target polynucleotide, the RNA construct attached to luciferase RNA and target RNA are placed into an in vitro translation system (Pierce Human in vitro protein expression kit (#88857, Thermo Scientific, Waltham, Mass.)). A 25 µL translation reaction is performed with 2 µg of RNA combined with 12.5 µL of lysate mixture, 2.5 µL accessory proteins, 1 µL salt solution B, 0.5 µL of amino acid minus methionine, 0.5 µL of amino acid minus leucine, 1 µL RNAse inhibitor (40 U/µL), 1.5 µL energy mix, and nuclease-free water. The reaction is assembled in a 0.5 mL centrifuge tube on ice, and the lysate is preincubated with accessory proteins for 5 minutes before adding the subsequent components to enable better translation. Nuclease-free water is substituted with varying quantities of MS2-PABP fusion protein. The reaction is mixed thoroughly by stirring with the pipette tip and gently flicking the tube before incubating at 30° C. overnight. The reaction is stopped by placing the centrifuge tube on ice. Translation products are then analyzed using Western blotting. SDS-PAGE electrophoresis is performed using 4-20% linear gradient polyacrylamide precast gels (#161-1105, Bio-Rad, Hercules, Calif.) before transferring to a nitrocellulose membrane. The nitrocellulose is developed by ONE-HOUR WESTERN™ (#L00228, Genscript, Piscataway, N.J.) using 10 µg of goat monoclonal anti-Luciferase antibody (Millipore, Billerica, Mass.). The intensity of the expression is analyzed by the BioRad Versa Doc™ 4000 imaging system (BioRad, Hercules, Calif.). An increase in intensity of luciferase expression is expected to be seen in tubes containing both RNA construct and target, compared to tubes containing RNA construct or target alone. The target stabilizes the RNA construct, which allows the RNA construct to be stably hound by the MS2-PABP fusion RBP, leading to an increase in expression of the attached luciferase polypeptide coding region.

Example 4

Naturally-Occurring RNA Switch

This example relates to a naturally-occurring RNA switch. The principles described in this example further validate RNA constructs of the invention.

MicroRNAs Target mRNA-Binding Protein Sites

Several recent studies suggested that the biological targets of microRNAs reside in the 3'UTRs of many mRNAs. The present invention contemplated that the cis-regulatory code targeted by trans-acting microRNAs was, at least in part, the same as that read by trans-acting RNA binding proteins. This model provides a new mechanism for gene regulation that provides a biochemical means to explain how the expression patterns of genes are selected for the required needs of a cell. It also provides a novel strategy for turning ON or OFF a polynucleotide coding region.

Confirmation that MicroRNAs Target mRNA-Binding Protein Sites

To confirm this model, it was determined whether any of the presently known microRNAs targeted a well-characterized mRNA regulatory element, such as the stem-loop structure, which is present in the 3'-untranslated region (UTR) of many higher eukaryotic histone mRNAs. Unlike most mRNAs, histone messages are not poly-adenylated. Instead, this family of mRNAs utilizes a 26 base stem-loop structure in its 3'-UTR called the histone stem-loop (HSL), which is regulated by the histone stem-loop binding protein (SLBP) and facilitates efficient translation.

Twenty-five human histone mRNA sequences containing the HSL (FIG. 53) were compared with a dataset containing the presently characterized microRNAs. This comparison was done in parallel with several control datasets matched for the histone mRNA dataset. The box labeled "Structure" in FIG. 53 is a consensus sequence for the twenty-file HSL sequence in FIG. 53. This sequence is the same as Consensus Sequence III, above.

Found microRNA and RBP Target Overlapping Code

Figure 55:
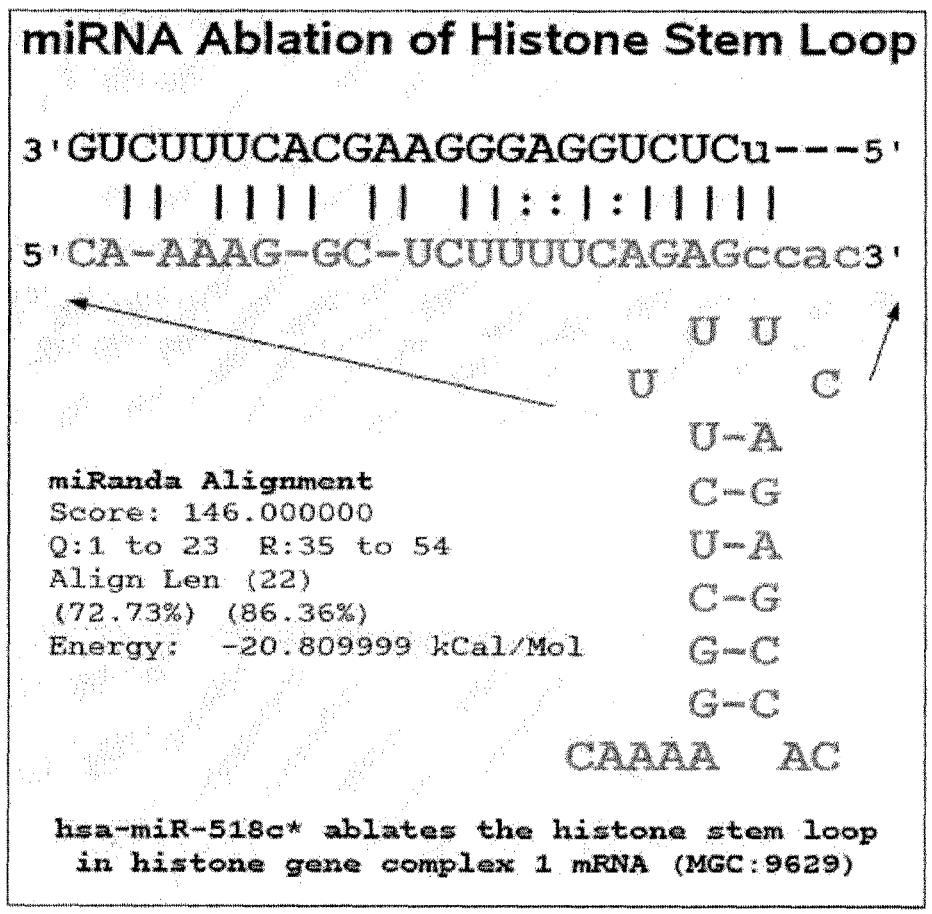
FIG. 55 shows a specific example of a histone stem-loop sequence (5'-CAAAAGGCUCUUUUCAGAGCCAC-3' (SEQ ID NO:170)) and its potential targeting by a microRNA. The upper sequences of the figure show the alignment of the stem-loop sequence to hsa-mir-518c* sequence (5'-UCUCUGGAGGGAAGCACUUUCUG-3' (SEQ ID NO:171)). This interaction is predicted to have a energy of −20.81 kcal/mol.

A group of microRNAs were identified that are contemplated to specifically interact with the HSL sequence with binding activity centered on the HSL regulatory element. These included the mir-518 and mir-319 microRNA families (FIG. 54). Strikingly, the microRNA-mRNA interaction is predicted to bind the HSL in a manner that melts the stem-loop portion, making the microRNA-mRNA complex and the SLBP binding site (or HSL regulatory element) mutually exclusive, in a scenario similar to that which is depicted in FIG. 55. More specifically, this model presents a mechanism that can be exploited whereby trans-acting non-coding RNAs are used to modulate an RNA construct in a manner that masks or reveals the regulatory targets of RBPs.

This first informatic search focused on human microRNAs. It was then expanded to include all presently characterized microRNAs. This expanded search additionally identified a microRNA encoded by SV40 (first example listed in FIG. 54) that has predicted binding affinity for the HSL sequence that is even higher than that predicted for the earlier identified cellular microRNAs (FIG. 54). It should be noted that all of the miRNAs of FIG. 54 are predicted to bind and melt all of the HSL mRNA elements.

It is likely that this SV40 microRNA represents a viral counterpart to what was a scavenged cellular microRNA, both performing a similar function, but in one case to perform a cellular need and the other case to satisfy a viral function. The cellular microRNA mir-518 family as well as the SV40 microRNA are likely all competing with the SLBP for binding to the HSL. When the SLBP binds, the histone mRNA that it is attached to is actively translated and the histone protein readily produced. When the microRNA binds the HSL, the histone protein is not expressed and translation is repressed.

The cell likely uses the mir-518 to help regulate SLBP binding, and thus the expression of histones, in an elaborate post-transcriptional regulatory mechanism that affords tight control that is directly linked to the cell cycle. SV40 may have developed to use this pathway for its own purposes so that it can better control the cellular production of histone protein, around which it wraps its genomic DNA as part of its replication process. Therefore, the mir-518/SLBP system appears to represent a naturally occurring RNA-based structural switch that has been scavenged by the SV40 virus.

Example 5

An RNA Construct that Turns Off a Reporter Gene

The inventive concept has been validated using an SV40-specific non-coding RNA (a microRNA), a target polynucleotide, that melts a stem-loop structured element based upon those known to exist in the 3'-untranslated region of many human histone-mRNAs (the RNA construct). This structure, called the histone stem-loop (HSL), is the natural target of a regulatory RNA-binding-protein called the stem-loop binding protein (SLBP). When SLBP binds to the HSL present in the histone mRNA, it activates translation, resulting in the increased production of histone protein. The SV40 non-coding RNA can act as a competitor to this process because it base pairs with the HSL in a manner that melts the stem-loop structure and thus destroys the natural binding site for SLBP (an example of the schema depicted in FIG. 2B and FIG. 3B). Thus, the SV40 non-coding RNA and SLBP interact with the HSL RNA construct in a mutually exclusive manner.

The naturally occurring histone mRNA has been rationally designed into a RNA construct with improved base-pairing kinetics for the SV40 non-coding RNA, and the histone mRNA coding region has been replaced with that of a green fluorescent protein (GFP) reporter gene. This trans-acting RNA switch strategy can be used as a molecular tool for biological research as a post-transcriptional reporter assay by inserting a gene of interest to then be turned ON or OFF, post-transcriptionally when the RNA switch is activated. An anti-viral strategy is specifically contemplated that utilizes virally-encoded RNA as the target to turn ON or OFF the RNA construct, resulting in cell death or inhibition of viral replication using one or more of the following additional strategies. The SV40/HSL construct, more fully described below, is able to be used as an antiviral compound when the reporter gene is replaced with, for example, a death gene.

The SV40/HSL/GFP construct was engineered such that the expression of the SV40 microRNA (the first entry in FIG. 54) will be in direct competition with SLBP for the HSL-RNA construct. Binding of the SLBP to the HSL is required for efficient GFP translation and, therefore, protein expression. In the presence of sufficient SV40 microRNA expression, the amount of GFP expression is decreased. Thus, this experiment involved modifying the naturally occurring HSL-containing, histone-mRNA/microRNA structural-RNA switch system (which is an example of a negative switch) to effect the expression of a reporter gene. Any fluorescent protein, for example luciferase, may be used in place of GFP.

The following approach was used to create a trans-acting RNA-structural switch.

(1) A hybrid gene (construct) was made containing the reporter gene, GFP, coding sequence (CDS) fused to a histone stem-loop (HSL) regulatory element (conforming to Consensus Sequence I), which serves as the RNA construct. This hybrid gene is shown in FIG. 56 (and the hold, underlined, italic sequence codes for the stem-loop sequence included in the RNA construct). These fused gene constructs were then transfected into mammalian cell culture lines, and the amount of reporter protein expression was determined.

(2) After optimizing the amount of reporter protein being expressed, the human mir518 or viral SV40 microRNAs were simultaneously expressed in the RNA construct-containing cell lines using a standard retroviral based shRNA delivery approach. The subsequent expressed microRNAs represent the target polynucleotides. The sequences used to produce viral SV40 microRNA or human mir518 microRNA are listed in the first two rows of the table in FIG. 57 (and one further microRNAs to be tested is listed in the final row of the table). The portion of the sequences in the column "antisense sequence" represents the sequence of the microRNA targets of interest (i.e., the sequence of microRNA target is as listed in the "antisense sequence" column, but as DNA, and thus the U's are listed as T's in the shRNA sequences).

(3) The effect of presence or absence of target RNA on the expression of GFP reporter protein was then assessed as a degree of fluorescence.

The HSL is the natural target of the stem-loop binding protein (SLBP), and this protein needs to bind in order for the upstream gene to be efficiently translated into protein (in this case it is the reporter GFP). In the presence of the SV40 miRNA, which is the target polynucleotide for this RNA construct, it base-pairs with the melted HSL, preventing SLBP binding and reducing GFP expression.

Figure 58:
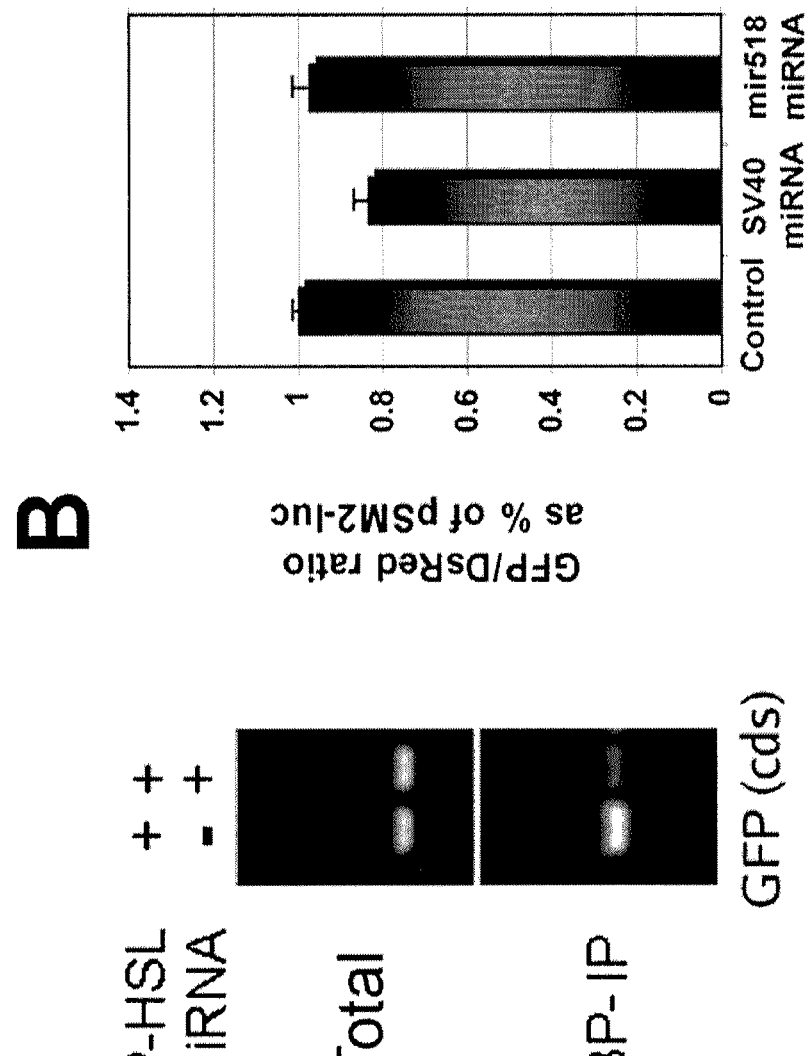
FIGS. 58A-B show direct (FIG. 58A) and indirect (FIG. 58B) evidence of the ON/OFF activity of the GFP-HSL trans-acting structural RNA switch.

The On-Off nature of the RNA-structural switch can be directly measured by assessing the amount of GFP-HSL-RNA construct that can be immunoprecipitated with the SLBP in the presence or absence of the SV40 miRNA. This is what is depicted in FIG. 58A in which RT-PCR is used to determine the amount of immunoprecipitated GFP-HSL hound to SLBP, with and without the SV40 miRNA. As can be seen, there is a substantial reduction in the amount of GFP-HSL-RNA construct that can be immunoprecipitated with SLBP when the SV40 miRNA is co-expressed (because the target polynucleotide is preventing binding of SLBP to the RNA construct).

The activity of the switch can also be indirectly assessed by determining the amount of reporter gene being expressed. As can be seen in FIG. 58B, there is about a 20% reduction in GFP expression when the GFP-HSL RNA construct is expressed in the presence of the SV40 miRNA. Interestingly, the human mir518 RNA did not have the same effect on the expression of GFP. There are several nucleotide differences between the SV40 miRNA and the mir518 so this was not that surprising because the HSL sequence that was used for RNA construct was specifically designed to interact preferentially with the SV40 miRNA. While there is overlap with the random fluctuation of the reporter, the experiment serves as an initial example validating this technology. The assay will be optimized to enhance the effect on reporter gene expression. Optimizing and titrating the amount of reporter gene basal expression as well as the amount of microRNA-target expression are accomplishing this.

Additional Experimental Validation

Further experimental work is contemplated to confirm and develop an RNA construct which can bind a viral RNA.

(1) The existing technology as described above will be optimized to show a greater difference in reporter gene expression in cells that contain the mir-518 or SV40 microRNA versus cells that do not. This will be accomplished by adjusting the amount of basal reporter gene expression as well as the amount of mir-518 or SV40 microRNA co-expressed in the cells.

(2) Once a change (reduction) in reporter gene expression by approximately 50% is achieved, use of mir-518 or SV40 microRNA co-expression will be replaced with actual SV40 virus infection in cell culture. This system will be used to determine the effect of SV40 virus on the expression of the reporter gene. It is contemplated that those cells infected with SV40 virus will show a decrease in reporter gene expression.

(3) The present version of the trans-acting RNA structural switch used in the experiment described above acts as a repressor and decreases the translation (protein production) of the gene fused to it. To produce an effective anti-viral biological (or other anti-pathogen or anti-neoplastic biological), it is desired to activate the expression of a death gene. To accomplish this, the approach of a repressor and an operator will be used. The RNA construct will be fused downstream of a gene coding for a repressor protein (such as the lac-repressor) instead of a reporter gene. This repressor protein will be constitutively expressed because the switch is in the "ON" state in the absence of target polynucleotide (e.g., virus microRNA) and therefore, translationally active. Additionally, the expression of a "Death-gene" will be driven by an inducible promoter, which is the target of the repressor gene being expressed from the RNA construct. This will keep the death-gene expression in the basal "OFF" state because the repressor protein binds it. In the presence of SV40, or the expression of the mir-518 or SV40 microRNA, the repressor gene expression will be reduced or shut OFF, which will activate the expression of the death-gene, thus killing the infected cell.

(4) Specificity could then be determined by measuring the degree to which virally infected cells or those expressing mir-518 or SV40 microRNA are selectively killed and the degree to which the anti-viral drug is inert in non-infected cells.

Although the anti-viral described above reverses a negative-type switch (i.e. is an indirect mechanism), it is contemplated that activating a positive-type regulating switch also will be a useful anti-viral mechanism. A rationally designed positive-activating RNA structural switch can be used to directly turn on a death gene when it is activated by a viral target polynucleotide, such as the mechanism depicted in FIG. 1A. Upon completion of the anti-viral (either negative or positive acting), the biological drug would be further optimized and delivery systems would be implemented. Next, animal testing would confirm that the drug does not affect some other functioning of the cells throughout the animals, and subsequent clinical testing will show efficacy within the human population.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

The entire disclosure of each of the patent documents, scientific publications, and other database references disclosed hereinabove is expressly incorporated herein by reference for all purposes.

What is claimed is:

1. An RNA construct comprising a non-naturally occurring, continuous sequence of ribonucleotide bases defining:
   a stem-loop structure;
   simulated, three way junction joining regions 3' and 5' of the stem-loop structure;
   a first region 5' of the 5' joining region comprising bases complementary to a 3' region of a target polynucleotide, wherein the target polynucleotide is not continuous with the RNA construct;
   a second region 3' of the 3' joining region comprising bases complementary to a 5' region of the target polynucleotide;
   the base sequence of the first and second regions being selected to base pair with complementary bases on the target polynucleotide spaced apart by an intermediate region on the target polynucleotide defining another three way junction joining region, whereby,
   in the presence of the target polynucleotide, a stem-loop conformation of said construct is stabilized.

2. The construct of claim 1, wherein at least one base in the stem of the stem-loop structure is mismatched with its potential binding partner so as to reduce the stability of the stem-loop conformation.

3. The construct of claim 1 wherein the RNA construct further comprises RNA defining a polypeptide coding region and wherein
   in the absence of the target polynucleotide, the construct assumes a conformation inhibiting association with an RNA binding protein and suppressing translation of the polypeptide-coding region, and
   in the presence of the target polynucleotide, the construct assumes a stem-loop conformation promoting association with the RNA binding protein and promoting translation of the polypeptide coding region.

4. The construct of claim 3 wherein the polypeptide coding region is disposed 5' of the first region.

5. The construct of claim 1, wherein the target polynucleotide is characteristic of a pathogen.

6. The construct of claim 5 wherein the pathogen is a virus or a single-celled microorganism.

7. The construct of claim 1, wherein the target polynucleotide is expressed preferentially in a cell type of a multicellular organism.

8. The construct of claim 7 wherein the cell type is a neoplastic cell.

9. The construct of claim 1, wherein the target polynucleotide comprises a synthetic target polynucleotide or ssDNA for transfection into a cell.

10. A DNA vector comprising a transcription unit encoding a construct as in claim 1.

11. A cell comprising a construct as in claim 1.

12. The construct of claim 1, wherein a joining region comprises no more than about 10 nucleotides.

13. The construct of claim 3, wherein the polypeptide coding region encodes a polypeptide needed for survival of a cell whereby only in the presence of the construct and the target polynucleotide in the cell can the cell survive.

14. The construct of claim 3, wherein the polypeptide coding region is expressed in a cell and encodes a polypeptide lethal to the cell.

15. The construct of claim 14 wherein the cell is an infected cell or a neoplastic cell, and the target polynucleotide is expressed by an organism infecting the cell or by the neoplastic cell.

16. The construct of claim 3, wherein the polypeptide coding region encodes a detectable marker polypeptide whose detection indicates the presence of an analyte comprising the target polynucleotide.

17. The construct of claim 1, wherein the construct comprises more than one said stem-loop structure.

* * * * *

SEQUENCE LISTING

```
<160> NUMBER OF SEQ ID NOS: 194

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (9)..(10)
<223> OTHER INFORMATION: a, c, u, g, unknown or other
<220> FEATURE:
<221> NAME/KEY: modified_base
<222> LOCATION: (12)..(12)
<223> OTHER INFORMATION: a, c, u, g, unknown or other
<220> FEATURE:
<221> NAME/KEY: modified_base
<222> LOCATION: (18)..(19)
<223> OTHER INFORMATION: a, c, u, g, unknown or other

<400> SEQUENCE: 1
nnnggggann cnuccccnn                                                19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (9)..(10)
<223> OTHER INFORMATION: a, c, u, g, unknown or other
<220> FEATURE:
<221> NAME/KEY: modified_base
<222> LOCATION: (12)..(12)
<223> OTHER INFORMATION: a, c, u, g, unknown or other
<220> FEATURE:
<221> NAME/KEY: modified_base
<222> LOCATION: (18)..(19)
<223> OTHER INFORMATION: a, c, u, g, unknown or other

<400> SEQUENCE: 2
nnnugggann cnucuuunn                                                19

<210> SEQ ID NO 3
<211> LENGTH: 22
<212> TYPE: RNA
<213> ORGANISM: Human cytomegalovirus

<400> SEQUENCE: 3
cgacauggac gugcaggggg au                                            22
```

```
<210> SEQ ID NO 4
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(12)
<223> OTHER INFORMATION: a, c, u, g, unknown or other
<220> FEATURE:
<221> NAME/KEY: modified_base
<222> LOCATION: (18)..(19)
<223> OTHER INFORMATION: a, c, u, g, unknown or other
<220> FEATURE:
<221> NAME/KEY: modified_base
<222> LOCATION: (21)..(21)
<223> OTHER INFORMATION: a, c, u, g, unknown or other
<220> FEATURE:
<221> NAME/KEY: modified_base
<222> LOCATION: (27)..(28)
<223> OTHER INFORMATION: a, c, u, g, unknown or other

<400> SEQUENCE: 4
auccccugcn nnugggannc nucuuunngu ccgugucg                          38

<210> SEQ ID NO 5
<211> LENGTH: 23
<212> TYPE: RNA
<213> ORGANISM: Homo sapiens

<400> SEQUENCE: 5
gaagugcuuc gauuuugggg ugu                                         23

<210> SEQ ID NO 6
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6 acacccaaa a                                                       11

<210> SEQ ID NO 7
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ucgaagcacu uc                                                     12

<210> SEQ ID NO 8
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cgaagcacuu c                                                      11
```

```
<210> SEQ ID NO 9
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
acacccaaa                                                             10

<210> SEQ ID NO 10
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
aaaggcucuu uuca                                                       14

<210> SEQ ID NO 11
<211> LENGTH: 23
<212> TYPE: RNA
<213> ORGANISM: Homo sapiens

<400> SEQUENCE: 11
gaagugcuuc gauuuugggg ugu                                             23

<210> SEQ ID NO 12
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12 acacccaaa aaaagguucu uuucagaguu acucgaagca cuuc                       44

<210> SEQ ID NO 13
<211> LENGTH: 21
<212> TYPE: RNA
<213> ORGANISM: Unknown
<220> FEATURE:
<223> OTHER INFORMATION: Description of Unknown: Iron Response Element
      motif sequence
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (4)..(8)
<223> OTHER INFORMATION: a, c, u, g, unknown or other
<220> FEATURE:
<221> NAME/KEY: modified_base
<222> LOCATION: (15)..(21)
<223> OTHER INFORMATION: a, c, u, g, unknown or other

<400> SEQUENCE: 13
nncnnnnnca gwghnnnnnn n                                               21

<210> SEQ ID NO 14
<211> LENGTH: 24
<212> TYPE: RNA
<213> ORGANISM: Unknown
```

```
<220> FEATURE:
<223> OTHER INFORMATION: Description of Unknown: Iron Response Element
      motif sequence
<220> FEATURE:
<221> NAME/KEY: modified_base
<222> LOCATION: (1)..(4)
<223> OTHER INFORMATION: a, c, u, g, unknown or other
<220> FEATURE:
<221> NAME/KEY: modified_base
<222> LOCATION: (6)..(10)
<223> OTHER INFORMATION: a, c, u, g, unknown or other
<220> FEATURE:
<221> NAME/KEY: modified_base
<222> LOCATION: (17)..(24)
<223> OTHER INFORMATION: a, c, u, g, unknown or other

<400> SEQUENCE: 14
nnnncnnnnn cagwghnnnn nnnn                                             24

<210> SEQ ID NO 15
<211> LENGTH: 22
<212> TYPE: RNA
<213> ORGANISM: Unknown
<220> FEATURE:
<223> OTHER INFORMATION: Description of Unknown: Iron Response Element
      motif sequence
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (4)..(8)
<223> OTHER INFORMATION: a, c, u, g, unknown or other
<220> FEATURE:
<221> NAME/KEY: modified_base
<222> LOCATION: (15)..(17)
<223> OTHER INFORMATION: a, c, u, g, unknown or other
<220> FEATURE:
<221> NAME/KEY: modified_base
<222> LOCATION: (19)..(22)
<223> OTHER INFORMATION: a, c, u, g, unknown or other

<400> SEQUENCE: 15
nncnnnnnca gwghnnnunn nn                                               22

<210> SEQ ID NO 16
<211> LENGTH: 52
<212> TYPE: RNA
<213> ORGANISM: Unknown
<220> FEATURE:
<223> OTHER INFORMATION: Description of Unknown: Selenocysteine
      insertion sequence element
<220> FEATURE:
<221> NAME/KEY: modified_base
<222> LOCATION: (1)..(7)
<223> OTHER INFORMATION: a, c, u, g, unknown or other
<220> FEATURE:
<221> NAME/KEY: modified_base
<222> LOCATION: (12)..(12)
<223> OTHER INFORMATION: a, c, u, g, unknown or other
<220> FEATURE:
<221> NAME/KEY: modified_base
<222> LOCATION: (15)..(21)
<223> OTHER INFORMATION: a, c, u, g, unknown or other
<220> FEATURE:
<221> NAME/KEY: modified_base
<222> LOCATION: (25)..(38)
<223> OTHER INFORMATION: a, c, u, g, unknown or other
<220> FEATURE:
<221> NAME/KEY: modified_base
<222> LOCATION: (44)..(52)
<223> OTHER INFORMATION: a, c, u, g, unknown or other

<400> SEQUENCE: 16
```

```
nnnnnnnaug anrrnnnnnn naarnnnnnn nnnnnnnnyy bgannnnnnn nn          52
```

```
<210> SEQ ID NO 17
<211> LENGTH: 383
<212> TYPE: RNA
<213> ORGANISM: Hepatitis C virus

<400> SEQUENCE: 17
gccagccccc ugauggggc gacacuccac caugaaucac uccccuguga ggaacuacug     60
ucuucacgca gaaagcgucu agccaugqcg uuaguaugag ugucgugcag ccuccaggac    120
ccccccuccc gggagagcca uaguggucug cggaaccggu gaguacaccg gaauugccag    180
gacgaccggg uccuuucuug gauaaacccg cucaaugccu ggagauuugg gcgugccccc    240
gcaagacugc uagccgagua uguuggguc gcgaaaggcc uugugguacu gccugauagg    300
gugcuugcga gugccccggg aggucucgua gaccgugcac caugagcacg aauccuaaac    360
cucaaagaaa aaccaaacgu aac                                           383
```

```
<210> SEQ ID NO 18
<211> LENGTH: 75
<212> TYPE: RNA
<213> ORGANISM: Hepatitis C virus

<400> SEQUENCE: 18
ccugugagga acuacugucu ucacgcagaa agcgucuagc cauggcguua guaugagugu    60
cgugcagccu ccagg                                                    75
```

```
<210> SEQ ID NO 19
<211> LENGTH: 68
<212> TYPE: RNA
<213> ORGANISM: Hepatitis C virus
<220> FEATURE:
<221> NAME/KEY: modified_base
<222> LOCATION: (1)..(5)
<223> OTHER INFORMATION: a, c, u, g, unknown or other
<220> FEATURE:
<221> NAME/KEY: modified_base
<222> LOCATION: (64)..(68)
<223> OTHER INFORMATION: a, c, u, g, unknown or other

<400> SEQUENCE: 19
nnnnnaacua cugucuucac gcagaaagcg ucuagccaug gcguuaguau gagugucgug    60 cagnnnnn                                                            68
```

```
<210> SEQ ID NO 20
<211> LENGTH: 311
<212> TYPE: DNA
<213> ORGANISM: Hepatitis C virus

<400> SEQUENCE: 20
cctgtgagga actactgtct tcacgcagaa agcgtctagc catggcgtta gtatgagtgt    60
cgtgcagcct ccaggacccc cctcccggg agagccatag tggtctgcgg aaccggtgag    120
tacaccggaa ttgccaggac gaccgggtcc tttcttggat aaacccgctc aatgcctgga    180
gatttgggcg tgccccgca agactgctag ccgagtagtt tgggtcgcg aaaggccttg     240 tggtactgcc tgatagggtg cttgcgagtg ccccgggagg tctcgtagac cgtgcaccat    300
gagcacgaat c                                                        311
```

```
<210> SEQ ID NO 21
```

```
<211> LENGTH: 311
<212> TYPE: DNA
<213> ORGANISM: Hepatitis C virus

<400> SEQUENCE: 21
cctgtgagga actactgtct tcacgcagaa agcgtctagc catggcgtta gtatgagtgt     60
cgtacagcct ccaggccccc ccctcccggg agagccatag tggtctgcgg aaccggtgag    120
tacaccggaa ttgccgggaa gactgggtcc tttcttggat aaacccactc tatgcccggc    180
catttgggcg tgccccgca agactgctag ccgagtagcg ttgggttgcg aaaggccttg     240
tggtactgcc tgatagggtg cttgcgagtg ccccgggagg tctcgtagac cgtgcaccat    300
gagcacaaat c                                                         311

<210> SEQ ID NO 22
<211> LENGTH: 311
<212> TYPE: DNA
<213> ORGANISM: Hepatitis C virus

<400> SEQUENCE: 22
cctgtgagga acttctgtct tcacgcggaa agcgcctagc catggcgtta gtacgagtgt     60
cgtgcagcct ccaggacccc ccctcccggg agagccatag tggtctgcgg aaccggtgag    120
tacaccggaa tcgctggggt gaccgggtcc tttcttggag caacccgctc aatacccaga    180
aatttgggcg tgccccgcg agatcactag ccgagtagtg ttgggtcgcg aaaggccttg     240
tggtactgcc tgatagggtg cttgcgagtg ccccgggagg tctcgtagac cgtgcaacat    300
gagcacactt c                                                         311

<210> SEQ ID NO 23
<211> LENGTH: 318
<212> TYPE: DNA
<213> ORGANISM: Classical swine fever virus

<400> SEQUENCE: 23
tccctccagc gacggccgaa ctgggctagc catgcccaca gtaggactag caaacggagg     60
gactagccgt agtggcgagc tccctgggtg gtctaagtcc tgagtacagg acagtcgtca    120
gtagttcgac gtgagcagaa gcccaccctcg agatgctatg tggacgaggg catgcccaag    180
acacacctta accctagcgg gggtcgctag ggtgaaatca caccacgtga tgggagtacg    240
acctgatagg gcgctgcaga ggcccactat taggctagta taaaaatctc tgctgtacat    300
ggcacatgga gttgaatc                                                  318

<210> SEQ ID NO 24
<211> LENGTH: 323
<212> TYPE: DNA
<213> ORGANISM: Bovine viral diarrhea virus

<400> SEQUENCE: 24
ccctctcagc gaaggccgaa aagaggctag ccatgccctt agtaggacta gcataatgag     60
gggggtagca acagtggtga gttcgttgga tggcttaagc cctgagtaca gggtagtcgt    120
cagtggttcg acgccttgga ataaaggtct cgagatgcca cgtggacgag gcatgccca     180 aagcacatct taacctgagc gggggtcgcc caggtaaaag cagttttaac cgactgttac    240
gaatacagcc tgatagggtg ctgcagaggc ccactgtatt gctactaaaa atctctgctg    300
tacatggcac atggagttga tca                                            323
```

```
<210> SEQ ID NO 25
<211> LENGTH: 75
<212> TYPE: DNA
<213> ORGANISM: Hepatitis C virus

<400> SEQUENCE: 25
cctgtgagga actactgtct tcacgcagaa agcgtctagc catggcgtta gtatgagtgt      60
cgtgcagcct ccagg                                                      75

<210> SEQ ID NO 26
<211> LENGTH: 75
<212> TYPE: DNA
<213> ORGANISM: Hepatitis C virus

<400> SEQUENCE: 26
cctgtgagga actactgtct tcacgcagaa agcgtctagc catggcgtta gtatgagtgt      60
cgtacagcct ccagg                                                      75

<210> SEQ ID NO 27
<211> LENGTH: 75
<212> TYPE: DNA
<213> ORGANISM: Hepatitis C virus

<400> SEQUENCE: 27
cctgtgagga acttctgtct tcacgcggaa agcgcctagc catggcgtta gtacgagtgt      60
cgtgcagcct ccagg                                                      75

<210> SEQ ID NO 28
<211> LENGTH: 62
<212> TYPE: DNA
<213> ORGANISM: Classical swine fever virus

<400> SEQUENCE: 28
tccctccagc gacggccgaa ctgggctagc catgcccaca gtaggactag caaacggagg      60
ga                                                                    62

<210> SEQ ID NO 29
<211> LENGTH: 65
<212> TYPE: DNA
<213> ORGANISM: Bovine viral diarrhea virus

<400> SEQUENCE: 29
ccctctcagc gaaggccgaa aagaggctag ccatgccctt agtaggacta gcataatgag      60
ggggg                                                                 65

<210> SEQ ID NO 30
<211> LENGTH: 20
<212> TYPE: RNA
<213> ORGANISM: Herpes simplex virus

<400> SEQUENCE: 30
uggcggcccg gcccggggcc                                                 20

<210> SEQ ID NO 31
<211> LENGTH: 21
<212> TYPE: RNA
<213> ORGANISM: Herpes simplex virus

<400> SEQUENCE: 31
uggaaggacg ggaaguggaa g                                               21
```

```
<210> SEQ ID NO 32
<211> LENGTH: 20
<212> TYPE: RNA
<213> ORGANISM: Human immunodeficiency virus

<400> SEQUENCE: 32
ccagggaggc gugccugggc                                              20

<210> SEQ ID NO 33
<211> LENGTH: 24
<212> TYPE: RNA
<213> ORGANISM: Human immunodeficiency virus

<400> SEQUENCE: 33
acugaccuuu ggauggugcu ucaa                                         24

<210> SEQ ID NO 34
<211> LENGTH: 22
<212> TYPE: RNA
<213> ORGANISM: Epstein Barr virus

<400> SEQUENCE: 34
uaaccugauc agccccggag uu                                           22

<210> SEQ ID NO 35
<211> LENGTH: 22
<212> TYPE: RNA
<213> ORGANISM: Epstein Barr virus

<400> SEQUENCE: 35 uaucuuugc ggcagaaauu ga                                            22

<210> SEQ ID NO 36
<211> LENGTH: 22
<212> TYPE: RNA
<213> ORGANISM: Epstein Barr virus

<400> SEQUENCE: 36
aaauucuguu gcagcagaua gc                                           22

<210> SEQ ID NO 37
<211> LENGTH: 22
<212> TYPE: RNA
<213> ORGANISM: Epstein Barr virus

<400> SEQUENCE: 37
uaacgggaag uguguaagca ca                                           22

<210> SEQ ID NO 38
<211> LENGTH: 24
<212> TYPE: RNA
<213> ORGANISM: Epstein Barr virus

<400> SEQUENCE: 38
ucuuagugga agugacgugc ugug                                         24

<210> SEQ ID NO 39
<211> LENGTH: 22
<212> TYPE: RNA
<213> ORGANISM: Epstein Barr virus

<400> SEQUENCE: 39
uagcaccgcu auccacuaug uc                                           22
```

<210> SEQ ID NO 40
<211> LENGTH: 22
<212> TYPE: RNA
<213> ORGANISM: Epstein Barr virus

<400> SEQUENCE: 40
uauuuucugc auucgcccuu gc                                           22

<210> SEQ ID NO 41
<211> LENGTH: 24
<212> TYPE: RNA
<213> ORGANISM: Epstein Barr virus

<400> SEQUENCE: 41
aaggagcgau uuggagaaaa uaaa                                         24

<210> SEQ ID NO 42
<211> LENGTH: 22
<212> TYPE: RNA
<213> ORGANISM: Epstein Barr virus

<400> SEQUENCE: 42
cgcaccacua gucaccaggu gu                                           22

<210> SEQ ID NO 43
<211> LENGTH: 21
<212> TYPE: RNA
<213> ORGANISM: Epstein Barr virus

<400> SEQUENCE: 43
accuaguguu aguguugugc u                                            21

<210> SEQ ID NO 44
<211> LENGTH: 22
<212> TYPE: RNA
<213> ORGANISM: Epstein Barr virus

<400> SEQUENCE: 44
gaccugaugc ugcuggugug cu                                           22

<210> SEQ ID NO 45
<211> LENGTH: 24
<212> TYPE: RNA
<213> ORGANISM: Epstein Barr virus

<400> SEQUENCE: 45
caaggugaau auagcugccc aucg                                         24

<210> SEQ ID NO 46
<211> LENGTH: 22
<212> TYPE: RNA
<213> ORGANISM: Epstein Barr virus

<400> SEQUENCE: 46
uaagguuggu ccaauccaua gg                                           22

<210> SEQ ID NO 47
<211> LENGTH: 22
<212> TYPE: RNA
<213> ORGANISM: Epstein Barr virus

<400> SEQUENCE: 47
cggggaucgg acuagccuua ga                                               22

<210> SEQ ID NO 48
<211> LENGTH: 22
<212> TYPE: RNA
<213> ORGANISM: Epstein Barr virus

<400> SEQUENCE: 48
caucauaguc caguguccag gg                                               22

<210> SEQ ID NO 49
<211> LENGTH: 22
<212> TYPE: RNA
<213> ORGANISM: Epstein Barr virus

<400> SEQUENCE: 49
ccuggaccuu gacuaugaaa ca                                               22

<210> SEQ ID NO 50
<211> LENGTH: 22
<212> TYPE: RNA
<213> ORGANISM: Epstein Barr virus

<400> SEQUENCE: 50
uacgguuucc uagauuguac ag                                               22

<210> SEQ ID NO 51
<211> LENGTH: 23
<212> TYPE: RNA
<213> ORGANISM: Epstein Barr virus

<400> SEQUENCE: 51
gucacaaucu auggggucgu aga                                              23

<210> SEQ ID NO 52
<211> LENGTH: 23
<212> TYPE: RNA
<213> ORGANISM: Epstein Barr virus

<400> SEQUENCE: 52
uaacacuuca uggucccgu agu                                               23

<210> SEQ ID NO 53
<211> LENGTH: 22
<212> TYPE: RNA
<213> ORGANISM: Epstein Barr virus

<400> SEQUENCE: 53
uacuggaccc ugaauuggaa ac                                               22

<210> SEQ ID NO 54
<211> LENGTH: 23
<212> TYPE: RNA
<213> ORGANISM: Epstein Barr virus

<400> SEQUENCE: 54
uacauaacca uggaguuggc ugu                                              23

<210> SEQ ID NO 55
<211> LENGTH: 22
<212> TYPE: RNA
<213> ORGANISM: Epstein Barr virus

<400> SEQUENCE: 55
gccaccucuu ugguucugua ca                                                    22

<210> SEQ ID NO 56
<211> LENGTH: 24
<212> TYPE: RNA
<213> ORGANISM: Epstein Barr virus

<400> SEQUENCE: 56
ucagacaguu uggugcgcua guug                                                  24

<210> SEQ ID NO 57
<211> LENGTH: 21
<212> TYPE: RNA
<213> ORGANISM: Epstein Barr virus

<400> SEQUENCE: 57
acgcacacca ggcugacugc c                                                     21

<210> SEQ ID NO 58
<211> LENGTH: 22
<212> TYPE: RNA
<213> ORGANISM: Epstein Barr virus

<400> SEQUENCE: 58
uccuguggug uuuggugugg uu                                                    22

<210> SEQ ID NO 59
<211> LENGTH: 23
<212> TYPE: RNA
<213> ORGANISM: Epstein Barr virus

<400> SEQUENCE: 59
uguaacuugc cagggacggc uga                                                   23

<210> SEQ ID NO 60
<211> LENGTH: 22
<212> TYPE: RNA
<213> ORGANISM: Epstein Barr virus

<400> SEQUENCE: 60
aaccggcucg uggcucguac ag                                                    22

<210> SEQ ID NO 61
<211> LENGTH: 22
<212> TYPE: RNA
<213> ORGANISM: Epstein Barr virus

<400> SEQUENCE: 61
uaaaugcugc aguaguaggg au                                                    22

<210> SEQ ID NO 62
<211> LENGTH: 22
<212> TYPE: RNA
<213> ORGANISM: Epstein Barr virus

<400> SEQUENCE: 62
uacccuacgc ugccgauuua ca                                                    22

<210> SEQ ID NO 63
<211> LENGTH: 22
<212> TYPE: RNA
<213> ORGANISM: Epstein Barr virus

```
<400> SEQUENCE: 63
gucagugguu uuguuccuu ga                                                    22

<210> SEQ ID NO 64
<211> LENGTH: 24
<212> TYPE: RNA
<213> ORGANISM: Epstein Barr virus

<400> SEQUENCE: 64
uuagauagag ugggugugug cucu                                                 24

<210> SEQ ID NO 65
<211> LENGTH: 22
<212> TYPE: RNA
<213> ORGANISM: Epstein Barr virus

<400> SEQUENCE: 65
uaagaggacg caggcauaca ag                                                   22

<210> SEQ ID NO 66
<211> LENGTH: 23
<212> TYPE: RNA
<213> ORGANISM: Epstein Barr virus

<400> SEQUENCE: 66
uguaugccug gugucccuu agu                                                   23

<210> SEQ ID NO 67
<211> LENGTH: 22
<212> TYPE: RNA
<213> ORGANISM: Epstein Barr virus

<400> SEQUENCE: 67
ucaaguucgc acuuccuaua ca                                                   22

<210> SEQ ID NO 68
<211> LENGTH: 22
<212> TYPE: RNA
<213> ORGANISM: Epstein Barr virus

<400> SEQUENCE: 68
uaucggaagu uugggcuucg uc                                                   22

<210> SEQ ID NO 69
<211> LENGTH: 23
<212> TYPE: RNA
<213> ORGANISM: Epstein Barr virus

<400> SEQUENCE: 69
acauuccccg caaacaugac aug                                                  23

<210> SEQ ID NO 70
<211> LENGTH: 21
<212> TYPE: RNA
<213> ORGANISM: Epstein Barr virus

<400> SEQUENCE: 70
uuuuguuugc uugggaaugc u                                                    21

<210> SEQ ID NO 71
<211> LENGTH: 21
<212> TYPE: RNA
<213> ORGANISM: Epstein Barr virus
```

-continued

```
<400> SEQUENCE: 71
uagcaggcau gucuucauuc c                                               21

<210> SEQ ID NO 72
<211> LENGTH: 22
<212> TYPE: RNA
<213> ORGANISM: Epstein Barr virus

<400> SEQUENCE: 72
caugaaggca cagccuguua cc                                              22

<210> SEQ ID NO 73
<211> LENGTH: 20
<212> TYPE: RNA
<213> ORGANISM: Human cytomegalovirus

<400> SEQUENCE: 73
uaacuagccu ucccgugaga                                                 20

<210> SEQ ID NO 74
<211> LENGTH: 22
<212> TYPE: RNA
<213> ORGANISM: Human cytomegalovirus

<400> SEQUENCE: 74
ucaccagaau gcuaguuugu ag                                              22

<210> SEQ ID NO 75
<211> LENGTH: 21
<212> TYPE: RNA
<213> ORGANISM: Human cytomegalovirus

<400> SEQUENCE: 75
aaccgcucag uggcucggac c                                               21

<210> SEQ ID NO 76
<211> LENGTH: 22
<212> TYPE: RNA
<213> ORGANISM: Human cytomegalovirus

<400> SEQUENCE: 76
uccgaacgcu aggucgguuc uc                                              22

<210> SEQ ID NO 77
<211> LENGTH: 22
<212> TYPE: RNA
<213> ORGANISM: Human herpesvirus 8

<400> SEQUENCE: 77
uaguguuguc cccccgagug gc                                              22

<210> SEQ ID NO 78
<211> LENGTH: 22
<212> TYPE: RNA
<213> ORGANISM: Human herpesvirus 8

<400> SEQUENCE: 78
ugguguuguc cccccgagug gc                                              22

<210> SEQ ID NO 79
<211> LENGTH: 23
<212> TYPE: RNA
```

```
<213> ORGANISM: Human herpesvirus 8

<400> SEQUENCE: 79
auuacaggaa acugggugua agc                                        23

<210> SEQ ID NO 80
<211> LENGTH: 22
<212> TYPE: RNA
<213> ORGANISM: Human herpesvirus 8

<400> SEQUENCE: 80
aacuguaguc cgggucgauc ug                                         22

<210> SEQ ID NO 81
<211> LENGTH: 22
<212> TYPE: RNA
<213> ORGANISM: Human herpesvirus 8

<400> SEQUENCE: 81
cuggguauac gcagcugcgu aa                                         22

<210> SEQ ID NO 82
<211> LENGTH: 22
<212> TYPE: RNA
<213> ORGANISM: Human herpesvirus 8

<400> SEQUENCE: 82
acccagcugc guaaaccccg cu                                         22

<210> SEQ ID NO 83
<211> LENGTH: 22
<212> TYPE: RNA
<213> ORGANISM: Human herpesvirus 8

<400> SEQUENCE: 83
uaggcgcgac ugagagagca cg                                         22

<210> SEQ ID NO 84
<211> LENGTH: 21
<212> TYPE: RNA
<213> ORGANISM: Human herpesvirus 8

<400> SEQUENCE: 84
ugaucccaug uugcuggcgc u                                          21

<210> SEQ ID NO 85
<211> LENGTH: 22
<212> TYPE: RNA
<213> ORGANISM: Human herpesvirus 8

<400> SEQUENCE: 85
ccagcagcac cuaauccauc gg                                         22

<210> SEQ ID NO 86
<211> LENGTH: 22
<212> TYPE: RNA
<213> ORGANISM: Human herpesvirus 8

<400> SEQUENCE: 86
ugaugguuuu cgggcuguug ag                                         22

<210> SEQ ID NO 87
<211> LENGTH: 22
```

```
<212> TYPE: RNA
<213> ORGANISM: Human herpesvirus 8

<400> SEQUENCE: 87
uaggaugccu ggaacuugcc gg                                              22

<210> SEQ ID NO 88
<211> LENGTH: 22
<212> TYPE: RNA
<213> ORGANISM: Human herpesvirus 8

<400> SEQUENCE: 88
agcuaaaccg caguacucua gg                                              22

<210> SEQ ID NO 89
<211> LENGTH: 22
<212> TYPE: RNA
<213> ORGANISM: Human herpesvirus 8

<400> SEQUENCE: 89
uagaauacug aggccuagcu ga                                              22

<210> SEQ ID NO 90
<211> LENGTH: 23
<212> TYPE: RNA
<213> ORGANISM: Human herpesvirus 8

<400> SEQUENCE: 90
ucacauucug aggacggcag cga                                             23

<210> SEQ ID NO 91
<211> LENGTH: 21
<212> TYPE: RNA
<213> ORGANISM: Human herpesvirus 8

<400> SEQUENCE: 91
ucgcggucac agaaugugac a                                               21

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 92

His His His His His His
1               5

<210> SEQ ID NO 93
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
gggauacgcu caggcuagac ggugggguga aauccacccg ugacgcugag gcgcggagua     60
acgaaccuau ccguaacaua auu                                             83

<210> SEQ ID NO 94
<211> LENGTH: 25
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
gcguguaggc ggccuggggc guccc                                           25

<210> SEQ ID NO 95
<211> LENGTH: 789
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Gly Ser Ser His His His His His Ser Ser Gly Leu Val Pro
1               5                   10                  15

Arg Gly Ser His Met Gly Pro Arg Ala Ser Asn Phe Thr Gln Phe Val
            20                  25                  30

Leu Val Asp Asn Gly Gly Thr Gly Asp Val Thr Val Ala Pro Ser Asn
        35                  40                  45

Phe Ala Asn Gly Val Ala Glu Trp Ile Ser Ser Asn Ser Arg Ser Gln
    50                  55                  60

Ala Tyr Lys Val Thr Cys Ser Val Arg Gln Ser Ser Ala Gln Asn Arg
65                  70                  75                  80

Lys Tyr Thr Ile Lys Val Glu Val Pro Lys Val Ala Thr Gln Thr Val
                85                  90                  95

Gly Gly Glu Glu Leu Pro Val Ala Gly Trp Arg Ser Tyr Leu Asn Met
            100                 105                 110

Glu Leu Thr Ile Pro Ile Phe Ala Thr Asn Ser Asp Cys Glu Leu Ile
        115                 120                 125

Val Lys Ala Met Gln Gly Leu Leu Lys Asp Gly Asn Pro Ile Pro Ser
    130                 135                 140

Ala Ile Ala Ala Asn Ser Gly Ile Tyr Ala Ser Pro Ser Ala Pro Ser
145                 150                 155                 160

Tyr Pro Met Ala Ser Leu Tyr Val Gly Asp Leu His Pro Asp Val Thr
                165                 170                 175

Glu Ala Met Leu Tyr Glu Lys Phe Ser Pro Ala Gly Pro Ile Leu Ser
            180                 185                 190

Ile Arg Val Cys Arg Asp Met Ile Thr Arg Arg Ser Leu Gly Tyr Ala
        195                 200                 205

Tyr Val Asn Phe Gln Gln Pro Ala Asp Ala Glu Arg Ala Leu Asp Thr
    210                 215                 220

Met Asn Phe Asp Val Ile Lys Gly Lys Pro Val Arg Ile Met Trp Ser
225                 230                 235                 240

Gln Arg Asp Pro Ser Leu Arg Lys Ser Gly Val Gly Asn Ile Phe Ile
                245                 250                 255

Lys Asn Leu Asp Lys Ser Ile Asp Asn Lys Ala Leu Tyr Asp Thr Phe
            260                 265                 270

Ser Ala Phe Gly Asn Ile Leu Ser Cys Lys Val Val Cys Asp Glu Asn
        275                 280                 285

Gly Ser Lys Gly Tyr Gly Phe Val His Phe Glu Thr Gln Glu Ala Ala
    290                 295                 300

Glu Arg Ala Ile Glu Lys Met Asn Gly Met Leu Leu Asn Asp Arg Lys

```
        305                 310                 315                 320
Val Phe Val Gly Arg Phe Lys Ser Arg Lys Glu Arg Glu Ala Glu Leu
                325                 330                 335

Gly Ala Arg Ala Lys Glu Phe Thr Asn Val Tyr Ile Lys Asn Phe Gly
                340                 345                 350

Glu Asp Met Asp Asp Glu Arg Leu Lys Asp Leu Phe Gly Lys Phe Gly
                355                 360                 365

Pro Ala Leu Ser Val Lys Val Met Thr Asp Glu Ser Gly Lys Ser Lys
370                 375                 380

Gly Phe Gly Phe Val Ser Phe Glu Arg His Glu Asp Ala Gln Lys Ala
385                 390                 395                 400

Val Asp Glu Met Asn Gly Lys Glu Leu Asn Gly Lys Gln Ile Tyr Val
                405                 410                 415

Gly Arg Ala Gln Lys Lys Val Glu Arg Gln Thr Glu Leu Lys Arg Lys
                420                 425                 430

Phe Glu Gln Met Lys Gln Asp Arg Ile Thr Arg Tyr Gln Gly Val Asn
                435                 440                 445

Leu Tyr Val Lys Asn Leu Asp Asp Gly Ile Asp Asp Glu Arg Leu Arg
                450                 455                 460

Lys Glu Phe Ser Pro Phe Gly Thr Ile Thr Ser Ala Lys Val Met Met
465                 470                 475                 480

Glu Gly Gly Arg Ser Lys Gly Phe Gly Phe Val Cys Phe Ser Ser Pro
                485                 490                 495

Glu Glu Ala Thr Lys Ala Val Thr Glu Met Asn Gly Arg Ile Val Ala
                500                 505                 510

Thr Lys Pro Leu Tyr Val Ala Leu Ala Gln Arg Lys Glu Glu Arg Gln
                515                 520                 525

Ala His Leu Thr Asn Gln Tyr Met Gln Arg Met Ala Ser Val Arg Ala
                530                 535                 540

Val Pro Asn Pro Val Ile Asn Pro Tyr Gln Pro Ala Pro Pro Ser Gly
545                 550                 555                 560

Tyr Phe Met Ala Ala Ile Pro Gln Thr Gln Asn Arg Ala Ala Tyr Tyr
                565                 570                 575

Pro Pro Ser Gln Ile Ala Gln Leu Arg Pro Ser Pro Arg Trp Thr Ala
                580                 585                 590

Gln Gly Ala Arg Pro His Pro Phe Gln Asn Met Pro Gly Ala Ile Arg
                595                 600                 605

Pro Ala Ala Pro Arg Pro Pro Phe Ser Thr Met Arg Pro Ala Ser Ser
610                 615                 620

Gln Val Pro Arg Val Met Ser Thr Gln Arg Val Ala Asn Thr Ser Thr
625                 630                 635                 640

Gln Thr Met Gly Pro Arg Pro Ala Ala Ala Ala Ala Ala Ala Thr Pro
                645                 650                 655

Ala Val Arg Thr Val Pro Gln Tyr Lys Tyr Ala Ala Gly Val Arg Asn
                660                 665                 670

Pro Gln Gln His Leu Asn Ala Gln Pro Gln Val Thr Met Gln Gln Pro
                675                 680                 685

Ala Val His Val Gln Gly Gln Glu Pro Leu Thr Ala Ser Met Leu Ala
                690                 695                 700

Ser Ala Pro Pro Gln Glu Gln Lys Gln Met Leu Gly Glu Arg Leu Phe
705                 710                 715                 720

Pro Leu Ile Gln Ala Met His Pro Thr Leu Ala Gly Lys Ile Thr Gly
                725                 730                 735
```

```
Met Leu Leu Glu Ile Asp Asn Ser Glu Leu Leu His Met Leu Glu Ser
            740                 745                 750

Pro Glu Ser Leu Arg Ser Lys Val Asp Glu Ala Val Ala Val Leu Gln
        755                 760                 765

Ala His Gln Ala Lys Glu Ala Ala Gln Lys Ala Val Asn Ser Ala Thr
770                 775                 780

Gly Val Pro Thr Val
785

<210> SEQ ID NO 96
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gggauacgcu caggcuagac ggugggguga auccacccg ugacgcugag gcgcggagua      60
acgaaccuau ccguaacaua auu                                            83

<210> SEQ ID NO 97
<211> LENGTH: 25
<212> TYPE: RNA
<213> ORGANISM: Thermus thermophilus

<400> SEQUENCE: 97
gcguguaggc ggccuggggc guccc                                          25

<210> SEQ ID NO 98
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gggauacgcu caggcaaagg cucuuuucag agccagcuga ggcgcggagu aacgaaccua    60
uccguaacau aauu                                                      74

<210> SEQ ID NO 99
<211> LENGTH: 21
<212> TYPE: RNA
<213> ORGANISM: Unknown
<220> FEATURE:
<223> OTHER INFORMATION: Description of Unknown: MS2 Motif
      sequence

<400> SEQUENCE: 99
aaacaugagg auuacccaug u                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      MS2 binding site consensus sequence
<220> FEATURE:
<221> NAME/KEY: modified_base
<222> LOCATION: (1)..(7)
<223> OTHER INFORMATION: a, c, u, g, unknown or other
<220> FEATURE:
```

```
<221> NAME/KEY: modified_base
<222> LOCATION: (9)..(10)
<223> OTHER INFORMATION: a, c, u, g, unknown or other
<220> FEATURE:
<221> NAME/KEY: modified_base
<222> LOCATION: (12)..(12)
<223> OTHER INFORMATION: a, c, u, g, unknown or other
<220> FEATURE:
<221> NAME/KEY: modified_base
<222> LOCATION: (15)..(21)
<223> OTHER INFORMATION: a, c, u, g, unknown or other

<400> SEQUENCE: 100
nnnnnnnrnn anyannnnnn n                                              21

<210> SEQ ID NO 101
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ccgcgggagc ucguuuugg gcgccaucag gguuuuugc caaguggau                   49

<210> SEQ ID NO 102
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
ccgcgggagc ucguuuugg ggcgccauca ggguuuuug ccaaguggau                  50

<210> SEQ ID NO 103
<211> LENGTH: 23
<212> TYPE: RNA
<213> ORGANISM: Human cytomegalovirus

<400> SEQUENCE: 103
auccacuugg agagcucccg cgg                                            23

<210> SEQ ID NO 104
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
aacuauacaa ccguuuugg ggcgccauua ggguuuuug ccuaccuca                   49

<210> SEQ ID NO 105
<211> LENGTH: 22
<212> TYPE: RNA
<213> ORGANISM: Homo sapiens

<400> SEQUENCE: 105
ugagguagga gguuguauag uu                                             22

<210> SEQ ID NO 106
<211> LENGTH: 49
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 106
aacuauacaa ccguuuuugg ggcgccauca ggguuuuuug ccuaccuca                    49

<210> SEQ ID NO 107
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
aaagugucag aguuuuuggg gcgccauuag gguuuuuuga cggugugg                     48

<210> SEQ ID NO 108
<211> LENGTH: 21
<212> TYPE: RNA
<213> ORGANISM: Homo sapiens

<400> SEQUENCE: 108
ccacaccgua ucugacacuu u                                                  21

<210> SEQ ID NO 109
<211> LENGTH: 22
<212> TYPE: RNA
<213> ORGANISM: Artificial Sequence
<220> FEATURE:
<223> OTHER INFORMATION: Description of Artificial Sequence: Synthetic
      HSL consensus sequence

<400> SEQUENCE: 109
mmmmggyyyu hhuharrrcc mm                                                 22

<210> SEQ ID NO 110
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
agguuccauc guauccaaaa ggcucuuuuc agagcuaccc a                            41

<210> SEQ ID NO 111
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
agguuccauc guauccaaaa gguucuuuuc agggcuaccc a                            41

<210> SEQ ID NO 112
<211> LENGTH: 22
<212> TYPE: RNA
<213> ORGANISM: Homo sapiens

<400> SEQUENCE: 112
```

```
cggguggauc acgaugcaau uu                                              22

<210> SEQ ID NO 113
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gugggccaca gguuucuuu aaaucccag cuccg                                  35

<210> SEQ ID NO 114
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gaagagagcc gcccaaaaca gaaagaaagg cucuuuucag agcuacacuu u              51

<210> SEQ ID NO 115
<211> LENGTH: 21
<212> TYPE: RNA
<213> ORGANISM: Homo sapiens

<400> SEQUENCE: 115
acggugcugg auguggccuu u                                               21

<210> SEQ ID NO 116
<211> LENGTH: 22
<212> TYPE: RNA
<213> ORGANISM: Xenopus laevis

<400> SEQUENCE: 116
aaagugcuuu cuguuuggg cg                                               22

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ccaaaggctc ttttcagagc cac                                             23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ccaaaggctc ttttcagagc ccc                                             23

<210> SEQ ID NO 119
<211> LENGTH: 23
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 119
ccaaaggctc ttttaagagc cac                                              23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tcaaaggctc ttttcagagc cac                                              23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
caaaaggctc ttttcagagc cac                                              23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccaaaggctc ttttcagagc cac                                              23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
acaaaggccc ttttaagggc cac                                              23

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
caaaaggctc ttttcagagc cac                                              23

<210> SEQ ID NO 125
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 125
aaaaaggccc tttttagggc ccc                                              23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ccaacggctc ttttcagggc cac                                              23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
taaaaggccc ttttcagggc cac                                              23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ccaaaggctc ttttcagagc cac                                              23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
caaaaggctc ttttcagagc cac                                              23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
caaaaggccc ttttcagggc ccc                                              23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 131
ccaaaggctc ttttcagagc caa                                              23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
caaaaggctc ttttcagagc cac                                              23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ccaaaggctc ttttcagagc caa                                              23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ccaaaggctc ttctcagagc caa                                              23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gcaaaggctc ttttcagagc cac                                              23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ccaaaggctc ttttcagagc cac                                              23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide -continued <210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ccaacggctc ttttcagggc cac                                              23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
acaaaggccc ttttaagggc cac                                              23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ccaaaggctc ttttcagagc ccc                                              23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
acccaggctt tatttagggc caa                                              23

<210> SEQ ID NO 142
<211> LENGTH: 22
<212> TYPE: RNA
<213> ORGANISM: Simian virus

<400> SEQUENCE: 142
ugaggggccu gaaaugagcc uu                                               22

<210> SEQ ID NO 143
<211> LENGTH: 21
<212> TYPE: RNA
<213> ORGANISM: Physcomitrella patens

<400> SEQUENCE: 143
cuuggacuga agggagcucc c                                                21

<210> SEQ ID NO 144

```
<211> LENGTH: 21
<212> TYPE: RNA
<213> ORGANISM: Physcomitrella patens

<400> SEQUENCE: 144
cuuggacuga agggagcucc c                                              21

<210> SEQ ID NO 145
<211> LENGTH: 20
<212> TYPE: RNA
<213> ORGANISM: Populus trichocarpa

<400> SEQUENCE: 145
uugggcugaa gggagcuccc                                                20

<210> SEQ ID NO 146
<211> LENGTH: 23
<212> TYPE: RNA
<213> ORGANISM: Homo sapiens

<400> SEQUENCE: 146
ucucuggagg gaagcacuuu cug                                            23

<210> SEQ ID NO 147
<211> LENGTH: 20
<212> TYPE: RNA
<213> ORGANISM: Physcomitrella patens

<400> SEQUENCE: 147
cuuggacuga agggagcucc                                                20

<210> SEQ ID NO 148
<211> LENGTH: 20
<212> TYPE: RNA
<213> ORGANISM: Physcomitrella patens

<400> SEQUENCE: 148
cuuggacuga agggagcucc                                                20

<210> SEQ ID NO 149
<211> LENGTH: 21
<212> TYPE: RNA
<213> ORGANISM: Arabidopsis thaliana

<400> SEQUENCE: 149
uuggacugaa gggagcuccu u                                              21

<210> SEQ ID NO 150
<211> LENGTH: 21
<212> TYPE: RNA
<213> ORGANISM: Arabidopsis thaliana

<400> SEQUENCE: 150
uuggacugaa gggagcuccc u                                              21

<210> SEQ ID NO 151
<211> LENGTH: 20
<212> TYPE: RNA
<213> ORGANISM: Populus trichocarpa

<400> SEQUENCE: 151
uuggacugaa gggagcuccu                                                20
```

```
<210> SEQ ID NO 152
<211> LENGTH: 70
<212> TYPE: RNA
<213> ORGANISM: Human cytomegalovirus

<400> SEQUENCE: 152
cacgguugau ugugcccgga ccgugggcgc gacgaaaccc accgucacgg uccgagcaca    60
uccaaacgug                                                          70

<210> SEQ ID NO 153
<211> LENGTH: 20
<212> TYPE: RNA
<213> ORGANISM: Populus trichocarpa

<400> SEQUENCE: 153
uuggacugaa gggagcuccc                                               20

<210> SEQ ID NO 154
<211> LENGTH: 28
<212> TYPE: RNA
<213> ORGANISM: Apis mellifera

<400> SEQUENCE: 154
gauuuagccu cuccuaggcu uugucugu                                      28

<210> SEQ ID NO 155
<211> LENGTH: 20
<212> TYPE: RNA
<213> ORGANISM: Populus trichocarpa

<400> SEQUENCE: 155
uuggacugaa gggagcuccu                                               20

<210> SEQ ID NO 156
<211> LENGTH: 20
<212> TYPE: RNA
<213> ORGANISM: Glycine max

<400> SEQUENCE: 156
uuggacugaa gggagcuccc                                               20

<210> SEQ ID NO 157
<211> LENGTH: 20
<212> TYPE: RNA
<213> ORGANISM: Glycine max

<400> SEQUENCE: 157
uuggacugaa gggagcuccc                                               20

<210> SEQ ID NO 158
<211> LENGTH: 23
<212> TYPE: RNA
<213> ORGANISM: Caenorhabditis elegans

<400> SEQUENCE: 158
uggcggaucc auuuuggguu gua                                           23

<210> SEQ ID NO 159
<211> LENGTH: 20
<212> TYPE: RNA
<213> ORGANISM: Populus trichocarpa

<400> SEQUENCE: 159
```

-continued

```
uuggacugaa gggagcuccc                                              20

<210> SEQ ID NO 160
<211> LENGTH: 21
<212> TYPE: RNA
<213> ORGANISM: Arabidopsis thaliana

<400> SEQUENCE: 160
uuggacugaa gggagcuccc u                                            21

<210> SEQ ID NO 161
<211> LENGTH: 20
<212> TYPE: RNA
<213> ORGANISM: Populus trichocarpa

<400> SEQUENCE: 161
uuggacugaa gggagcuccu                                              20

<210> SEQ ID NO 162
<211> LENGTH: 20
<212> TYPE: RNA
<213> ORGANISM: Populus trichocarpa

<400> SEQUENCE: 162
uuggacugaa gggagcuccc                                              20

<210> SEQ ID NO 163
<211> LENGTH: 20
<212> TYPE: RNA
<213> ORGANISM: Populus trichocarpa

<400> SEQUENCE: 163
uuggacugaa gggagcuccu                                              20

<210> SEQ ID NO 164
<211> LENGTH: 20
<212> TYPE: RNA
<213> ORGANISM: Medicago truncatula

<400> SEQUENCE: 164
uuggacugaa gggagcuccc                                              20

<210> SEQ ID NO 165
<211> LENGTH: 20
<212> TYPE: RNA
<213> ORGANISM: Populus trichocarpa

<400> SEQUENCE: 165
uuggacugaa gggagcuccc                                              20

<210> SEQ ID NO 166
<211> LENGTH: 20
<212> TYPE: RNA
<213> ORGANISM: Human cytomegalovirus

<400> SEQUENCE: 166
ggggaugggc uggcgcgcgg                                              20

<210> SEQ ID NO 167
<211> LENGTH: 22
<212> TYPE: RNA
<213> ORGANISM: Arabidopsis thaliana

<400> SEQUENCE: 167
```

```
uuggggacga caucuuuugu ug                                              22

<210> SEQ ID NO 168
<211> LENGTH: 22
<212> TYPE: RNA
<213> ORGANISM: Drosophila melanogaster

<400> SEQUENCE: 168
gggggucacu cugugccugu gc                                              22

<210> SEQ ID NO 169
<211> LENGTH: 24
<212> TYPE: RNA
<213> ORGANISM: Populus trichocarpa

<400> SEQUENCE: 169
caaaagcugu uggguuuggc uggg                                            24

<210> SEQ ID NO 170
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
caaaaggcuc uuuucagagc cac                                             23

<210> SEQ ID NO 171
<211> LENGTH: 23
<212> TYPE: RNA
<213> ORGANISM: Homo sapiens

<400> SEQUENCE: 171
ucucuggagg gaagcacuuu cug                                             23

<210> SEQ ID NO 172
<211> LENGTH: 5289
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
tagttattaa tgtacgtaaa tccctcttaa atcttgtgac ctgaaacagg aaatttagtc     60
accgtatgta aactgaaaac tgcactaaaa aataacaaga tccaagttaa gcaatttctg   120
acccaaaaga caagttactt cacagacgcc tccgatgctg atactttaat aaatggactg   180
cctaatgctt tcctacattc tgacaatata ttaacactaa ttttatgtaa ctcccctaca   240
cttatactcc tcattcaagg gcacatgtaa acttgagtag aaatgatttc taatgtcaat   300
gggagggagg tagaagagaa aaaacaaaaa aacaaaaaac ccagaagcag cagagacccg   360
tgggtggttt catacaggaa acagggtaag gctgcctggc tctgcgggac gactcgccag   420
tttgggcaca aagatggagc gtaggaaaga actcacagcc gtgtccagtc acctacacct   480
ggtacaccat gccctgtggc aagtttacg cgtgctaccg gctctatcct gttagcttcc   540
tcagcaggag aaacagcgag caggcccagc cgcccggcga cccgcggagt gtcgcaacga   600
cggccgcacg caaatgaagc caccgagcac gcgcgtcgtg attcgcgcgt tccagggcgg   660
```

-continued

```
cgccggggcg agggagccgg tcttatgtaa atgagaggct tctgtccgcg cgctcctatt    720
ggccacggcg tcaggacgcg tgtgagccaa tgagagcgtc gggcggacaa tcgggtctgc    780
gtctatcaaa gggtgaggcg tcggcgccgg agtaccgttt cctggttgtg gccgttcgag    840
atctgatctc gagctcaagc ttcgaattct gcagtcgacg gtaccgcggg cccgggatcc    900
accggtcgcc accatggtga gcaagggcga ggagctgttc accggggtgg tgcccatcct    960
ggtcgagctg gacggcgacg taaacggcca caagttcagc gtgtccggcg agggcgaggg   1020
cgatgccacc tacggcaagc tgaccctgaa gttcatctgc accaccggca agctgcccgt   1080
gccctggccc accctcgtga ccaccctgac ctacggcgtg cagtgcttca gccgctaccc   1140
cgaccacatg aagcagcacg acttcttcaa gtccgccatg cccgaaggct acgtccagga   1200
gcgcaccatc ttcttcaagg acgacggcaa ctacaagacc cgcgccgagg tgaagttcga   1260
gggcgacacc ctggtgaacc gcatcgagct gaagggcatc gacttcaagg aggacggcaa   1320
catcctgggg cacaagctgg agtacaacta caacagccac aacgtctata tcatggccga   1380
caagcagaag aacggcatca aggtgaactt caagatccgc cacaacatcg aggacggcag   1440
cgtgcagctc gccgaccact accagcagaa caccccatc ggcgacggcc ccgtgctgct   1500
gcccgacaac cactacctga gcacccagtc cgccctgagc aaagaccca acgagaagcg   1560
cgatcacatg gtcctgctgg agttcgtgac cgccgccggg atcactctcg gcatggacga   1620
gctgtacaag aagcttagcc atggcttccc gccggaggtg gaggagcagg atgatgcgc   1680
gctgcccatg tcttgtgccc aggagagcgg gatggaccgt caccctgcag cctgtgcttc   1740
tgctaggatc aatgtgtaga tgcgcggccg cactgctcgc gtcggcccgc gtctctgtga   1800
tataaccccc gcgagctccc aaaaaggctc ttttcagagc cacccactga atcagataaa   1860
gagttgtgtc acggtagccg gtcttggtgg cctttcctgg ccctgcccca aaagtaagag   1920
tgttcgtgtt cctctgcttc cttgcccatc tgccgtggtt taccctggtt agtttagtct   1980
gttgtcgctt ctttggtttc atgccctgcc tcgcgagcgg ataacgcggt tctcgctgac   2040
cgtcccaagc atttagcccc tatctgccca cacccttgtc ctacacaaca ctgtccctca   2100
ctcagcgtcc acccgcctga cccttcccag gactaagact caactaggac gtctaggcat   2160
tctagttgtg gtttgtccaa actcatcaat gtatcttaag gcgtaaattg taagcgttaa   2220
tattttgtta aaattcgcgt taaattttg ttaaatcagc tcattttta accaataggc   2280
cgaaatcggc aaaatccctt ataaatcaaa agaatagacc gagatagggt tgagtgttgt   2340
tccagtttgg aacaagagtc cactattaaa gaacgtggac tccaacgtca agggcgaaa   2400
aaccgtctat cagggcgatg gcccactacg tgaaccatca cctaatcaa gttttttggg   2460
gtcgaggtgc cgtaaagcac taaatcggaa ccctaaaggg agccccgat ttagagcttg   2520
acggggaaag ccggcgaacg tggcgagaaa ggaagggaag aaagcgaaag gagcgggcgc   2580
tagggcgctg gcaagtgtag cggtcacgct gcgcgtaacc accacaccg ccgcgcttaa   2640
tgcgccgcta cagggcgcgt caggtggcac ttttcgggga atgtgcgcg gaacccctat   2700
ttgtttattt ttctaaatac attcaaatat gtatccgctc atgagacaat aaccctgata   2760
aatgcttcaa taatattgaa aaggaagag tcctgaggcg gaaagaacca gctgtggaat   2820
gtgtgtcagt tagggtgtgg aaagtcccca ggctcccag caggcagaag tatgcaaagc   2880
atgcatctca attagtcagc aaccaggtgt ggaaagtccc caggctcccc agcaggcaga   2940
agtatgcaaa gcatgcatct caattagtca gcaaccatag tcccgcccct aactccgccc   3000
atcccgcccc taactccgcc cagttccgcc cattctccgc cccatggctg actaattttt   3060
```

```
tttatttatg cagaggccga ggccgcctcg gcctctgagc tattccagaa gtagtgagga    3120 ggctttttg gaggcctagg cttttgcaaa gatcgatcaa gagacaggat gaggatcgtt     3180
tcgcatgatt gaacaagatg gattgcacgc aggttctccg gccgcttggg tggagaggct    3240
attcggctat gactgggcac aacagacaat cggctgctct gatgccgccg tgttccggct    3300
gtcagcgcag gggcgcccgg ttcttttgt caagaccgac ctgtccggtg ccctgaatga     3360
actgcaagac gaggcagcgc ggctatcgtg gctggcacg acgggcgttc cttgcgcagc     3420
tgtgctcgac gttgtcactg aagcgggaag ggactggctg ctattgggcg aagtgccggg    3480
gcaggatctc ctgtcatctc accttgctcc tgccgagaaa gtatccatca tggctgatgc    3540
aatgcggcgg ctgcatacgc ttgatccggc tacctgccca ttcgaccacc aagcgaaaca    3600
tcgcatcgag cgagcacgta ctcggatgga agccggtctt gtcgatcagg atgatctgga    3660
cgaagagcat caggggctcg cgccagccga actgttcgcc aggctcaagg cgagcatgcc    3720
cgacggcgag gatctcgtcg tgacccatgg cgatgcctgc ttgccgaata tcatggtgga    3780
aaatggccgc ttttctggat tcatcgactg tggccggctg ggtgtggcgg accgctatca    3840
ggacatagcg ttggctaccc gtgatattgc tgaagagctt ggcggcgaat gggctgaccg    3900
cttcctcgtg ctttacggta tcgccgctcc cgattcgcag cgcatcgcct tctatcgcct    3960
tcttgacagg ttcttctgag cgggactctg gggttcgaaa tgaccgacca agcgacgccc    4020
aacctgccat cacgagattt cgattccacc gccgccttct atgaaaggtt gggcttcgga    4080
atcgttttcc gggacgccgg ctggatgatc ctccagcgcg gggatctcat gctggagttc    4140
ttcgcccacc ctagggggag gctaactgaa acacggaagg agacaatacc ggaaggaacc    4200
cgcgctatga cggcaataaa aagacagaat aaaacgcacg gtgttgggtc gtttgttcat    4260
aaacgcgggg ttcggtccca gggctggcac tctgtcgata ccccaccgag accccattgg    4320
ggccaatacg cccgcgtttc ttccttttcc ccaccccacc ccccaagttc gggtgaaggc    4380
ccagggctcg cagccaacgt cggggcggca ggccctgcca tagcctcagg ttactcatat    4440
atactttaga ttgatttaaa acttcatttt taatttaaaa ggatctaggt gaagatcctt    4500
tttgataatc tcatgaccaa aatcccttaa cgtgagtttt cgttccactg agcgtcagac    4560
cccgtagaaa agatcaaagg atcttcttga gatccttttt ttctgcgcgt aatctgctgc    4620
ttgcaaacaa aaaaaccacc gctaccagcg gtggtttgtt tgccggatca agagctacca    4680
actctttttc cgaaggtaac tggcttcagc agagcgcaga taccaaatac tgtccttcta    4740
gtgtagccgt agttaggcca ccacttcaag aactctgtag caccgcctac atacctcgct    4800
ctgctaatcc tgttaccagt ggctgctgcc agtggcgata agtcgtgtct taccgggttg    4860
gactcaagac gatagttacc ggataaggcg cagcggtcgg gctgaacggg gggttcgtgc    4920
acacagccca gcttggagcg aacgacctac accgaactga gatacctaca gcgtgagcta    4980
tgagaaagcg ccacgcttcc cgaagggaga aaggcggaca ggtatccggt aagcggcagg    5040
gtcggaacag gagagcgcac gagggagctt ccaggggaa acgcctggta tctttatagt     5100
cctgtcgggt ttcgccacct ctgacttgag cgtcgatttt tgtgatgctc gtcaggggg     5160 cggagcctat ggaaaaacgc cagcaacgcg gcctttttac ggttcctggc cttttgctgg    5220
ccttttgctc acatgttctt tcctgcgtta tcccctgatt ctgtggataa ccgtattacc    5280
gccatgcat                                                            5289
```

<210> SEQ ID NO 173

```
<211> LENGTH: 97
<212> TYPE: DNA
<213> ORGANISM: Simian virus

<400> SEQUENCE: 173
tgctgttgac agtgagcgca ggctcatttc aggcccctca tagtgaagcc acagatgtat    60
gagggccctg aaatgagcct ttgcctactg cctcgga                             97

<210> SEQ ID NO 174
<211> LENGTH: 97
<212> TYPE: DNA
<213> ORGANISM: Homo sapiens

<400> SEQUENCE: 174
tgctgttgac agtgagcgcg aaagtgcttc cctccagaga tagtgaagcc acagatgtat    60
ctctggaggg aagcactttc ttgcctactg cctcgga                             97

<210> SEQ ID NO 175
<211> LENGTH: 97
<212> TYPE: DNA
<213> ORGANISM: Mus musculus

<400> SEQUENCE: 175
tgctgttgac agtgagcgac cctctggtca accagtcaca tagtgaagcc acagatgtat    60
gtgactggtt gaccagaggg gtgcctactg cctcgga                             97

<210> SEQ ID NO 176
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Ala Cys Arg Pro Arg Ser Pro Pro Arg His Gln Ser Arg Cys Asp
1               5                   10                  15

Gly Asp Ala Ser Pro Pro Ser Pro Ala Arg Trp Ser Leu Gly Arg Lys
            20                  25                  30

Arg Arg Ala Asp Gly Arg Arg Trp Arg Pro Glu Asp Ala Glu Glu Ala
        35                  40                  45

Glu His Arg Gly Ala Glu Arg Arg Pro Glu Ser Phe Thr Thr Pro Glu
    50                  55                  60

Gly Pro Lys Pro Arg Ser Arg Cys Ser Asp Trp Ala Ser Ala Val Glu
65                  70                  75                  80

Glu Asp Glu Met Arg Thr Arg Val Asn Lys Glu Met Ala Arg Tyr Lys
                85                  90                  95

Arg Lys Leu Leu Ile Asn Asp Phe Gly Arg Glu Arg Lys Ser Ser Ser
            100                 105                 110

Gly Ser Ser Asp Ser Lys Glu Ser Met Ser Thr Val Pro Ala Asp Phe
        115                 120                 125

Glu Thr Asp Glu Ser Val Leu Met Arg Arg Gln Lys Gln Ile Asn Tyr
    130                 135                 140

Gly Lys Asn Thr Ile Ala Tyr Asp Arg Tyr Ile Lys Glu Val Pro Arg
145                 150                 155                 160

His Leu Arg Gln Pro Gly Ile His Pro Lys Thr Pro Asn Lys Phe Lys
                165                 170                 175

Lys Tyr Ser Arg Arg Ser Trp Asp Gln Gln Ile Lys Leu Trp Lys Val
```

```
                180                 185                 190
Ala Leu His Phe Trp Asp Pro Pro Ala Glu Glu Gly Cys Asp Leu Gln
            195                 200                 205

Glu Ile His Pro Val Asp Leu Glu Ser Ala Glu Ser Ser Glu Pro
            210                 215                 220

Gln Thr Ser Ser Gln Asp Asp Phe Asp Val Tyr Ser Gly Thr Pro Thr
225                 230                 235                 240

Lys Val Arg His Met Asp Ser Gln Val Glu Asp Glu Phe Asp Leu Glu
                245                 250                 255

Ala Cys Leu Thr Glu Pro Leu Arg Asp Phe Ser Ala Met Ser
            260                 265                 270

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      HSL consensus sequence

<400> SEQUENCE: 177
mmmggyyyuh huhadddyym m                                              21

<210> SEQ ID NO 178
<211> LENGTH: 22
<212> TYPE: RNA
<213> ORGANISM: Artificial Sequence
<220> FEATURE:
<223> OTHER INFORMATION: Description of Artificial Sequence: Synthetic
      HSL consensus sequence
<220> FEATURE:
<221> NAME/KEY: modified_base
<222> LOCATION: (14)..(14)
<223> OTHER INFORMATION: a, c, u, g, unknown or other

<400> SEQUENCE: 178
mmmmggyyyu uyunarrrcc mm                                             22

<210> SEQ ID NO 179
<211> LENGTH: 23
<212> TYPE: RNA
<213> ORGANISM: Artificial Sequence
<220> FEATURE:
<223> OTHER INFORMATION: Description of Artificial Sequence: Synthetic
      HSL consensus sequence
<220> FEATURE:
<221> NAME/KEY: modified_base
<222> LOCATION: (1)..(1)
<223> OTHER INFORMATION: a, c, u, g, unknown or other

<400> SEQUENCE: 179
nmmmmggyyy uhhuharrrc cmm                                            23

<210> SEQ ID NO 180
<211> LENGTH: 21
<212> TYPE: RNA
<213> ORGANISM: Homo sapiens

<400> SEQUENCE: 180
cuccagaggg aaguacuuuc u                                              21

<210> SEQ ID NO 181
<211> LENGTH: 22
<212> TYPE: RNA
<213> ORGANISM: Homo sapiens
```

```
<400> SEQUENCE: 181
aaagugcuuc ccuuuggacu gu                                      22

<210> SEQ ID NO 182
<211> LENGTH: 21
<212> TYPE: RNA
<213> ORGANISM: Homo sapiens

<400> SEQUENCE: 182
aaagugcuuc cuuuuagagg g                                       21

<210> SEQ ID NO 183
<211> LENGTH: 22
<212> TYPE: RNA
<213> ORGANISM: Homo sapiens

<400> SEQUENCE: 183
cucuagaggg aagcacuuuc ug                                      22

<210> SEQ ID NO 184
<211> LENGTH: 22
<212> TYPE: RNA
<213> ORGANISM: Homo sapiens

<400> SEQUENCE: 184
aaagugcuuc cuuuuagagg gu                                      22

<210> SEQ ID NO 185
<211> LENGTH: 20
<212> TYPE: RNA
<213> ORGANISM: Homo sapiens

<400> SEQUENCE: 185
cuacaaaggg aagcccuuuc                                         20

<210> SEQ ID NO 186
<211> LENGTH: 22
<212> TYPE: RNA
<213> ORGANISM: Homo sapiens

<400> SEQUENCE: 186
aaagugcuuc ucuuuggugg gu                                      22

<210> SEQ ID NO 187
<211> LENGTH: 21
<212> TYPE: RNA
<213> ORGANISM: Homo sapiens

<400> SEQUENCE: 187
aaagugcuuc cuuuuugagg g                                       21

<210> SEQ ID NO 188
<211> LENGTH: 22
<212> TYPE: RNA
<213> ORGANISM: Homo sapiens

<400> SEQUENCE: 188
aagugcuucc uuuuagaggg uu                                      22

<210> SEQ ID NO 189
<211> LENGTH: 24
<212> TYPE: RNA
```

<213> ORGANISM: Homo sapiens

<400> SEQUENCE: 189
acaaagugcu ucccuuuaga gugu                                              24

<210> SEQ ID NO 190
<211> LENGTH: 22
<212> TYPE: RNA
<213> ORGANISM: Homo sapiens

<400> SEQUENCE: 190
acaaagugcu ucccuuuaga gu                                                22

<210> SEQ ID NO 191
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
agagaaacau gaggaucacc caugugagag agagagagag                             40

<210> SEQ ID NO 192
<211> LENGTH: 1522
<212> TYPE: RNA
<213> ORGANISM: Thermus thermophilus

<400> SEQUENCE: 192
uuuguuggag aguuugaucc uggcucaggg ugaacgcugg cggcgugccu aagacaugca       60
agucgugcgg gccgcggggu uuuacuccgu ggucagcggc ggacggguga guaacgcgug      120
ggugaccuac ccggaagagg gggacaaccc ggggaaacuc gggcuaaucc cccaugugga     180
cccgccccuu ggggugugcuc caaagggcuu ugcccgcuuc cggaugggcc cgcgucccau    240
cagcuaguug gugggguaau ggcccaccaa ggcgacgacg gguagccggu cugagaggau     300
ggccggccac agggggcacug agacacgggc cccacuccua cgggaggcag caguuaggaa    360
ucuuccgcaa ugggcgcaag ccugacgag cgacgccgcu uggaggaaga agcccuucgg     420
gguguaaacu ccugaacccg ggacgaaacc cccgacgagg ggacugacgg uaccggggua    480
auagcgccgg ccaacuccgu gccagcagcc gcgguaauac ggagggcgcg agcguuaccc     540
ggauucacug ggcguaaagg gcguguaggc ggccuggggc gucccaugug aaagaccacg    600
gcucaaccgu ggggagcgu gggauacgcu caggcuagac ggugggagag gguggugga     660 uucccggagu agcggugaaa ugcgcagaua ccggaggaa cgccgauggc gaaggcagcc   720
accuggucca cccgugacgc ugaggcgcga agcgugggg agcaaaccgg auuagauacc    780 cgggagucc acgcccuaaa cgaugcgcgc uaggucucug ggucuccugg gggccgaagc    840
uaacgcguua agcgccgc cugggagua cggccgcaag gcugaaacuc aaaggaauug    900 acggggggccc gcacaagcgg uggagcaugu gguuuaauuc gaagcaacgc gaagaaccuu     960
accaggccuu gacaugcuag gaacccggg ugaaagccug ggugcccccg cgaggggagc    1020
ccuagcacag gugcugcaug gccgucguca gcucgugccg ugagguguug gguuaagucc    1080
cgcaacgagc gcaaccccg ccguuaguug ccagcgguuc ggccgggcac ucuacggga     1140 cugcccgcga aagcgggagg aaggagggga cgacgucugg ucagcauggc ccuuacggcc    1200
ugggcgacac acgugcuaca augcccacua caaagcgaug ccaccggca acggggagcu    1260

```
aaucgcaaaa agguggyccc aguucggauu gggucugca acccgaccc  augaagccgg    1320 aaucgcuagu aaucgcggau cagccaugcc gcggugaaua cguucccggg ccuuguacac    1380
accgcccguc acgccauggg agcgggcucu acccgaaguc gccgggagcc uacgggcagg    1440
cgccgagggu agggcccgug acugggggcga agucguaaca agguagcugu accggaaggu    1500
gcggcuggau caccuccuuu cu                                              1522

<210> SEQ ID NO 193
<211> LENGTH: 41
<212> TYPE: RNA
<213> ORGANISM: Homo sapiens

<400> SEQUENCE: 193
agguuccauc guauccaaaa ggcucuuuuc agagccaccc a                         41

<210> SEQ ID NO 194
<211> LENGTH: 23
<212> TYPE: RNA
<213> ORGANISM: Artificial Sequence
<220> FEATURE:
<223> OTHER INFORMATION: Description of Artificial Sequence: Synthetic
      HSL consensus sequence
<220> FEATURE:
<221> NAME/KEY: modified_base
<222> LOCATION: (1)..(1)
<223> OTHER INFORMATION: a, c, u, g, unknown or other

<400> SEQUENCE: 194
nmmmmggyyy uhhuharrrc cmm                                             23
```